(12) United States Patent
Ammendola et al.

(10) Patent No.: US 11,795,478 B2
(45) Date of Patent: **\*Oct. 24, 2023**

(54) ADENOVIRUS POLYNUCLEOTIDES AND POLYPEPTIDES

(71) Applicant: GLAXOSMITHKLINE BIOLOGICALS SA, Rixensart (BE)

(72) Inventors: Virginia Ammendola, Rome (IT); Stefania Capone, Rome (IT); Stefano Colloca, Rome (IT); Antonella Folgori, Rome (IT); Rossella Merone, Rome (IT)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

This patent is subject to a terminal disclaimer.

(21) Appl. No.: 17/742,221

(22) Filed: May 11, 2022

(65) Prior Publication Data

US 2022/0275397 A1    Sep. 1, 2022

Related U.S. Application Data

(63) Continuation of application No. 16/466,683, filed as application No. PCT/IB2017/057738 on Dec. 7, 2017, now Pat. No. 11,414,679.

(30) Foreign Application Priority Data

Dec. 9, 2016 (GB) ........................... 1620968

(51) Int. Cl.
| | |
|---|---|
| *C12N 15/86* | (2006.01) |
| *A61K 39/12* | (2006.01) |
| *A61K 39/21* | (2006.01) |
| *C07K 14/005* | (2006.01) |
| *A61P 31/18* | (2006.01) |
| *A61P 31/14* | (2006.01) |
| *A61K 39/00* | (2006.01) |

(52) U.S. Cl.
CPC .............. *C12N 15/86* (2013.01); *A61K 39/12* (2013.01); *A61K 39/21* (2013.01); *A61P 31/14* (2018.01); *A61P 31/18* (2018.01); *C07K 14/005* (2013.01); *A61K 2039/572* (2013.01); *C12N 2710/10343* (2013.01); *C12N 2740/16034* (2013.01); *C12N 2740/16234* (2013.01); *C12N 2760/20134* (2013.01)

(58) Field of Classification Search
None
See application file for complete search history.

(56) References Cited

U.S. PATENT DOCUMENTS

| | | | |
|---|---|---|---|
| 8,216,834 | B2 | 7/2012 | Colloca et al. |
| 8,673,319 | B2 | 3/2014 | Colloca et al. |
| 11,414,679 | B2 * | 8/2022 | Ammendola ........ C07K 14/005 |
| 2010/0260799 | A1 | 10/2010 | Roy et al. |

FOREIGN PATENT DOCUMENTS

| | | |
|---|---|---|
| JP | 2007-518414 A | 7/2007 |
| JP | 2008-543295 A | 12/2008 |
| WO | WO 2005/071093 A2 | 8/2005 |
| WO | WO 2006/133911 A2 | 12/2006 |
| WO | WO 2016/198621 A1 | 12/2016 |

OTHER PUBLICATIONS

Molinier-Frenkel et al. "The maturation of murine dendritic cells induced by human adenovirus is mediated by the fiber knob domain," The Journal of Biological Chemistry, vol. 278, No. 39, Sep. 26, 2003, pp. 37175-37185.
Castro-Chavez, Fernando, "The rules of variation: Amino acid exchange according to the rotating circular genetic code" J Theor Biol, vol. 264(3): Jun. 7, 2010, pp. 711-721.
Roy et al. 2008 (accession No. FJ025904).

\* cited by examiner

*Primary Examiner* — Agnieszka Boesen
(74) *Attorney, Agent, or Firm* — Birch, Stewart, Kolasch & Birch, LLP

(57) ABSTRACT

The present invention relates to isolated polynucleotide and polypeptide sequences derived from novel chimpanzee adenovirus ChAd157, as well as to recombinant polynucleotides, vectors, adenoviruses, cells and compositions comprising said polynucleotide and polypeptide sequences.

24 Claims, 10 Drawing Sheets

Specification includes a Sequence Listing.

Figure 1B

```
                  170        180        190        200        210        220        230        240
                    +          +          +          +          +          +          +          +
12_ChAd157  QTSAPLTAADSSTLTVSATPP------GSLGDMEDPKYTNGKLGTIGSPLHVVDSLRLTVVTGGLTVNALQTRV   240
01_ChAd3    QTSAPLTAADSSTLTVSATPP------GSLGDMEDPKYTNGKLGTIGSPLHVVDSLRLTVVTGGLTVNALQTRV   240
02_PanAd3   QTSAPLTAADSSTLTVSTTPPSVSGSLGDMEDPKYTHGKLGTIGSPLHVVDSLRLTVVTGGLTVNALQTRV      239
03_ChAd17   QTSAPLTAADSSTLTVSATPPSVSGSLGDMEDPKYTNGKLGTIGSPLHVVDSLRLTVVTGGLTVNALQTRV      240
04_ChAd19   QTSAPLTAADSSTLTVSATPPSVSGSLGDMEDPNYTNGKLGTIGSPLHVVDSLRLTVVTGGLTVNALQTRV      240
05_ChAd24   QTSAPLTAADSSTLTVSATPPSVSGSLGDMEDPKYTNGKLGTIGSPLHVVDSLRLTVVTGGLTVNALQTRV      240
06_ChAd155  QTSAPLTAADSSTLTVSATPPSVSGSLGDMQAPTYTTNGKLGTIGSPLHVVDSLRLTVVTGGLTVNALQTRV     240
07_ChAd11   QTSAPLTAADSSTLTVSATPPSVSGSLGDMQAPTYTTNGKLGTIGAPLHVVDSIRLTVVTGGLTVNALQTRV     240
08_ChAd20   QTSAPLTAADSSTLTVSATPPSVSGSLGDMQAPTYTTNGKLGNIGAPLHVVDSIRLTVVTGGLTVNALQTRV     240
09_ChAd31   QTSAPLTAADSSTLTVSATPPSVSGSLGDMQAPTYTTNGKLGTIGAPLHVVDSIRLTVVTGGLTVNALQTRV     240
10_PanAd1   QTSAPLTAADSSTLTVSATPP------GSLSDMQAPTYTTNGKLGTIGAPLHVVDPIRLTVVTGGLTVNALQTRV  239
11_PanAd2   QTSAPLTAADSSTLTVSATPP------GSLSDMQAPTYTTNGKLGTINGAPLHVVDPIRLTVVTGGLTVNALQTRV 239

250        260        270        280        290        300        310        320
                    +          +          +          +          +          +          +          +
12_ChAd157  TGALGYDTSGNLQLRAAGGMRIDANGQLILVAYPFDAQNNLSLRLGQGPLYVNHNLDLNCNRGINTKKLEV      320
01_ChAd3    TGALGYDTSGNLQLRAAGGMRIDANGQLILVAYPFDAQNNLSLRLGQGPLYVNHNLDLNCNRGINTKKLEV      320
02_PanAd3   KGALGYDTSGNIRLRAAGGMRIGQLILGQLILVAYPFDAQNNLSLRLGQGPLYVNHNLDLNCNRGITSNTKKLEV  319
03_ChAd17   TGALGYDTSGNLQLRAAGGMRIDANGQLILVAYPFDAQNNLSLRLGQGPLYVNHNLDLNCNRGITNTKKLEV     320
04_ChAd19   TGALGYDTSGNLQLRAAGGMRIDANGQLILVAYPFDAQNNLSLRLGQGPLYVNHNLDLNCNRGITNTKKLEV     320
05_ChAd24   TGALGYDTSGNLQLRAAGGMRIDANGQLILVAYPFDAQNNLSLRLGQGPLYVNHNLDLNCNRGITNTKKLEV     320
06_ChAd155  GALYDTSGNILRAAGGMRDANGQLILVAYPFDAQNNLSLRLGQGPLYVNAHNLDLNQNRGITSGNTKKLEV      320
07_ChAd11   GALYDTSGNILRAAGGMRDANGQLILVAYPFDAQNNLSLRLGQGPLYVNAHNLDLNQNRGITSGNTKKLEV      320
08_ChAd20   GALYDTSGNLRAAGGMPRDANGQLILVAYPFDAQNNLSLRLGQGPLYVNAHNLDLNNRGITSGNTKKLEV       320
09_ChAd31   GALYDTSGNLRAAGGMRDANGQLILVAYPFDAQNNLSLRLGQGPLYVNAHNLDLNNRGITSGNTKKLEV        320
10_PanAd1   TGAIYDTNQLQIAGGMRIDANGQLILVAYPFDAQNNLSLRLGQGPLYVNAHNLDLNNRGILNRGITSGNTKKLEV  319
11_PanAd2   TGAIYDTNQLQIAGGMRIDANGQLILVAYPFDAQNNLSLRLGQGPLYVNAHNLDLNNRGILNRGITSGNTKKLEV  319
```

ADENOVIRUS POLYNUCLEOTIDES AND POLYPEPTIDES

CROSS-REFERENCE TO RELATED APPLICATIONS

This application is a Continuation of copending application Ser. No. 16/466,683, filed on Jun. 5, 2019, which is the National Phase under 35 U.S.C. § 371 of International Application No. PCT/IB2017/057738, filed on Dec. 7, 2017, which claims priority under 35 U.S.C. § 119(a) to Application No. 1620968.6, filed in United Kingdom on Dec. 9, 2016, all of which are hereby expressly incorporated by reference into the present application.

FIELD OF THE INVENTION

The present invention relates to isolated polynucleotide and polypeptide sequences derived from novel chimpanzee adenovirus ChAd157, as well as to recombinant polynucleotides, vectors, adenoviruses, cells and compositions comprising said polynucleotide and polypeptide sequences.

BACKGROUND OF THE INVENTION

Adenovirus has been widely used for gene transfer applications due to its ability to achieve highly efficient gene transfer in a variety of target tissues and large transgene capacity. Conventionally, E1 genes of adenovirus are deleted and replaced with a transgene cassette consisting of the promoter of choice, cDNA sequence of the gene of interest and a poly A signal, resulting in a replication defective recombinant virus.

Recombinant adenoviruses are useful in gene therapy and as vaccines. Viral vectors based on chimpanzee adenovirus represent an alternative to the use of human derived adenovirus vectors for the development of genetic vaccines. Adenoviruses isolated from chimpanzees are closely related to adenoviruses isolated from humans as demonstrated by their efficient propagation in cells of human origin. However, since human and chimpanzee adenoviruses are close relatives, serologic cross reactivity between the two virus species is possible.

There is a demand for vectors which effectively deliver molecules to a target and minimize the effect of pre-existing immunity to selected adenovirus serotypes in the population. One aspect of pre-existing immunity that is observed in humans is humoral immunity, which can result in the production and persistence of antibodies that are specific for adenoviral proteins. The humoral response elicited by adenovirus is mainly directed against the three major structural capsid proteins: fiber, penton and hexon.

SUMMARY OF THE INVENTION

There is provided an isolated polynucleotide, wherein the polynucleotide encodes a polypeptide selected from the group consisting of:
  (a) a polypeptide having the amino acid sequence according to SEQ ID NO: 1; and
  (b) a functional derivative of a polypeptide having the amino acid sequence according to SEQ ID NO: 1, wherein the functional derivative has an amino acid sequence which is at least 99.8% identical over its entire length to the amino acid sequence of SEQ ID NO: 1.

Also provided is a recombinant polynucleotide comprising a polynucleotide selected from the group consisting of:
  (a) a polynucleotide which encodes a polypeptide having the amino acid sequence according to SEQ ID NO: 1; and
  (b) a polynucleotide which encodes a functional derivative of a polypeptide having the amino acid sequence according to SEQ ID NO: 1, wherein the functional derivative has an amino acid sequence which is at least 99.8% identical over its entire length to the amino acid sequence of SEQ ID NO: 1.

Also provided is a recombinant vector comprising a polynucleotide selected from the group consisting of:
  (a) a polynucleotide which encodes a polypeptide having the amino acid sequence according to SEQ ID NO: 1; and
  (b) a polynucleotide which encodes a functional derivative of a polypeptide having the amino acid sequence according to SEQ ID NO: 1, wherein the functional derivative has an amino acid sequence which is at least 99.8% identical over its entire length to the amino acid sequence of SEQ ID NO: 1.

Also provided is a recombinant adenovirus comprising at least one polynucleotide or polypeptide selected from the group consisting of:
  (a) a polynucleotide which encodes a polypeptide having the amino acid sequence according to SEQ ID NO: 1;
  (b) a polynucleotide which encodes a functional derivative of a polypeptide having the amino acid sequence according to SEQ ID NO: 1, wherein the functional derivative has an amino acid sequence which is at least 99.8% identical over its entire length to the amino acid sequence of SEQ ID NO: 1;
  (c) a polypeptide having the amino acid sequence according to SEQ ID NO: 1; and
  (d) a functional derivative of a polypeptide having the amino acid sequence according to SEQ ID NO: 1, wherein the functional derivative has an amino acid sequence which is at least 99.8% identical over its entire length to the amino acid sequence of SEQ ID NO: 1.

Also provided is a composition comprising at least one of the following:
  (a) an isolated polynucleotide which encodes a polypeptide having the amino acid sequence according to SEQ ID NO: 1;
  (b) an isolated polynucleotide which encodes a functional derivative of a polypeptide having the amino acid sequence according to SEQ ID NO: 1, wherein the functional derivative has an amino acid sequence which is at least 99.8% identical over its entire length to the amino acid sequence of SEQ ID NO: 1;
  (c) an isolated polypeptide having the amino acid sequence according to SEQ ID NO: 1;
  (d) an isolated functional derivative of a polypeptide having the amino acid sequence according to SEQ ID NO: 1, wherein the functional derivative has an amino acid sequence which is at least 99.8% identical over its entire length to the amino acid sequence of SEQ ID NO: 1;
  (e) a vector comprising a polynucleotide as described in (a) or (b) above; and
  (f) a recombinant adenovirus comprising a polynucleotide as described in (a) or (b) above,
  and a pharmaceutically acceptable excipient.

Also provided is a cell comprising at least one of the following:
  (a) an isolated polynucleotide which encodes a polypeptide having the amino acid sequence according to SEQ ID NO: 1,
  (b) an isolated polynucleotide which encodes a functional derivative of a polypeptide having the amino acid sequence according to SEQ ID NO: 1, wherein the functional derivative has an amino acid sequence which is at least 99.8% identical over its entire length to the amino acid sequence of SEQ ID NO: 1;
  (c) a vector comprising a polynucleotide as described in (a) or (b) above, and
  (d) a recombinant adenovirus comprising a polynucleotide as described in (a) or (b) above.

Also provided is an isolated adenoviral polypeptide selected from the group consisting of:
  (a) a polypeptide having the amino acid sequence according to SEQ ID NO: 1; and
  (b) a functional derivative of a polypeptide having the amino acid sequence according to SEQ ID NO: 1, wherein the functional derivative has an amino acid sequence which is at least 99.8% identical over its entire length to the amino acid sequence of SEQ ID NO: 1.

DESCRIPTION OF THE FIGURES

FIG. 1A-1D—Alignment of fiber protein sequences from the indicated simian adenoviruses.
  ChAd157 (SEQ ID NO:1)
  ChAd3 (SEQ ID NO:27)
  PanAd3 (SEQ ID NO:28)
  ChAd17 (SEQ ID NO:29)
  ChAd19 (SEQ ID NO:30)
  ChAd24 (SEQ ID NO:31)
  ChAd155 (SEQ ID NO:7)
  ChAd11 (SEQ ID NO:32)
  ChAd20 (SEQ ID NO:33)
  ChAd31 (SEQ ID NO:34)
  PanAd1 (SEQ ID NO:35)
  PanAd2 (SEQ ID NO:36)
FIG. 2—Subgroup C BAC Shuttle schematic representation
FIG. 3—Subgroup C Plasmid Shuttle schematic representation
FIG. 4—pChAd157 ΔE1/TetO hCMV GAG vector schematic representation
FIG. 5—pARS SpeciesC Ad5orf6-2 shuttle schematic representation
FIG. 6—plasmid carrying the ChAd157 RG schematic representation
FIG. 7—Transgene Expression by ChAd157/GAG, ChAd19/GAG and ChAd155/GAG
FIG. 8—Western Blot analysis of lysates of Hela cells infected with ChAd155/RG and ChAd157/RG
FIG. 9—Immunological potency of ChAd157/GAG, ChAd155/GAG and ChAd19 GAG in BALB/c mice
FIG. 10—Immunological potency of ChAd157/RG and ChAd155/RG in BALB/c mice
FIG. 11—Neutralization titers following preimmunization of mice with different ChAd vectors
FIG. 12—IFN-γ ELISpot following vaccination of mice with ChAd157/GAG after various preimmunization regimes

DESCRIPTION OF THE SEQUENCES

Figure 1A:
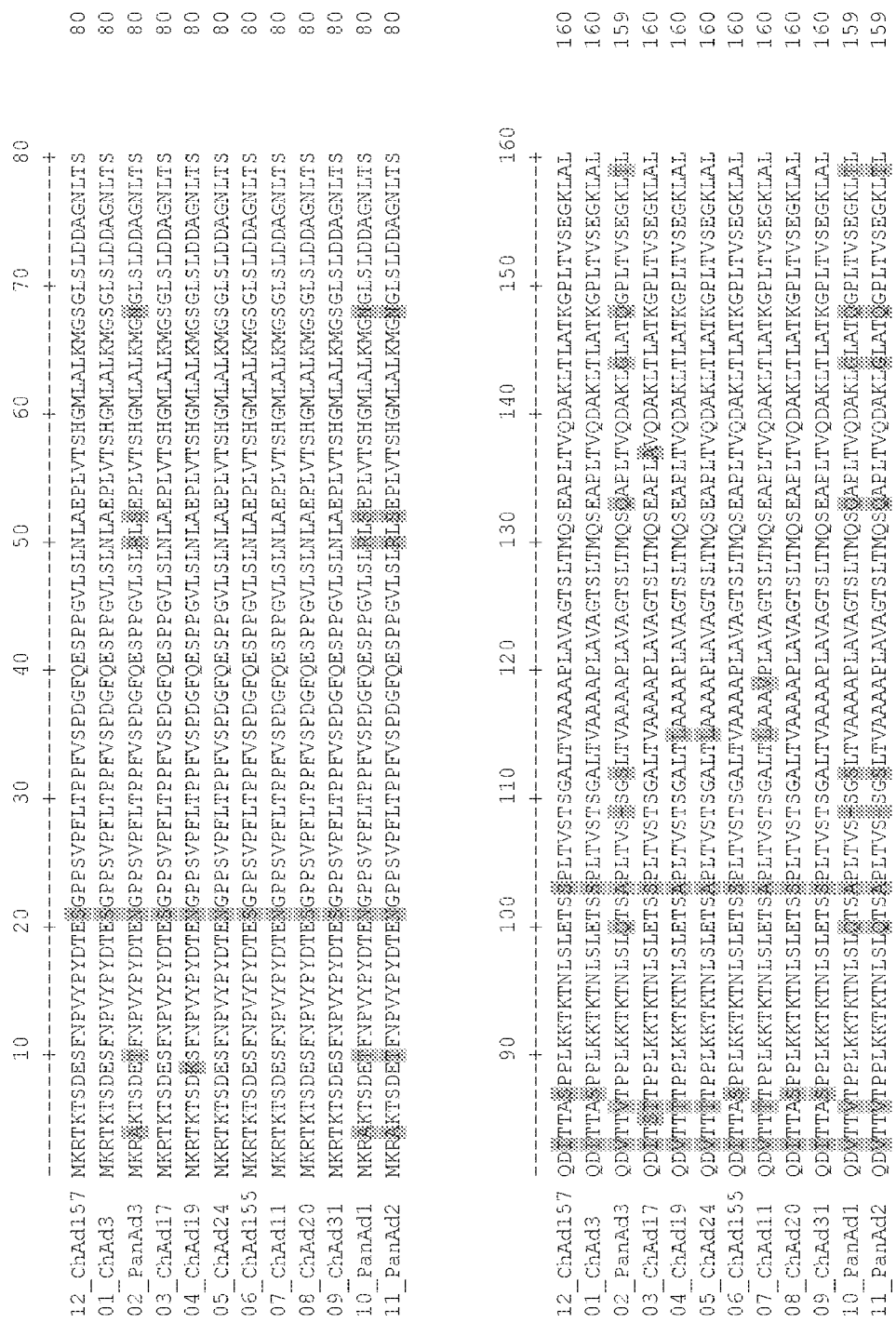

SEQ ID NO: 1—Polypeptide sequence of ChAd157 fiber
SEQ ID NO: 2—Polynucleotide sequence encoding ChAd157 fiber
SEQ ID NO: 3—Polypeptide sequence of ChAd157 penton
SEQ ID NO: 4—Polynucleotide sequence encoding ChAd157 penton
SEQ ID NO: 5—Polypeptide sequence of ChAd157 hexon
SEQ ID NO: 6—Polynucleotide sequence encoding ChAd157 hexon
SEQ ID NO: 7—Polypeptide sequence of ChAd155 fiber
SEQ ID NO: 8—Polynucleotide sequence encoding ChAd155 fiber
SEQ ID NO: 9—Polypeptide sequence of ChAd155 penton
SEQ ID NO: 10—Polynucleotide sequence encoding ChAd155 penton
SEQ ID NO: 11—Polypeptide sequence of ChAd155 hexon
SEQ ID NO: 12—Polynucleotide sequence encoding ChAd155 hexon
SEQ ID NO: 13—Polynucleotide sequence encoding wide type ChAd155
SEQ ID NO: 14—Polynucleotide sequence of Subgroup C BAC Shuttle (#1365)
SEQ ID NO: 15—Polynucleotide sequence of pChAd157ΔE1 TetO hCMV RpsL-Kana #1551
SEQ ID NO: 16—HIV Gag polynucleotide sequence
SEQ ID NO: 17—Polynucleotide sequence of pChAd157 ΔE1/TetO hCMV GAG #1557
SEQ ID NO: 18—Ad5orf6 primer 1 polynucleotide sequence
SEQ ID NO: 19—Ad5orf6 primer 2 polynucleotide sequence
SEQ ID NO: 20—Fiber-E4 polyA primer 1 polynucleotide sequence
SEQ ID NO: 21—Fiber-E4 polyA primer 2 polynucleotide sequence
SEQ ID NO: 22—Polynucleotide sequence of ChAd157 ΔE1E4_Ad5E4orf6/TetO hCMV RpsL-Kana #1594
SEQ ID NO: 23—Rabies Glycoprotein polynucleotide sequence
SEQ ID NO: 24—Polynucleotide sequence of pChAd157 ΔE1E4_Ad5E4orf6/TetO hCMV RG #1559
SEQ ID NO: 25—CMVfor primer polynucleotide sequence
SEQ ID NO: 26—CMVrev primer polynucleotide sequence
SEQ ID NO: 27—Amino acid sequence for the fiber protein of ChAd3
SEQ ID NO: 28—Amino acid sequence for the fiber protein of PanAd3
SEQ ID NO: 29—Amino acid sequence for the fiber protein of ChAd17
SEQ ID NO: 30—Amino acid sequence for the fiber protein of ChAd19
SEQ ID NO: 31—Amino acid sequence for the fiber protein of ChAd24
SEQ ID NO: 32—Amino acid sequence for the fiber protein of ChAd11
SEQ ID NO: 33—Amino acid sequence for the fiber protein of ChAd20
SEQ ID NO: 34—Amino acid sequence for the fiber protein of ChAd31
SEQ ID NO: 35—Amino acid sequence for the fiber protein of PanAd1

SEQ ID NO: 36—Amino acid sequence for the fiber protein of PanAd2

SEQ ID NO: 37—Polynucleotide sequence of hCMV (tetO)

SEQ ID NO: 38—Polynucleotide sequence of Subgroup C Plasmid Shuttle #1376

SEQ ID NO: 39—Polynucleotide sequence of BGH polyA

SEQ ID NO: 40—Polynucleotide sequence of pARS SpeciesC Ad5orf6-2

SEQ ID NO: 41—Polynucleotide sequence of CMVFAM-TAMRA probe

SEQ ID NO: 42—Polynucleotide sequence encoding the enhanced hCMV promoter

DETAILED DESCRIPTION OF THE INVENTION

Vectors, compositions and methods of the present invention may have one or more following improved characteristics over the prior art, including but not limited to higher productivity, improved immunogenicity, increased transgene expression or a distinct serologic cross reactivity profile.

Vectors, compositions and methods of the present invention may demonstrate a combination of properties, such as productivity, immunogenicity, transgene expression and/or serologic cross reactivity which mean they provide are a valuable alternative to known approaches.

Adenovirus

Adenoviruses have a characteristic morphology with an icosahedral capsid comprising three major proteins, hexon (II), penton base (III) and a knobbed fiber (IV), along with a number of other minor proteins, VI, VIII, IX, IIIa and IVa2. The virus genome is a linear, double-stranded DNA. The virus DNA is intimately associated with the highly basic protein VII and a small peptide pX (formerly termed mu). Another protein, V, is packaged with this DNA-protein complex and provides a structural link to the capsid via protein VI. The virus also contains a virus-encoded protease, which is necessary for processing of some of the structural proteins to produce mature infectious virus.

The adenoviral genome is well characterized. There is general conservation in the overall organization of the adenoviral genome with respect to specific open reading frames being similarly positioned, e.g. the location of the E1A, E1B, E2A, E2B, E3, E4, L1, L2, L3, L4 and L5 genes of each virus. Each extremity of the adenoviral genome comprises a sequence known as an inverted terminal repeat (ITR), which is necessary for viral replication. The virus also comprises a virus-encoded protease, which is necessary for processing some of the structural proteins required to produce infectious virions. The structure of the adenoviral genome is described on the basis of the order in which the viral genes are expressed following host cell transduction. More specifically, the viral genes are referred to as early (E) or late (L) genes according to whether transcription occurs prior to or after onset of DNA replication. In the early phase of transduction, the E1A, E1B, E2A, E2B, E3 and E4 genes of adenovirus are expressed to prepare the host cell for viral replication. During the late phase of infection, expression of the late genes L1-L5, which encode the structural components of the virus particles, is activated.

Adenoviruses are species-specific and different serotypes, i.e., types of viruses that are not cross-neutralized by antibodies, have been isolated from a variety of mammalian species. For example, more than 50 serotypes have been isolated from humans which are divided into six subgroups (A-F; B is subdivided into B1 and B2) based on sequence homology and on their ability to agglutinate red blood cells (Tatsis and Ertl *Molecular Therapy* (2004) 10:616-629). Numerous adenoviruses have been isolated from nonhuman simians such as chimpanzees, bonobos, rhesus macaques and gorillas, and they are classified into the same human groups based on phylogenetic relationships based on hexon or fiber sequences (Colloca et al. (2012) *Science Translational Medicine* 4:1-9; Roy et al. (2004) *Virology* 324: 361-372; Roy et al. (2010) *Journal of Gene Medicine* 13:17-25).

WO2005071093 discloses chimpanzee adenoviruses including ChAd19. WO2016198621 (PCT/EP2016/063329) discloses the chimpanzee adenoviruses ChAd155, which is incorporated herein by reference for the purpose of defining ChAd155 derived vectors.

Adenovirus Capsid Proteins Including the Fiber Protein and Polynucleotides Encoding these Proteins As outlined above, the adenoviral capsid comprises three major proteins, hexon, penton and fiber. The hexon accounts for the majority of the structural components of the capsid, which consists of 240 trimeric hexon capsomeres and 12 penton bases. The hexon has three conserved double barrels, while the top has three towers, each tower containing a loop from each subunit that forms most of the capsid. The base of hexon is highly conserved between adenoviral serotypes, while the surface loops are variable (Tatsis and Ertl *Molecular Therapy* (2004) 10:616-629).

Penton is another adenoviral capsid protein that forms a pentameric base to which fiber attaches. The trimeric fiber protein protrudes from the penton base at each of the 12 vertices of the capsid and is a knobbed rod-like structure. A remarkable difference in the surface of adenovirus capsids compared to that of most other icosahedral viruses is the presence of the long, thin fiber protein. The primary role of the fiber protein is the tethering of the viral capsid to the cell surface via its interaction with a cellular receptor.

The fiber proteins of many adenovirus serotypes share a common architecture: an N-terminal tail, a central shaft made of repeating sequences, and a C-terminal globular knob domain (or "head"). The central shaft domain consists of a variable number of beta-repeats. The beta-repeats connect to form an elongated structure of three intertwined spiraling strands that is highly rigid and stable. The shaft connects the N-terminal tail with the globular knob structure, which is responsible for interaction with the target cellular receptor. The globular nature of the adenovirus knob domain presents large surfaces for binding the receptor laterally and apically. The effect of this architecture is to project the receptor-binding site far from the virus capsid, thus freeing the virus from steric constraints presented by the relatively flat capsid surface.

Although fibers of many adenovirus serotypes have the same overall architecture, they have variable amino acid sequences that influence their function as well as structure. For example, a number of exposed regions on the surface of the fiber knob present an easily adaptable receptor binding site. The globular shape of the fiber knob allows receptors to bind at the sides of the knob or on top of the fiber knob. These binding sites typically lie on surface-exposed loops connecting beta-strands that are poorly conserved among human adenoviruses. The exposed side chains on these loops give the knob a variety of surface features while preserving the tertiary and quaternary structure. For example, the electrostatic potential and charge distributions at the knob surfaces can vary due to the wide range of isoelectric points in the fiber knob sequences, from pI approximately 9 for Ad 8, Ad 19, and Ad 37 to approximately 5 for subgroup B adenoviruses. As a structurally complex virus ligand, the fiber protein allows the presentation of a variety of binding surfaces (knob) in a number of orientations and distances (shaft) from the viral capsid.

One of the most obvious variations between some serotypes is fiber length. Studies have shown that the length of the fiber shaft strongly influences the interaction of the knob and the virus with its target receptors. Further, fiber proteins between serotypes can also vary in their ability to bend. Although beta-repeats in the shaft form a highly stable and regular structure, electron microscopy (EM) studies have shown distinct hinges in the fiber. Analysis of the protein sequence from several adenovirus serotype fibers pinpoints a disruption in the repeating sequences of the shaft at the third beta-repeat from the N-terminal tail, which correlates strongly with one of the hinges in the shaft, as seen by EM. The hinges in the fiber allow the knob to adopt a variety of orientations relative to the virus capsid, which may circumvent steric hindrances to receptor engagement requiring the correct presentation of the receptor binding site on the knob. For example, the rigid fibers of subgroup D Ads thus require a flexible receptor or one prepositioned for virus attachment, as they are unable to bend themselves. (Nicklin et al *Molecular Therapy* 2005 12:384-393)

The identification of specific cell receptors for different Ad serotypes and the knowledge of how they contribute to tissue tropism have been achieved through the use of fiber pseudotyping technology. Although Ads of some subgroups use CAR as a primary receptor, it is becoming clear that many Ads use alternate primary receptors, leading to vastly different tropism in vitro and in vivo. The fibers of these serotypes show clear differences in their primary and tertiary structures, such as fiber shaft rigidity, the length of the fiber shaft, and the lack of a CAR binding site and/or the putative HSPG binding motif, together with the differences in net charge within the fiber knob. Pseudotyping Ad 5 particles with an alternate fiber shaft and knob therefore provides an opportunity to remove important cell binding domains and, in addition, may allow more efficient (and potentially more cell-selective) transgene delivery to defined cell types compared to that achieved with Ad 5. Neutralization of fiber-pseudotyped Ad particles may also be reduced if the fibers used are from Ads with lower seroprevalence in humans or experimental models, a situation that favours successful administration of the vector (Nicklin et al *Molecular Therapy* (2005) 12:384-393). Furthermore, full length fiber as well as isolated fiber knob regions, but not hexon or penton alone, are capable of inducing dendritic cell maturation and are associated with induction of a potent CD8+ T cell response (Molinier-Frenkel et al. *J. Biol. Chem.* (2003) 278:37175-37182). Taken together, adenoviral fiber plays an important role in at least receptor-binding and immunogenicity of adenoviral vectors.

Figure 1C:
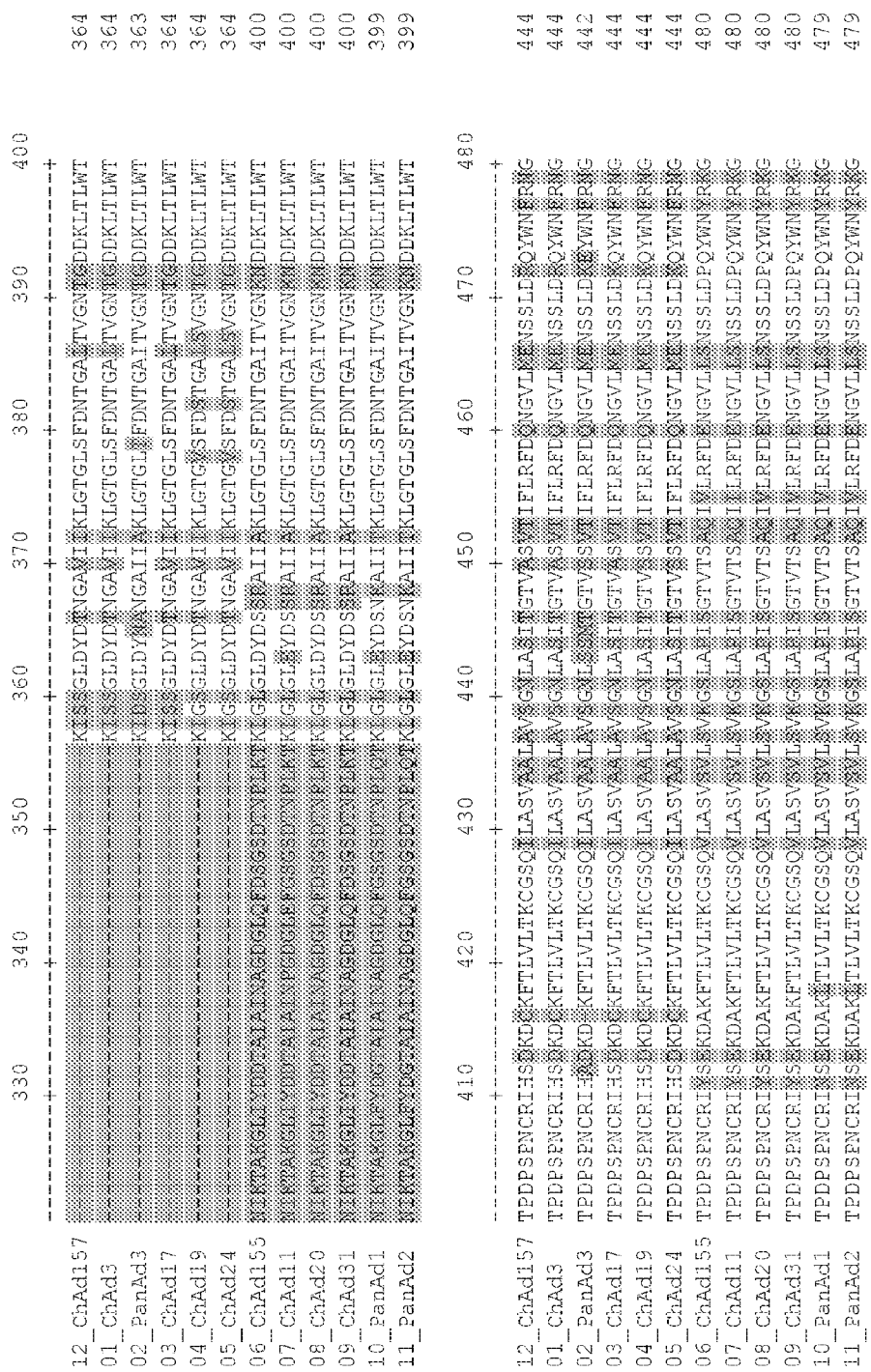
Figure 1D:
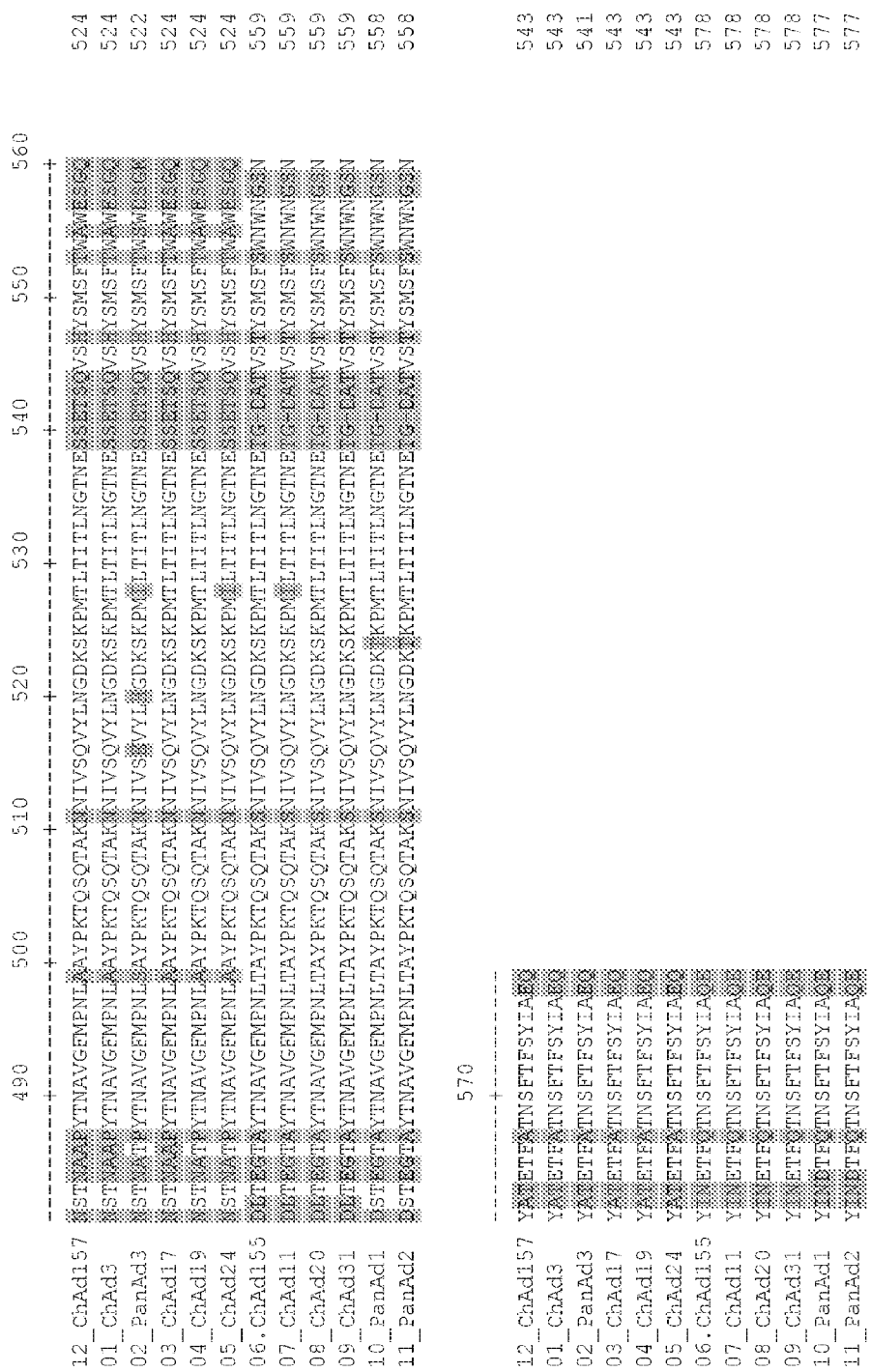

Illustrating the differences between the fiber proteins of Group C simian adenoviruses is the alignment provided in FIG. 1. A striking feature is that the fiber sequences of these adenoviruses can be broadly grouped into having a short fiber, such as ChAd157, or long fiber, such as ChAd155. This length differential is due to a 36 amino acid deletion at approximately position 321 in the short fiber relative to the long fiber. In addition, there are a number of amino acid substitutions that differ between the short versus long fiber subgroup yet are consistent within each subgroup. While the exact function of these differences have not yet been elucidated, given the function and immunogenicity of fiber, they are likely to be significant. It has been shown that one of the determinants of viral tropism is the length of the fiber shaft. It has been demonstrated that an Ad5 vector with a shorter shaft has a lower efficiency of binding to CAR receptor and a lower infectivity (Ambriović-Ristov A. et al.: Virology. (2003) 312(2):425-33): It has been speculated that this impairment is the result of an increased rigidity of the shorter fiber leading to a less efficient attachment to the cell receptor (Wu, E et al.: J Virol. (2003) 77(13): 7225-7235).

In one aspect of the invention there is provided an isolated fiber polypeptide of chimpanzee adenovirus ChAd157 and isolated polynucleotides encoding the fiber polypeptide of chimpanzee adenovirus ChAd157.

The fiber protein is expected to contribute to low seroprevalence and can, thus, be used independently from the hexon and penton polypeptides from ChAd157 or in combination (with one or both of the hexon and penton) to suppress the affinity of an adenovirus to preexisting neutralizing antibodies, e.g. to manufacture a recombinant adenovirus with a reduced seroprevalence. Such a recombinant adenovirus may be a chimeric adenovirus with capsid proteins from different serotypes with at least a fiber protein from ChAd157.

The ChAd157 fiber polypeptide sequence is provided in SEQ ID NO: 1.

The ChAd157 penton polypeptide sequence is provided in SEQ ID NO: 3.

The ChAd157 hexon polypeptide sequence is provided in SEQ ID NO: 5.

Polypeptides, Recombinant Adenoviruses, Compositions or Cells Comprising Polypeptide Sequences of ChAd157 Fiber or a Functional Derivative Thereof Suitably the isolated polypeptide, recombinant adenovirus, composition or cell of the invention comprises a polypeptide having the amino acid sequence according to SEQ ID NO: 1.

The polypeptide, recombinant adenovirus, composition or cell of the invention may comprise a polypeptide which is a functional derivative of a polypeptide having the amino acid sequence according to SEQ ID NO: 1, wherein the functional derivative has an amino acid sequence which is at least 99.8% identical over its entire length to the amino acid sequence of SEQ ID NO: 1.

Alternatively the functional derivative has no more than one addition, deletion or substitution compared to SEQ ID NO: 1, such as one substitution compared to SEQ ID NO: 1.

Suitably the polypeptide, recombinant adenovirus, composition or cell according to the invention further comprises:
(a) a polypeptide having the amino acid sequence according to SEQ ID NO: 3; or
(b) a functional derivative of a polypeptide having the amino acid sequence according to SEQ ID NO: 3, wherein the functional derivative has an amino acid sequence which is at least 60% identical over its entire length to the amino acid sequence of SEQ ID NO: 3, and/or
(a) a polypeptide having the amino acid sequence according to SEQ ID NO: 5; or
(b) a functional derivative of a polypeptide having the amino acid sequence according to SEQ ID NO: 5, wherein the functional derivative has an amino acid sequence which is at least 60% identical over its entire length to the amino acid sequence of SEQ ID NO: 5.

Suitably, the functional derivative of a polypeptide having the amino acid sequence according to SEQ ID NO: 3 has an amino acid sequence which is at least 70% identical over its entire length to the amino acid sequence of SEQ ID NO: 3, such as at least 80%, especially at least 90%, for example at least 95% or at least 98%.

Suitably, the functional derivative of a polypeptide having the amino acid sequence according to SEQ ID NO: 5 has an amino acid sequence which is at least 70% identical over its entire length to the amino acid sequence of SEQ ID NO: 5, such as at least 80%, especially at least 90%, for example at least 95% or at least 98%.

In particular, the polypeptide, recombinant adenovirus, composition or cell according to the invention further comprises:
(a) a polypeptide having the amino acid sequence according to SEQ ID NO: 3;
and/or
(b) a polypeptide having the amino acid sequence according to SEQ ID NO: 5.

Isolated Polynucleotides, Vectors, Recombinant Adenoviruses, Compositions or Cells Comprising Polynucleotides Encoding ChAd157 Fiber or a Functional Derivative Thereof Suitably the isolated polynucleotide, vector, recombinant adenovirus, composition or cell of the invention comprises a polynucleotide which encodes a polypeptide having the amino acid sequence according to SEQ ID NO: 1. Suitably the polynucleotide has a sequence according to SEQ ID NO: 2.

When the isolated polynucleotide, vector, recombinant adenovirus, composition or cell of the invention comprises a polynucleotide which encodes a functional derivative of a polypeptide having the amino acid sequence according to SEQ ID NO: 1, wherein the functional derivative has an amino acid sequence which is at least 99.8% identical over its entire length to the amino acid sequence of SEQ ID NO: 1, suitably the polynucleotide has a sequence according to SEQ ID NO: 2 wherein one codon has been added, deleted or altered to encode a different amino acid.

Suitably the polynucleotide, vector, recombinant adenovirus, composition or cell of the invention further comprises a polynucleotide encoding:
(a) a polypeptide having the amino acid sequence according to SEQ ID NO: 3; or
(b) a functional derivative of a polypeptide having the amino acid sequence according to SEQ ID NO: 3, wherein the functional derivative has an amino acid sequence which is at least 60% identical over its entire length to the amino acid sequence of SEQ ID NO: 3,
and/or
(a) a polypeptide having the amino acid sequence according to SEQ ID NO: 5; or
(b) a functional derivative of a polypeptide having the amino acid sequence according to SEQ ID NO: 5, wherein the functional derivative has an amino acid sequence which is at least 60% identical over its entire length to the amino acid sequence of SEQ ID NO: 5.

Suitably, the functional derivative of a polypeptide having the amino acid sequence according to SEQ ID NO: 3 has an amino acid sequence which is at least 70% identical over its entire length to the amino acid sequence of SEQ ID NO: 3, such as at least 80%, especially at least 90%, for example at least 95% or at least 98%.

Suitably, the functional derivative of a polypeptide having the amino acid sequence according to SEQ ID NO: 5 has an amino acid sequence which is at least 70% identical over its entire length to the amino acid sequence of SEQ ID NO: 5, such as at least 80%, especially at least 90%, for example at least 95% or at least 98%.

In particular, the polynucleotide, vector, recombinant adenovirus, composition or cell of the invention further comprises a polynucleotide encoding:
(a) a polypeptide having the amino acid sequence according to SEQ ID NO: 3;
and/or
(b) a polypeptide having the amino acid sequence according to SEQ ID NO: 5.

The polynucleotide, vector, recombinant adenovirus, composition or cell of the invention may further comprise:
(a) a polynucleotide according to SEQ ID NO: 4;
and/or
(b) a polynucleotide according to SEQ ID NO: 6.

ChAd157 Backbones

The invention provides isolated polynucleotide sequences of chimpanzee adenovirus ChAd157, including that of wild type, unmodified ChAd157 and modified backbone constructs of ChAd157. These modified backbone constructs include those exemplified herein, such as pChAd157 \E1 TetO hCMV RpsL-Kana #1551 (SEQ ID NO: 15) and ChAd157 ΔE1E4_Ad5E4orf6/TetO hCMV RpsL-Kana #1594 (SEQ ID NO: 22). ChAd157 backbones may be used in the construction of recombinant replication-competent or replication-incompetent adenoviruses for example for the delivery of transgenes.

Annotation of the pChAd157 ΔE1/TetO hCMV GAG (SEQ ID NO: 17) sequence is provided below.

| Annotations ChAd157DE1_TetOhCMV_GAG | |
|---|---|
| IX | 3187 . . . 3651 |
| IVa2 | Complement (3710 . . . 5045, 5325 . . . 5337) |
| Pol | Complement (4816 . . . 8397, 13762 . . . 13770) |
| VA RNAI | 10230 . . . 10391 |
| pTP | Complement(8196 . . . 10199, 13762 . . . 13770) |
| 48K | 10652 . . . 11914 |
| pIIIa | 11938 . . . 13714 |
| III | 13807 . . . 15588 |
| pVII | 15603 . . . 16199 |
| V | 16275 . . . 17390 |
| pX | 17415 . . . 17660 |
| pVI | 17750 . . . 18508 |
| Hexon | 18623 . . . 21499 |
| Protease | 21529 . . . 22158 |
| DBP | Complement (22274 . . . 23926) |
| 92K | 23976 . . . 26447 |
| 22K | 26164 . . . 26739 |
| 33K | Join (26164 . . . 26473, 26679 . . . 27061) |
| E2e promoter | Complement(27027 . . . 27274) |
| pVIII | 27136 . . . 27819 |
| E3 12K | 27820 . . . 28137 |
| E3 CR1-alphap0 | 28635 . . . 28835 |
| E3 gp18K | 28838 . . . 29329 |
| E3A 11K | 30776 . . . 31072 |
| E3 RID alpha | 31084 . . . 31356 |
| E3 RID beta | 31359 . . . 31757 |
| E3 15K | 31750 . . . 32136 |
| U exon | Complement (32167 . . . 32331) |
| fibre | 32342 . . . 33973 |
| E4 ORF6/7 | Complement (34181 . . . 34456, 35168 . . . 35341) |
| E4 ORF6 | Complement (34457 . . . 35341) |
| E4 ORF4 | Complement (35241 . . . 35606) |
| E4 ORF3 | Complement (35622 . . . 35969) |
| E4 ORF2 | Complement (35966 . . . 36358) |
| E4 ORF1 | Complement (36411 . . . 36797) |

In one embodiment, fragments of the sequences of SEQ ID NO: 15, 22 and their complementary strands, cDNA and RNA complementary thereto are provided. Suitably, fragments are at least 15 nucleotides in length, more suitably 30 nucleotides in length, more suitably 60 nucleotides in length, more suitably 120 nucleotides in length, more suitably 240, more suitably 480 nucleotides in length and encompass functional fragments, i.e., fragments which are of biological interest. For example, a functional fragment can express a desired adenoviral product or may be useful in production of recombinant viral vectors. Such fragments include the gene sequences listed above. In certain embodiments isolated sequences of SEQ ID NO: 15, 22 and their complementary strands, cDNA and RNA complementary thereto are provided.

Gene products of the ChAd157 adenovirus, such as proteins, enzymes, and fragments thereof, which are encoded by the adenoviral nucleic acids, and the aforementioned fragments thereof, described herein are provided. Such proteins include those encoded by the open reading frames identified above and the proteins encoded by the polynucleotides provided in the Sequence Listing.

Further ChAd157 Polynucleotides and Polypeptides

In some embodiments the polynucleotide of the invention comprises a polynucleotide encoding a fiber polypeptide; a hexon polypeptide and fiber polypeptide; penton polypeptide and fiber polypeptide; or hexon polypeptide, penton polypeptide and fiber polypeptide of the invention; and may further comprise additional adenoviral polynucleotides, suitably ChAd157 polynucleotides. Thus, suitably the polynucleotide according to the invention comprises one or more of the following:

(a) an adenoviral 5'-inverted terminal repeat (ITR);
(b) an adenoviral E1A region, or a fragment thereof selected from among the E1A_280R and E1A_243R regions;
(c) an adenoviral E1B or IX region, or a fragment thereof selected from among the group consisting of the E1B_19K, E1B_55K and IX regions;
(d) an adenoviral E2B region; or a fragment thereof selected from among the group consisting of the E2B_pTP, E2B_polymerase and E2B_IVa2 regions;
(e) an adenoviral L1 region, or a fragment thereof, said fragment encoding an adenoviral protein selected from the group consisting of the L1_13.6K, L1_52K and L1_pIIIa protein;
(f) an adenoviral L2 region or a L2 region comprising a polynucleotide encoding the penton protein of the invention, or a fragment thereof, said fragment encoding an adenoviral protein selected from the group consisting of the L2_penton protein, the L2_pVII protein, the L2_V protein and the L2_pX protein;
(g) an adenoviral L3 region or a L3 region comprising a polynucleotide encoding the hexon protein of the invention, or a fragment thereof, said fragment encoding an adenoviral protein selected from the group consisting of the L3_pVI protein, the L3_hexon protein and the L3_protease protein;
(h) an adenoviral E2A region;
(i) an adenoviral L4 region, or a fragment thereof said fragment encoding an adenoviral protein selected from the group consisting of the L4_100 k protein, the L4_33K protein, the L4_22K protein and protein L4_VIII;
(j) an adenoviral E3 region, or a fragment thereof selected from the group consisting of E3 ORF1, E3 ORF2, E3 ORF3, E3 ORF4, E3 ORF5, E3 ORF6, E3 ORF7, E3 ORF8, and E3 ORF9;
(k) an adenoviral L5 region or a L5 region comprising a polynucleotide encoding the L5_fiber fiber polypeptide of the invention
(l) an adenoviral (such as Ad5) E4 region, or a fragment thereof selected from the group consisting of E4 ORF7, E4 ORF6, E4 ORF4, E4 ORF3, E4 ORF2, and E4 ORF1; in particular ORF6 of said E4 region;
(m) an adenoviral 3'-ITR; and/or
(n) an adenoviral VAI or VAII RNA region, preferably an adenoviral VAI or VAII RNA region from an adenovirus other than ChAd157, more preferably from Ad5.

Definitions

Suitably the polynucleotides or polypeptides of the invention are isolated. An "isolated" polynucleotide is one that is removed from its original environment. For example, a naturally-occurring polynucleotide is isolated if it is separated from some or all of the coexisting materials in the natural system. A polynucleotide is considered to be isolated if, for example, it is cloned into a vector that is not a part of its natural environment or if it is comprised within cDNA.

Suitably the polynucleotides of the invention are recombinant. Recombinant means that the polynucleotide is the product of at least one of cloning, restriction or ligation steps, or other procedures that result in a polynucleotide that is distinct from a polynucleotide found in nature. A recombinant adenovirus is an adenovirus comprising a recombinant polynucleotide. A recombinant vector is a vector comprising a recombinant polynucleotide. 'A recombinant virus' includes progeny of the original recombinant virus. 'A recombinant vector' includes replicates of the original recombinant vector. 'A recombinant polynucleotide' includes replicates of the original recombinant polynucleotide.

Suitably, the polypeptide sequence of the present invention contains at least one alteration with respect to a native sequence. Suitably, the polynucleotide sequences of the present invention contain at least one alteration with respect to a native sequence. For example, a polynucleotide introduced by genetic engineering techniques into a plasmid or vector derived from a different species (and often a different genus, subfamily or family) is a heterologous polynucleotide. A promoter removed from its native coding sequence and operatively linked to a coding sequence with which it is not naturally found linked is a heterologous promoter. A specific recombination site that has been cloned into a genome of a virus or viral vector, wherein the genome of the virus does not naturally contain it, is a heterologous recombination site. A heterologous nucleic acid sequence also includes a sequence naturally found in an adenoviral genome, but located at a non-native position within the adenoviral vector.

Typically, "heterologous" means derived from a genotypically distinct entity from that of the rest of the entity to which it is being compared. A heterologous nucleic acid sequence refers to any nucleic acid sequence that is not isolated from, derived from, or based upon a naturally occurring nucleic acid sequence of the adenoviral vector. A heterologous protein sequence refers to any protein sequence that is not isolated from, derived from, or based upon a naturally occurring protein sequence of the adenoviral vector "Naturally occurring" means a sequence found in nature and not synthetically prepared or modified. A sequence is "derived" from a source when it is isolated from a source but modified (e.g., by deletion, substitution (mutation), insertion, or other modification), suitably so as not to disrupt the normal function of the source gene.

A "functional derivative" of a polypeptide suitably refers to a modified version of a polypeptide, e.g. wherein one or more amino acids of the polypeptide may be deleted, inserted, modified and/or substituted. A derivative of an unmodified adenoviral capsid protein is considered functional if, for example:
- (a) an adenovirus comprising the derivative capsid protein within its capsid retains substantially the same or a lower seroprevalence compared to an adenovirus comprising the unmodified capsid protein and/or
- (b) an adenovirus comprising the derivative capsid protein within its capsid retains substantially the same or a higher host cell infectivity compared to an adenovirus comprising the unmodified capsid protein and/or
- (c) an adenovirus comprising the derivative capsid protein within its capsid retains substantially the same or a higher immunogenicity compared to an adenovirus comprising the unmodified capsid protein and/or
- (d) an adenovirus comprising the derivative capsid protein within its capsid retains substantially the same or a higher level of transgene productivity compared to an adenovirus comprising the unmodified capsid protein.

Properties (a)-(d) above may suitably be measured using the methods described in the Examples section below.

Suitably, the polypeptide, vector or recombinant adenovirus has a low seroprevalence in a human population. "Low seroprevalence" may mean having a reduced pre-existing neutralizing antibody level as compared to human adenovirus 5 (Ad5). Similarly or alternatively, "low seroprevalence" may mean less than about 20% seroprevalence, less than about 15% seroprevalence, less than about 10% seroprevalence, less than about 5% seroprevalence, less than about 4% seroprevalence, less than about 3% seroprevalence, less than about 2% seroprevalence, less than about 1% seroprevalence or no detectable seroprevalence. Seroprevalence can be measured as the percentage of individuals having a clinically relevant neutralizing titre (defined as a 50% neutralisation titer >200) using methods as described in Aste-Amézaga et al., *Hum. Gene Ther*. (2004) 15(3):293-304.

The terms polypeptide, peptide and protein are used interchangeably herein.

The term "simian" is typically meant to encompass non-human primates, for example Old World monkeys, New World monkeys, apes and gibbons. In particular, simian may refer to nonhuman apes such as chimpanzees (*Pan troglodyte*), bonobos (*Pan paniscus*) and gorillas (genus *Gorilla*). Non-ape simians may include rhesus macaques (*Macaca mulatta*).

Sequence Comparison

For the purposes of comparing two closely-related polynucleotide or polypeptide sequences, the "% identity" between a first sequence and a second sequence may be calculated using an alignment program, such as BLAST® (available at blast.ncbi.nlm.nih.gov, last accessed 9 Mar. 2015) using standard settings. The % identity is the number of identical residues divided by the number of residues in the reference sequence, multiplied by 100. The % identity figures referred to above and in the claims are percentages calculated by this methodology. An alternative definition of % identity is the number of identical residues divided by the number of aligned residues, multiplied by 100. Alternative methods include using a gapped method in which gaps in the alignment, for example deletions in one sequence relative to the other sequence, are accounted for in a gap score or a gap cost in the scoring parameter. For more information, see the BLAST® fact sheet available at ftp.ncbi.nlm.nih.gov/pub/factsheets/HowTo_BLASTGuide.pdf, last accessed on 9 Mar. 2015.

Sequences that preserve the functionality of the polynucleotide or a polypeptide encoded thereby are likely to be more closely identical. Polypeptide or polynucleotide sequences are said to be the same as or identical to other polypeptide or polynucleotide sequences, if they share 100% sequence identity over their entire length.

A "difference" between sequences refers to an insertion, deletion or substitution of a single amino acid residue in a position of the second sequence, compared to the first sequence. Two polypeptide sequences can contain one, two or more such amino acid differences. Insertions, deletions or substitutions in a second sequence which is otherwise identical (100% sequence identity) to a first sequence result in reduced percent sequence identity. For example, if the identical sequences are 9 amino acid residues long, one substitution in the second sequence results in a sequence identity of 88.9%. If the identical sequences are 17 amino acid residues long, two substitutions in the second sequence results in a sequence identity of 88.2%. If the identical sequences are 7 amino acid residues long, three substitutions in the second sequence results in a sequence identity of 57.1%. If first and second polypeptide sequences are 9 amino acid residues long and share 6 identical residues, the first and second polypeptide sequences share greater than 66% identity (the first and second polypeptide sequences share 66.7% identity). If first and second polypeptide sequences are 17 amino acid residues long and share 16 identical residues, the first and second polypeptide sequences share greater than 94% identity (the first and second polypeptide sequences share 94.1% identity). If first and second polypeptide sequences are 7 amino acid residues long and share 3 identical residues, the first and second polypeptide sequences share greater than 42% identity (the first and second polypeptide sequences share 42.9% identity).

Alternatively, for the purposes of comparing a first, reference polypeptide sequence to a second, comparison polypeptide sequence, the number of additions, substitutions and/or deletions made to the first sequence to produce the second sequence may be ascertained. An addition is the addition of one amino acid residue into the sequence of the first polypeptide (including addition at either terminus of the first polypeptide). A substitution is the substitution of one amino acid residue in the sequence of the first polypeptide with one different amino acid residue. A deletion is the deletion of one amino acid residue from the sequence of the first polypeptide (including deletion at either terminus of the first polypeptide).

For the purposes of comparing a first, reference polynucleotide sequence to a second, comparison polynucleotide sequence, the number of additions, substitutions and/or deletions made to the first sequence to produce the second sequence may be ascertained. An addition is the addition of one nucleotide residue into the sequence of the first polynucleotide (including addition at either terminus of the first polynucleotide). A substitution is the substitution of one nucleotide residue in the sequence of the first polynucleotide with one different nucleotide residue. A deletion is the deletion of one nucleotide residue from the sequence of the first polynucleotide (including deletion at either terminus of the first polynucleotide).

Suitably substitutions in the sequences of the present invention may be conservative substitutions. A conservative substitution comprises the substitution of an amino acid with another amino acid having a chemical property similar to the amino acid that is substituted (see, for example, Stryer et al, *Biochemistry*, 5$^{th}$ Edition 2002, pages 44-49). Preferably, the conservative substitution is a substitution selected from the group consisting of: (i) a substitution of a basic amino acid with another, different basic amino acid; (ii) a substitution of an acidic amino acid with another, different acidic amino acid; (iii) a substitution of an aromatic amino acid with another, different aromatic amino acid; (iv) a substitution of a non-polar, aliphatic amino acid with another, different non-polar, aliphatic amino acid; and (v) a substitution of a polar, uncharged amino acid with another, different polar, uncharged amino acid. A basic amino acid is preferably selected from the group consisting of arginine, histidine, and lysine. An acidic amino acid is preferably aspartate or glutamate. An aromatic amino acid is preferably selected from the group consisting of phenylalanine, tyrosine and tryptophane. A non-polar, aliphatic amino acid is preferably selected from the group consisting of glycine, alanine, valine, leucine, methionine and isoleucine. A polar, uncharged amino acid is preferably selected from the group consisting of serine, threonine, cysteine, proline, asparagine and glutamine. In contrast to a conservative amino acid substitution, a non-conservative amino acid substitution is the exchange of one amino acid with any amino acid that does not fall under the above-outlined conservative substitutions (i) through (v).

Vectors and Recombinant Adenovirus

The ChAd157 sequences of the invention are useful as therapeutic agents and in construction of a variety of vector systems, recombinant adenovirus and host cells. Suitably the term "vector" refers to a nucleic acid that has been substantially altered (e.g., a gene or functional region that has been deleted and/or inactivated) relative to a wild type sequence and/or incorporates a heterologous sequence, i.e., nucleic acid obtained from a different source (also called an "insert"), and replicating and/or expressing the inserted polynucleotide sequence, when introduced into a cell (e.g., a host cell). For example, the insert may be all or part of the ChAd157 sequences described herein. In addition or alternatively, a ChAd157 vector may be a ChAd157 adenovirus comprising one or more deletions or inactivations of viral genes, such as E1 or other viral gene or functional region described herein. Such a ChAd157, which may or may not comprise a heterologous sequence, is often called a "backbone" and may be used as is or as a starting point for additional modifications to the vector.

A vector may be any suitable nucleic acid molecule including naked DNA, a plasmid, a virus, a cosmid, phage vector such as lambda vector, an artificial chromosome such as a BAC (bacterial artificial chromosome), or an episome. Alternatively, a vector may be a transcription and/or expression unit for cell-free in vitro transcription or expression, such as a T7-compatible system. The vectors may be used alone or in combination with other adenoviral sequences or fragments, or in combination with elements from non-adenoviral sequences. The ChAd157 sequences are also useful in antisense delivery vectors, gene therapy vectors, or vaccine vectors. Thus, further provided are gene delivery vectors, and host cells which contain the ChAd157 sequences.

The term "replication-competent" adenovirus refers to an adenovirus which can replicate in a host cell in the absence of any recombinant helper proteins comprised in the cell. Suitably, a "replication-competent" adenovirus comprises the following intact or functional essential early genes: E1A, E1B, E2A, E2B, E3 and E4. Wild type adenoviruses isolated from a particular animal will be replication competent in that animal.

The term "replication-incompetent" or "replication-defective" adenovirus refers to an adenovirus which is incapable of replication because it has been engineered to comprise at least a functional deletion (or "loss-of-function" mutation), i.e. a deletion or mutation which impairs the function of a gene without removing it entirely, e.g. introduction of artificial stop codons, deletion or mutation of active sites or interaction domains, mutation or deletion of a regulatory sequence of a gene etc, or a complete removal of a gene encoding a gene product that is essential for viral replication, such as one or more of the adenoviral genes selected from E1A, E1B, E2A, E2B, E3 and E4 (such as E3 ORF1, E3 ORF2, E3 ORF3, E3 ORF4, E3 ORF5, E3 ORF6, E3 ORF7, E3 ORF8, E3 ORF9, E4 ORF7, E4 ORF6, E4 ORF4, E4 ORF3, E4 ORF2 and/or E4 ORF1). Particularly suitably E1 and optionally E3 and/or E4 are deleted. If deleted, the aforementioned deleted gene region will suitably not be considered in the alignment when determining % identity with respect to another sequence.

The present invention provides vectors such as recombinant adenovirus that deliver a protein, suitably a heterologous protein, to cells, either for therapeutic or vaccine purposes. A vector may include any genetic element including naked DNA, a phage, transposon, cosmid, episome, plasmid, or a virus. Such vectors contain DNA of ChAd157 as disclosed herein and a minigene. By "minigene" (or "expression cassette") is meant the combination of a selected heterologous gene (transgene) and the other regulatory elements necessary to drive translation, transcription and/or expression of the gene product in a host cell.

Typically, a ChAd157-derived adenoviral vector is designed such that the minigene is located in a nucleic acid molecule which contains other adenoviral sequences in the region native to a selected adenoviral gene. The minigene may be inserted into an existing gene region to disrupt the function of that region, if desired. Alternatively, the minigene may be inserted into the site of a partially or fully deleted adenoviral gene. For example, the minigene may be located in the site of a mutation, insertion or deletion which renders non-functional at least one gene of a genomic region selected from the group consisting of E1A, E1B, E2A, E2B, E3 and E4. The term "renders non-functional" means that a sufficient amount of the gene region is removed or otherwise disrupted, so that the gene region is no longer capable of producing functional products of gene expression. If desired, the entire gene region may be removed (and suitably replaced with the minigene).

For example, for a production vector useful for generation of a recombinant virus, the vector may contain the minigene and either the 5' end of the adenoviral genome or the 3' end of the adenoviral genome, or both the 5' and 3' ends of the adenoviral genome. The 5' end of the adenoviral genome contains the 5 ' cis-elements necessary for packaging and replication; i.e., the 5' ITR sequences (which function as origins of replication) and the native 5 ' packaging enhancer domains (that contain sequences necessary for packaging linear Ad genomes and enhancer elements for the E1 promoter). The 3' end of the adenoviral genome includes the 3 ' cis-elements (including the ITRs) necessary for packaging and encapsidation. Suitably, a recombinant adenovirus contains both 5' and 3' adenoviral cis-elements and the minigene (suitably containing a transgene) is located between the 5' and 3' adenoviral sequences. A ChAd157-based adenoviral vector may also contain additional adenoviral sequences.

Suitably, ChAd157-based vectors contain one or more adenoviral elements derived from the adenoviral ChAd157 genome of the invention. In one embodiment, the vectors contain adenoviral ITRs from ChAd157 and additional adenoviral sequences from the same adenoviral serotype. In another embodiment, the vectors contain adenoviral sequences that are derived from a different adenoviral serotype than that which provides the ITRs.

As defined herein, a pseudotyped adenovirus refers to an adenovirus in which the capsid proteins of the adenovirus are from a different adenovirus than the adenovirus which provides the ITRs.

Further, chimeric or hybrid adenoviruses may be constructed using the adenoviruses described herein using techniques known to those of skill in the art (e.g., U.S. Pat. No. 7,291,498).

ITRs and any other adenoviral sequences present in the vector of the present invention may be obtained from many sources. A variety of adenovirus strains are available from the American Type Culture Collection, Manassas, Va., or available by request from a variety of commercial and institutional sources. Further, the sequences of many such strains are available from a variety of databases including, e.g., PubMed and GenBank. Homologous adenovirus vectors prepared from other chimpanzee or from human adenoviruses are described in the published literature (for example, U.S. Pat. No. 5,240,846). The DNA sequences of a number of adenovirus types are available from GenBank, including type Ad5 (GenBank Accession Number M73370). The adenovirus sequences may be obtained from any known adenovirus serotype, such as serotypes 2, 3, 4, 7, 12 and 40, and further including any of the presently identified human types. Similarly adenoviruses known to infect nonhuman animals (e.g., simians) may also be employed in the vector constructs of this invention (e.g., U.S. Pat. No. 6,083,716). The viral sequences, helper viruses (if needed), and recombinant viral particles, and other vector components and sequences employed in the construction of the vectors described herein may be obtained as described below.

Sequence, Vector and Adenovirus Production

The sequences of the invention may be produced by any suitable means, including recombinant production, chemical synthesis, or other synthetic means. Suitable production techniques are well known to those of skill in the art. Alternatively, peptides can also be synthesized by well-known solid phase peptide synthesis methods.

The adenoviral plasmids (or other vectors) may be used to produce adenoviral vectors. In one embodiment, the adenoviral vectors are adenoviral particles which are replication-incompetent. In one embodiment, the adenoviral particles are rendered replication-incompetent by deletions in the E1A and/or E1B genes, in particular the E1A and E1B. Alternatively, the adenoviruses are rendered replication-incompetent by another means, optionally while retaining the E1A and/or E1B genes. Similarly, in some embodiments, reduction of an immune response to the vector may be accomplished by deletions in the E2B and/or DNA polymerase genes. The adenoviral vectors can also contain other mutations to the adenoviral genome, e.g., temperature-sensitive mutations or deletions in other genes. In other embodiments, it is desirable to retain an intact E1A and/or E1B region in the adenoviral vectors. Such an intact E1 region may be located in its native location in the adenoviral genome or placed in the site of a deletion in the native adenoviral genome (e.g., in the E3 region).

In the construction of adenovirus vectors for delivery of a gene to a mammalian (such as human) cell, a range of modified adenovirus nucleic acid sequences can be employed in the vectors. For example, all or a portion of the adenovirus delayed early gene E3 may be eliminated from the adenovirus sequence which forms a part of the recombinant virus. The function of E3 is believed to be irrelevant to the function and production of the recombinant virus particle. Adenovirus vectors may also be constructed having a deletion of at least the ORF6 region of the E4 gene, and more desirably because of the redundancy in the function of this region, the entire E4 region. Still another vector of the invention contains a deletion in the delayed early gene E2A. Deletions may also be made in any of the late genes L1 to L5 of the adenovirus genome. Similarly, deletions in the intermediate genes IX and IVa2 may be useful for some purposes.

Other deletions may be made in the other structural or non-structural adenovirus genes. The above discussed deletions may be used individually, i.e., an adenovirus sequence for use as described herein may contain deletions in only a single region. Alternatively, deletions of entire genes or portions thereof effective to destroy their biological activity may be used in any combination. For example, in one exemplary vector, the adenovirus sequence may have deletions of the E1 genes and the E4 gene, or of the E1, E2A and E3 genes, or of the E1 and E3 genes, or of E1, E2A and E4 genes, with or without deletion of E3, and so on. Any one or more of the E genes may suitably be replaced with an E gene (or one or more E gene open reading frames) sourced from a different strain of adenovirus. Particularly suitably the ChAd157 E1 and E3 genes are deleted and the ChAd157E4 gene is replaced with E4Ad5orf6. As discussed above, such deletions and/or substitutions may be used in combination with other mutations, such as temperature-sensitive mutations, to achieve a desired result.

An adenoviral vector lacking one or more essential adenoviral sequences (e.g., DA, E1B, E2A, E2B, E4 ORF6, L1, L2, L3, L4 and L5) may be cultured in the presence of the missing adenoviral gene products which are required for viral infectivity and propagation of an adenoviral particle. These helper functions may be provided by culturing the adenoviral vector in the presence of one or more helper constructs (e.g., a plasmid or virus) or a packaging host cell.

Complementation of Replication-Incompetent Vectors

To generate recombinant adenoviruses deleted in any of the genes described above, the function of the deleted gene region, if essential to the replication and infectivity of the virus, must be supplied to the recombinant virus by a helper virus or cell line, i.e., a complementation or packaging cell line.

Helper Viruses

Depending upon the adenovirus gene content of the viral vectors employed to carry the minigene, a helper adenovirus or non-replicating virus fragment may be used to provide sufficient adenovirus gene sequences necessary to produce an infective recombinant viral particle containing the minigene. Useful helper viruses contain selected adenovirus gene sequences not present in the adenovirus vector construct and/or not expressed by the packaging cell line in which the vector is transfected. In one embodiment, the helper virus is replication-defective and contains adenovirus genes in addition, suitably, to one or more of the sequences described herein. Such a helper virus is suitably used in combination with an E1 expressing (and optionally additionally E3 expressing) cell line.

A helper virus may optionally contain a reporter gene. A number of such reporter genes are known to the art as well as described herein. The presence of a reporter gene on the helper virus which is different from the transgene on the adenovirus vector allows both the adenoviral vector and the helper virus to be independently monitored. This reporter is used to enable separation between the resulting recombinant virus and the helper virus upon purification.

Complementation Cell Lines

In many circumstances, a cell line expressing the one or more missing genes which are essential to the replication and infectivity of the virus, such as human E1, can be used to transcomplement a chimpanzee adenoviral vector. This is particularly advantageous because, due to the diversity between the chimpanzee adenovirus sequences of the invention and the human adenovirus sequences found in currently available packaging cells, the use of the current human E1-containing cells prevents the generation of replication-competent adenoviruses during the replication and production process.

Alternatively, if desired, one may utilize the sequences provided herein to generate a packaging cell or cell line that expresses, at a minimum, the E1 gene from ChAd157 or from another adenovirus (such as human adenovirus, e.g. hAd5 E1, or another ChAd E1) under the transcriptional control of a promoter for expression in a selected parent cell line. Inducible or constitutive promoters may be employed for this purpose. Examples of such promoters are described in detail elsewhere in this document. A parent cell is selected for the generation of a novel cell line expressing any desired ChAd157 gene. Without limitation, such a parent cell line may be HeLa [ATCC Accession No. CCL 2], A549 [ATCC Accession No. CCL 185], HEK 293, KB [CCL 17], Detroit [e.g., Detroit 510, CCL 72] and WI-38 [CCL 75] cells, among others. These cell lines are all available from the American Type Culture Collection, 10801 University Boulevard, Manassas, Va. 20110-2209.

Such E1-expressing cell lines are useful in the generation of recombinant adenovirus E1 deleted vectors. Additionally, or alternatively, cell lines that express one or more adenoviral gene products, e.g., E1A, E1B, E2A, E3 and/or E4, can be constructed using essentially the same procedures as used in the generation of recombinant viral vectors. Such cell lines can be utilised to transcomplement adenovirus vectors deleted in the essential genes that encode those products, or to provide helper functions necessary for packaging of a helper-dependent virus (e.g., adeno-associated virus). The preparation of a host cell involves techniques such as assembly of selected DNA sequences.

In another alternative, the essential adenoviral gene products are provided in trans by the adenoviral vector and/or helper virus. In such an instance, a suitable host cell can be selected from any biological organism, including prokaryotic (e.g., bacterial) cells, and eukaryotic cells, including, insect cells, yeast cells and mammalian cells.

Host cells may be selected from among any mammalian species, including, without limitation, cells such as A549, WEHI, 3T3, 10T1/2, HEK 293 cells or Per.C6 (both of which express functional adenoviral E1) [Fallaux, F J et al, (1998), Hum Gene Ther, 9:1909-1917], Saos, C2C12, L cells, HT1080, HepG2 and primary fibroblast, hepatocyte and myoblast cells derived from mammals including human, monkey, mouse, rat, rabbit, and hamster.

A particularly suitable complementation cell line is the Procell92 cell line. The Procell92 cell line is based on HEK 293 cells which express adenoviral E1 genes, transfected with the Tet repressor under control of the human phosphoglycerate kinase-1 (PGK) promoter, and the G418-resistance gene (Vitelli et al. PLOS One (2013) 8(e55435):1-9). Procell92.S is adapted for growth in suspension conditions and is useful for producing adenoviral vectors expressing toxic proteins (www.okairos.com/e/inners.php?m=00084, last accessed 13 Apr. 2015).

Assembly of a Viral Particle and Transfection of a Cell Line

Generally, when delivering the vector comprising the minigene by transfection, the vector is delivered in an amount from about 5 µg to about 100 µg DNA, and preferably about 10 to about 50 µg DNA to about $1 \times 10^4$ cells to about $1 \times 10^{13}$ cells, and preferably about $10^5$ cells. However, the relative amounts of vector DNA to host cells may be adjusted, taking into consideration such factors as the selected vector, the delivery method and the host cells selected.

Introduction into the host cell of the vector may be achieved by any means known in the art, including transfection, and infection. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently.

Introduction of vectors into the host cell may also be accomplished using techniques known to the skilled person. Suitably, standard transfection techniques are used, e.g., CaPC transfection or electroporation.

Assembly of the selected DNA sequences of the adenovirus (as well as the transgene and other vector elements) into various intermediate plasmids, and the use of the plasmids and vectors to produce a recombinant viral particle are all achieved using conventional techniques. Such techniques include conventional cloning techniques of cDNA, use of overlapping oligonucleotide sequences of the adenovirus genomes, polymerase chain reaction, and any suitable method which provides the desired nucleotide sequence. Standard transfection and co-transfection techniques are employed, e.g., CaPC precipitation techniques. Other conventional methods employed include homologous recombination of the viral genomes, plaquing of viruses in agar overlay, methods of measuring signal generation, and the like.

For example, following the construction and assembly of the desired minigene-containing viral vector, the vector is transfected in vitro in the presence of a helper virus into the packaging cell line. Homologous recombination occurs between the helper and the vector sequences, which permits the adenovirus-transgene sequences in the vector to be replicated and packaged into virion capsids, resulting in the recombinant viral vector particles. The resulting recombinant adenoviruses are useful in transferring a selected transgene to a selected cell. In in vivo experiments with the recombinant virus grown in the packaging cell lines, the E1-deleted recombinant adenoviral vectors of the invention demonstrate utility in transferring a transgene to a non-simian mammal, preferably a human, cell.

Transgenes

The transgene is a nucleic acid sequence, heterologous to the vector sequences flanking the transgene, which encodes a protein of interest. The nucleic acid coding sequence is operatively linked to regulatory components in a manner which permits transgene transcription, translation, and/or expression in a host cell.

The composition of the transgene sequence will depend upon the use to which the resulting vector will be put. For example, the transgene may be a therapeutic transgene or an immunogenic transgene. Alternatively, a transgene sequence may include a reporter sequence, which upon expression produces a detectable signal. Such reporter sequences include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc. These coding sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry.

In one embodiment, the transgene is a non-marker sequence encoding a product which is useful in biology and medicine, such as a therapeutic transgene or an immunogenic transgene such as proteins, RNA, enzymes, or catalytic RNAs. Desirable RNA molecules include tRNA, dsRNA, ribosomal RNA, catalytic RNAs, and antisense RNAs. One example of a useful RNA sequence is a sequence which extinguishes expression of a targeted nucleic acid sequence in the treated animal.

The transgene may be used for treatment, e.g., of genetic deficiencies, as a cancer therapeutic or vaccine, for induction of an immune response, and/or for prophylactic vaccine purposes. As used herein, induction of an immune response refers to the ability of a protein to induce a T cell and/or a humoral immune response to the protein.

The term prophylaxis means the provision of a medicament in advance, this may be in advance of exposure to a pathogen (pre-exposure prophylaxis) or in advance of the development of disease symptoms (post-exposure prophylaxis). The terms treatment and therapy are used interchangeably herein and mean the administration of medicament during disease.

By the term disease is meant a disorder of structure or function in a subject, especially one that produces specific symptoms or that affects a specific location and is not simply a direct result of physical injury.

Regulatory Elements

In addition to the transgene the vector also includes conventional control elements which are operably linked to the transgene in a manner that permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (poly A) signals including rabbit beta-globin polyA; sequences that stabilize cytoplasmic mRNA; sequences that enhance translation efficiency (e.g., Kozak consensus sequence); sequences that enhance protein stability; and when desired, sequences that enhance secretion of the encoded product. Among other sequences, chimeric introns may be used.

In some embodiments, the Woodchuck Hepatitis Virus Posttranscriptional Regulatory Element (WPRE) (Zuffrey et al. (1999) *J Virol;* 73(4):2886-9) may be operably linked to the transgene. An exemplary WPRE is provided in SEQ ID NO: 26.

A "promoter" is a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and mammals (including humans). A great number of expression control sequences, including promoters which are internal, native, constitutive, inducible and/or tissue-specific, are known in the art and may be utilized.

Examples of constitutive promoters include, without limitation, the TBG promoter, the retroviral Rous sarcoma virus LTR promoter (optionally with the enhancer), the cytomegalovirus (CMV) promoter (optionally with the CMV enhancer, see, e.g., Boshart et al, Cell, 41:521-530 (1985)), the CASI promoter, the SV40 promoter, the dihydrofolate reductase promoter, the β-actin promoter, the phosphoglycerol kinase (PGK) promoter, and the EF1a promoter (Invitrogen).

In some embodiments, the promoter is a CASI promoter (see, for example, WO2012/115980). The CASI promoter is a synthetic promoter which contains a portion of the CMV enhancer, a portion of the chicken beta-actin promoter, and a portion of the UBC enhancer. In some embodiments, the CASI promoter can include a nucleic acid sequence having at least about 90%, at least about 95%, at least about 96%, at least about 97%, at least about 98%, at least about 99%, or more, sequence identity to SEQ ID NO: 12. In some embodiments, the promoter comprises or consists of a nucleic acid sequence of SEQ ID NO: 12.

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. For example, inducible promoters include the zinc-inducible sheep metallothionine (MT) promoter and the dexamethasone (Dex)-inducible mouse mammary tumor virus (MMTV) promoter. Other inducible systems include the T7 polymerase promoter system (WO 98/10088); the ecdysone insect promoter (No et al, Proc. Natl. Acad. Sci. USA, 93:3346-3351 (1996)), the tetracycline-repressible system (Gossen et al, Proc. Natl. Acad. Sci. USA, 89:5547-5551 (1992)), the tetracycline-inducible system (Gossen et al, Science, 378:1766-1769 (1995), see also Harvey et al, Curr. Opin. Chem. Biol, 2:512-518 (1998)). Other systems include the FK506 dimer, VP16 or p65 using castradiol, diphenol murislerone, the RU486-inducible system (Wang et al, Nat. Biotech., 15:239-243 (1997) and Wang et al, Gene Ther., 4:432-441 (1997)) and the rapamycin-inducible system (Magari et al, J. Clin. Invest., 100:2865-2872 (1997)). The effectiveness of some inducible promoters increases over time. In such cases one can enhance the effectiveness of such systems by inserting multiple repressors in tandem, e.g., TetR linked to a TetR by an IRES.

In some embodiments the promotor is an enhanced hCMV promoter, such as provided in SEQ ID NO. 42.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

The transgene may be operably linked to a tissue-specific promoter. For instance, if expression in skeletal muscle is desired, a promoter active in muscle should be used. These include the promoters from genes encoding skeletal β-actin, myosin light chain 2A, dystrophin, muscle creatine kinase, as well as synthetic muscle promoters with activities higher than naturally occurring promoters (see Li et al, Nat. Biotech., 17:241-245 (1999)). Examples of promoters that are tissue-specific are known for liver (albumin, Miyatake et al, J. Virol, 71:5124-32 (1997); hepatitis B virus core promoter, Sandig et al, Gene Ther., 3:1002-9 (1996); alpha-fetoprotein (AFP), Arbuthnot et al., Hum. Gene Ther., 7: 1503-14 (1996)), bone osteocalcin (Stein et al, Mol. Biol. Rep., 24:185-96 (1997)); bone sialoprotein (Chen et al., J. Bone Miner. Res., 11:654-64 (1996)), lymphocytes (CD2, Hansal et al, J. Immunol, 161:1063-8 (1998); immunoglobulin heavy chain; T cell receptor chain), neuronal such as neuron-specific enolase (NSE) promoter (Andersen et al, Cell. Mol. Neurobiol, 13:503-15 (1993)), neurofilament light-chain gene (Piccioli et al, Proc. Natl. Acad. Sci. USA, 88:5611-5 (1991)), and the neuron-specific vgf gene (Piccioli et al, Neuron, 15:373-84 (1995)), among others.

Optionally, vectors carrying transgenes encoding therapeutically useful or immunogenic products may also include selectable markers or reporter genes which may include sequences encoding geneticin, hygromycin or puromycin resistance, among others. Such selectable reporters or marker genes (preferably located outside the viral genome to be packaged into a viral particle) can be used to signal the presence of the plasmids in bacterial cells, such as ampicillin resistance. Other components of the vector may include an origin of replication.

These vectors are generated using the techniques and sequences provided herein, in conjunction with techniques known to those of skill in the art. Such techniques include conventional cloning techniques of cDNA such as those described in texts, use of overlapping oligonucleotide sequences of the adenovirus genomes, polymerase chain reaction, and any suitable method which provides the desired nucleotide sequence.

Therapeutics and Prophylaxis

The recombinant ChAd157-based vectors are useful for gene transfer to a human or non-simian mammal in vitro, ex vivo, and in vivo.

The recombinant adenovirus vectors described herein can be used as expression vectors for the production of the products encoded by the heterologous transgenes in vitro. For example, the recombinant replication-incompetent adenovirus containing a transgene may be transfected into a complementation cell line as described above.

A ChAd157-derived recombinant adenoviral vector provides an efficient gene transfer vehicle that can deliver a selected transgene to a selected host cell in vivo or ex vivo even where the organism has neutralizing antibodies to one or more adenovirus serotypes. In one embodiment, the vector and the cells are mixed ex vivo; the infected cells are cultured using conventional methodologies; and the transduced cells are re-infused into the patient. These techniques are particularly well suited to gene delivery for therapeutic purposes and for immunisation, including inducing protective immunity.

Immunogenic Transgenes

The recombinant ChAd157 vectors may also be as administered in immunogenic compositions. An immunogenic composition as described herein is a composition comprising one or more recombinant ChAd157 vector capable of inducing an immune response, for example a humoral (e.g., antibody) and/or cell-mediated (e.g., a cytotoxic T cell) response, against a transgene product delivered by the vector following delivery to a mammal, suitably a human. A recombinant adenovirus may comprise (suitably in any of its gene deletions) a gene encoding a desired immunogen and may therefore be used in a vaccine. The recombinant adenoviruses can be used as prophylactic or therapeutic vaccines against any pathogen for which the antigen(s) crucial for induction of an immune response and able to limit the spread of the pathogen has been identified and for which the cDNA is available.

By the term immunogen is meant a polypeptide which is capable of eliciting an immune response. Suitably the immunogen is an antigen which comprises at least one B or T cell epitope. The elicited immune response may be an antigen specific B cell response, which produces neutralizing antibodies. The elicited immune response may be an antigen specific T cell response, which may be a systemic and/or a local response. The antigen specific T cell response may comprise a CD4+ T cell response, such as a response involving CD4+ T cells expressing a plurality of cytokines, e.g. IFNgamma, TNFalpha and/or IL2. Alternatively, or additionally, the antigen specific T cell response comprises a CD8+ T cell response, such as a response involving CD8+ T cells expressing a plurality of cytokines, e.g., IFNgamma, TNFalpha and/or IL2.

The term immunise therefore means the administration of an immunogen (or polynucleotide encoding the immunogen as appropriate to the context), to elicit an immune response.

Such vaccine or other immunogenic compositions may be formulated in a suitable delivery vehicle. Generally, doses for the immunogenic compositions are in the range defined below under 'Delivery Methods and Dosage'. The levels of immunity of the selected gene can be monitored to determine the need, if any, for boosters. Following an assessment of antibody titers in the serum, optional booster immunizations may be desired.

Optionally, a vaccine or immunogenic composition of the invention may be formulated to contain other components, including, e.g., adjuvants, stabilizers, pH adjusters, preservatives and the like. Examples of suitable adjuvants are provided below under 'Adjuvants'. Such an adjuvant can be administered with a priming DNA vaccine encoding an antigen to enhance the antigen-specific immune response compared with the immune response generated upon priming with a DNA vaccine encoding the antigen only. Alternatively, such an adjuvant can be administered with a polypeptide antigen which is administered in an administration regimen involving the ChAd157 vectors of the invention (as described below under 'Administration Regimens'.

The recombinant adenoviruses are administered in an immunogenic amount, that is, an amount of recombinant adenovirus that is effective in a route of administration to transfect the desired target cells and provide sufficient levels of expression of the selected gene to induce an immune response. Where protective immunity is provided, the recombinant adenoviruses are considered to be vaccine compositions useful in preventing infection and/or recurrent disease.

The recombinant vectors described herein are expected to be highly efficacious at inducing cytolytic T cells and antibodies directed to the inserted heterologous antigenic protein expressed by the vector.

Immunogens expressed by the inventive vectors which are useful to immunize a human or non-human animal against other pathogens include, e.g., bacteria, fungi, parasitic microorganisms or multicellular parasites which infect human and non-human vertebrates, or from a cancer cell or tumor cell. For example, immunogens may be selected from a variety of viral families. Examples of viral families against which an immune response would be desirable include Lyssaviruses such as rabies viruses, respiratory viruses such as respiratory syncytial virus (RSV) and other paramyxoviruses such as human metapneumovirus, hMPV and parainfluenza viruses (PIV).

Suitable rabies antigens which are useful as immunogens to immunize a human or non-human animal can be selected from the rabies viral glycoprotein (G), RNA polymerase (L), matrix protein (M), nucleoprotein (N) and phosphoprotein (P). The term "G protein" or "glycoprotein" or "G protein polypeptide" or "glycoprotein polypeptide" refers to a polypeptide or protein having all or part of an amino acid sequence of a rabies glycoprotein polypeptide. The term "L protein" or "RNA polymerase protein" or "L protein polypeptide" or "RNA polymerase protein polypeptide" refers to a polypeptide or protein having all or part of an amino acid sequence of a rabies RNA polymerase protein polypeptide. The term "M protein" or "matrix protein" or "M protein polypeptide" or "matrix protein polypeptide" refers to a polypeptide or protein having all or part of an amino acid sequence of a rabies matrix protein polypeptide. The term "N protein" or "nucleoprotein" or "N protein polypeptide" or "nucleoprotein polypeptide" refers to a polypeptide or protein having all or part of an amino acid sequence of a rabies nucleoprotein polypeptide. The term "P protein" or "phosphoprotein" or "P protein polypeptide" or "phosphoprotein polypeptide" refers to a polypeptide or protein having all or part of an amino acid sequence of a rabies phosphoprotein polypeptide.

Suitable antigens of RSV which are useful as immunogens to immunize a human or non-human animal can be selected from: the fusion protein (F), the attachment protein (G), the matrix protein (M2) and the nucleoprotein (N). The term "F protein" or "fusion protein" or "F protein polypeptide" or "fusion protein polypeptide" refers to a polypeptide or protein having all or part of an amino acid sequence of an RSV Fusion protein polypeptide. Similarly, the term "G protein" or "G protein polypeptide" refers to a polypeptide or protein having all or part of an amino acid sequence of an RSV Attachment protein polypeptide. The term "M protein" or "matrix protein" or "M protein polypeptide" refers to a polypeptide or protein having all or part of an amino acid sequence of an RSV Matrix protein and may include either or both of the M2-1 (which may be written herein as M2.1) and M2-2 gene products. Likewise, the term "N protein" or "Nucleocapsid protein" or "N protein polypeptide" refers to a polypeptide or protein having all or part of an amino acid sequence of an RSV Nucleoprotein.

Two groups of human RSV strains have been described, the A and B groups, based mainly on differences in the antigenicity of the G glycoprotein. Numerous strains of RSV have been isolated to date, any of which are suitable in the context of the antigens of the immunogenic combinations disclosed herein. Exemplary strains indicated by GenBank and/or EMBL Accession number can be found in US published application number 2010/0203071 (WO2008114149), which is incorporated herein by reference for the purpose of disclosing the nucleic acid and polypeptide sequences of RSV F and G proteins suitable for use in present invention. In an embodiment, the RSV F protein can be an ectodomain of an RSV F Protein (FΔTM).

Exemplary M and N protein nucleic acids and protein sequences can be found, e.g., in US published application number 2014/0141042 (WO2012/089833), which are incorporated herein for purpose of disclosing the nucleic acid and polypeptide sequences of RSV M and N proteins suitable for use in present invention.

Suitably, for use with in present invention, a nucleic acid encodes an RSV F antigen and RSV, M and N antigens. More specifically, the nucleic acid encodes an RSV FΔTM antigen and RSV M2-1 and N antigens, wherein a self-cleavage site is included between the RSV FΔTM antigen and the RSV M2-1 and a flexible linker is included between the RSV M2-1 and N antigens. In one embodiment a suitable nucleic acid encodes the polypeptide represented by SEQ ID NO:37

In one embodiment, the immunogen may be from a retrovirus, for example a lentivirus such as the Human Immunodeficiency Virus (HIV). In such an embodiment, immunogens may be derived from HIV-1 or HIV-2.

The HIV genome encodes a number of different proteins, each of which can be immunogenic in its entirety or as a fragment when expressed by vectors of the present invention. Envelope proteins include gp120, gp41 and Env precursor gp160, for example. Non-envelope proteins of HIV include for example internal structural proteins such as the products of the gag and pol genes and other non-structural proteins such as Rev, Nef, Vif and Tat. In an embodiment the vector of the invention encodes one or more polypeptides comprising HIV Gag.

The Gag gene is translated as a precursor polyprotein that is cleaved by protease to yield products that include the matrix protein (p17), the capsid (p24), the nucleocapsid (p9), p6 and two space peptides, p2 and p1, all of which are examples of fragments of Gag.

The Gag gene gives rise to the 55-kilodalton (kD) Gag precursor protein, also called p55, which is expressed from the unspliced viral mRNA. During translation, the N terminus of p55 is myristoylated, triggering its association with the cytoplasmic aspect of cell membranes. The membrane-associated Gag polyprotein recruits two copies of the viral genomic RNA along with other viral and cellular proteins that triggers the budding of the viral particle from the surface of an infected cell. After budding, p55 is cleaved by the virally encoded protease (a product of the pol gene) during the process of viral maturation into four smaller proteins designated MA (matrix [p17]), CA (capsid [p24]), NC (nucleocapsid [p9]), and p6, all of which are examples of fragments of Gag. In one embodiment, the vectors of the present invention comprise a Gag polypeptide of SEQ ID NO: 16.

Adjuvants

An "adjuvant" as used herein refers to a composition that enhances the immune response to an immunogen. Examples of such adjuvants include but are not limited to inorganic adjuvants (e.g. inorganic metal salts such as aluminium phosphate or aluminium hydroxide), organic adjuvants (e.g. saponins, such as QS21, or squalene), oil-based adjuvants (e.g. Freund's complete adjuvant and Freund's incomplete adjuvant), cytokines (e.g. IL-1β, IL-2, IL-7, IL-12, IL-18, GM-CFS, and INF-y) particulate adjuvants (e.g. immunostimulatory complexes (ISCOMS), liposomes, or biodegradable microspheres), virosomes, bacterial adjuvants (e.g. monophosphoryl lipid A, such as 3-de-O-acylated monophosphoryl lipid A (3D-MPL), or muramyl peptides), synthetic adjuvants (e.g. non-ionic block copolymers, muramyl peptide analogues, or synthetic lipid A), synthetic polynucleotides adjuvants (e.g polyarginine or polylysine) and immunostimulatory oligonucleotides containing unmethylated CpG dinucleotides ("CpG").

One suitable adjuvant is monophosphoryl lipid A (MPL), in particular 3-de-O-acylated monophosphoryl lipid A (3D-MPL). Chemically it is often supplied as a mixture of 3-de-O-acylated monophosphoryl lipid A with either 4, 5, or 6 acylated chains. It can be purified and prepared by the methods taught in GB 2122204B, which reference also discloses the preparation of diphosphoryl lipid A, and 3-O-deacylated variants thereof. Other purified and synthetic lipopolysaccharides have been described (U.S. Pat. No. 6,005,099 and EP 0 729 473 B1; Hilgers et al., 1986, Int. Arch. Allergy. Immunol., 79(4):392-6; Hilgers et al., 1987, Immunology, 60(1):141-6; and EP 0 549 074 B11).

Saponins are also suitable adjuvants (see Lacaille-Dubois, M and Wagner H, A review of the biological and pharmacological activities of saponins. Phytomedicine vol 2 pp 363-386 (1996)). For example, the saponin Quil A (derived from the bark of the South American tree Quillaja *Saponaria* Molina), and fractions thereof, are described in U.S. Pat. No. 5,057,540 and Kensil, Crit. Rev. Ther. Drug Carrier Syst., 1996, 12:1-55; and EP 0 362 279 B1. Purified fractions of Quil A are also known as immunostimulants, such as QS21 and QS17; methods of their production is disclosed in U.S. Pat. No. 5,057,540 and EP 0 362 279 B1. Also described in these references is QS7 (a non-haemolytic fraction of Quil-A). Use of QS21 is further described in Kensil et al. (1991, J. Immunology, 146: 431-437). Combinations of QS21 and polysorbate or cyclodextrin are also known (WO 99/10008). Particulate adjuvant systems comprising fractions of QuilA, such as QS21 and QS7 are described in WO 96/33739 and WO 96/11711.

Another adjuvant is an immunostimulatory oligonucleotide containing unmethylated CpG dinucleotides ("CpG") (Krieg, Nature 374:546 (1995)). CpG is an abbreviation for cytosine-guanosine dinucleotide motifs present in DNA. CpG is known as an adjuvant when administered by both systemic and mucosal routes (WO 96/02555, EP 468520, Davis et al, J. Immunol, 1998, 160:870-876; McCluskie and Davis, J. Immunol., 1998, 161:4463-6). CpG, when formulated into vaccines, may be administered in free solution together with free antigen (WO 96/02555) or covalently conjugated to an antigen (WO 98/16247), or formulated with a carrier such as aluminium hydroxide (Brazolot-Millan et al., Proc. Natl. Acad. Sci., USA, 1998, 95:15553-8).

Adjuvants such as those described above may be formulated together with carriers, such as liposomes, oil in water emulsions, and/or metallic salts (including aluminum salts such as aluminum hydroxide). For example, 3D-MPL may be formulated with aluminum hydroxide (EP 0 689 454) or oil in water emulsions (WO 95/17210); QS21 may be formulated with cholesterol containing liposomes (WO 96/33739), oil in water emulsions (WO 95/17210) or alum (WO 98/15287); CpG may be formulated with alum (Brazolot-Millan, supra) or with other cationic carriers.

Combinations of adjuvants may be utilized in the present invention, in particular a combination of a monophosphoryl lipid A and a saponin derivative (see, e.g., WO 94/00153; WO 95/17210; WO 96/33739; WO 98/56414; WO 99/12565; WO 99/11241), more particularly the combination of QS21 and 3D-MPL as disclosed in WO 94/00153, or a composition where the QS21 is quenched in cholesterol-containing liposomes (DQ) as disclosed in WO 96/33739. Alternatively, a combination of CpG plus a saponin such as QS21 is an adjuvant suitable for use in the present invention. A potent adjuvant formulation involving QS21, 3D-MPL & tocopherol in an oil in water emulsion is described in WO 95/17210 and is another formulation for use in the present invention. Saponin adjuvants may be formulated in a liposome and combined with an immunostimulatory oligonucleotide. Thus, suitable adjuvant systems include, for example, a combination of monophosphoryl lipid A, preferably 3D-MPL, together with an aluminium salt (e.g. as described in WO00/23105). A further exemplary adjuvant comprises QS21 and/or MPL and/or CpG. QS21 may be quenched in cholesterol-containing liposomes as disclosed in WO 96/33739.

Other suitable adjuvants include alkyl Glucosaminide phosphates (AGPs) such as those disclosed in WO9850399 or U.S. Pat. No. 6,303,347 (processes for preparation of AGPs are also disclosed), or pharmaceutically acceptable salts of AGPs as disclosed in U.S. Pat. No. 6,764,840. Some AGPs are TLR4 agonists, and some are TLR4 antagonists. Both are thought to be useful as adjuvants.

It has been found (WO 2007/062656, which published as US 2011/0293704 and is incorporated by reference for the purpose of disclosing invariant chain sequences) that the fusion of the invariant chain to an antigen which is comprised by an expression system used for vaccination increases the immune response against said antigen, if it is administered with an adenovirus. Accordingly, in one embodiment of the invention, the immunogenic transgene may be co-expressed with invariant chain in a recombinant ChAd157 viral vector.

In another embodiment, the invention provides the use of the capsid of ChAd157 (optionally an intact or recombinant viral particle or an empty capsid is used) to induce an immunomodulatory effect response, or to enhance or adjuvant a cytotoxic T cell response to another active agent by delivering a ChAd157 capsid to a subject. The ChAd157 capsid can be delivered alone or in a combination regimen with an active agent to enhance the immune response thereto. Advantageously, the desired effect can be accomplished without infecting the host with an adenovirus.

Administration Regimens

Commonly, the ChAd157 recombinant adenoviral vectors will be utilized for delivery of therapeutic or immunogenic molecules (such as proteins). It will be readily understood for both applications, that the recombinant adenoviral vectors of the invention are particularly well suited for use in regimens involving repeat delivery of recombinant adenoviral vectors. Such regimens typically involve delivery of a series of viral vectors in which the viral capsids are alternated. The viral capsids may be changed for each subsequent administration, or after a pre-selected number of administrations of a particular serotype capsid (e.g. one, two, three, four or more). Thus, a regimen may involve delivery of a recombinant adenovirus with a first capsid, delivery with a recombinant adenovirus with a second capsid, and delivery with a recombinant adenovirus with a third capsid. A variety of other regimens which use the adenovirus capsids of the invention alone, in combination with one another, or in combination with other adenoviruses (which are preferably immunologically non-cross reactive) will be apparent to those of skill in the art. Optionally, such a regimen may involve administration of recombinant adenovirus with capsids of other non-human primate adenoviruses, human adenoviruses, or artificial sequences such as are described herein.

The adenoviral vectors of the invention are particularly well suited for therapeutic regimens in which multiple adenoviral-mediated deliveries of transgenes are desired, e.g., in regimens involving redelivery of the same transgene or in combination regimens involving delivery of other transgenes. Such regimens may involve administration of a ChAd157 adenoviral vector, followed by re-administration with a vector from the same serotype adenovirus. Particularly desirable regimens involve administration of a ChAd157 adenoviral vector, in which the source of the adenoviral capsid sequences of the vector delivered in the first administration differs from the source of adenoviral capsid sequences of the viral vector utilized in one or more of the subsequent administrations. For example, a therapeutic regimen involves administration of a ChAd157 vector and repeat administration with one or more adenoviral vectors of the same or different serotypes.

In another example, a therapeutic regimen involves administration of an adenoviral vector followed by repeat administration with a ChAd157 vector which has a capsid which differs from the source of the capsid in the first delivered adenoviral vector, and optionally further administration with another vector which is the same or, preferably, differs from the source of the adenoviral capsid of the vector in the prior administration steps. These regimens are not limited to delivery of adenoviral vectors constructed using the ChAd157 sequences. Rather, these regimens can readily utilize other adenoviral sequences, including, without limitation, other adenoviral sequences including other non-human primate adenoviral sequences, or human adenoviral sequences, in combination with the ChAd157 vectors.

In a further example, a therapeutic regimen may involve either simultaneous (such as co-administration) or sequential (such as a prime-boost) delivery of (i) one or more ChAd157 adenoviral vectors and (ii) a further component such as non-adenoviral vectors, non-viral vectors, and/or a variety of other therapeutically useful compounds or molecules such as antigenic proteins optionally simultaneously administered with adjuvant. Examples of co-administration include homo-lateral co-administration and contra-lateral co-administration (further described below under 'Delivery Methods and Dosage').

Suitable non-adenoviral vectors for use in simultaneous or particularly in sequential delivery (such as prime-boost) with one or more ChAd157 adenoviral vectors include one or more poxviral vectors. Suitably, the poxviral vector belongs to the subfamily chordopoxvirinae, more suitably to a genus in said subfamily selected from the group consisting of orthopox, parapox, yatapox, avipox (suitably canarypox (ALVAC) or fowlpox (FPV)) and molluscipox. Even more suitably, the poxviral vector belongs to the orthopox and is selected from the group consisting of vaccinia virus, NYVAC (derived from the Copenhagen strain of vaccinia), Modified Vaccinia Ankara (MVA), cowpoxvirus and monkeypox virus. Most suitably, the poxviral vector is MVA.

"Simultaneous" administration suitably refers to the same ongoing immune response. Preferably both components are administered at the same time (such as simultaneous administration of both DNA and protein), however, one component could be administered within a few minutes (for example, at the same medical appointment or doctor's visit), within a few hours. Such administration is also referred to as co-administration. In some embodiments, co-administration may refer to the administration of an adenoviral vector, an adjuvant and a protein component. In other embodiments, co-administration refers to the administration of an adenoviral vector and another viral vector, for example a second adenoviral vector or a poxvirus such as MVA. In other embodiments, co-administration refers to the administration of an adenoviral vector and a protein component, which is optionally adjuvanted.

A prime-boost regimen may be used. Prime-boost refers to two separate immune responses: (i) an initial priming of the immune system followed by (ii) a secondary or boosting of the immune system many weeks or months after the primary immune response has been established.

Such a regimen may involve the administration of a recombinant ChAd157 vector to prime the immune system to second, booster, administration with a traditional antigen, such as a protein (optionally co-administered with adjuvant), or a recombinant virus carrying the sequences encoding such an antigen (e.g., WO 00/11140). Alternatively, an immunization regimen may involve the administration of a recombinant ChAd157 vector to boost the immune response to a vector (either viral or DNA-based) encoding an antigen. In another alternative, an immunization regimen involves administration of a protein followed by booster with a recombinant ChAd157 vector encoding the antigen. In one example, the prime-boost regimen can provide a protective immune response to the virus, bacteria or other organism from which the antigen is derived. In another embodiment, the prime-boost regimen provides a therapeutic effect that can be measured using conventional assays for detection of the presence of the condition for which therapy is being administered.

Preferably, a boosting composition is administered about 2 to about 27 weeks after administering the priming composition to the subject. The administration of the boosting composition is accomplished using an effective amount of a boosting composition containing or capable of delivering the same antigen or a different antigen as administered by the priming vaccine. The boosting composition may be composed of a recombinant viral vector derived from the same viral source or from another source. Alternatively, the boosting composition can be a composition containing the same antigen as encoded in the priming vaccine, but in the form of a protein, which composition induces an immune response in the host. The primary requirements of the boosting composition are that the antigen of the composition is the same antigen, or a cross-reactive antigen, as that encoded by the priming composition.

A low cross-reactivity between neutralizing antibodies for ChAd157 and certain other adenoviral vectors, such as ChAd155, is beneficial in contexts where multiple vector administrations are required. Multiple administrations may be for the purpose of the separate delivery of different transgenes (e.g. encoding immunogens associated different medical indications) or delivery of the same or similar transgenes (e.g. in a prime-boost regime to increase the immune response for a particular medical indication).

Consequently, there is provided a recombinant adenoviral vector of the invention encoding a transgene, for administration to a subject which has previously been exposed to a recombinant adenoviral vector which does not comprise a ChAd157 fiber, or functional derivative thereof, as described herein (e.g. does not comprise a ChAd157 fiber, hexon or penton as described herein, such as a recombinant adenoviral vector comprising a ChAd155 fiber, hexon and/or penton, especially a recombinant adenoviral vector comprising a ChAd155 fiber, hexon and penton). In particular, there is provided a recombinant adenoviral vector of the invention encoding a transgene for administration to a subject which has previously been administered a recombinant adenoviral vector which does not comprise a ChAd157 fiber, or functional derivative thereof, as described herein (e.g. does not comprise a ChAd157 fiber, hexon or penton as described herein, such as a recombinant adenoviral vector comprising a ChAd155 fiber, hexon and/or penton, especially a recombinant adenoviral vector comprising a ChAd155 fiber, hexon and penton). Suitably the recombinant adenoviral vector which does not comprise a ChAd157 fiber is one which has low cross-reactivity with ChAd157. In one embodiment the recombinant adenoviral vector which does not comprise a ChAd157 fiber encodes a transgene directed at a different medical indication or indications as the recombinant adenoviral vector of the invention transgene. In another embodiment the recombinant adenoviral vector which does not comprise a ChAd157 fiber encodes a transgene directed at the same medical indication or indications as the recombinant adenoviral vector of the invention transgene (e.g. such as the same transgene).

Also provided is a recombinant adenoviral vector of the invention encoding a transgene for administration to a subject which may (i.e. it is intended or expected will) subsequently be exposed to a recombinant adenoviral vector which does not comprise a ChAd157 fiber, or functional derivative thereof, as described herein (e.g. does not comprise a ChAd157 fiber, hexon or penton as described herein, such as a recombinant adenoviral vector comprising a ChAd155 fiber, hexon and/or penton, especially a recombinant adenoviral vector comprising a ChAd155 fiber, hexon and penton). In particular, there is provided a recombinant adenoviral vector of the invention encoding a transgene for administration to a subject which may subsequently be administered a recombinant adenoviral vector which does not comprise a ChAd157 fiber, or functional derivative thereof, as described herein (e.g. does not comprise a ChAd157 fiber, hexon or penton as described herein, such as a recombinant adenoviral vector comprising a ChAd155 fiber, hexon and/or penton, especially a recombinant adenoviral vector comprising a ChAd155 fiber, hexon and penton). Suitably the recombinant adenoviral vector which does not comprise a ChAd157 fiber is one which has low cross-reactivity with ChAd157. In one embodiment the recombinant adenoviral vector which does not comprise a ChAd157 fiber encodes a transgene directed at a different medical indication or indications as the recombinant adenoviral vector of the invention transgene. In another embodiment the recombinant adenoviral vector which does not comprise a ChAd157 fiber encodes a transgene directed at the same medical indication or indications as the recombinant adenoviral vector of the invention transgene (e.g. such as the same transgene).

The present invention therefore provides a method for eliciting an immune response in a subject, said method comprising:
  (a) administering to the subject a recombinant adenoviral vector of the invention encoding a first transgene; and
  (b) administering to the subject a recombinant adenoviral vector which does not comprise a ChAd157 fiber, or functional derivative thereof as described herein, the vector encoding a second transgene;
  wherein steps (a) and (b) may be undertaken in either order and the first and second transgenes may be the same or different.

The first and second transgenes will typically encode immunogens which are useful to immunize a human or non-human animal against a pathogen such as bacteria, fungi, parasitic microorganisms or multicellular parasites which infect human and non-human vertebrates, or against a cancer cell or tumor cell. The first and second transgenes may encode the same or different immunogens. When encoding different immunogens, these may be directed to the same or different pathogen or cancer cell or tumor cell.

Consequently, there is also provided a method for the prophylaxis or treatment of a subject, said method comprising:
  (a) administering to the subject a recombinant adenoviral vector of the invention encoding a first transgene encoding an immunogen which is useful to immunize a human or non-human animal against a pathogen such as bacteria, fungi, parasitic microorganisms or multicellular parasites which infect human and non-human vertebrates, or against a cancer cell or tumor cell; and
  (b) administering to the subject a recombinant adenoviral vector which does not comprise a ChAd157 fiber, or functional derivative thereof as described herein, the vector encoding a second transgene encoding an immunogen which is useful to immunize a human or non-human animal against a different pathogen such as bacteria, fungi, parasitic microorganisms or multicellular parasites which infect human and non-human vertebrates, or against a cancer cell or tumor cell;
  wherein steps (a) and (b) may be undertaken in either order.

The recombinant adenoviral vector which does not comprise a ChAd157 fiber, or functional derivative thereof as described herein, suitably does not comprise a ChAd157 fiber, ChAd157 hexon or ChAd157 fiber, such as does not comprise a ChAd157 fiber, ChAd157 hexon or ChAd157 fiber or functional derivatives thereof having at least 98% identity thereto.

The recombinant adenoviral vector which does not comprise a ChAd157 fiber, or functional derivative thereof as described herein may be a recombinant adenoviral vector comprising a ChAd155 fiber, hexon and/or penton, especially a recombinant adenoviral vector comprising a ChAd155 fiber, hexon and penton.

As mentioned, a recombinant adenoviral vector of the invention may be used for delivery of therapeutic or immunogenic molecules in conjunction with a recombinant adenoviral vector comprising a ChAd155 fiber, hexon and/or penton. The recombinant adenoviral vector comprising a ChAd155 fiber, hexon and/or penton will comprise a fiber, penton and/or hexon according to SEQ ID NOs: 7, 9 and 11, in particular a fiber, penton and hexon according to SEQ ID NOs: 7, 9 and 11.

By the term low cross-reactivity is meant that immunisation with a first vector does not elicit a notable neutralising antibody response to a second vector, i.e. not significantly impacting the immunological potency of the second vector. Neutralising antibody responses can be determined with methods analogous to Example 7 herein. Desirably, immunisation with a first vector twice elicits a neutralising titer which is on average less than 50% of the level arising from immunisation with the second vector, such as less than 75%, suitably less than 90%.

By the term "subject" is meant any animal, suitably a mammal, and in particular a human.

Delivery Methods and Dosage

The vector may be prepared for administration by being suspended or dissolved in a pharmaceutically or physiologically acceptable carrier such as isotonic saline; isotonic salts solution or other formulations that will be apparent to those skilled in the art. The appropriate carrier will be evident to those skilled in the art and will depend in large part upon the route of administration. The compositions described herein may be administered to a mammal in a sustained release formulation using a biodegradable biocompatible polymer, or by on-site delivery using micelles, gels and liposomes.

In some embodiments, the recombinant adenovirus of the invention is administered to a subject by intramuscular injection, intravaginal administration, intravenous injection, intraperitoneal injection, subcutaneous injection, epicutaneous administration, intradermal administration, nasal administration, rectal administration or oral administration. Sublingual administration may also be of interest.

If the therapeutic regimen involves co-administration of one or more ChAd157 adenoviral vectors and a further component, each formulated in different compositions, they are favourably administered co-locationally at or near the same site. For example, the components can be administered (e.g. via an administration route selected from intramuscular, transdermal, intradermal, sub-cutaneous) to the same side or extremity ("co-lateral" administration) or to opposite sides or extremities ("contra-lateral" administration).

Dosages of the viral vector will depend primarily on factors such as the condition being treated, the age, weight and health of the patient, and may thus vary among patients. For example, a therapeutically effective adult human or veterinary dosage of the viral vector generally contains $1 \times 10^5$ to $1 \times 10^{15}$ viral particles, such as from $1 \times 10^8$ to $1 \times 10^{12}$ (e.g., $1 \times 10^8$, $2.5 \times 10^8$, $5 \times 10^8$, $1 \times 10^9$, $1.5 \times 10^9$, $2.5 \times 10^9$, $5 \times 10^9$, $1 \times 10^{10}$, $1.5 \times 10^{10}$, $2.5 \times 10^{10}$, $5 \times 10^{10}$, $1 \times 10^{11}$ $1.5 \times 10^{11}$, $2.5 \times 10^{11}$, $5 \times 10^{11}$, $1 \times 10^{12}$ particles). Alternatively, a viral vector can be administered at a dose that is typically from $1 \times 10^5$ to $1 \times 10^{10}$ plaque forming units (PFU), such as $1 \times 10^5$ PFU, $2.5 \times 10^5$ PFU, $5 \times 10^5$ PFU, $1 \times 10^6$ PFU, $2.5 \times 10^6$ PFU, $5 \times 10^6$ PFU $1 \times 10^7$ PFU, $2.5 \times 10^7$ PFU, $5 \times 10^7$ PFU, $1 \times 10^8$ PFU, $2.5 \times 10^8$ PFU, $5 \times 10^8$ PFU, $1 \times 10^9$ PFU, $2.5 \times 10^9$ PFU, $5 \times 10^9$ PFU, or $1 \times 10^{10}$ PFU. Dosages will vary depending upon the size of the animal and the route of administration. For example, a suitable human or veterinary dosage (for about an 80 kg animal) for intramuscular injection is in the range of about $1 \times 10^9$ to about $5 \times 10^{12}$ particles per mL, for a single site. Optionally, multiple sites of administration may be used. In another example, a suitable human or veterinary dosage may be in the range of about $1 \times 10^{11}$ to about $1 \times 10^{15}$ particles for an oral formulation.

The viral vector can be quantified by Quantitative PCR Analysis (Q-PCR), for example with primers and probe designed on CMV promoter region using as standard curve serial dilution of plasmid DNA containing the vector genome with expression cassette including HCMV promoter. The copy number in the test sample is determined by the parallel line analysis method. Alternative methods for vector particle quantification can be analytical HPLC or spectrophotometric method based on A260 nm.

An immunologically effective amount of a nucleic acid may suitably be between 1 ng and 100 mg. For example, a suitable amount can be from 1 μg to 100 mg. An appropriate amount of the particular nucleic acid (e.g., vector) can readily be determined by those of skill in the art. Exemplary effective amounts of a nucleic acid component can be between 1 ng and 100 μg, such as between 1 ng and 1 μg (e.g., 100 ng-1 μg), or between 1 μg and 100 μg, such as 10 ng, 50 ng, 100 ng, 150 ng, 200 ng, 250 ng, 500 ng, 750 ng, or 1 μg. Effective amounts of a nucleic acid can also include from 1 μg to 500 μg, such as between 1 μg and 200 μg, such as between 10 and 100 μg, for example 1 μg, 2 μg, 5 μg, 10 μg, 20 μg, 50 μg, 75 μg, 100 μg, 150 μg, or 200 μg.

Alternatively, an exemplary effective amount of a nucleic acid can be between 100 μg and 1 mg, such as from 100 μg to 500 μg, for example, 100 μg, 150 μg, 200 μg, 250 μg, 300 μg, 400 μg, 500 μg, 600 μg, 700 μg, 800 μg, 900 μg or 1 mg.

Generally a human dose will be in a volume of between 0.1 ml and 2 ml. Thus the composition described herein can be formulated in a volume of, for example 0.1, 0.15, 0.2, 0.5, 1.0, 1.5 or 2.0 ml human dose per individual or combined immunogenic components.

One of skill in the art may adjust these doses, depending on the route of administration and the therapeutic or vaccine application for which the recombinant vector is employed. The levels of expression of the transgene, or for an adjuvant, the level of circulating antibody, can be monitored to determine the frequency of dosage administration.

If one or more priming and/or boosting steps are used, this step may include a single dose that is administered hourly, daily, weekly or monthly, or yearly. As an example, mammals may receive one or two doses containing between about 10 μg to about 50 μg of plasmid in carrier. The amount or site of delivery is desirably selected based upon the identity and condition of the mammal.

The therapeutic levels of, or level of immune response against, the protein encoded by the selected transgene can be monitored to determine the need, if any, for boosters. Following an assessment of CD8+ T cell response, or optionally, antibody titers, in the serum, optional booster immunizations may be desired. Optionally, the recombinant ChAd157 vectors may be delivered in a single administration or in various combination regimens, e.g., in combination with a regimen or course of treatment involving other active ingredients or in a prime-boost regimen.

The present invention will now be further described by means of the following non-limiting examples.

EXAMPLES

Example 1: Isolation of ChAd157 and Vector Construction 29 different wild type chimpanzee adenoviruses were isolated from healthy young chimpanzees housed in different European facilities using standard procedures as described in Colloca et al. Sci Transl Med. 2012 Jan. 4; 4(115):115ra2 and WO2010/086189, which is hereby incorporated by reference for the purpose of describing adenoviral isolation and characterization techniques.

Figure 2:
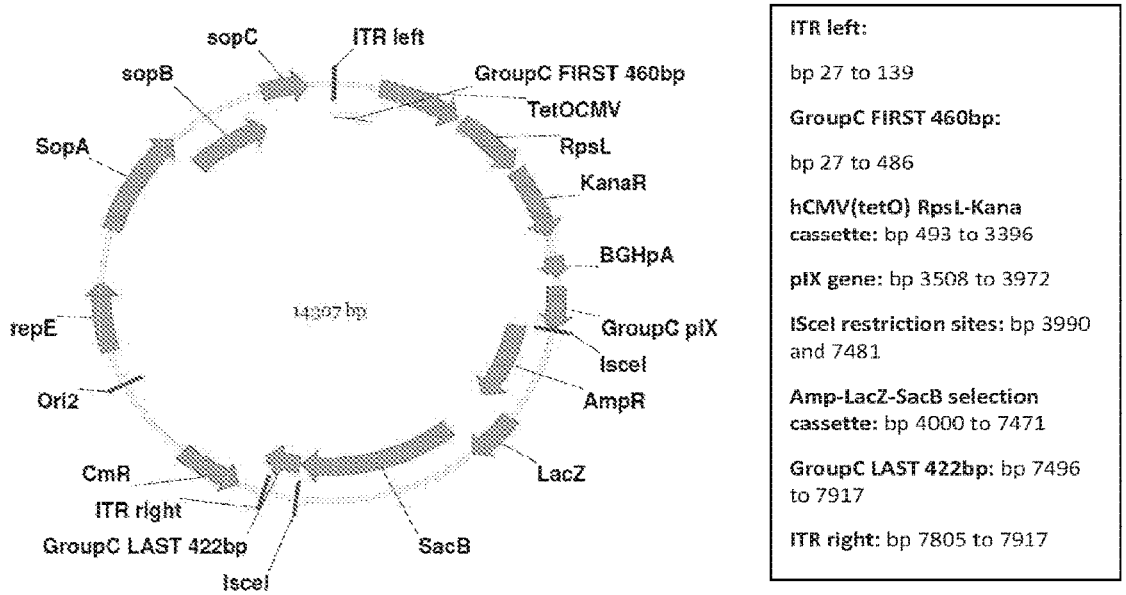

The 29 wild type viruses were subsequently pooled; the viral genome of the pool was cloned by homologous recombination in E. coli BJ5183 cells using a BAC shuttle, to create a minilibrary of vectors carrying the deletion of E1 region. The minilibrary of ΔE1 vectors was transfected into the Procell 92 cell line; the rescued vectors were serially passaged for 16 passages of infection. At passage 16 the viral DNA was prepared from the amplified vector and cloned by homologous recombination in E. coli BJ5183 cells using a plasmid shuttle. The prevalent vector species was identified as ChAd157ΔE1 vector and subsequently modified to include the following additional modifications of the vector backbone:
  a) deletion of the E4 region (from bp 34413 to bp 37127) of the ΔE1 virus;
  b) insertion of the E4orf6 derived from human Ad5.
  1.1: ΔE1 Minilibrary Generation The pool of 29 wild type virus was used to obtain a pooled viral genome. The pooled viral genome was cloned into a BAC vector by homologous recombination in E. coli strain BJ5183 co-transformed with pooled viral DNA and Subgroup C BAC Shuttle (#1365) (SEQ ID NO: 14). As shown in the schematic of FIG. 2, the Subgroup C Shuttle is a BAC vector dedicated to the cloning of ChAd belonging to species C and therefore contains the pIX gene and DNA fragments derived from right and left ends (including right and left ITRs) of species C ChAd viruses.

The Species C BAC Shuttle also contains a RpsL-Kana cassette inserted between left end and the pIX gene. In addition, an Amp-LacZ-SacB selection cassette, flanked by IScel restriction sites, is present between the pIX gene and right end of the viral genome. In particular, the BAC Shuttle comprised the following features: Left ITR: bp 27 to 139, hCMV(tetO) RpsL-Kana cassette: bp 493 to 3396, pIX gene: bp 3508 to 3972, IScel restriction sites: bp 3990 and 7481, Amp-LacZ-SacB selection cassette: bp 4000 to 7471, Right ITR: bp 7805 to 7917. hCMV(tetO) is provided in SEQ ID NO: 37.

BJ5183 cells were co-transformed by electroporation with the pool of purified viral DNAs and with Subgroup C BAC Shuttle vector digested with IScel restriction enzyme and then purified from gel. Homologous recombination occurring between pIX gene and right ITR sequences (present at the ends of Species C BAC Shuttle linearized DNA) and homologous sequences present in pooled viral DNA lead to the insertion of the different viral genomic DNA in the BAC shuttle vector. At the same time, the viral E1 regions were deleted and substituted by the RpsL-Kana cassette, generating BAC/MinilibraryΔE1/TetO hCMV RpsL-Kana.

1.2: ΔE1 Minilibrary Amplification in Procell 92 Cell Line and Cloning of ChAd157ΔE1 Vector.

Figure 3:
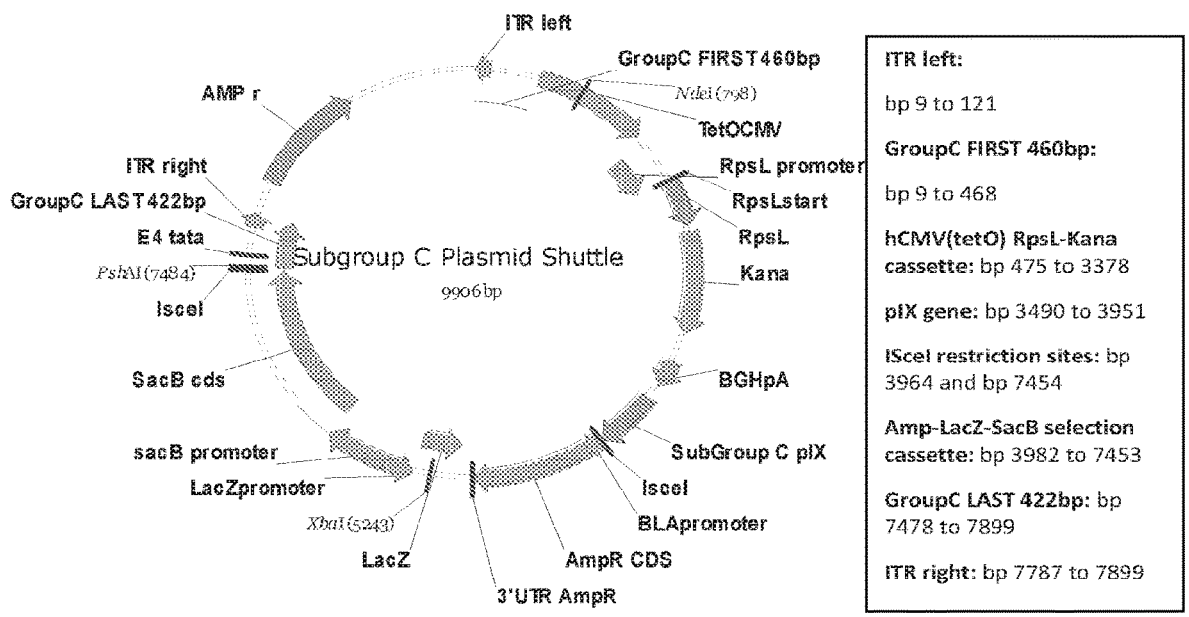

The ΔE1 minilibrary was digested with PmeI and used to transfect Procell 92 packaging cell line, in order to rescue the library of different viruses in bulk. 10 days post transfection; the cells were harvested and the cell lysate was subjected to three cycle of freeze (−70° C.) and thaw (+37° C.), clarified by centrifugation at 2000 rpm and used to infect fresh cells, 16 serial passages of virus amplification were performed; in order to select the viral species for efficiency of propagation in Procell92 cells. The virus (-es) at passage 16 were purified by two CsCl gradient centrifugations and viral DNA was extracted and cloned by homologous recombination in *E. coli* BJ5183 cells using a plasmid shuttle. In detail, BJ5183 cells were co-transformed with purified viral DNA and Subgroup C Plasmid Shuttle (SEQ ID NO: 38). As shown in the diagram of FIG. 3, the Subgroup C Plasmid Shuttle is a plasmid vector dedicated to the cloning of ChAd belonging to species C and therefore contains the DNA fragments derived from right and left ends (including right and left ITRs) of species C ChAd viruses.

Homologous recombination between right and left ITR DNA sequences present at the ends of linearized Subgroup C Plasmid Shuttle (digested with PshAI/NdeI/XbaI) and viral genomic DNAs allowed its insertion in the plasmid vector. 30 different clones were amplified and analysed by Restriction analysis and 9 different species were identified. 19/30 clones showed the same restriction patterns and represented the predominant species; one of these clones was selected and identified as pChAd157ΔE1 TetO hCMV RpsL-Kana #1551 (SEQ ID NO: 15).

1.3: Construction of ChAd157 ΔE1/TetO hCMV GAG #1557

The GAG cassette (GAG polynucleotide sequence SEQ ID NO: 16) was cloned into a linearised pre-adeno acceptor vector via homologous recombination in *E. coli* by exploiting the homology existing between HCMV promoter and BGH polyA sequences (SEQ ID NO: 39).

The plasmid pARS CV32TetOhCMV GAG was cleaved with SpeI and SphI to excise the 2.44 Kb fragment containing HCMV promoter with tetO, HIV-GAG and BGH polyA sequence.

The HIV-GAG 2.44 Kb fragment was cloned by homologous recombination into pChAd157 ΔE1/TetO hCMV RpsL-Kana (#1551) acceptor vector (SnabI digested) carrying the RpsL-Kana selection cassette under control of HCMV and BGHpA. The resulting construct was pChAd157 ΔE1/TetO hCMV GAG #1557 vector (SEQ ID NO: 17).

Figure 4:
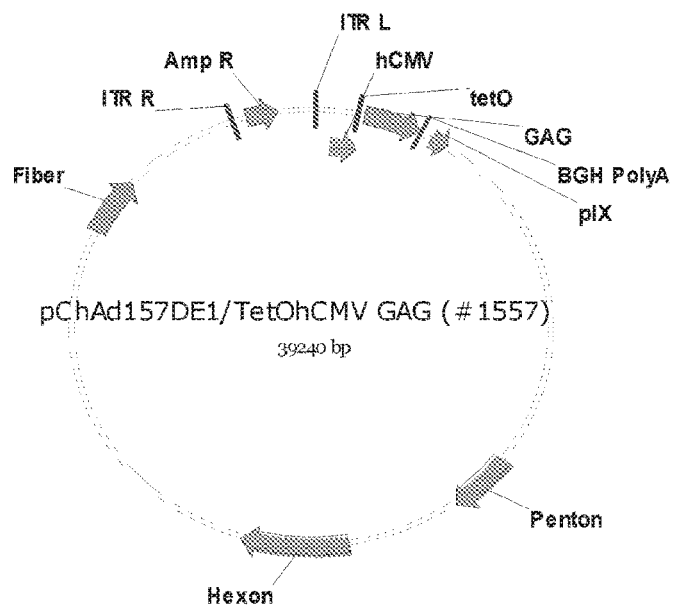
Figure 5:
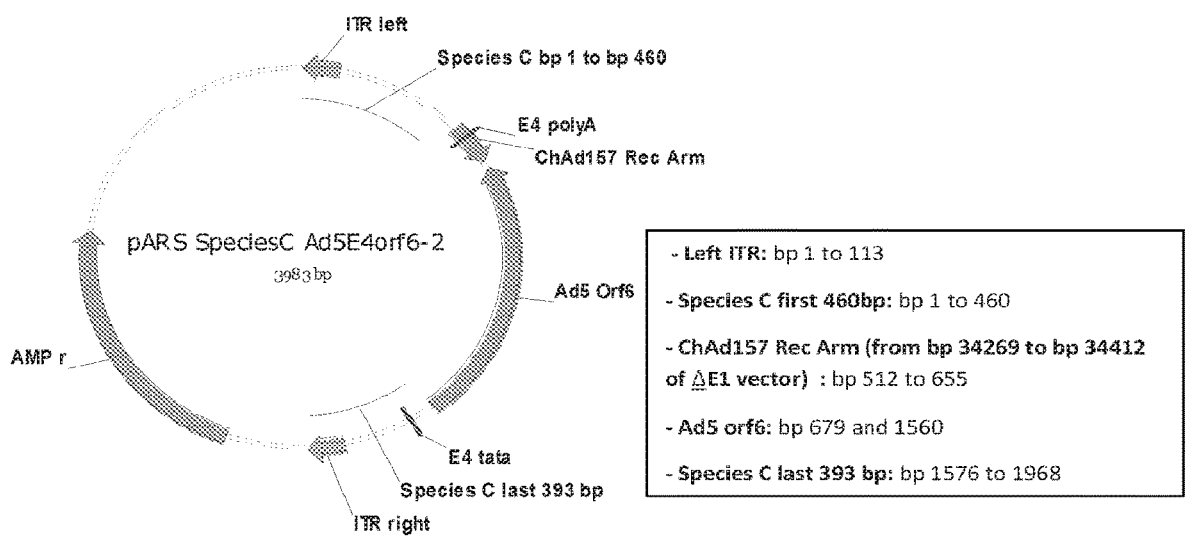

The structure of the plasmid carrying the ChAd157 GAG is reported in FIG. 4.

1.4: Construction of ChAd157 ΔE1E4 Ad5E4orf6/TetO hCMV RpsL-Kana #1594.

ChAd157ΔE1 vector was subsequently modified to carry the following modifications in the backbone:
  a) deletion of the E4 region (from bp 34413 to bp 37127) of the AEI virus;
  b) insertion of the E4orf6 derived from human Ad5.

A deletion of E4 region spanning from nucleotide 34413 to 37127 (ΔE1 vector sequence coordinates) was introduced in the vector backbone by replacing the native E4 region with Ad5 E4orf6 coding sequence by using a strategy involving several steps of cloning and homologous recombination in *E. coli*. E4 coding region was completely deleted while E4 native promoter and polyadenylation signal were conserved. To this end, a shuttle vector was constructed to allow the insertion of Ad5orf6 by replacing ChAd157 native E4 region by homologous recombination in *E. coli* BJ5183 as detailed below.

Construction of pARS SpeciesC Ad5E4orf6-1:
Ad5orf6 containing DNA fragment was obtained by PCR using Ad5 DNA as template, with the oligonucleotides: 5'-ATACGGACTAGTGGAGAAGTACTCGCCTACATG-3' (SEQ ID NO: 18) and 5'-ATACGGAAGATCTAA-GACTTCAGGAAATATGACTAC-3' (SEQ ID NO: 19). The PCR fragment was digested with BglII and SpeI and cloned into pARS Species C RLD-EGFP shuttle digested with BglII and SpeI, generating the plasmid pARS Species C Ad5orf6-1.

Construction of pARS SpeciesC Ad5E4orf6-2:
A 144 bp DNA fragment containing the Fiber-E4 polyA (from bp 34269 to bp 34412 of ChAd157ΔE1 vector) was amplified by PCR using as template the plasmid pChAd157 ΔE1/TetO hCMV RpsL-Kana (#1551) with the following oligonucleotides: 5'-ATTCAGTGTACAGGCGCGC-CAAAGCATGACACTGATGTTCATTTC-3' (SEQ ID NO: 20) and 5'-ACTAGGACTAGTTATAAGCTAGA ATGGGGCTTTGC-3' (SEQ ID NO: 21). The PCR fragment was digested with BsrGI and SpeI and cloned into pARS SubGroupC Ad5orf6-1 digested with BsrGI and SpeI, generating the plasmid pARS SpeciesC Ad5orf6-2 (SEQ ID NO: 40).

The resulting plasmid pARS SpeciesC Ad5orf6-2 was then used to replace the E4 with Ad5orf6 within ChAd157 backbone. To this end, the plasmid pChAd157ΔE1 TetO hCMV RpsL-Kana #1551 was digested with PacI and co-transformed into BJ5183 cells with the plasmid pARS SpeciesC Ad5orf6-2 BamHI/AscI digested, to obtain the pChAd157 ΔE1E4_Ad5E4orf6/TetO hCMV RpsL-Kana (#1594) preadeno plasmid (SEQ ID NO: 22).

1.5: Construction of ChAd157 ΔE1E4 Ad5E4orf6/TetO hCMV RG #1559.

The Rabies viral Glycoprotein (RG) expression cassette (Rabies Glycoprotein polynucleotide sequence SEQ ID NO: 23) was cloned into a linearised pre-adeno acceptor vector via homologous recombination in E. coli by exploiting the homology existing between HCMV promoter and BGH polyA sequences.

The plasmid pvjTetOhCMV-bghpolyA_RG was cleaved with SpeI and AsiSI to excise the 2.59 Kb fragment containing HCMV promoter with tetO, RG and BGHpolyA sequence.

The resulting RG 2.59 Kb fragment was cloned by homologous recombination into pChAd157 ΔE1E4_Ad5E4orf6/TetO hCMV RpsL-Kana (#1594) acceptor vector carrying the RpsL-Kana selection cassette under control of HCMV and BGHpA. The acceptor preAd plasmid was linearized with the restriction endonuclease SnaBI. The resulting construct was pChAd157 ΔE1E4_Ad5E4orf6/TetO hCMV RG #1559 vector (SEQ ID NO: 24).

Figure 6:
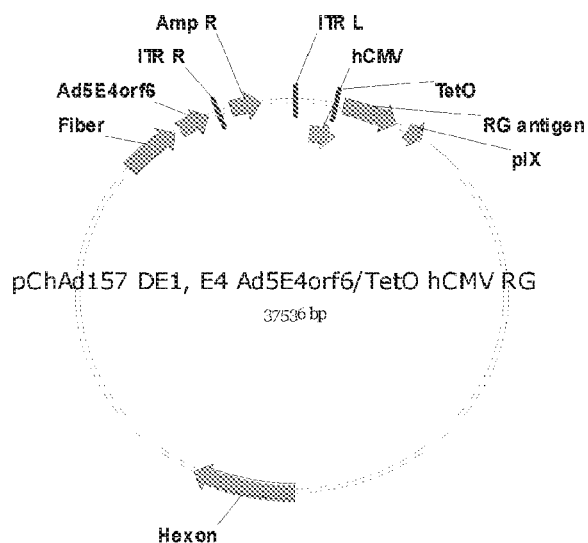

The structure of the plasmid carrying the ChAd157 RG is reported in FIG. 6.

Example 2: Vector Production

The productivity of ChAd157 was evaluated in comparison to ChAd19 and ChAd155 in the Procell 92 cell line.

2.1: Production of Vectors Comprising an HIV Gag Transgene

ChAd157/GAG, ChAd19/GAG, ChAd155/GAG (ChAd157, ChAd19 and ChAd155 vectors expressing an HIV Gag transgene) were rescued and amplified in Procell 92; the lysates were used to infect 1 T25 flask of Procell 92 cultivated in monolayer with each vector. A multiplicity of infection (MOI) of 300 vp/cell was used and the infections were performed in presence of tetracycline because ChAd19/GAG lacked the transcriptional control mediated by the insertion of the TetO operator in the hCMV promoter. The infected cells were harvested when full cytopathic effect was evident (48 hours post-infection for ChAd157/GAG and ChAd155/GAG and 5 days post-infections for ChAd19/GAG); the viruses were released from the infected cells by 3 cycles of freeze/thaw (−70° to 37° C.) then the lysate was clarified by centrifugation. The clarified lysates were quantified by Quantitative PCR Analysis with primers and probe complementary to the CMV promoter region. The oligonucleotide sequences are the following: CMVfor 5'-CATCTACGTATTAGTCATCGCTATTACCA-3' (SEQ ID NO: 25), CMVrev 5'-GACTTGGAAATCCCCGTGAGT-3' (SEQ ID NO: 26), CMVFAM-TAMRA probe 5'-ACATCAATGGGCGTGGATAGCGGTT-3' (SEQ ID NO: 41) (QPCRs were run on ABI Prism 7900 Sequence detector—Applied Biosystem).

The resulting volumetric titers (vp/ml) measured on clarified lysates and the specific productivity expressed in virus particles per cell (vp/cell) are provided in Table 1 below.

TABLE 1

| GAG vector productivity. | | | |
|---|---|---|---|
| Vector | Volumetric productivity (vp/ml) | Total vp | Cell specific productivity (vp/cell) |
| ChAd157/GAG | 4.61E+09 | 2.30E+10 | 7.68E+03 |
| ChAd155/GAG | 5.42E+09 | 2.71E+10 | 9.04E+03 |
| ChAd19/GAG | 4.80E+08 | 2.40E+09 | 8.00E+02 |

2.2: Production of Vectors Comprising an RG Transgene

A different set of experiments were performed to evaluate the productivity of RG vaccine vectors in Procell 92 cultivated in suspension. The experiment compared ChAd157/RG and ChAd155/RG in parallel by infecting Procell 92 at a cell density of $5 \times 10^5$ cells/ml. A multiplicity of infection (MOI) of 300 vp/cell was used. The infected cells were harvested 4 days post infection; the virus was released from the infected cells by 3 cycles of freeze/thaw and the lysate was clarified by centrifugation. The clarified lysates were then quantified by QPCR as reported above.

The volumetric productivity and the cell specific productivity are provided in Table 2 below.

TABLE 2

| RG vector productivity. | | | |
|---|---|---|---|
| Vector | Volumetric productivity (vp/ml) | Total vp | Cell specific productivity (vp/cell) |
| ChAd157/RG | 9.39E+09 | 4.69E+11 | 1.88E+04 |
| ChAd155/RG | 1.41E+10 | 7.04E+11 | 2.81E+04 |

Example 3: Transgene Expression Levels 3.1: Expression Level of HIV Gag Transgene Expression levels were compared in parallel experiments by infecting HeLa cells with ChAd19, ChAd155 and ChAd157 vectors comprising an HIV Gag transgene.

HeLa cells were seeded in 35 mm dishes and infected with ChAd19/GAG, ChAd157/GAG and ChAd155/GAG purified viruses using a MOI=250 vp/cell. The supernatants of infected HeLa cells were harvested 48 hours post-infection, and the production of secreted HIV GAG protein was quantified by using a commercial ELISA Kit (HIV-1 p24 ELISA Kit, PerkinElmer Life Science). The quantification was performed according to the manufacturer's instruction by using an HIV-1 p24 antigen standard curve.

Figure 7:
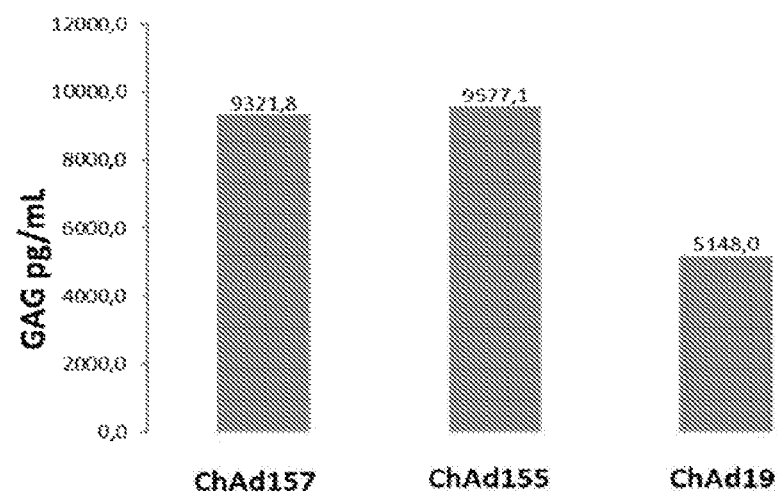

The results, expressed in pg/ml of GAG protein, are illustrated in FIG. 7.

3.2: Expression Level of RG Transgene

A western blot analysis was also performed to evaluate the rabies glycoprotein expression provided by the ChAd157/RG vector in comparison to ChAd155/RG vector. To this end, HeLa cells were seeded in 35 mm dishes and infected with ChAd157/RG and ChAd155/RG purified viruses using a MOI=250 vp/cell. Cell lysates were harvested 48 hours post-infection and the transgene expression level was evaluated by reducing SDS-PAGE followed by Western Blot analysis.

Figure 8:
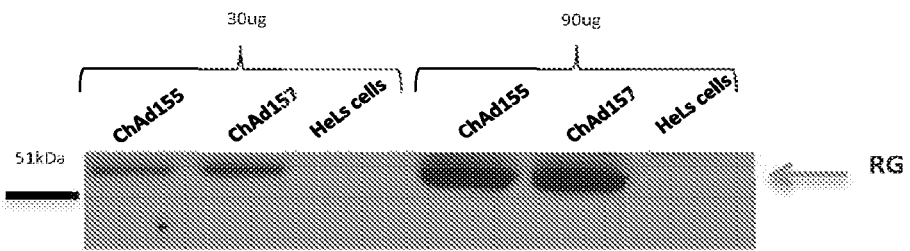

Equivalent quantities of proteins extracts were loaded on reducing SDS gel; after electrophoresis separation, the proteins were transferred to a nitrocellulose membrane to be probed with a Rabbit Polyclonal anti-GP (Cat. No. RBVGP11-S αDiagnostic, diluted 1:1000). After the incubation with primary antibody, the membrane was washed and then incubated with anti-rabbit horseradish peroxidase (HRP) conjugate secondary antibody. Finally the assay was developed by chemiluminescence using enhanced chemiluminescence (ECL) detection reagents (W3252282 PIERCE). The Western Blot results are shown in FIG. 8.

A band of about 57 kD indicated by the arrow was revealed by polyclonal antibody anti-GP, which corresponds to the expected weight of rabies glycoprotein.

The result demonstrated that the expression level of ChAd157 vector appears comparable to that provided by ChAd155.

Example 4: Evaluation of Immunological Potency by Mouse Immunization Experiments

4.1: Immunogenicity of Vectors Comprising the HIV Gaq Transgene

Figure 9:
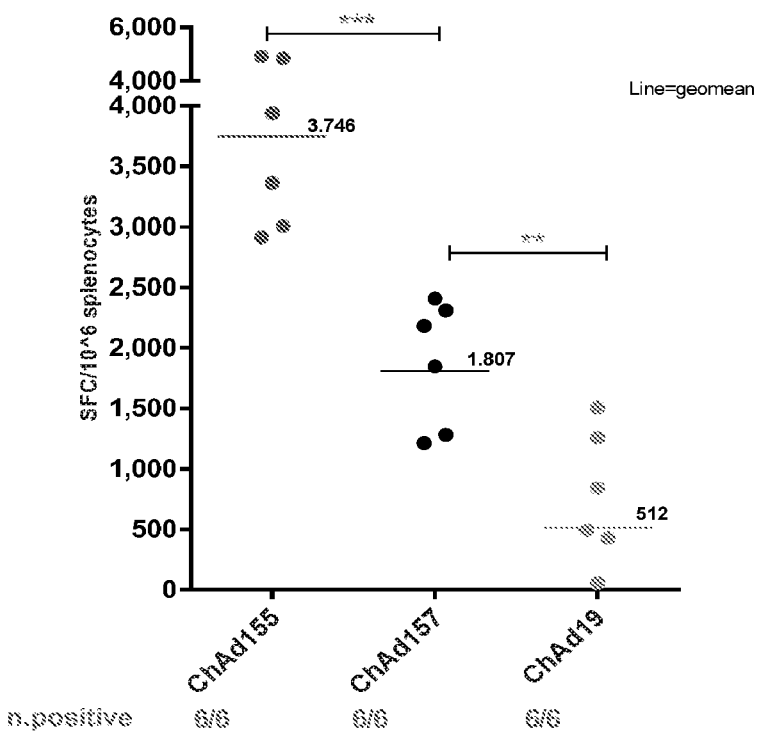

The immunogenicity ChAd157/GAG vector was evaluated in parallel with ChAd155/GAG and ChAd19/GAG in BALB/c mice (6 per group). The experiment was performed by injecting $10^7$ viral particles intramuscularly. T-cell response was measured 3 weeks after the immunization by ex vivo interferon-γ (IFN-γ) enzyme-linked immunospot (ELISpot) using a GAG CD8+ T cell epitope mapped in BALB/c mice. The results obtained are reported in FIG. 9, expressed as IFNs Spot Forming Cells (SFC) per million of splenocytes.

Each dot represents the response in a single mouse, and the line corresponds to the geomean for each dose group. Frequency of positive mice to the CD8 immunodominant peptide is shown on the x axis.

4.2 Immunogenicity of Vectors Comprising the RG Transgene

The immunological potency of ChAd157/RG and ChAd155/RG vectors was evaluated in BALB/c mice. Both vectors were injected intramuscularly with $10^7$ and $10^6$ vp doses. The splenocytes of immunized mice were isolated seven weeks after vaccination and analysed by IFNγ ELISpot (FIG. 10), using peptide pools from RG as antigen.

Figure 10:
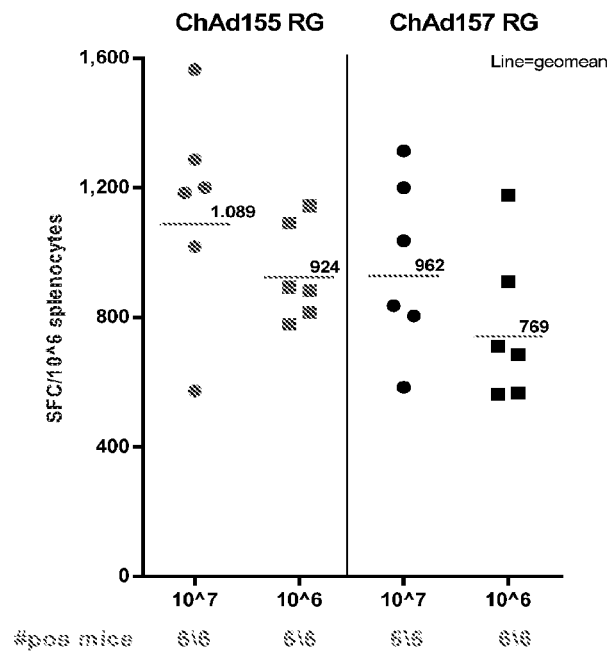

The levels of immune response were reduced in line with decreasing dosage, as expected. Moreover, ChAd155RG vector induced higher T cell response than ChAd157 RG, although they were not significantly different (FIG. 10).

Example 5: Evaluation of Infectivity

5.1 Infectivity of Vectors Comprising the HIV Gaq Transgene

The infectivity of purified viruses was evaluated in adherent Procell 92 cells utilizing an antibody against adenovirus hexon protein to visualize infected cells by immunocytochemistry staining. The antibody against hexon protein recognizes all serotypes of adenoviruses. To this end, Procell92 cells were seeded in 24 well plate at a cell density of $2\times10^5$ viable cell/ml and infected in duplicate with ChAd157/GAG and ChAd155/GAG and ChAd19/GAG vectors using a MOI=1 vp/cell, 0.5 vp/cell and 0.25 vp/cell. 48 hours post-infection, infected cells were fixed by cold methanol and then labelled with the anti-hexon antibody. Excess antibody is removed. The labelled cells are then incubated with a secondary antibody conjugated with horseradish peroxidase and the detection is performed by using a commercial kit VECTOR NOVARED Substrate Kit (SK-4800). Detection is accomplished when the horseradish peroxidase enzyme label reacts with the DAB substrate resulting in a dark brown product. The labelled, dark brown cells were then quantified by light microscopy and the infectious titer calculated. The results are shown in the table below

| Virus | Vp/ml | ifu/ml | R (vp/ifu) |
|---|---|---|---|
| ChAd155 GAG | 1.32E+11 | 1.58E+09 | 84 |
| ChAd157 GAG | 1.17E+11 | 1.23E+09 | 95 |
| ChAd19 GAG | 4.46E+10 | 3.86E+08 | 116 |

The result demonstrated that the infectivity of ChAd155 and ChAd157 viruses are comparable and higher than ChAd19.

5.2 Infectivity of Vectors Comprising the RG Transgene

The infectivity of ChAd157/RG and ChAd155/RG purified viruses was evaluated in adherent Procell 92 cells by Hexon Immunostaining as reported above. The results are shown in the table below

| Virus | Vp/ml | ifu/ml | R (vp/ifu) |
|---|---|---|---|
| ChAd155/RG | 4.23E+11 | 4.06E+09 | 104 |
| ChAd157/RG | 1.97E+11 | 1.46E+09 | 133 |

The result demonstrated that the infectivity of ChAd155 and ChAd157 viruses are comparable

Example 6: Evaluation of Cross-Neutralization Between ChAd155 and ChAd157 Vectors

6.1 Testing In Vivo if ChAd155 and ChAd157 Vectors are Different Serotypes

The cross-neutralization between ChAd155 and ChAd157 vectors was assessed in BALB/c mice (6 per group). Mice were preimmunized twice at week 0 and week 3 with $10^9$ vp of ChAd155 or ChAd157 expressing RG or were mock-vaccinated with saline buffer. Three weeks later, all mice were then immunized once with $10^9$ vp of ChAd157 encoding HIV gag

| Groups | n | Pre-immunization 2× w0 and w3 | dose (vp) | Immunization w6 | dose (vp) |
|---|---|---|---|---|---|
| 1 | 6 | PBS | — | ChAd157-GAG | $10^9$ |
| 2 | 6 | ChAd155-RG | $10^9$ | ChAd157-GAG | $10^9$ |
| 3 | 6 | ChAd157-RG | $10^9$ | ChAd157-GAG | $10^9$ |

Figure 11:
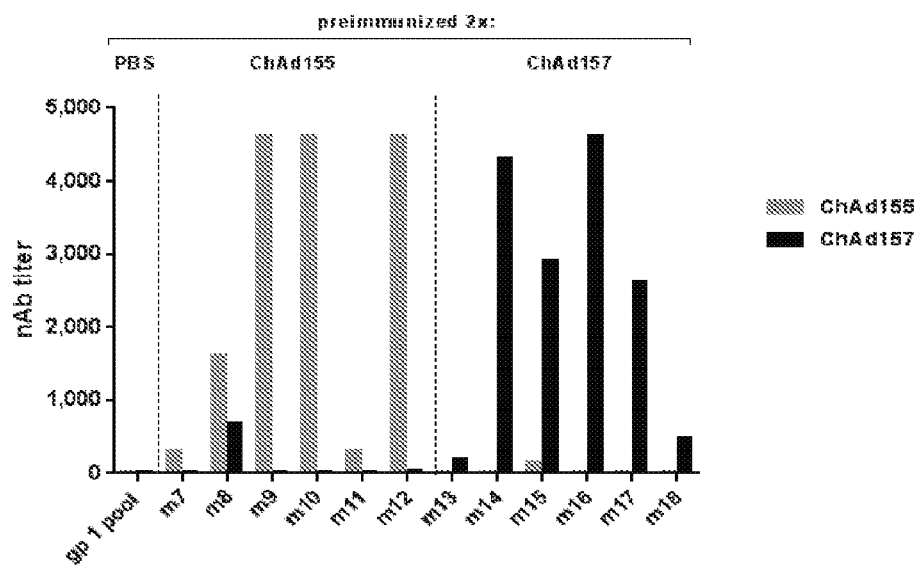
Figure 12:
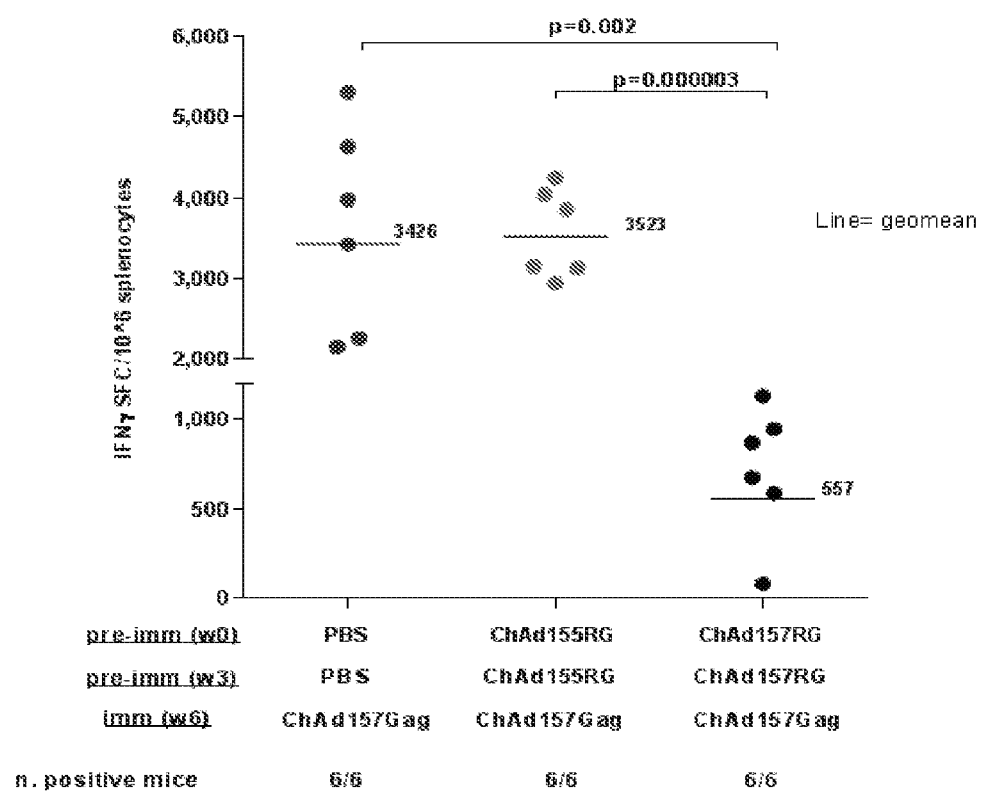

Neutralization titers to the preimmunizing vectors were measured in sera at week 5 (2 weeks post second injection) by in vitro neutralization assay (FIG. 11). Finally, T cell response against gag was tested on splenocytes 3 weeks after immunization by IFN-γ ELISpot, using a GAG CD8+ T cell epitope mapped in BALB/c mice (FIG. 12). The doses of vectors used for preimmunization were able to elicit good neutralizing activities against the two Ad vectors, although with some variability. Anti ChAd155 neutralizing antibodies do not cross-react against ChAd157 and vice-versa (FIG. 11). Moreover, ChAd157-Gag T-cell response was not affected by anti-ChAd155 preimmunity, confirming that cross-neutralization was not observed (FIG. 12).

Taken together, these data suggest that ChAd155 and ChAd157 viruses are distinct adenovirus serotypes.

The invention claimed is:

1. An isolated recombinant polynucleotide simian adenoviral vector, wherein the polynucleotide encodes a polypeptide selected from the group consisting of:
   (a) a polypeptide having the amino acid sequence according to SEQ ID NO: 1, and
   (b) a functional derivative of a polypeptide having the amino acid sequence according to SEQ ID NO: 1, wherein the functional derivative has an amino acid sequence which is at least 99.8% identical over its entire length to the amino acid sequence of SEQ ID NO: 1,
wherein the polynucleotide further encodes a heterologous polypeptide and polynucleotide encoding the heterologous polypeptide is operatively linked to one or more sequences which direct expression of the heterologous polypeptide.

2. A composition comprising the isolated recombinant polynucleotide simian adenoviral vector according to claim 1, and a pharmaceutically acceptable excipient.

3. A cell comprising the isolated recombinant polynucleotide simian adenoviral vector of claim 1.

4. The isolated recombinant polynucleotide simian adenoviral vector according to claim 1, wherein the polynucleotide has a sequence according to SEQ ID NO: 2.

5. The isolated recombinant polynucleotide simian adenoviral vector according to claim 1, further comprising a polynucleotide encoding:
   (a) a polypeptide having the amino acid sequence according to SEQ ID NO: 3; or
   (b) a functional derivative of a polypeptide having the amino acid sequence according to SEQ ID NO: 3, wherein the functional derivative has an amino acid sequence which is at least 60% identical over its entire length to the amino acid sequence of SEQ ID NO: 3.

6. The isolated recombinant polynucleotide simian adenoviral vector according to claim 1, wherein the polynucleotide comprises a sequence according to SEQ ID NO: 4.

7. The isolated recombinant polynucleotide simian adenoviral vector according to claim 1, further comprising a polynucleotide encoding:
   (a) a polypeptide having the amino acid sequence according to SEQ ID NO: 5; or
   (b) a functional derivative of a polypeptide having the amino acid sequence according to SEQ ID NO: 5, wherein the functional derivative has an amino acid sequence which is at least 60% identical over its entire length to the amino acid sequence of SEQ ID NO: 5.

8. The isolated recombinant polynucleotide simian adenoviral vector according to claim 1, wherein the polynucleotide comprises a sequence according to SEQ ID NO: 6.

9. The isolated recombinant polynucleotide simian adenoviral vector according to claim 1, wherein the polynucleotide comprises at least one of the following:

(a) an adenoviral 5' inverted terminal repeat;
(b) an adenoviral E1A region, or a fragment thereof selected from an E1A_280R region and an E1A_243R region;
(c) an adenoviral E1B or IX region, or a fragment thereof selected from an E1B_19K region, an E1B_55K region and an IX region;
(d) an adenoviral E2b region; or a fragment thereof selected from an E2B_pTP region, an E2B_Polymerase region and an E2B_IVa2 region;
(e) an adenoviral L1 region, or a fragment thereof, said fragment encoding an adenoviral protein selected from an L1_13.6k protein, an L1_52k protein and an L1_IIIa protein;
(f) an adenoviral L2 region, or a fragment thereof, said fragment encoding an adenoviral protein selected from an L2_penton protein, an L2_pVII, L2_V protein, and an L2_pX protein;
(g) an adenoviral L3 region, or a fragment thereof, said fragment encoding an adenoviral protein selected from an L3_pVI protein, an L3_hexon protein and an L3_protease;
(h) an adenoviral E2A region;
(i) an adenoviral L4 region, or a fragment thereof said fragment encoding an adenoviral protein selected from an L4_100k protein, an L4_33k protein and an protein L4_VIII protein;
(j) an adenoviral E3 region, or a fragment thereof selected from E3 ORF1, E3 ORF2, E3 ORF3, E3 ORF4, E3 ORF5, E3 ORF6, E3 ORF7, E3 ORF8, and E3 ORF9;
(k) an adenoviral L5 region, or a fragment thereof said fragment encoding an L5_fiber protein;
(l) an adenoviral E4 region, or a fragment thereof selected from E4 ORF7, E4 ORF6, E4 ORF4, E4 ORF3, E4 ORF2, and E4 ORF1;
(m) an adenoviral 3' inverted terminal repeat; and/or
(n) an adenoviral VAI or VAII RNA region from an adenovirus other than ChAd157.

10. The isolated recombinant polynucleotide simian adenoviral vector according to claim 1, wherein the polynucleotide comprises a polynucleotide which is at least 95% identical over its entire length to a reference sequence that consists essentially of SEQ ID NO: 15 or 22.

11. The isolated recombinant polynucleotide simian adenoviral vector according to claim 10, wherein the polynucleotide comprises or consists of a polynucleotide which is at least 99.5% identical over its entire length to the reference sequence.

12. The isolated recombinant polynucleotide simian adenoviral vector according to claim 11, wherein the polynucleotide comprises or consists of a polynucleotide which is identical over its entire length to the reference sequence.

13. The isolated recombinant polynucleotide simian adenoviral vector according to claim 1, wherein the adenoviral vector is replication competent.

14. The isolated recombinant polynucleotide simian adenoviral vector according to claim 1, wherein the adenoviral vector is replication incompetent.

15. The isolated recombinant polynucleotide simian adenoviral vector according to claim 14, wherein the adenoviral vector comprises a functional inactivation.

16. The isolated recombinant polynucleotide simian adenoviral vector according to claim 1, wherein the functional inactivation is a deletion.

17. The isolated recombinant polynucleotide simian adenoviral vector according to claim 1, wherein the functional inactivation comprises a mutation or deletion which renders non-functional at least one gene of a genomic region selected from the group consisting of E1A, E1B, E2A, E2B, E3 and E4.

18. The isolated recombinant polynucleotide simian adenoviral vector according to claim 1, wherein the heterologous polypeptide is an antigenic protein or a fragment thereof.

19. The isolated recombinant polynucleotide simian adenoviral vector of claim 1, wherein the one or more sequences which direct expression of the heterologous polypeptide is selected from one or more of the group consisting of transcription initiation, transcription termination, promoter and enhancer sequences.

20. The composition according to claim 2, further comprising an adjuvant.

21. The cell according to claim 3, wherein the cell is a host cell that expresses at least one adenoviral gene selected from the group consisting of E1A, E1B, E2A, E2B, E3 E4, L1, L2, L3, L4 and L5.

22. A method for eliciting an immune response in a subject comprising
(a) administering to the subject the recombinant adenoviral vector according to claim 1 encoding a first heterologous polypeptide; and
(b) administering to the subject a recombinant adenoviral vector which does not comprise a ChAd157 fiber, the vector encoding a second heterologous polypeptide,
wherein steps (a) and (b) may be undertaken in either order and the first and second heterologous polypeptides may be the same or different.

23. The method according to claim 22, wherein the subject has previously been exposed to a recombinant adenoviral vector which does not comprise a ChAd157 fiber, or functional derivative thereof.

24. The method according to claim 23, wherein the recombinant vector to which the subject has been previously exposed is a recombinant adenoviral vector comprising a ChAd155 fiber, hexon and/or penton.

* * * * *

SEQUENCE LISTING

<160> NUMBER OF SEQ ID NOS: 42

<210> SEQ ID NO 1

```
<211> LENGTH: 543
<212> TYPE: PRT
<213> ORGANISM: Pan troglodytes

<400> SEQUENCE: 1

Met Lys Arg Thr Lys Thr Ser Asp Glu Ser Phe Asn Pro Val Tyr Pro
1               5                   10                  15

Tyr Asp Thr Glu Ser Gly Pro Pro Ser Val Pro Phe Leu Thr Pro Pro
                20                  25                  30

Phe Val Ser Pro Asp Gly Phe Gln Glu Ser Pro Pro Gly Val Leu Ser
            35                  40                  45

Leu Asn Leu Ala Glu Pro Leu Val Thr Ser His Gly Met Leu Ala Leu
        50                  55                  60

Lys Met Gly Ser Gly Leu Ser Leu Asp Asp Ala Gly Asn Leu Thr Ser
65                  70                  75                  80

Gln Asp Ile Thr Thr Ala Ser Pro Pro Leu Lys Lys Thr Lys Thr Asn
                85                  90                  95

Leu Ser Leu Glu Thr Ser Ser Pro Leu Thr Val Ser Thr Ser Gly Ala
            100                 105                 110

Leu Thr Val Ala Ala Ala Ala Pro Leu Ala Val Ala Gly Thr Ser Leu
        115                 120                 125

Thr Met Gln Ser Glu Ala Pro Leu Thr Val Gln Asp Ala Lys Leu Thr
130                 135                 140

Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Thr Leu Thr Val
                165                 170                 175

Ser Ala Thr Pro Pro Ile Asn Val Ser Ser Gly Ser Leu Gly Leu Asp
            180                 185                 190

Met Glu Asp Pro Met Tyr Thr His Asn Gly Lys Leu Gly Ile Arg Ile
        195                 200                 205

Gly Gly Pro Leu Arg Val Val Asp Ser Leu His Thr Leu Thr Val Val
210                 215                 220

Thr Gly Asn Gly Leu Thr Val Asp Asn Asn Ala Leu Gln Thr Lys Val
225                 230                 235                 240

Thr Gly Ala Leu Gly Tyr Asp Thr Ser Gly Asn Leu Gln Leu Arg Ala
                245                 250                 255

Ala Gly Gly Met Arg Ile Asp Ala Asn Gly Gln Leu Ile Leu Asn Val
            260                 265                 270

Ala Tyr Pro Phe Asp Ala Gln Asn Asn Leu Ser Leu Arg Leu Gly Gln
        275                 280                 285

Gly Pro Leu Tyr Ile Asn Thr Asp His Asn Leu Asp Leu Asn Cys Asn
290                 295                 300

Arg Gly Leu Thr Thr Thr Thr Asn Asn Thr Lys Lys Leu Glu Thr
305                 310                 315                 320

Lys Ile Ser Ser Gly Leu Asp Tyr Asp Thr Asn Gly Ala Val Ile Ile
                325                 330                 335

Lys Leu Gly Thr Gly Leu Ser Phe Asp Asn Thr Gly Ala Leu Thr Val
            340                 345                 350

Gly Asn Thr Gly Asp Asp Lys Leu Thr Leu Trp Thr Thr Pro Asp Pro
        355                 360                 365

Ser Pro Asn Cys Arg Ile His Ser Asp Lys Asp Cys Lys Phe Thr Leu
370                 375                 380

Val Leu Thr Lys Cys Gly Ser Gln Ile Leu Ala Ser Val Ala Ala Leu
```

```
                385                390                395                400
Ala Val Ser Gly Asn Leu Ala Ser Ile Thr Gly Thr Val Ala Ser Val
                    405                410                415

Thr Ile Phe Leu Arg Phe Asp Gln Asn Gly Val Leu Met Glu Asn Ser
            420                425                430

Ser Leu Asp Arg Gln Tyr Trp Asn Phe Arg Asn Gly Asn Ser Thr Asn
        435                440                445

Ala Ala Pro Tyr Thr Asn Ala Val Gly Phe Met Pro Asn Leu Ala Ala
    450                455                460

Tyr Pro Lys Thr Gln Ser Gln Thr Ala Lys Asn Asn Ile Val Ser Gln
465                470                475                480

Val Tyr Leu Asn Gly Asp Lys Ser Lys Pro Met Thr Leu Thr Ile Thr
                485                490                495

Leu Asn Gly Thr Asn Glu Ser Ser Glu Thr Ser Gln Val Ser His Tyr
            500                505                510

Ser Met Ser Phe Thr Trp Ala Trp Glu Ser Gly Gln Tyr Ala Thr Glu
        515                520                525

Thr Phe Ala Thr Asn Ser Phe Thr Phe Ser Tyr Ile Ala Glu Gln
    530                535                540

<210> SEQ ID NO 2
<211> LENGTH: 1629
<212> TYPE: DNA
<213> ORGANISM: Pan troglodytes

<400> SEQUENCE: 2
atgaagcgca ccaaaacgtc tgacgagagc ttcaaccccg tgtacccta tgacacggaa      60 agcggccctc cctccgtccc tttcctcacc cctcccttcg tgtctcccga tggattccaa    120
gaaagtcccc ccggggtcct gtctctgaac ctggccgagc cctggtcac ttcccacggc     180 atgctcgccc tgaaaatggg aagtggcctc tccctggacg acgctggcaa cctcacctct    240
caagatatca ccaccgctag ccctcccctc aaaaaaacca agaccaacct cagcctagaa    300
acctcatccc ccctaactgt gagcacctca ggcgccctca ccgtagcagc cgccgctccc    360
ctggcggtgg ccggcacctc cctcaccatg caatcagagg ccccctgac agtacaggat    420 gcaaaactca ccctggccac caaaggcccc ctgaccgtgt ctgaaggcaa actggccttg    480
caaacatcgg ccccgctgac ggccgctgac agcagcaccc tcaccgttag cgccacacca    540
ccaattaatg taagcagtgg aagtttaggc ttagacatgg aagacctat gtatactcac    600 aatggaaaac tgggaataag aattgggggt ccactaagag tagtagacag cttgcataca    660
ctcactgtag ttaccggaaa tggactaact gtagataaca atgccctcca aactaaagtt    720
acgggcgccc taggttatga cacatcagga aatctacaat taagagctgc aggaggtatg    780
cgaattgacg caaatggcca acttatcctt aatgtggcat acccatttga tgctcagaac    840
aatctcagcc ttagacttgg tcagggaccc ctgtatataa acacagacca aacctggat    900 ttgaattgca acagaggtct aaccacaact accaccaaca acacaaaaaa acttgagact    960
aaaattagct caggcttaga ctatgacacc aatggtgctg tcattattaa acttggcact   1020
ggtctaagct tcgacaacac aggcgcccta actgtgggaa acactggtga tgataaactg   1080
actctgtgga cgaccccaga cccatctcca aattgcagaa ttcactcaga caaagactgc   1140
aagtttactc tagtcctaac taagtgtgga agccaaatcc tggcctctgt cgccgcccta   1200
gcggtatcag gaaatctggc ttcgataaca ggcaccgttg ccagcgttac catctttctc   1260
```

-continued

```
agatttgatc agaatggagt gcttatggaa aactcctcgc tagacaggca gtactggaac    1320
ttcagaaatg gcaactcaac taacgctgcc ccctacacca atgcagttgg gttcatgcca    1380
aacctcgcag catacCccaa aacgcaaagc cagactgcta aaacaacat tgtaagtcag     1440 gtttacttga atggagacaa atccaaaccc atgacccta ccatcaccct caatggaact    1500
aatgaatcca gtgaaactag ccaggtgagt cactactcca tgtcatttac atgggcttgg    1560
gaaagtgggc aatatgccac tgaaaccttt gccaccaact ccttcacctt ttcttacatt    1620
gctgaacaa                                                            1629
```

<210> SEQ ID NO 3
<211> LENGTH: 593
<212> TYPE: PRT
<213> ORGANISM: Pan troglodytes

<400> SEQUENCE: 3

```
Met Arg Arg Ala Ala Met Tyr Gln Glu Gly Pro Pro Ser Tyr Glu
1               5                  10                 15

Ser Val Val Gly Ala Ala Ala Ala Pro Ser Ser Pro Phe Ala Ser
                20                  25                 30

Gln Leu Leu Glu Pro Pro Tyr Val Pro Pro Arg Tyr Leu Arg Pro Thr
         35                  40                 45

Gly Gly Arg Asn Ser Ile Arg Tyr Ser Glu Leu Ala Pro Leu Phe Asp
     50                  55                 60

Thr Thr Arg Val Tyr Leu Val Asp Asn Lys Ser Ala Asp Val Ala Ser
65               70                  75                 80

Leu Asn Tyr Gln Asn Asp His Ser Asn Phe Leu Thr Thr Val Ile Gln
                85                  90                 95

Asn Asn Asp Tyr Ser Pro Ser Glu Ala Ser Thr Gln Thr Ile Asn Leu
            100                 105                110

Asp Asp Arg Ser His Trp Gly Gly Asp Leu Lys Thr Ile Leu His Thr
        115                 120                 125

Asn Met Pro Asn Val Asn Glu Phe Met Phe Thr Asn Lys Phe Lys Ala
    130                 135                 140

Arg Val Met Val Ser Arg Ser His Thr Lys Glu Asp Arg Val Glu Leu
145                 150                 155                 160

Lys Tyr Glu Trp Val Glu Phe Glu Leu Pro Glu Gly Asn Tyr Ser Glu
                165                 170                 175

Thr Met Thr Ile Asp Leu Met Asn Asn Ala Ile Val Glu His Tyr Leu
            180                 185                 190

Lys Val Gly Arg Gln Asn Gly Val Leu Glu Ser Asp Ile Gly Val Lys
        195                 200                 205

Phe Asp Thr Arg Asn Phe Arg Leu Gly Leu Asp Pro Val Thr Gly Leu
    210                 215                 220

Val Met Pro Gly Val Tyr Thr Asn Glu Ala Phe His Pro Asp Ile Ile
225                 230                 235                 240

Leu Leu Pro Gly Cys Gly Val Asp Phe Thr Tyr Ser Arg Leu Ser Asn
                245                 250                 255

Leu Leu Gly Ile Arg Lys Arg Gln Pro Phe Gln Glu Gly Phe Arg Ile
            260                 265                 270

Thr Tyr Glu Asp Leu Glu Gly Gly Asn Ile Pro Ala Leu Leu Asp Val
        275                 280                 285

Glu Ala Tyr Gln Asp Ser Leu Lys Glu Asn Glu Ala Gly Gln Glu Asp
    290                 295                 300
```

| | | | | | | | | | | | | |
|---|---|---|---|---|---|---|---|---|---|---|---|---|
|Thr|Ala|Pro|Ala|Ala|Ser|Ala|Ala|Glu|Gln|Gly|Glu|Asp|Ala|Ala|
|305| | | |310| | | |315| | | |320|

Thr Ala Pro Ala Ala Ser Ala Ala Glu Gln Gly Glu Asp Ala Ala
305                 310                 315                 320

Asp Thr Ala Ala Ala Asp Gly Ala Glu Ala Asp Pro Ala Met Val Val
            325                 330                 335

Glu Ala Ala Glu Gln Glu Glu Asp Met Asn Asp Ser Ala Val Arg Gly
            340                 345                 350

Asp Thr Phe Val Thr Arg Gly Glu Glu Lys Gln Ala Glu Ala Glu Ala
            355                 360                 365

Ala Ala Glu Glu Lys Gln Leu Ala Ala Ala Ala Ala Ala Leu
            370                 375                 380

Ala Ala Ala Glu Ala Glu Ser Glu Gly Thr Lys Pro Ala Lys Glu Pro
385                 390                 395                 400

Val Ile Lys Pro Leu Thr Glu Asp Ser Lys Lys Arg Ser Tyr Asn Leu
            405                 410                 415

Leu Lys Asp Ser Thr Asn Thr Ala Tyr Arg Ser Trp Tyr Leu Ala Tyr
            420                 425                 430

Asn Tyr Gly Asp Pro Ser Thr Gly Val Arg Ser Trp Thr Leu Leu Cys
            435                 440                 445

Thr Pro Asp Val Thr Cys Gly Ser Glu Gln Val Tyr Trp Ser Leu Pro
450                 455                 460

Asp Met Met Gln Asp Pro Val Thr Phe Arg Ser Thr Arg Gln Val Ser
465                 470                 475                 480

Asn Phe Pro Val Val Gly Ala Glu Leu Leu Pro Val His Ser Lys Ser
            485                 490                 495

Phe Tyr Asn Asp Gln Ala Val Tyr Ser Gln Leu Ile Arg Gln Phe Thr
            500                 505                 510

Ser Leu Thr His Val Phe Asn Arg Phe Pro Glu Asn Gln Ile Leu Ala
            515                 520                 525

Arg Pro Pro Ala Pro Thr Ile Thr Thr Val Ser Glu Asn Val Pro Ala
            530                 535                 540

Leu Thr Asp His Gly Thr Leu Pro Leu Arg Asn Ser Ile Gly Gly Val
545                 550                 555                 560

Gln Arg Val Thr Val Thr Asp Ala Arg Arg Thr Cys Pro Tyr Val
            565                 570                 575

Tyr Lys Ala Leu Gly Ile Val Ser Pro Arg Val Leu Ser Ser Arg Thr
            580                 585                 590

Phe

<210> SEQ ID NO 4
<211> LENGTH: 1779
<212> TYPE: DNA
<213> ORGANISM: Pan troglodytes

<400> SEQUENCE: 4

```
atgcggcgcg cggcgatgta ccaggaggga cctcctccct cttacgagag cgtggtgggc      60
gcggcggcgg cggcgccctc ttctcccttt gcgtcgcagc tgctggagcc gccgtacgtg     120
cctccgcgct acctgcggcc tacggggggg agaaacagca tccgttactc ggagctggcg     180
cccctgttcg acaccacccg ggtgtacctg gtggacaaca gtcggcgga cgtgccctcc     240 ctgaactacc agaacgacca cagcaatttt ttgaccacgg tcatccagaa caatgactac     300
agcccgagcg aggccagcac ccagaccatc aatctggatg accggtcgca ctggggcggc     360
gacctgaaaa ccatcctgca caccaacatg cccaacgtga cgagttcat gttcaccaat     420 aagttcaagg cgcgggtgat ggtgtcgcgc tcgcacacca aggaagaccg gtggagctg     480
```

```
aagtacgagt gggtggagtt cgagctgcca gagggcaact actccgagac catgaccatt    540
gacctgatga acaacgcgat cgtggagcac tatctgaaag tgggcaggca gaacggggtc    600
ctggagagcg catcggggt caagttcgac accaggaact ccgcctggg gctggacccc     660 gtgaccgggc tggttatgcc cggggtgtac accaacgagg ccttccatcc cgacatcatc    720
ctgctgcccg gctgcggggt ggacttcact tacagccgcc tgagcaacct cctgggcatc    780
cgcaagcggc agcccttcca ggagggcttc aggatcacct acgaggacct ggagggggc    840 aacatccccg cgctcctcga tgtggaggcc taccaggata gcttgaagga aaatgaggcg    900
ggacaggagg ataccgcccc cgccgcctcc gccgccgccg agcagggcga ggatgctgct    960
gacaccgcgg ccgcggacgg ggcggaggcc gaccccgcta tggtggtgga ggctgccgag   1020
caggaggagg acatgaatga cagtgcggtg cgcggagaca ccttcgtcac ccggggggag   1080
gaaaagcaag cggaggccga ggccgcggcc gaggaaaagc aactggcggc agcagcggcg   1140
gcggcggcgt tggccgcggc ggaggctgag tctgagggga ccaagcccgc caaggagccc   1200
gtgattaagc ccctgaccga agatagcaag aagcgcagtt acaacctgct caaggacagc   1260
accaacaccg cgtaccgcag ctggtacctg gcctacaact acggcgaccc gtcgacgggg   1320
gtgcgctcct ggaccctgct gtgcacgccg gacgtgacct gcggctcgga gcaggtgtac   1380
tggtcgctgc ccgacatgat gcaagacccc gtgaccttcc gctccacgcg gcaggtcagc   1440
aacttcccgg tggtgggcgc cgagctgctg cccgtgcact ccaagagctt ctacaacgac   1500
caggccgtct actcccagct catccgccag ttcacctctc tgacccacgt gttcaatcgc   1560
tttcctgaga accagattct ggcgcgcccg ccgcccccca ccatcaccac cgtcagtgaa   1620
aacgttcctg ctctcacaga tcacgggacg ctaccgctgc gcaacagcat cggaggagtc   1680
cagcgagtga ccgttactga cgccagacgc cgcacctgcc cctacgttta caaggccttg   1740
ggcatagtct cgccgcgcgt cctttccagc cgcactttt                         1779
```

<210> SEQ ID NO 5
<211> LENGTH: 958
<212> TYPE: PRT
<213> ORGANISM: Pan troglodytes

<400> SEQUENCE: 5

```
Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Ser Tyr Phe Ser Leu Ser Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ser Leu Ala Pro Lys Gly
        115                 120                 125

Ala Pro Asn Ser Cys Glu Trp Glu Gln Leu Glu Glu Ala Gln Ala Ala
    130                 135                 140
```

```
Val Glu Asp Glu Glu Leu Glu Asp Glu Asp Glu Pro Gln Asp Glu
145                 150                 155                 160

Ala Pro Val Lys Lys Thr His Val Tyr Ala Gln Ala Pro Leu Ser Gly
            165                 170                 175

Glu Glu Ile Thr Lys Asn Gly Leu Gln Ile Gly Ser Asp Asn Thr Glu
            180                 185                 190

Ala Gln Ser Lys Pro Ile Tyr Ala Asp Pro Thr Phe Gln Pro Glu Pro
            195                 200                 205

Gln Ile Gly Glu Ser Gln Trp Asn Glu Ala Asp Ala Thr Val Ala Gly
210                 215                 220

Gly Arg Val Leu Lys Lys Ser Thr Pro Met Lys Pro Cys Tyr Gly Ser
225                 230                 235                 240

Tyr Ala Arg Pro Thr Asn Ser Asn Gly Gly Gln Gly Val Leu Val Ala
            245                 250                 255

Asp Asp Lys Gly Val Leu Gln Ser Lys Val Glu Leu Gln Phe Phe Ser
            260                 265                 270

Asn Thr Thr Thr Leu Asn Gln Arg Glu Gly Asn Asp Thr Lys Pro Lys
            275                 280                 285

Val Val Leu Tyr Ser Glu Asp Val His Met Glu Thr Pro Asp Thr His
            290                 295                 300

Ile Ser Tyr Lys Pro Thr Lys Ser Asp Asp Asn Ser Lys Ile Met Leu
305                 310                 315                 320

Gly Gln Gln Ser Met Pro Asn Arg Pro Asn Tyr Ile Gly Phe Arg Asp
            325                 330                 335

Asn Phe Ile Gly Leu Met Tyr Tyr Asn Ser Thr Gly Asn Met Gly Val
            340                 345                 350

Leu Ala Gly Gln Ala Ser Gln Leu Asn Ala Val Val Asp Leu Gln Asp
            355                 360                 365

Arg Asn Thr Glu Leu Ser Tyr Gln Leu Leu Leu Asp Ser Met Gly Asp
            370                 375                 380

Arg Thr Arg Tyr Phe Ser Met Trp Asn Gln Ala Val Asp Ser Tyr Asp
385                 390                 395                 400

Pro Asp Val Arg Ile Ile Glu Asn His Gly Thr Glu Asp Glu Leu Pro
            405                 410                 415

Asn Tyr Cys Phe Pro Leu Gly Gly Ile Gly Val Thr Asp Thr Tyr Gln
            420                 425                 430

Ala Ile Lys Thr Asn Gly Asn Gly Gln Glu Asn Pro Thr Trp Glu Lys
            435                 440                 445

Asp Thr Glu Phe Ala Asp Arg Asn Glu Ile Gly Val Gly Asn Asn Phe
            450                 455                 460

Ala Met Glu Ile Asn Leu Ser Ala Asn Leu Trp Arg Asn Phe Leu Tyr
465                 470                 475                 480

Ser Asn Val Ala Leu Tyr Leu Pro Asp Lys Leu Lys Tyr Asn Pro Ser
            485                 490                 495

Asn Val Asp Ile Ser Asp Asn Pro Asn Thr Tyr Asp Tyr Met Asn Lys
            500                 505                 510

Arg Val Val Ala Pro Gly Leu Val Asp Cys Tyr Ile Asn Leu Gly Ala
            515                 520                 525

Arg Trp Ser Leu Asp Tyr Met Asp Asn Val Asn Pro Phe Asn His His
            530                 535                 540

Arg Asn Ala Gly Leu Arg Tyr Arg Ser Met Leu Leu Gly Asn Gly Arg
545                 550                 555                 560
```

-continued

Tyr Val Pro Phe His Ile Gln Val Pro Gln Lys Phe Ala Ile Lys
                565                 570                 575

Asn Leu Leu Leu Leu Pro Gly Ser Tyr Thr Tyr Glu Trp Asn Phe Arg
        580                 585                 590

Lys Asp Val Asn Met Val Leu Gln Ser Ser Leu Gly Asn Asp Leu Arg
            595                 600                 605

Val Asp Gly Ala Ser Ile Lys Phe Glu Ser Ile Cys Leu Tyr Ala Thr
610                 615                 620

Phe Phe Pro Met Ala His Asn Thr Ala Ser Thr Leu Glu Ala Met Leu
625                 630                 635                 640

Arg Asn Asp Thr Asn Asp Gln Ser Phe Asn Asp Tyr Leu Ser Ala Ala
                645                 650                 655

Asn Met Leu Tyr Pro Ile Pro Ala Asn Ala Thr Asn Val Pro Ile Ser
            660                 665                 670

Ile Pro Ser Arg Asn Trp Ala Ala Phe Arg Gly Trp Ala Phe Thr Arg
        675                 680                 685

Leu Lys Thr Lys Glu Thr Pro Ser Leu Gly Ser Gly Phe Asp Pro Tyr
    690                 695                 700

Tyr Thr Tyr Ser Gly Ser Ile Pro Tyr Leu Asp Gly Thr Phe Tyr Leu
705                 710                 715                 720

Asn His Thr Phe Lys Lys Val Ser Val Thr Phe Asp Ser Ser Val Ser
                725                 730                 735

Trp Pro Gly Asn Asp Arg Leu Leu Thr Pro Asn Glu Phe Glu Ile Lys
            740                 745                 750

Arg Ser Val Asp Gly Glu Gly Tyr Asn Val Ala Gln Cys Asn Met Thr
        755                 760                 765

Lys Asp Trp Phe Leu Val Gln Met Leu Ala Asn Tyr Asn Ile Gly Tyr
    770                 775                 780

Gln Gly Phe Tyr Ile Pro Glu Ser Tyr Lys Asp Arg Met Tyr Ser Phe
785                 790                 795                 800

Phe Arg Asn Phe Gln Pro Met Ser Arg Gln Val Val Asp Gln Thr Lys
                805                 810                 815

Tyr Lys Asp Tyr Gln Glu Val Gly Ile Ile His Gln His Asn Asn Ser
            820                 825                 830

Gly Phe Val Gly Tyr Leu Ala Pro Thr Met Arg Glu Gly Gln Ala Tyr
        835                 840                 845

Pro Ala Asn Phe Pro Tyr Pro Leu Ile Gly Lys Thr Ala Val Asp Ser
    850                 855                 860

Ile Thr Gln Lys Lys Phe Leu Cys Asp Arg Thr Leu Trp Arg Ile Pro
865                 870                 875                 880

Phe Ser Ser Asn Phe Met Ser Met Gly Ala Leu Ser Asp Leu Gly Gln
                885                 890                 895

Asn Leu Leu Tyr Ala Asn Ser Ala His Ala Leu Asp Met Thr Phe Glu
            900                 905                 910

Val Asp Pro Met Asp Glu Pro Thr Leu Leu Tyr Val Leu Phe Glu Val
        915                 920                 925

Phe Asp Val Val Arg Val His Gln Pro His Arg Gly Val Ile Glu Thr
    930                 935                 940

Val Tyr Leu Arg Thr Pro Phe Ser Ala Gly Asn Ala Thr Thr
945                 950                 955

<210> SEQ ID NO 6
<211> LENGTH: 2874
<212> TYPE: DNA

<213> ORGANISM: Pan troglodytes

<400> SEQUENCE: 6

```
atggcgaccc catcgatgat gccgcagtgg tcgtacatgc acatctcggg ccaggacgcc      60
tcggagtacc tgagcccggg gctggtgcag ttcgcccgcg ccaccgagag ctacttcagc     120
ctgagtaaca agtttaggaa ccccacggtg gcgcccacgc acgatgtgac caccgaccgg     180
tctcagcgcc tgacgctgcg gttcattccc gtggaccgcg aggacaccgc gtactcgtac     240
aaggcgcggt tcaccctggc cgtgggcgac aaccgcgtgc tggacatggc ctccacctac     300
tttgacatcc gcggggtgct ggaccggggc cccactttca agccttactc tggcaccgcc     360
tacaactccc tggcccccaa gggcgctccc aactcctgcg agtgggagca attagaagaa     420
gcccaggccg ctgtggaaga cgaagaatta gaagatgaag acgaggaacc acaggatgag     480
gcacctgtga aaaaacccca tgtatacgct caggctcccc tttctggaga agaaattact     540
aaaaacggtt tgcaaatagg gtcagataac acagaagccc agtctaagcc catatatgca     600
gatcctacat tccagcctga accccaaatc ggggaatccc agtggaatga ggcagatgct     660
acagttgccg gcggtagagt gctaaagaaa tccactccca tgaagccatg ctatggttcc     720
tatgcaagac ccacaaactc caatggaggt caaggtgtgc tggtggctga tgataagggg     780
gttcttcaat ctaaagttga attgcaattt ttttcaaata ctactactct taatcagcgg     840
gagggtaacg atacaaaacc aaaagtggtg ctgtatagcg aagatgtgca catggaaact     900
ccagacaccc acatttctta caagcccaca aaaagcgatg acaattcaaa aatcatgctg     960
ggtcagcagt ccatgcccaa cagacctaat tacatcggct tcagagacaa ctttatcggc    1020
ctcatgtatt acaatagcac tggcaacatg ggagtgcttg caggtcaggc ctctcagttg    1080
aatgcagtgg tggacttgca agacagaaac acagaactgt cctaccagct cttgcttgat    1140
tccatggggtg acagaaccag atacttttcc atgtggaatc aggcagtgga cagttatgac    1200
ccagatgtca gaattattga aaatcatgga actgaagacg agctccccaa ctattgtttc    1260
cctctgggcg gcataggggt aactgacact taccaggcca ttaaaaccaa tggcaatggt    1320
caagaaaacc caacctggga aaaagataca gagtttgcag accgcaatga aataggggtg    1380
ggaaacaatt tcgctatgga gatcaacctc agtgccaacc tgtggagaaa cttcctgtac    1440
tccaacgtgg cgctgtacct gccagacaag cttaagtaca ccccctccaa tgtggacatc    1500
tctgacaacc ccaacaccta cgattacatg aacaagcgag tggtggcccc ggggctggtg    1560
gactgctaca tcaacctggg cgcgcgctgg tcgctggact acatggacaa cgtcaacccc    1620
ttcaaccacc accgcaatgc gggcctgcgc taccgctcca tgctcctggg caacgggcgc    1680
tacgtgccct tccacatcca ggtgcccag aagttctttg ccatcaagaa cctcctcctc    1740
ctgccgggct cctacaccta cgagtggaac ttcaggaagg atgtcaacat ggtcctccag    1800
agctctctgg gtaacgatct cagggtggac ggggccagca tcaagttcga gagcatctgc    1860
ctctacgcca ccttcttccc catggcccac aacacggcct ccacgctcga ggccatgctc    1920
aggaacgaca ccaacgacca gtccttcaat gactacctct ccgccgccaa catgctctac    1980
cccataccccg ccaacgccac caacgtcccc atctccatcc cctcgcgcaa ctgggcggcc    2040
ttccgcggct gggccttcac ccgcctcaag accaaggaga cccctcccct gggctcggga    2100
ttcgaccccc actacaccta tcgggctcc attccctacc tggacggcac cttctacctc    2160
aaccacactt tcaagaaggt ctcggtcacc ttcgactcct cggtcagctg gccgggcaac    2220
gaccgtctgc tcaccccaa cgagttcgaa atcaagcgct cggtcgacgg ggagggctac    2280
```

-continued

```
aacgtggccc agtgcaacat gaccaaggac tggttcctgg tccagatgct ggccaactac    2340
aacatcggct accagggctt ctacatccca gagagctaca aggacaggat gtactccttc    2400
ttcaggaact tccagcccat gagccggcag gtggtggacc agaccaagta caaggactac    2460
caggaggtgg gcatcatcca ccagcacaac aactcgggct tcgtgggcta cctcgccccc    2520
accatgcgcg agggacaggc ctaccccgcc aacttcccct acccgctcat aggcaagacc    2580
gcggtcgaca gcatcaccca gaaaaagttc ctctgcgatc gcaccctctg gcgcatcccc    2640
ttctccagca acttcatgtc catgggtgcg ctctcggacc tgggccagaa cttgctctac    2700
gccaactccg cccacgccct cgacatgacc ttcgaggtcg accccatgga cgagcccacc    2760
cttctctatg ttctgttcga agtctttgac gtggtccggg tccaccagcc gcaccgcggc    2820
gtcatcgaga ccgtgtacct gcgtacgccc ttctcggccg gcaacgccac cacc          2874
```

<210> SEQ ID NO 7
<211> LENGTH: 578
<212> TYPE: PRT
<213> ORGANISM: Pan troglodytes

<400> SEQUENCE: 7

```
Met Lys Arg Thr Lys Thr Ser Asp Glu Ser Phe Asn Pro Val Tyr Pro
1               5                   10                  15

Tyr Asp Thr Glu Ser Gly Pro Pro Ser Val Pro Phe Leu Thr Pro Pro
            20                  25                  30

Phe Val Ser Pro Asp Gly Phe Gln Glu Ser Pro Pro Gly Val Leu Ser
        35                  40                  45

Leu Asn Leu Ala Glu Pro Leu Val Thr Ser His Gly Met Leu Ala Leu
    50                  55                  60

Lys Met Gly Ser Gly Leu Ser Leu Asp Asp Ala Gly Asn Leu Thr Ser
65                  70                  75                  80

Gln Asp Ile Thr Thr Ala Ser Pro Pro Leu Lys Lys Thr Lys Thr Asn
                85                  90                  95

Leu Ser Leu Glu Thr Ser Ser Pro Leu Thr Val Ser Thr Ser Gly Ala
            100                 105                 110

Leu Thr Val Ala Ala Ala Pro Leu Ala Val Ala Gly Thr Ser Leu
        115                 120                 125

Thr Met Gln Ser Glu Ala Pro Leu Thr Val Gln Asp Ala Lys Leu Thr
    130                 135                 140

Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Thr Leu Thr Val
                165                 170                 175

Ser Ala Thr Pro Pro Leu Ser Thr Ser Asn Gly Ser Leu Gly Ile Asp
            180                 185                 190

Met Gln Ala Pro Ile Tyr Thr Thr Asn Gly Lys Leu Gly Leu Asn Phe
        195                 200                 205

Gly Ala Pro Leu His Val Val Asp Ser Leu Asn Ala Leu Thr Val Val
    210                 215                 220

Thr Gly Gln Gly Leu Thr Ile Asn Gly Thr Ala Leu Gln Thr Arg Val
225                 230                 235                 240

Ser Gly Ala Leu Asn Tyr Asp Thr Ser Gly Asn Leu Glu Leu Arg Ala
                245                 250                 255

Ala Gly Gly Met Arg Val Asp Ala Asn Gly Gln Leu Ile Leu Asp Val
            260                 265                 270
```

Ala Tyr Pro Phe Asp Ala Gln Asn Asn Leu Ser Leu Arg Leu Gly Gln
        275                 280                 285

Gly Pro Leu Phe Val Asn Ser Ala His Asn Leu Asp Val Asn Tyr Asn
    290                 295                 300

Arg Gly Leu Tyr Leu Phe Thr Ser Gly Asn Thr Lys Lys Leu Glu Val
305                 310                 315                 320

Asn Ile Lys Thr Ala Lys Gly Leu Ile Tyr Asp Asp Thr Ala Ile Ala
                325                 330                 335

Ile Asn Ala Gly Asp Gly Leu Gln Phe Asp Ser Gly Ser Asp Thr Asn
                340                 345                 350

Pro Leu Lys Thr Lys Leu Gly Leu Gly Leu Asp Tyr Asp Ser Ser Arg
            355                 360                 365

Ala Ile Ala Lys Leu Gly Thr Gly Leu Ser Phe Asp Asn Thr Gly
370                 375                 380

Ala Ile Thr Val Gly Asn Lys Asn Asp Asp Lys Leu Thr Leu Trp Thr
385                 390                 395                 400

Thr Pro Asp Pro Ser Pro Asn Cys Arg Ile Tyr Ser Glu Lys Asp Ala
                405                 410                 415

Lys Phe Thr Leu Val Leu Thr Lys Cys Gly Ser Gln Val Leu Ala Ser
                420                 425                 430

Val Ser Val Leu Ser Val Lys Gly Ser Leu Ala Pro Ile Ser Gly Thr
            435                 440                 445

Val Thr Ser Ala Gln Ile Val Leu Arg Phe Asp Glu Asn Gly Val Leu
    450                 455                 460

Leu Ser Asn Ser Ser Leu Asp Pro Gln Tyr Trp Asn Tyr Arg Lys Gly
465                 470                 475                 480

Asp Leu Thr Glu Gly Thr Ala Tyr Thr Asn Ala Val Gly Phe Met Pro
                485                 490                 495

Asn Leu Thr Ala Tyr Pro Lys Thr Gln Ser Gln Thr Ala Lys Ser Asn
            500                 505                 510

Ile Val Ser Gln Val Tyr Leu Asn Gly Asp Lys Ser Lys Pro Met Thr
        515                 520                 525

Leu Thr Ile Thr Leu Asn Gly Thr Asn Glu Thr Gly Asp Ala Thr Val
    530                 535                 540

Ser Thr Tyr Ser Met Ser Phe Ser Trp Asn Trp Asn Gly Ser Asn Tyr
545                 550                 555                 560

Ile Asn Glu Thr Phe Gln Thr Asn Ser Phe Thr Phe Ser Tyr Ile Ala
                565                 570                 575

Gln Glu

<210> SEQ ID NO 8
<211> LENGTH: 1734
<212> TYPE: DNA
<213> ORGANISM: Pan troglodytes

<400> SEQUENCE: 8
atgaagcgca ccaaaacgtc tgacgagagc ttcaaccccg tgtaccccta tgacacggaa      60
agcggccctc cctccgtccc tttcctcacc cctcccttcg tgtctcccga tggattccaa     120
gaaagtcccc ccggggtcct gtctctgaac ctggccgagc ccctggtcac ttcccacggc     180
atgctcgccc tgaaaatggg aagtggcctc tccctggacg acgctggcaa cctcacctct     240
caagatatca ccaccgctag ccctcccctc aaaaaaacca agaccaacct cagcctagaa     300
acctcatccc ccctaactgt gagcacctca ggcgccctca ccgtagcagc cgccgctccc     360

```
ctggcggtgg ccggcacctc cctcaccatg caatcagagg ccccctgac agtacaggat      420 gcaaaactca ccctggccac caaaggcccc ctgaccgtgt ctgaaggcaa actggccttg     480
caaacatcgg ccccgctgac ggccgctgac agcagcaccc tcacagtcag tgccacacca     540
ccccttagca caagcaatgg cagcttgggt attgacatgc aagcccccat ttacaccacc     600
aatggaaaac taggacttaa ctttggcgct ccctgcatg tggtagacag cctaaatgca      660
ctgactgtag ttactggcca aggtcttacg ataaacggaa cagccctaca aactagagtc     720
tcaggtgccc tcaactatga cacatcagga aacctagaat tgagagctgc agggggtatg    780
cgagttgatg caaatggtca acttatcctt gatgtagctt acccatttga tgcacaaaac    840
aatctcagcc ttaggcttgg acagggaccc ctgtttgtta actctgccca caacttggat     900
gttaactaca acagaggcct ctacctgttc acatctggaa ataccaaaaa gctagaagtt    960
aatatcaaaa cagccaaggg tctcatttat gatgacactg ctatagcaat caatgcgggt    1020
gatgggctac agtttgactc aggctcagat acaaatccat taaaaactaa acttggatta    1080
ggactggatt atgactccag cagagccata attgctaaac tgggaactgg cctaagcttt    1140
gacaacacag gtgccatcac agtaggcaac aaaaatgatg acaagcttac cttgtggacc    1200
acaccagacc catcccctaa ctgtagaatc tattcagaga agatgctaa attcacactt     1260 gttttgacta aatgcggcag tcaggtgttg ccagcgtttt ctgttttatc tgtaaaaggt    1320
agccttgcgc ccatcagtgg cacagtaact agtgctcaga ttgtcctcag atttgatgaa    1380
aatggagttc tactaagcaa ttcttcccct gaccctcaat actggaacta cagaaaaggt    1440
gaccttacag agggcactgc atataccaac gcagtgggat ttatgcccaa cctcacagca    1500
tacccaaaaa cacagagcca aactgctaaa gcaacattg taagtcaggt ttacttgaat     1560
ggggacaaat ccaaacccat gaccctcacc attaccctca atggaactaa tgaaacagga    1620
gatgccacag taagcactta ctccatgtca ttctcatgga actggaatgg aagtaattac    1680
attaatgaaa cgttccaaac caactccttc accttctcct acatcgccca agaa          1734
```

<210> SEQ ID NO 9
<211> LENGTH: 593
<212> TYPE: PRT
<213> ORGANISM: Pan troglodytes

<400> SEQUENCE: 9

Met Arg Arg Ala Ala Met Tyr Gln Glu Gly Pro Pro Ser Tyr Glu
1               5                   10                  15

Ser Val Val Gly Ala Ala Ala Ala Pro Ser Ser Pro Phe Ala Ser
                20                  25                  30

Gln Leu Leu Glu Pro Pro Tyr Val Pro Pro Arg Tyr Leu Arg Pro Thr
                35                  40                  45

Gly Gly Arg Asn Ser Ile Arg Tyr Ser Glu Leu Ala Pro Leu Phe Asp
        50                  55                  60

Thr Thr Arg Val Tyr Leu Val Asp Asn Lys Ser Ala Asp Val Ala Ser
65                  70                  75                  80

Leu Asn Tyr Gln Asn Asp His Ser Asn Phe Leu Thr Thr Val Ile Gln
                85                  90                  95

Asn Asn Asp Tyr Ser Pro Ser Glu Ala Ser Thr Gln Thr Ile Asn Leu
                100                 105                 110

Asp Asp Arg Ser His Trp Gly Gly Asp Leu Lys Thr Ile Leu His Thr
            115                 120                 125

```
Asn Met Pro Asn Val Asn Glu Phe Met Phe Thr Asn Lys Phe Lys Ala
    130                 135                 140
Arg Val Met Val Ser Arg Ser His Thr Lys Glu Asp Arg Val Glu Leu
145                 150                 155                 160
Lys Tyr Glu Trp Val Glu Phe Glu Leu Pro Glu Gly Asn Tyr Ser Glu
                165                 170                 175
Thr Met Thr Ile Asp Leu Met Asn Asn Ala Ile Val Glu His Tyr Leu
            180                 185                 190
Lys Val Gly Arg Gln Asn Gly Val Leu Glu Ser Asp Ile Gly Val Lys
                195                 200                 205
Phe Asp Thr Arg Asn Phe Arg Leu Gly Leu Asp Pro Val Thr Gly Leu
    210                 215                 220
Val Met Pro Gly Val Tyr Thr Asn Glu Ala Phe His Pro Asp Ile Ile
225                 230                 235                 240
Leu Leu Pro Gly Cys Gly Val Asp Phe Thr Tyr Ser Arg Leu Ser Asn
                245                 250                 255
Leu Leu Gly Ile Arg Lys Arg Gln Pro Phe Gln Glu Gly Phe Arg Ile
                260                 265                 270
Thr Tyr Glu Asp Leu Glu Gly Gly Asn Ile Pro Ala Leu Leu Asp Val
            275                 280                 285
Glu Ala Tyr Gln Asp Ser Leu Lys Glu Asn Glu Ala Gly Gln Glu Asp
    290                 295                 300
Thr Ala Pro Ala Ala Ser Ala Ala Glu Gln Gly Glu Asp Ala Ala
305                 310                 315                 320
Asp Thr Ala Ala Ala Asp Gly Ala Glu Ala Asp Pro Ala Met Val Val
                325                 330                 335
Glu Ala Pro Glu Gln Glu Glu Asp Met Asn Asp Ser Ala Val Arg Gly
            340                 345                 350
Asp Thr Phe Val Thr Arg Gly Glu Glu Lys Gln Ala Glu Ala Glu Ala
    355                 360                 365
Ala Ala Glu Glu Lys Gln Leu Ala Ala Ala Ala Ala Ala Ala Ala Leu
370                 375                 380
Ala Ala Ala Glu Ala Glu Ser Glu Gly Thr Lys Pro Ala Lys Glu Pro
385                 390                 395                 400
Val Ile Lys Pro Leu Thr Glu Asp Ser Lys Lys Arg Ser Tyr Asn Leu
                405                 410                 415
Leu Lys Asp Ser Thr Asn Thr Ala Tyr Arg Ser Trp Tyr Leu Ala Tyr
            420                 425                 430
Asn Tyr Gly Asp Pro Ser Thr Gly Val Arg Ser Trp Thr Leu Leu Cys
            435                 440                 445
Thr Pro Asp Val Thr Cys Gly Ser Glu Gln Val Tyr Trp Ser Leu Pro
    450                 455                 460
Asp Met Met Gln Asp Pro Val Thr Phe Arg Ser Thr Arg Gln Val Ser
465                 470                 475                 480
Asn Phe Pro Val Val Gly Ala Glu Leu Leu Pro Val His Ser Lys Ser
                485                 490                 495
Phe Tyr Asn Asp Gln Ala Val Tyr Ser Gln Leu Ile Arg Gln Phe Thr
            500                 505                 510
Ser Leu Thr His Val Phe Asn Arg Phe Pro Glu Asn Gln Ile Leu Ala
            515                 520                 525
Arg Pro Pro Ala Pro Thr Ile Thr Thr Val Ser Glu Asn Val Pro Ala
530                 535                 540
Leu Thr Asp His Gly Thr Leu Pro Leu Arg Asn Ser Ile Gly Gly Val
```

|     |     |     |     |     |     |     |     |     |     |
| --- | --- | --- | --- | --- | --- | --- | --- | --- | --- |
| 545 |     |     |     | 550 |     |     |     | 555 |     |     |     | 560 |

Gln Arg Val Thr Val Thr Asp Ala Arg Arg Thr Cys Pro Tyr Val
                        565                 570                 575

Tyr Lys Ala Leu Gly Ile Val Ser Pro Arg Val Leu Ser Ser Arg Thr
                580                 585                 590

Phe

<210> SEQ ID NO 10
<211> LENGTH: 1779
<212> TYPE: DNA
<213> ORGANISM: Pan troglodytes

<400> SEQUENCE: 10

| | | | | | |
|---|---|---|---|---|---|
| atgcggcgcg | cggcgatgta | ccaggaggga | cctcctccct | cttacgagag | cgtggtgggc | 60 |
| gcggcggcgg | cggcgccctc | ttctcccttt | gcgtcgcagc | tgctggagcc | gccgtacgtg | 120 |
| cctccgcgct | acctgcggcc | tacggggggg | agaaacagca | tccgttactc | ggagctggcg | 180 |
| cccctgttcg | acaccacccg | ggtgtacctg | gtggacaaca | agtcggcgga | cgtggcctcc | 240 |
| ctgaactacc | agaacgacca | cagcaatttt | ttgaccacgg | tcatccagaa | caatgactac | 300 |
| agcccgagcg | aggccagcac | ccagaccatc | aatctggatg | accggtcgca | ctggggcggc | 360 |
| gacctgaaaa | ccatcctgca | caccaacatg | cccaacgtga | acgagttcat | gttcaccaat | 420 |
| aagttcaagg | cgcgggtgat | ggtgtcgcgc | tcgcacacca | aggaagaccg | ggtggagctg | 480 |
| aagtacgagt | gggtggagtt | cgagctgcca | gagggcaact | actccgagac | catgaccatt | 540 |
| gacctgatga | caacgcgcat | cgtggagcac | tatctgaaag | tgggcaggca | gaacggggtc | 600 |
| ctggagagcg | acatcggggt | caagttcgac | accaggaact | tccgcctggg | gctggacccc | 660 |
| gtgaccgggc | tggttatgcc | cggggtgtac | accaacgagg | ccttccatcc | cgacatcatc | 720 |
| ctgctgcccg | gctgcggggt | ggacttcact | tacagccgcc | tgagcaacct | cctgggcatc | 780 |
| cgcaagcggc | agcccttcca | ggagggcttc | aggatcaccct | acgaggacct | ggaggggggc | 840 |
| aacatccccg | cgctcctcga | tgtggaggcc | taccaggata | gcttgaagga | aaatgaggcg | 900 |
| ggacaggagg | ataccgcccc | cgccgcctcc | gccgccgccg | agcagggcga | ggatgctgct | 960 |
| gacaccgcgg | ccgcggacgg | ggcagaggcc | gaccccgcta | tggtggtgga | ggctcccgag | 1020 |
| caggaggagg | acatgaatga | cagtgcggtg | cgcggagaca | ccttcgtcac | ccgggggggag | 1080 |
| gaaaagcaag | cggaggccga | ggccgcggcc | gaggaaaagc | aactggcggc | agcagcggcg | 1140 |
| gcggcggcgt | tggccgcggc | ggaggctgag | tctgagggga | ccaagcccgc | caaggagccc | 1200 |
| gtgattaagc | ccctgaccga | agatagcaag | aagcgcagtt | acaacctgct | caaggacagc | 1260 |
| accaacaccg | cgtaccgcag | ctggtacctg | gcctacaact | acggcgaccc | gtcgacgggg | 1320 |
| gtgcgctcct | ggaccctgct | gtgcacgccg | gacgtgacct | gcggctcgga | gcaggtgtac | 1380 |
| tggtcgctgc | ccgacatgat | gcaagacccc | gtgaccttcc | gctccacgcg | gcaggtcagc | 1440 |
| aacttcccgg | tggtgggcgc | cgagctgctg | cccgtgcact | ccaagagctt | ctacaacgac | 1500 |
| caggccgtct | actcccagct | catccgccag | ttcacctctc | tgacccacgt | gttcaatcgc | 1560 |
| tttcctgaga | accagattct | ggcgcgcccg | ccgcccccca | ccatcaccac | cgtcagtgaa | 1620 |
| aacgttcctg | ctctcacaga | tcacgggacg | ctaccgctgc | gcaacagcat | cggaggagtc | 1680 |
| cagcgagtga | ccgttactga | cgccagacgc | cgcacctgcc | cctacgttta | caaggccttg | 1740 |
| ggcatagtct | cgccgcgcgt | cctttccagc | cgcactttt  |            |            | 1779 |

-continued

```
<210> SEQ ID NO 11
<211> LENGTH: 960
<212> TYPE: PRT
<213> ORGANISM: Pan troglodytes

<400> SEQUENCE: 11
```

| | | | | | | | | | | | | | | | |
|---|---|---|---|---|---|---|---|---|---|---|---|---|---|---|---|
| Met | Ala | Thr | Pro | Ser | Met | Met | Pro | Gln | Trp | Ser | Tyr | Met | His | Ile | Ser |
| 1 | | | | 5 | | | | | 10 | | | | | 15 | |
| Gly | Gln | Asp | Ala | Ser | Glu | Tyr | Leu | Ser | Pro | Gly | Leu | Val | Gln | Phe | Ala |
| | | | 20 | | | | | 25 | | | | | 30 | | |
| Arg | Ala | Thr | Glu | Ser | Tyr | Phe | Ser | Leu | Ser | Asn | Lys | Phe | Arg | Asn | Pro |
| | | | 35 | | | | | 40 | | | | | 45 | | |
| Thr | Val | Ala | Pro | Thr | His | Asp | Val | Thr | Thr | Asp | Arg | Ser | Gln | Arg | Leu |
| | 50 | | | | | 55 | | | | | 60 | | | | |
| Thr | Leu | Arg | Phe | Ile | Pro | Val | Asp | Arg | Glu | Asp | Thr | Ala | Tyr | Ser | Tyr |
| 65 | | | | | 70 | | | | | 75 | | | | | 80 |
| Lys | Ala | Arg | Phe | Thr | Leu | Ala | Val | Gly | Asp | Asn | Arg | Val | Leu | Asp | Met |
| | | | | 85 | | | | | 90 | | | | | 95 | |
| Ala | Ser | Thr | Tyr | Phe | Asp | Ile | Arg | Gly | Val | Leu | Asp | Arg | Gly | Pro | Thr |
| | | | 100 | | | | | 105 | | | | | 110 | | |
| Phe | Lys | Pro | Tyr | Ser | Gly | Thr | Ala | Tyr | Asn | Ser | Leu | Ala | Pro | Lys | Gly |
| | | | 115 | | | | | 120 | | | | | 125 | | |
| Ala | Pro | Asn | Ser | Cys | Glu | Trp | Glu | Gln | Glu | Thr | Gln | Ala | Val | Glu |
| | 130 | | | | | 135 | | | | | 140 | | | | |
| Glu | Ala | Ala | Glu | Glu | Glu | Glu | Asp | Ala | Asp | Gly | Gln | Ala | Glu | Glu |
| 145 | | | | | 150 | | | | | 155 | | | | | 160 |
| Glu | Gln | Ala | Ala | Thr | Lys | Lys | Thr | His | Val | Tyr | Ala | Gln | Ala | Pro | Leu |
| | | | | 165 | | | | | 170 | | | | | 175 | |
| Ser | Gly | Glu | Lys | Ile | Ser | Lys | Asp | Gly | Leu | Gln | Ile | Gly | Thr | Asp | Ala |
| | | | 180 | | | | | 185 | | | | | 190 | | |
| Thr | Ala | Thr | Glu | Gln | Lys | Pro | Ile | Tyr | Ala | Asp | Pro | Thr | Phe | Gln | Pro |
| | | | 195 | | | | | 200 | | | | | 205 | | |
| Glu | Pro | Gln | Ile | Gly | Glu | Ser | Gln | Trp | Asn | Glu | Ala | Asp | Ala | Thr | Val |
| | 210 | | | | | 215 | | | | | 220 | | | | |
| Ala | Gly | Gly | Arg | Val | Leu | Lys | Lys | Ser | Thr | Pro | Met | Lys | Pro | Cys | Tyr |
| 225 | | | | | 230 | | | | | 235 | | | | | 240 |
| Gly | Ser | Tyr | Ala | Arg | Pro | Thr | Asn | Ala | Asn | Gly | Gly | Gln | Gly | Val | Leu |
| | | | | 245 | | | | | 250 | | | | | 255 | |
| Thr | Ala | Asn | Ala | Gln | Gly | Gln | Leu | Glu | Ser | Gln | Val | Glu | Met | Gln | Phe |
| | | | 260 | | | | | 265 | | | | | 270 | | |
| Phe | Ser | Thr | Ser | Glu | Asn | Ala | Arg | Asn | Glu | Ala | Asn | Asn | Ile | Gln | Pro |
| | | | 275 | | | | | 280 | | | | | 285 | | |
| Lys | Leu | Val | Leu | Tyr | Ser | Glu | Asp | Val | His | Met | Glu | Thr | Pro | Asp | Thr |
| | 290 | | | | | 295 | | | | | 300 | | | | |
| His | Leu | Ser | Tyr | Lys | Pro | Ala | Lys | Ser | Asp | Asp | Asn | Ser | Lys | Ile | Met |
| 305 | | | | | 310 | | | | | 315 | | | | | 320 |
| Leu | Gly | Gln | Gln | Ser | Met | Pro | Asn | Arg | Pro | Asn | Tyr | Ile | Gly | Phe | Arg |
| | | | | 325 | | | | | 330 | | | | | 335 | |
| Asp | Asn | Phe | Ile | Gly | Leu | Met | Tyr | Tyr | Asn | Ser | Thr | Gly | Asn | Met | Gly |
| | | | 340 | | | | | 345 | | | | | 350 | | |
| Val | Leu | Ala | Gly | Gln | Ala | Ser | Gln | Leu | Asn | Ala | Val | Val | Asp | Leu | Gln |
| | | | 355 | | | | | 360 | | | | | 365 | | |
| Asp | Arg | Asn | Thr | Glu | Leu | Ser | Tyr | Gln | Leu | Leu | Leu | Asp | Ser | Met | Gly |
| | 370 | | | | | 375 | | | | | 380 | | | | |

-continued

```
Asp Arg Thr Arg Tyr Phe Ser Met Trp Asn Gln Ala Val Asp Ser Tyr
385                 390                 395                 400

Asp Pro Asp Val Arg Ile Ile Glu Asn His Gly Thr Glu Asp Glu Leu
            405                 410                 415

Pro Asn Tyr Cys Phe Pro Leu Gly Gly Ile Gly Val Thr Asp Thr Tyr
            420                 425                 430

Gln Ala Val Lys Thr Asn Asn Gly Asn Asn Gly Gly Gln Val Thr Trp
            435                 440                 445

Thr Lys Asp Glu Thr Phe Ala Asp Arg Asn Glu Ile Gly Val Gly Asn
450                 455                 460

Asn Phe Ala Met Glu Ile Asn Leu Ser Ala Asn Leu Trp Arg Asn Phe
465                 470                 475                 480

Leu Tyr Ser Asn Val Ala Leu Tyr Leu Pro Asp Lys Leu Lys Tyr Asn
            485                 490                 495

Pro Ser Asn Val Asp Ile Ser Asp Asn Pro Asn Thr Tyr Asp Tyr Met
            500                 505                 510

Asn Lys Arg Val Val Ala Pro Gly Leu Val Asp Cys Tyr Ile Asn Leu
            515                 520                 525

Gly Ala Arg Trp Ser Leu Asp Tyr Met Asp Asn Val Asn Pro Phe Asn
530                 535                 540

His His Arg Asn Ala Gly Leu Arg Tyr Arg Ser Met Leu Leu Gly Asn
545                 550                 555                 560

Gly Arg Tyr Val Pro Phe His Ile Gln Val Pro Gln Lys Phe Phe Ala
            565                 570                 575

Ile Lys Asn Leu Leu Leu Leu Pro Gly Ser Tyr Thr Tyr Glu Trp Asn
            580                 585                 590

Phe Arg Lys Asp Val Asn Met Val Leu Gln Ser Ser Leu Gly Asn Asp
            595                 600                 605

Leu Arg Val Asp Gly Ala Ser Ile Lys Phe Glu Ser Ile Cys Leu Tyr
            610                 615                 620

Ala Thr Phe Phe Pro Met Ala His Asn Thr Ala Ser Thr Leu Glu Ala
625                 630                 635                 640

Met Leu Arg Asn Asp Thr Asn Asp Gln Ser Phe Asn Asp Tyr Leu Ser
            645                 650                 655

Ala Ala Asn Met Leu Tyr Pro Ile Pro Ala Asn Ala Thr Asn Val Pro
            660                 665                 670

Ile Ser Ile Pro Ser Arg Asn Trp Ala Ala Phe Arg Gly Trp Ala Phe
            675                 680                 685

Thr Arg Leu Lys Thr Lys Glu Thr Pro Ser Leu Gly Ser Gly Phe Asp
            690                 695                 700

Pro Tyr Tyr Thr Tyr Ser Gly Ser Ile Pro Tyr Leu Asp Gly Thr Phe
705                 710                 715                 720

Tyr Leu Asn His Thr Phe Lys Lys Val Ser Val Thr Phe Asp Ser Ser
                725                 730                 735

Val Ser Trp Pro Gly Asn Asp Arg Leu Leu Thr Pro Asn Glu Phe Glu
            740                 745                 750

Ile Lys Arg Ser Val Asp Gly Glu Gly Tyr Asn Val Ala Gln Cys Asn
            755                 760                 765

Met Thr Lys Asp Trp Phe Leu Val Gln Met Leu Ala Asn Tyr Asn Ile
            770                 775                 780

Gly Tyr Gln Gly Phe Tyr Ile Pro Glu Ser Tyr Lys Asp Arg Met Tyr
785                 790                 795                 800

Ser Phe Phe Arg Asn Phe Gln Pro Met Ser Arg Gln Val Val Asp Gln
```

```
            805                 810                 815
Thr Lys Tyr Lys Asp Tyr Gln Glu Val Gly Ile Ile His Gln His Asn
            820                 825                 830

Asn Ser Gly Phe Val Gly Tyr Leu Ala Pro Thr Met Arg Glu Gly Gln
            835                 840                 845

Ala Tyr Pro Ala Asn Phe Pro Tyr Pro Leu Ile Gly Lys Thr Ala Val
        850                 855                 860

Asp Ser Ile Thr Gln Lys Lys Phe Leu Cys Asp Arg Thr Leu Trp Arg
865                 870                 875                 880

Ile Pro Phe Ser Ser Asn Phe Met Ser Met Gly Ala Leu Ser Asp Leu
                885                 890                 895

Gly Gln Asn Leu Leu Tyr Ala Asn Ser Ala His Ala Leu Asp Met Thr
            900                 905                 910

Phe Glu Val Asp Pro Met Asp Glu Pro Thr Leu Leu Tyr Val Leu Phe
            915                 920                 925

Glu Val Phe Asp Val Val Arg Val His Gln Pro His Arg Gly Val Ile
            930                 935                 940

Glu Thr Val Tyr Leu Arg Thr Pro Phe Ser Ala Gly Asn Ala Thr Thr
945                 950                 955                 960

<210> SEQ ID NO 12
<211> LENGTH: 2880
<212> TYPE: DNA
<213> ORGANISM: Pan troglodytes

<400> SEQUENCE: 12
atggcgaccc catcgatgat gccgcagtgg tcgtacatgc acatctcggg ccaggacgcc      60
tcggagtacc tgagccccgg gctggtgcag ttcgcccgcg ccaccgagag ctacttcagc     120
ctgagtaaca agtttaggaa ccccacggtg gcgcccacgc acgatgtgac caccgaccgg     180
tctcagcgcc tgacgctgcg gttcattccc gtggaccgcg aggacaccgc gtactcgtac     240
aaggcgcggt tcaccctggc cgtgggcgac aaccgcgtgc tggacatggc ctccacctac     300
tttgacatcc gcggggtgct ggaccggggt cccacttttca gccctactc tggcaccgcc     360 tacaactccc tggcccccaa gggcgctccc aactcctgcg agtgggagca agaggaaact     420
caggcagttg aagaagcagc agaagaggaa gaagaagatg ctgacggtca agctgaggaa     480
gagcaagcag ctaccaaaaa gactcatgta tatgctcagg ctcccctttc tggcgaaaaa     540
attagtaaag atggtctgca aataggaacg gacgctacag ctacagaaca aaaacctatt     600
tatgcagacc tacattcca gcccgaaccc caaatcgggg agtcccagtg gaatgaggca     660
gatgctacag tcgccggcgg tagagtgcta agaaatctac tcccatgaa accatgctat     720 ggttcctatg caagacccac aaatgctaat ggaggtcagg gtgtactaac ggcaaatgcc     780
cagggacagc tagaatctca ggttgaaatg caattctttt caacttctga aaacgcccgt     840
aacgaggcta acaacattca gcccaaattg gtgctgtata gtgaggatgt gcacatggag     900
accccggata cgcacctttc ttacaagccc gcaaaaagcg atgacaattc aaaaatcatg     960
ctgggtcagc agtccatgcc aacagacct aattacatcg gcttcagaga caactttatc    1020
ggcctcatgt attacaatag cactggcaac atggagtgc ttgcaggtca ggcctctcag    1080
ttgaatgcag tggtggactt gcaagacaga aacacagaac tgtcctacca gctcttgctt    1140
gattccatgg gtgacagaac cagatacttt tccatgtgga atcaggcagt ggacagttat    1200
gacccagatg ttagaattat tgaaaatcat ggaactgaag acgagctccc caactattgt    1260
```

```
ttccctctgg gtggcatagg ggtaactgac acttaccagg ctgttaaaac caacaatggc    1320
aataacgggg gccaggtgac ttggacaaaa gatgaaactt ttgcagatcg caatgaaata    1380
ggggtgggaa acaatttcgc tatggagatc aacctcagtg ccaacctgtg agaaacttc     1440 ctgtactcca acgtggcgct gtacctacca gacaagctta agtacaaccc ctccaatgtg    1500
gacatctctg acaaccccaa cacctacgat tacatgaaca agcgagtggt ggccccgggg    1560
ctggtggact gctacatcaa cctgggcgcg cgctggtcgc tggactacat ggacaacgtc    1620
aaccccttca accaccaccg caatgcgggc ctgcgctacc gctccatgct cctgggcaac    1680
gggcgctacg tgcccttcca catccaggtg ccccagaagt tctttgccat caagaacctc    1740
ctcctcctgc cgggctccta cacctacgag tggaacttca ggaaggatgt caacatggtc    1800
ctccagagct ctctgggtaa cgatctcagg gtggacgggg ccagcatcaa gttcgagagc    1860
atctgcctct acgccacctt cttccccatg ccccacaaca cggcctccac gctcgaggcc    1920
atgctcagga acgacaccaa cgaccagtcc ttcaatgact acctctccgc cgccaacatg    1980
ctctacccca tacccgccaa cgccaccaac gtccccatct ccatcccctc gcgcaactgg    2040
gcggccttcc gcggctgggc cttcacccgc ctcaagacca aggagacccc ctccctgggc    2100
tcgggattcg accctacta cacctactcg ggctccattc cctacctgga cggcaccttc    2160
tacctcaacc acactttcaa gaaggtctcg gtcaccttcg actcctcggt cagctggccg    2220
ggcaacgacc gtctgctcac ccccaacgag ttcgagatca agcgctcggt cgacggggag    2280
ggctacaacg tggcccagtg caacatgacc aaggactggt tcctggtcca gatgctggcc    2340
aactacaaca tcggctacca gggcttctac atcccagaga gctacaagga caggatgtac    2400
tccttcttca ggaacttcca gcccatgagc cggcaggtgg tggaccagac caagtacaag    2460
gactaccagg aggtgggcat catccaccag cacaacaact cgggcttcgt gggctacctc    2520
gcccccacca tgcgcgaggg acaggcctac cccgccaact tcccctatcc gctcataggc    2580
aagaccgcgg tcgacagcat cacccagaaa aagttcctct gcgaccgcac cctctggcgc    2640
atccccttct ccagcaactt catgtccatg ggtgcgctct cggacctggg ccagaacttg    2700
ctctacgcca actccgccca cgccctcgac atgaccttcg aggtcgaccc catggacgag    2760 cccaccttc tctatgttct gttcgaagtc tttgacgtgg tccgggtcca ccagccgcac    2820
cgcggcgtca tcgagaccgt gtacctgcgt acgcccttct cggccggcaa cgccaccacc    2880
```

<210> SEQ ID NO 13
<211> LENGTH: 37830
<212> TYPE: DNA
<213> ORGANISM: Pan troglodytes

<400> SEQUENCE: 13

```
catcatcaat aatataccct atttggatt gaagccaata tgataatgag atgggcggcg      60
cggggcggga ggcgggtccg ggggcgggcc ggcgggcggg gcggtgtggc ggaagtggac     120
tttgtaagtg tggcggatgt gacttgctag tgccgggcgc ggtaaaagtg acgttttccg     180
tgcgcgacaa cgcccacggg aagtgacatt tttcccgcgg ttttaccgg atgttgtagt      240 gaatttgggc gtaaccaagt aagatttggc cattttcgcg ggaaaactga acgggggaag    300
tgaaatctga ttaatttcgc gttagtcata ccgcgtaata tttgtcgagg gccgagggac    360
tttggccgat tacgtggagg actcgcccag gtgttttttg aggtgaattt ccgcgttccg    420
ggtcaaagtc tccgttttat tattatagtc agctgacgcg gagtgtattt ataccctctg    480
atctcgtcaa gtggccactc ttgagtgcca gcgagtagag ttttctcctc tgccgctctc    540
```

```
cgctccgctc cgctcggctc tgacaccggg gaaaaaatga gacatttcac ctacgatggc    600
ggtgtgctca ccggccagct ggctgctgaa gtcctggaca ccctgatcga ggaggtattg    660
gccgataatt atcctccctc gactccttt  gagccaccta cacttcacga actctacgat    720
```
(line 720 as read: `gccgataatt atcctccctc gactccttt  gagccaccta cacttcacga actctacgat`)

Replacing with faithful rendering:

```
cgctccgctc cgctcggctc tgacaccggg gaaaaaatga gacatttcac ctacgatggc    600
ggtgtgctca ccggccagct ggctgctgaa gtcctggaca ccctgatcga ggaggtattg    660
gccgataatt atcctccctc gactcctttt gagccaccta cacttcacga actctacgat    720
ctggatgtgg tggggcccag cgatccgaac gagcaggcgg tttccagttt ttttccagag    780
tccatgttgt tggccagcca ggaggggtc gaacttgaga cccctcctcc gatcgtggat    840
tcccccgatc cgccgcagct gactaggcag cccgagcgct gtgcgggacc tgagactatg    900
ccccagctgc tacctgaggt gatcgatctc acctgtaatg agtctggttt tccacccagc    960
gaggatgagg acgaagaggg tgagcagttt gtgttagatt ctgtggaaca acccgggcga   1020
ggatgcaggt cttgtcaata tcaccggaaa acacaggag  actcccagat tatgtgttct   1080
ctgtgttata tgaagatgac ctgtatgttt atttacagta agtttatcat ctgtgggcag   1140
gtgggctata gtgtgggtgg tggtcttgg  ggggttttt  aatatatgtc aggggttatg   1200
ctgaagactt ttttattgtg attttttaaag gtccagtgtc tgagcccgag caagaacctg   1260
aaccggagcc tgagccttct cgccccagga gaaagcctgt aatcttaact agacccagcg   1320
caccggtagc gagaggcctc agcagcgcgg agaccaccga ctccggtgct tcctcatcac   1380
ccccggagat tcaccccctg gtgcccctgt gtcccgttaa gcccgttgcc gtgagagtca   1440
gtgggcggcg gtctgctgtg gagtgcattg aggacttgct ttttgattca caggaacctt   1500
tggacttgag cttgaaacgc cccaggcatt aaacctggtc acctggactg aatgagttga   1560
cgcctatgtt tgcttttgaa tgacttaatg tgtatagata taaagagtg  agataatgtt   1620
ttaattgcat ggtgtgttta acttgggcgg agtctgctgg gtatataagc ttccctgggc   1680
taaacttggt tacacttgac ctcatggagg cctgggagtg tttggagaac tttgccggag   1740
ttcgtgcctt gctggacgag agctctaaca atacctcttg gtggtggagg tatttgtggg   1800
gctctcccca gggcaagtta gtttgtagaa tcaaggagga ttacaagtgg gaatttgaag   1860
agcttttgaa atcctgtggt gagctattgg attctttgaa tctaggccac caggctctct   1920
tccaggagaa ggtcatcagg actttggatt ttttccacacc ggggcgcatt gcagccgcgg   1980
ttgcttttct agcttttttg aaggatagat ggagcgaaga gacccacttg agttcgggct   2040
acgtcctgga ttttctggcc atgcaactgt ggagagcatg gatcagacac aagaacaggc   2100
tgcaactgtt gtcttccgtc cgcccgttgc tgattccggc ggaggagcaa caggccgggt   2160
cagaggaccg ggcccgtcgg gatccggagg agagggcacc gaggccgggc gagaggagcg   2220
cgctgaacct gggaaccggg ctgagcggcc atccacatcg ggagtgaatg tcgggcaggt   2280
ggtggatctt tttccagaac tgcggcggat tttgactatt agggaggatg ggcaatttgt   2340
taagggtctt aagagggaga gggggcttc  tgagcataac gaggaggcca gtaatttagc   2400
ttttagcttg atgaccagac accgtccaga gtgcatcact tttcagcaga ttaaggacaa   2460
ttgtgccaat gagttggatc tgtttgggtca aagtatagc  atagagcagc tgaccactta   2520
ctggctgcag ccgggtgatg atctggagga agctattagg gtgtatgcta aggtggccct   2580
gcggcccgat tgcaagtaca agctcaaggg gctggtgaat atcaggaatt gttgctacat   2640
ttctggcaac ggggcggagg tggagataga gaccgaagac agggtggctt tcagatgcag   2700
catgatgaat atgtggccgg gggtgctggg catggacggg gtggtgatta tgaatgtgag   2760
gttcacgggg cccaactta  acggcacggt tttttgggg  acaccaacc  tggtcctgca   2820
cggggtgagc ttctatgggt ttaacaacac ctgtgtggag gcctggaccg atgtgaaggt   2880
```

```
ccgcggttgc gccttttatg gatgttggaa ggccatagtg agccgccta agagcaggag    2940 ttccattaag aaatgcttgt ttgagaggtg caccttgggg atcctggccg agggcaactg    3000
cagggtgcgc cacaatgtgg cctccgagtg cggttgcttc atgctagtca agagcgtggc    3060
ggtaatcaag cataatatgg tgtgcggcaa cagcgaggac aaggcctcac agatgctgac    3120
ctgcacggat ggcaactgcc acttgctgaa gaccatccat gtaaccagcc acagccggaa    3180
ggcctggccc gtgttcgagc acaacttgct gacccgctgc tccttgcatc tgggcaacag    3240 gcgggggggtg ttcctgccct atcaatgcaa ctttagtcac accaagatct tgctagagcc    3300
cgagagcatg tccaaggtga acttgaacgg ggtgtttgac atgaccatga agatctggaa    3360
ggtgctgagg tacgacgaga ccaggtcccg gtgcagaccc tgcgagtgcg ggggcaagca    3420
tatgaggaac cagcccgtga tgctggatgt gaccgaggag ctgaggacag accacttggt    3480
tctggcctgc accagggccg agtttggttc tagcgatgaa gacacagatt gaggtgggtg    3540
agtgggcgtg gcctggggtg gtcatgaaaa tatataagtt gggggtctta gggtctcttt    3600
atttgtgttg cagagaccgc cggagccatg agcgggagca gcagcagcag cagtagcagc    3660
agcgccttgg atggcagcat cgtgagccct tatttgacga cgcggatgcc ccactgggcc    3720
ggggtgcgtc agaatgtgat gggctccagc atcgacggcc gacccgtcct gcccgcaaat    3780
tccgccacgc tgacctatgc gaccgtcgcg gggacgccgt tggacgccac cgccgccgcc    3840
gccgccaccg cagccgcctc ggccgtgcgc agcctggcca cggactttgc attcctggga    3900
ccactggcga caggggctac ttctcgggcc gctgctgccg ccgttcgcga tgacaagctg    3960
accgccctgc tggcgcagtt ggatgcgctt actcgggaac tgggtgacct ttctcagcag    4020
gtcatggccc tgcgccagca ggtctcctcc ctgcaagctg gcgggaatgc ttctcccaca    4080
aatgccgttt aagataaata aaaccagact ctgtttggat taaagaaaag tagcaagtgc    4140
attgctctct ttatttcata attttccgcg cgcgataggc cctagaccag cgttctcggt    4200
cgttgagggt gcggtgtatc ttctccagga cgtggtagag gtggctctgg acgttgagat    4260
acatgggcat gagcccgtcc cggggggtgga ggtagcacca ctgcagagct tcatgctccg    4320
gggtggtgtt gtagatgatc cagtcgtagc aggagcgctg ggcatggtgc ctaaaaatgt    4380
ccttcagcag caggccgatg ccaggggga ggcccttggt gtaagtgttt acaaaacggt    4440
taagttggga agggtgcatt cgggggagaga tgatgtgcat cttggactgt attttttagat    4500 tggcgatgtt tccgcccaga tcccttctgg gattcatgtt gtgcaggacc accagtacag    4560
tgtatccggt gcacttgggg aatttgtcat gcagcttaga gggaaaagcg tggaagaact    4620
tggagacgcc tttgtggcct cccagatttt ccatgcattc gtccatgatg atggcaatgg    4680
gcccgcggga ggcagcttgg gcaaagatat ttctggggtc gctgacgtcg tagttgtgtt    4740
ccagggtgag gtcgtcatag gccatttta caaagcgcgg gcggagggtg cccgactggg    4800
ggatgatggt cccctctggc cctggggcgt agttgccctc gcagatctgc atttcccagg    4860
ccttaatctc ggagggggga atcatatcca cctgcgggc gatgaagaaa acggtttccg    4920
gagccgggga gattaactgg gatgagagca ggtttctaag cagctgtgat tttccacaac    4980
cggtgggccc ataaataaca cctataaccg gttgcagctg gtagtttaga gagctgcagc    5040
tgccgtcgtc ccggaggagg ggggccacct cgttgagcat gtccctgacg cgcatgttct    5100
ccccgaccag atccgccaga aggcgctcgc cgcccaggga cagcagctct tgcaaggaag    5160
caaagttttt cagcggcttg aggccgtccg ccgtgggcat gttttttcagg gtctggctca    5220 gcagctccag gcggtcccag agctcggtga cgtgctctac ggcatctcta tccagcatat    5280
```

```
ctcctcgttt cgcgggttgg ggcgactttc gctgtagggc accaagcggt ggtcgtccag   5340
cggggccaga gtcatgtcct tccatgggcg cagggtcctc gtcagggtgg tctgggtcac   5400
ggtgaagggg tgcgctccgg gctgagcgct tgccaaggtg cgcttgaggc tggttctgct   5460
ggtgctgaag cgctgccggt cttcgccctg cgcgtcggcc aggtagcatt tgaccatggt   5520
gtcatagtcc agcccctccg cggcgtgtcc cttggcgcgc agcttgccct tggaggtggc   5580
gccgcacgag gggcagagca ggctcttgag cgcgtagagc ttgggggcga ggaagaccga   5640
ttcgggggag taggcgtccg cgccgcagac cccgcacacg gtctcgcact ccaccagcca   5700
ggtgagctcg gggcgcgccg ggtcaaaaac caggtttccc ccatgctttt tgatgcgttt   5760
cttacctcgg gtctccatga ggtggtgtcc ccgctcggtg acgaagaggc tgtccgtgtc   5820
tccgtagacc gacttgaggg gtcttttctc caggggggtc cctcggtctt cctcgtagag   5880
gaactcggac cactctgaga cgaaggcccg cgtccaggcc aggacgaagg aggctatgtg   5940
ggaggggtag cggtcgttgt ccactagggg gtccaccttc tccaaggtgt gaagacacat   6000
gtcgccttcc tcggcgtcca ggaaggtgat tggcttgtag gtgtaggcca cgtgaccggg   6060
ggttcctgac gggggggtat aaaggggggt ggggcgcgc tcgtcgtcac tctcttccgc   6120
atcgctgtct gcgagggcca gctgctgggg tgagtattcc ctctcgaagg cgggcatgac   6180
ctccgcgctg aggttgtcag tttccaaaaa cgaggaggat tgatgttca cctgtcccga   6240 ggtgatacct ttgagggtac ccgcgtccat ctggtcagaa aacacgatct ttttattgtc   6300
cagcttggtg gcgaacgacc cgtagagggc gttggagagc agcttggcga tggagcgcag   6360
ggtctggttc ttgtccctgt cggcgcgctc cttggccgcg atgttgagct gcacgtactc   6420
gcgcgcgacg cagcgccact cggggaagac ggtggtgcgc tcgtcgggca ccaggcgcac   6480
gcgccagccg cggttgtgca gggtgaccag gtccacgctg gtggcgacct cgccgcgcag   6540
gcgctcgttg gtccagcaga gacggccgcc cttgcgcgag cagaaggggg gcaggggtc   6600 gagctgggtc tcgtccgggg ggtccgcgtc cacggtgaaa accccgggc gcaggcgcgc   6660 gtcgaagtag tctatcttgc aaccttgcat gtccagcgcc tgctgccagt cgcgggcggc   6720
gagcgcgcgc tcgtagggggt tgagcggcgg gccccaggggc atgggtggg tgagtgcgga   6780 ggcgtacatg ccgcagatgt catagacgta gaggggctcc cgcaggaccc cgatgtaggt   6840
ggggtagcag cggccgccgc ggatgctggc gcgcacgtag tcatacagct cgtgcgaggg   6900
ggcgaggagg tcggggccca ggttggtgcg ggcggggcgc tccgcgcgga agacgatctg   6960
cctgaagatg gcatgcgagt tggaagagat ggtggggcgc tggaagacgt tgaagctggc   7020
gtcctgcagg ccgacggcgt cgcgcacgaa ggaggcgtag gagtcgcgca gcttgtgtac   7080
cagctcggcc gtgacctgca cgtcgagcgc gcagtagtcg agggtctcgc ggatgatgtc   7140
atatttagcc tgccccttct ttttccacag ctcgcggttg aggacaaact cttcgcggtc   7200
tttccagtac tcttggatcg ggaaaccgtc cggttccgaa cggtaagagc ctagcatgta   7260
gaactggttg acggcctggt aggcgcagca gcccttctcc acggggaggg cgtaggcctg   7320
cgcggccttg cggagcgagg tgtgggtcag ggcgaaggtg tccctgacca tgactttgag   7380
gtactggtgc ttgaagtcgg agtcgtcgca gccgccccgc tcccagagcg agaagtcggt   7440
gcgcttcttg gagcggggt tgggcagagc gaaggtgaca tcgttgaaga ggattttgcc   7500
cgcgcggggc atgaagttgc gggtgatgcg gaagggcccc ggcacttcag agcggttgtt   7560
gatgacctgg gcggcgagca cgatctcgtc gaagccgttg atgttgtggc ccacgatgta   7620
```

```
gagttccagg aagcggggcc ggcccttttac ggtgggcagc ttctttagct cttcgtaggt    7680
gagctcctcg ggcgaggcga ggccgtgctc ggccagggcc cagtccgcga ggtgcgggtt    7740
gtctctgagg aaggacttcc agaggtcgcg ggccaggagg gtctgcaggc ggtctctgaa    7800
ggtcctgaac tggcggccca cggccatttt ttcgggggtg atgcagtaga aggtgagggg    7860
gtcttgctgc cagcggtccc agtcgagctg cagggcgagg tcgcgcgcgg cggtgaccag    7920
gcgctcgtcg cccccgaatt tcatgaccag catgaagggc acgagctgct ttccgaaggc    7980
ccccatccaa gtgtaggtct ctacatcgta ggtgacaaag aggcgctccg tgcgaggatg    8040
cgagccgatc gggaagaact ggatctcccg ccaccagttg gaggagtggc tgttgatgtg    8100
gtggaagtag aagtcccgtc gccgggccga acactcgtgc tggcttttgt aaaagcgagc    8160
gcagtactgg cagcgctgca cgggctgtac ctcatgcacg agatgcacct ttcgcccgcg    8220
cacgaggaag ccgaggggaa atctgagccc cccgcctggc tcgcggcatg gctggttctc    8280
ttctactttg gatgcgtgtc cgtctccgtc tggctcctcg aggggtgtta cggtggagcg    8340
gaccaccacg ccgcgcgagc cgcaggtcca gatatcggcg cgcggcggtc ggagtttgat    8400
gacgacatcg cgcagctggg agctgtccat ggtctggagc tcccgcggcg gcggcaggtc    8460
agccgggagt tcttgcaggt tcacctcgca gagtcgggcc agggcgcggg gcaggtctag    8520
gtggtacctg atctctaggg gcgtgttggt ggcggcgtcg atggcttgca ggagcccgca    8580
gccccggggg gcgacgacgg tgcccgcgcg ggtggtggtg gtggtggcgg tgcagctcag    8640
aagcggtgcc gcgggcgggc ccccggaggt aggggggggct ccggtcccgc gggcaggggc    8700
ggcagcggca cgtcggcgtg gagcgcgggc aggagttggt gctgtgcccg gaggttgctg    8760
gcgaaggcga cgacgcggcg gttgatctcc tggatctggc gcctctgcgt gaagacgacg    8820
ggcccggtga gcttgaacct gaaagagagt tcgacagaat caatctcggt gtcattgacc    8880
gcggcctggc gcaggatctc ctgcacgtct cccgagttgt cttggtaggc gatctcggcc    8940
atgaactgct cgatctcttc ctcctggagg tctccgcgtc cggcgcgttc cacggtggcc    9000
gccaggtcgt tggagatgcg ccccatgagc tgcgagaagg cgttgagtcc gccctcgttc    9060
cagactcggc tgtagaccac gccccccctgg tcatcgcggg cgcgcatgac cacctgcgcg    9120
aggttgagct ccacgtgccg cgcgaagacg gcgtagttgc gcagacgctg gaagaggtag    9180
ttgagggtgg tggcggtgtg ctcggccacg aagaagttca tgacccagcg gcgcaacgtg    9240
gattcgttga tgtcccccaa ggcctccagc cgttccatgg cctcgtagaa gtccacggcg    9300
aagttgaaaa actgggagtt gcgcgccgac acggtcaact cctcctccag aagacggatg    9360
agctcggcga cggtgtcgcg cacctcgcgc tcgaaggcta tggggatctc ttcctccgct    9420 agcatccacca cctcctcctc ttcctcctct tctggcactt ccatgatggc ttcctcctct    9480 tcgggggggtg gcggcggcgg cggtgggggga ggggcgctc tgcgccggcg gcggcgcacc    9540
gggaggcggt ccacgaagcg cgcgatcatc tccccgcggc ggcggcgcat ggtctcggtg    9600
acggcgcggc cgttctcccg ggggcgcagt tggaagacgc cgccggacat ctggtgctgg    9660
ggcgggtggc cgtgaggcag cgagacggcg ctgacgatgc atctcaacaa ttgctgcgta    9720
ggtacgccgc cgagggacct gagggagtcc atatccaccg gatccgaaaa cctttcgagg    9780
aaggcgtcta accagtcgca gtcgcaaggt aggctgagca ccgtggcggg cggcggggggg    9840 tgggggggagt gtctggcgga ggtgctgctg atgatgtaat tgaagtaggc ggacttgaca    9900
cggcggatgg tcgacaggag caccatgtcc ttggtccgg cctgctggat gcggaggcgg    9960
tcggctatgc cccaggcttc gttctggcat cggcgcaggt ccttgtagta gtcttgcatg    10020
```

```
agcctttcca ccggcacctc ttctccttcc tcttctgctt cttccatgtc tgcttcggcc    10080
ctggggcggc gccgcgcccc cctgcccccc atgcgcgtga ccccgaaccc cctgagcggt    10140
tggagcaggg ccaggtcggc gacgacgcgc tcggccagga tggcctgctg cacctgcgtg    10200
agggtggttt ggaagtcatc caagtccacg aagcggtggt aggcgcccgt gttgatggtg    10260
taggtgcagt tggccatgac ggaccagttg acggtctggt ggcccggttg cgacatctcg    10320
gtgtacctga gtcgcgagta ggcgcgggag tcgaagacga gtcgttgca agtccgcacc    10380 aggtactggt agcccaccag gaagtgcggc ggcggctggc ggtagagggg ccagcgcagg    10440
gtggcggggg ctccggggc caggtcttcc agcatgaggc ggtggtaggc gtagatgtac    10500
ctggacatcc aggtgatacc cgcggcggtg gtggaggcgc gcgggaagtc gcgcacccgg    10560
ttccagatgt tgcgcagggg cagaaagtgc tccatggtag gcgtgctctg tccagtcaga    10620
cgcgcgcagt cgttgatact ctagaccagg gaaaacgaaa gccggtcagc gggcactctt    10680
ccgtggtctg gtgaatagat cgcaagggta tcatggcgga gggcctcggt tcgagccccg    10740
ggtccgggcc ggacggtccg ccatgatcca cgcggttacc gcccgcgtgt cgaacccagg    10800
tgtgcgacgt cagacaacgg tggagtgttc cttttggcgt ttttctggcc gggcgccggc    10860
gccgcgtaag agactaagcc gcgaaagcga aagcagtaag tggctcgctc cccgtagccg    10920
gagggatcct tgctaagggt tgcgttgcgg cgaaccccgg ttcgaatccc gtactcgggc    10980
cggccggacc cgcggctaag gtgttggatt ggcctccccc tcgtataaag ccccgcttg    11040 cggattgact ccggacacgg ggacgagccc ctttttatttt tgctttcccc agatgcatcc    11100
ggtgctgcgg cagatgcgcc ccccgcccca gcagcagcaa caacaccagc aagagcggca    11160
gcaacagcag cgggagtcat gcagggcccc ctcacccacc ctcggcgggc cggccacctc    11220
ggcgtccgcg gccgtgtctg gcgcctgcgg cggcggcggg gggccggctg acgaccccga    11280
ggagcccccg cggcgcaggg ccagacacta cctggacctg gagaggggcg agggcctggc    11340
gcggctgggg gcgccgtctc ccgagcgcca cccgcgggtg cagctgaagc gcgactcgcg    11400
cgaggcgtac gtgcctcggc agaacctgtt cagggaccgc gcgggcgagg agcccgagga    11460
gatgcgggac aggaggttca gcgcaggggcg ggagctgcgg caggggctga accgcgagcg    11520
gctgctgcgc gaggaggact ttgagcccga cgcgcggacg gggatcagcc ccgcgcgcgc    11580
gcacgtggcg gccgccgacc tggtgacggc gtacgagcag acggtgaacc aggagatcaa    11640
cttccaaaag agtttcaaca accacgtgcg cacgctggtg gcgcgcgagg aggtgaccat    11700
cgggctgatg cacctgtggg actttgtaag cgcgctggtc cagaacccca acagcaagcc    11760
tctgacggcg cagctgttcc tgatagtgca gcacagcagg gacaacgagg cgtttaggga    11820
cgcgctgctg aacatcaccg agcccgaggg tcggtggctg ctggacctga ttaacatcct    11880
gcagagcata gtggtgcagg agcgcagcct gagcctggcc gacaaggtgg cggccatcaa    11940
ctactcgatg ctgagcctgg gcaagtttta cgcgcgcaag atctaccaga cgccgtacgt    12000
gcccatagac aaggaggtga agatcgacgg ttttttacatg cgcatggcgc tgaaggtgct    12060
caccctgagc gacgacctgg gcgtgtaccg caacgagcgc atccacaagg ccgtgagcgt    12120
gagccggcgc cgcgagctga cgcgaccgcga gctgatgcac agcctgcagc gggcgctggc    12180
gggcgccggc agcggcgaca gggaggcgga gtcctacttc gatgcggggg cggacctgcg    12240
ctgggcgccc agccggcggg ccctggaggc gcgcggggtc cgcgaggact atgacgagga    12300
cggcgaggag gatgaggagt acgagctaga ggagggcgag tacctggact aaaccgcggg    12360
```

| | |
|---|---|
| tggtgtttcc ggtagatgca agacccgaac gtggtggacc cggcgctgcg ggcggctctg | 12420 |
| cagagccagc cgtccggcct taactcctca gacgactggc gacaggtcat ggaccgcatc | 12480 |
| atgtcgctga cggcgcgtaa cccggacgcg ttccggcagc agccgcaggc caacaggctc | 12540 |
| tccgccatcc tggaggcggt ggtgcctgcg cgctcgaacc ccacgcacga aaggtgctg | 12600 |
| gccatagtga acgcgctggc cgagaacagg gccatccgcc cggacgaggc cgggctggtg | 12660 |
| tacgacgcgc tgctgcagcg cgtggcccgc tacaacagcg gcaacgtgca gaccaacctg | 12720 |
| gaccggctgg tggggacgt gcgcgaggcg gtggcgcagc gcgagcgcgc ggatcggcag | 12780 |
| ggcaacctgg gctccatggt ggcgctgaat gccttcctga gcacgcagcc ggccaacgtg | 12840 |
| ccgcggggc aggaagacta caccaacttt gtgagcgcgc tgcggctgat ggtgaccgag | 12900 |
| acccccaga gcgaggtgta ccagtcgggc ccggactact tcttccagac cagcagacag | 12960 |
| ggcctgcaga cggtgaacct gagccaggct ttcaagaacc tgcgggggct gtggggcgtg | 13020 |
| aaggcgccca ccggcgaccg ggcgacggtg tccagcctgc tgacgcccaa ctcgcgcctg | 13080 |
| ctgctgctgc tgatcgcgcc gttcacggac agcggcagcg tgtcccggga cacctacctg | 13140 |
| gggcacctgc tgaccctgta ccgcgaggcc atcgggcagg cgcaggtgga cgagcacacc | 13200 |
| ttccaggaga tcaccagcgt gagccgcgcg ctggggcagg aggacacgag cagcctggag | 13260 |
| gcgactctga actacctgct gaccaaccgg cggcagaaga ttccctcgct gcacagcctg | 13320 |
| acctccgagg aggagcgcat cttgcgctac gtgcagcaga gcgtgagcct gaacctgatg | 13380 |
| cgcgacgggg tgacgcccag cgtggcgctg acatgaccg cgcgcaacat ggaaccgggc | 13440 |
| atgtacgccg cgcaccggcc ttacatcaac cgcctgatgg actacctgca tcgcgcggc | 13500 |
| gccgtgaacc ccgagtactt taccaacgcc atcctgaacc cgcactggct cccgccgccc | 13560 |
| ggggttctaca gcggggcctt cgaggtcccg gagaccaacg atggcttcct gtgggacgac | 13620 |
| atggacgaca gcgtgttctc cccgcggccg caggcgctgg cggaagcgtc cctgctgcgt | 13680 |
| cccaagaagg aggaggagga ggaggcgagt cgccgccgcg gcagcagcgg cgtggcttct | 13740 |
| ctgtccgagc tggggcggc agccgccgcg cgccccgggt ccctgggcgg cagcccctt | 13800 |
| ccgagcctgg tggggtctct gcacagcgag cgcaccaccc gccctcggct gctgggcgag | 13860 |
| gacgagtacc tgaataactc cctgctgcag ccggtgcggg agaaaaacct gcctcccgcc | 13920 |
| ttccccaaca acgggataga gagcctggtg gacaagatga gcagatggaa gacctatgcg | 13980 |
| caggagcaca gggacgcgcc tgcgctccgg ccgcccacgc ggcgccagcg ccacgaccgg | 14040 |
| cagcgggggc tggtgtggga tgacgaggac tccgcggacg atagcagcgt gctgacctg | 14100 |
| ggagggagcg gcaacccgtt cgcgcacctg cgccccgcc tggggaggat gttttaaaaa | 14160 |
| aaaaaaaaa aagcaagaag catgatgcaa aaattaaata aaactcacca aggccatggc | 14220 |
| gaccgagcgt tggtttcttg tgttcccttc agtatgcggc gcgcggcgat gtaccaggag | 14280 |
| ggacctcctc cctcttacga gagcgtggtg ggcgcggcgg cggcggcgcc ctcttctccc | 14340 |
| tttgcgtcgc agctgctgga ccgccgtac gtgcctccgc gctacctgcg gcctacgggg | 14400 |
| gggagaaaca gcatccgtta ctcggagctg gcgcccctgt tcgacaccac ccgggtgtac | 14460 |
| ctggtggaca caagtcggc ggacgtgccc tccctgaact accagaacga ccacagcaat | 14520 |
| ttttgacca cggtcatcca gaacaatgac tacagcccga gcgaggccag cacccagacc | 14580 |
| atcaatctgg atgaccggtc gcactggggc ggcgacctga aaaccatcct gcacaccaac | 14640 |
| atgcccaacg tgaacgagtt catgttcacc aataagttca aggcgcgggt gatggtgtcg | 14700 |
| cgctcgcaca ccaaggaaga ccgggtggag ctgaagtacg agtgggtgga gttcgagctg | 14760 |

```
ccagagggca actactccga gaccatgacc attgacctga tgaacaacgc gatcgtggag   14820
cactatctga aagtgggcag gcagaacggg gtcctggaga gcgacatcgg ggtcaagttc   14880
gacaccagga acttccgcct ggggctggac cccgtgaccg ggctggttat gcccggggtg   14940
tacaccaacg aggccttcca tcccgacatc atcctgctgc ccggctgcgg ggtggacttc   15000
acttacagcc gcctgagcaa cctcctgggc atccgcaagc ggcagcccct tccaggagggc  15060 ttcaggatca cctacgagga cctggagggg ggcaacatcc ccgcgctcct cgatgtggag   15120
gcctaccagg atagcttgaa ggaaaatgag gcgggacagg aggataccgc ccccgccgcc   15180
tccgccgccg ccgagcaggg cgaggatgct gctgacaccg cggccgcgga cggggcagag   15240
gccgaccccg ctatggtggt ggaggctccc gagcaggagg aggacatgaa tgacagtgcg   15300
gtgcgcggag acaccttcgt cacccggggg gaggaaaagc aagcggaggc cgaggccgcg   15360
gccgaggaaa agcaactggc ggcagcagcg gcggcggcgg cgttggccgc ggcggaggct   15420
gagtctgagg ggaccaagcc cgccaaggag cccgtgatta gcccctgac cgaagatagc   15480 aagaagcgca gttacaacct gctcaaggac agcaccaaca ccgcgtaccg cagctggtac   15540
ctggcctaca actacggcga cccgtcgacg ggggtgcgct cctggaccct gctgtgcacg   15600
ccggacgtga cctgcggctc ggagcaggtg tactggtcgc tgcccgacat gatgcaagac   15660
cccgtgacct tccgctccac gcggcaggtc agcaacttcc cggtggtggg cgccgagctg   15720
ctgcccgtgc actccaagag cttctacaac gaccaggccg tctactccca gctcatccgc   15780
cagttcacct ctctgaccca cgtgttcaat cgctttcctg agaaccagat tctggcgcgc   15840
ccgcccgccc ccaccatcac caccgtcagt gaaaacgttc ctgctctcac agatcacggg   15900
acgctaccgc tgcgcaacag catcggagga gtccagcgag tgaccgttac tgacgccaga   15960
cgccgcacct gccctacgt ttacaaggcc ttgggcatag tctcgccgcg cgtcctttcc   16020
agccgcactt tttgagcaac accaccatca tgtccatcct gatctcaccc agcaataact   16080
ccggctgggg actgctgcgc gcgcccagca agatgttcgg aggggcgagg aagcgttccg   16140
agcagcaccc cgtgcgcgtg cgcgggcact tccgcgcccc ctggggagcg cacaaacgcg   16200
gccgcgcggg gcgcaccacc gtggacgacg ccatcgactc ggtggtggag caggcgcgca   16260
actacaggcc cgcggtctct accgtggacg cggccatcca gaccgtggtg cggggcgcgc   16320
ggcggtacgc caagctgaag agccgccgga agcgcgtggc ccgccgccac cgccgccgac   16380
ccggggccgc cgccaaacgc gccgccgcgg ccctgcttcg ccgggccaag cgcacgggcc   16440
gccgcgccgc catgagggcc gcgcgccgct tggccgccgg catcaccgcc gccaccatgg   16500
ccccccgtac ccgaagacgc gcggccgccg ccgccgccgc cgccatcagt gacatggcca   16560
gcaggcgccg gggcaacgtg tactgggtgc gcgactcggt gaccggcacg cgcgtgcccg   16620
tgcgcttccg ccccccgcgg acttgagatg atgtgaaaaa acaacactga gtctcctgct   16680
gttgtgtgta tccagcggc ggcggcgcgc gcagcgtcat gtccaagcgc aaaatcaaag   16740
aagagatgct ccaggtcgtc gcgccggaga tctatgggcc cccgaagaag gaagagcagg   16800
attcgaagcc ccgcaagata aagcgggtca aaaagaaaaa gaaagatgat gacgatgccg   16860
atggggaggt ggagttcctg cgcgccacgg cgcccaggcg cccggtgcag tggaagggcc   16920
ggcgcgtaaa gcgcgtcctg cgcccccggca ccgcggtggt cttcacgccc ggcgagcgct   16980
ccaccccgga ctttcaagcgc gtctatgacg aggtgtacgg cgacgaagac ctgctggagc   17040
aggccaacga gcgcttcgga gagtttgctt acgggaagcg tcagcgggcg ctggggaagg   17100
```

```
aggacctgct ggcgctgccg ctggaccagg gcaaccccac ccccagtctg aagcccgtga   17160
ccctgcagca ggtgctgccg agcagcgcac cctccgaggc gaagcggggt ctgaagcgcg   17220
agggcggcga cctggcgccc accgtgcagc tcatggtgcc caagcggcag aggctggagg   17280
atgtgctgga gaaaatgaaa gtagacgccg gtctgcagcc ggacatcagg gtccgcccca   17340
tcaagcaggt ggcgccgggc ctcggcgtgc agaccgtgga cgtggtcatc cccaccggca   17400
actcccccgc cgccgccacc actaccgctg cctccacgga catggagaca cagaccgatc   17460
ccgccgcagc cgcagccgca gccgccgccg cgacctcctc ggcggaggtg cagacggacc   17520
cctggctgcc gccggcgatg tcagctcccc gcgcgcgtcg cgggcgcagg aagtacggcg   17580
ccgccaacgc gctcctgccc gagtacgcct tgcatccttc catcgcgccc acccccggct   17640
accgaggcta tacctaccgc ccgcgaagag ccaaggggtt cacccgccgt ccccgccgac   17700
gcgccgccgc caccacccgc cgccgccgcc gcagacgcca gcccgcactg gctccagtct   17760
ccgtgaggaa agtggcgcgc gacggacaca ccctggtgct gcccagggcg cgctaccacc   17820
ccagcatcgt ttaaaagcct gttgtggttc ttgcagatat ggccctcact tgccgcctcc   17880
gtttcccggt gccgggatac cgaggaggaa gatcgcgccg caggaggggt ctggccggcc   17940
gcggcctgag cggaggcagc cgccgcgcgc accggcggcg acgcgccacc agccgacgca   18000
tgcgcggcgg ggtgctgccc ctgttaatcc ccctgatcgc cgcggcgatc ggcgccgtgc   18060
ccgggatcgc ctccgtggcc ttgcaagcgt cccagaggca ttgacagact tgcaaacttg   18120
caaatatgga aaaaaaaacc ccaataaaaa agtctagact ctcacgctcg cttggtcctg   18180
tgactatttt gtagaatgga agacatcaac tttgcgtcgc tggccccgcg tcacggctcg   18240
cgcccgttcc tgggacactg gaacgatatc ggcaccagca acatgagcgg tggcgccttc   18300 agttgggggct ctctgtggag cggcattaaa agtatcgggt ctgccgttaa aaattacggc   18360
tcccgggcct ggaacagcag cacgggccag atgttgagag acaagttgaa agagcagaac   18420
ttccagcaga aggtggtgga gggcctggcc tccggcatca acggggtggt ggacctggcc   18480
aaccaggccg tgcagaataa gatcaacagc agactggacc cccggccgcc ggtggaggag   18540
gtgccgccgg cgctggagac ggtgtccccc gatgggcgtg gcgagaagcg cccgcggccc   18600
gatagggaag agaccactct ggtcacgcag accgatgagc cgccccgta tgaggaggcc   18660 ctgaagcaag gtctgccac cacgcggccc atcgcgccca tggccaccgg ggtggtgggc   18720
cgccacaccc ccgccacgct ggacttgcct ccgcccgccg atgtgccgca gcagcagaag   18780
gcggcacagc cgggccccgc cgcgaccgcc tcccgttcct ccgccggtcc tctgcgccgc   18840
gcggccagcg gcccccgcgg gggggtcgcg aggcacggca actggcagag cacgctgaac   18900
agcatcgtgg gtctggggt gcggtccgtg aagcgccgcc gatgctactg aatagcttag   18960
ctaacgtgtt gtatgtgtgt atgcgcccta tgtcgccgcc agaggagctg ctgagtcgcc   19020
gccgttcgcg cgcccaccac caccgccact ccgcccctca agatggcgac cccatcgatg   19080
atgccgcagt ggtcgtacat gcacatctcg ggccaggacg cctcggagta cctgagcccc   19140
gggctggtgc agttcgcccg cgccaccgag agctacttca gcctgagtaa caagtttagg   19200
aaccccacgt ggcgcccac gcacgatgtg accaccgacc ggtctcagcg cctgacgctg   19260
cggttcattc ccgtggaccg cgaggacacc gcgtactcgt acaaggcgcg gttcacctg   19320 gccgtgggcg acaaccgcgt gctggacatg gcctccacct actttgacat ccgcggggtg   19380
ctggaccggg gtcccacttt caagccctac tctggcaccg cctacaactc cctgcccccc   19440
aagggcgctc ccaactcctg cgagtgggag caagaggaaa ctcaggcagt tgaagaagca   19500
```

```
gcagaagagg aagaagaaga tgctgacggt caagctgagg aagagcaagc agctaccaaa   19560
aagactcatg tatatgctca ggctcccctt tctggcgaaa aaattagtaa agatggtctg   19620
caaataggaa cggacgctac agctacagaa caaaaaccta tttatgcaga ccctacattc   19680
cagcccgaac cccaaatcgg ggagtcccag tggaatgagg cagatgctac agtcgccggc   19740
ggtagagtgc taaagaaatc tactcccatg aaaccatgct atggttccta tgcaagaccc   19800
acaaatgcta atggaggtca gggtgtacta acggcaaatg cccagggaca gctagaatct   19860
caggttgaaa tgcaattctt ttcaacttct gaaaacgccc gtaacgaggc taacaacatt   19920
cagcccaaat tggtgctgta tagtgaggat gtgcacatgg agaccccgga tacgcacctt   19980
tcttacaagc ccgcaaaaag cgatgacaat tcaaaaatca tgctgggtca gcagtccatg   20040
cccaacagac ctaattacat cggcttcaga gacaacttta tcggcctcat gtattacaat   20100
agcactggca acatgggagt gcttgcaggt caggcctctc agttgaatgc agtggtggac   20160
ttgcaagaca gaaacacaga actgtcctac cagctcttgc ttgattccat gggtgacaga   20220
accagatact tttccatgtg gaatcaggca gtggacagtt atgacccaga tgttagaatt   20280
attgaaaatc atggaactga agacgagctc cccaactatt gtttccctct gggtggcata   20340
ggggtaactg acacttacca ggctgttaaa accaacaatg gcaataacgg gggccaggtg   20400
acttggacaa aagatgaaac ttttgcagat cgcaatgaaa taggggtggg aaacaatttc   20460
gctatggaga tcaacctcag tgccaacctg tggagaaact tcctgtactc caacgtggcg   20520
ctgtacctac cagacaagct taagtacaac ccctccaatg tggacatctc tgacaacccc   20580
aacacctacg attacatgaa caagcgagtg gtggccccgg ggctggtgga ctgctacatc   20640
aacctgggcg cgcgctggtc gctggactac atggacaacg tcaaccccct caaccaccac   20700
cgcaatgcgg gcctgcgcta ccgctccatg ctcctgggca cgggcgcta cgtgcccttc   20760 cacatccagg tgccccagaa gttctttgcc atcaagaacc tcctcctcct gccgggctcc   20820
tacacctacg agtggaactt caggaaggat gtcaacatgg tcctccagag ctctctgggt   20880
aacgatctca gggtggacgg ggccagcatc aagttcgaga gcatctgcct ctacgccacc   20940
ttcttcccca tggcccacaa cacggcctcc acgctcgagg ccatgctcag gaacgacacc   21000
aacgaccagt ccttcaatga ctacctctcc gccgccaaca tgctctaccc catacccgcc   21060
aacgccacca acgtccccat ctccatcccc tcgcgcaact gggcggcctt ccgcggctgg   21120
gccttcaccc gcctcaagac caaggagacc cctccctgg gctcgggatt cgacccctac   21180
tacacctact cgggctccat tccctacctg gacggcacct tctacctcaa ccacacttt c  21240 aagaaggtct cggtcacctt cgactcctcg gtcagctggc cgggcaacga ccgtctgctc   21300
acccccaacg agttcgagat caagcgctcg gtcgacgggg agggctacaa cgtggcccag   21360
tgcaacatga ccaaggactg gttcctggtc cagatgctgg ccaactacaa catcggctac   21420
cagggcttct catcccagga gagctacaag gacaggatgt actccttctt caggaacttc   21480
cagcccatga gccggcaggt ggtggaccag accaagtaca aggactacca ggaggtgggc   21540
atcatccacc agcacaacaa ctcgggcttc gtgggctacc tcgccccac catgcgcgag   21600 ggacaggcct accccgccaa cttccccta t ccgctcatag caagaccgc ggtcgacagc   21660 atcccccaga aaaagttcct ctgcgaccgc accctctggc gcatccccttc tccagcaac   21720 ttcatgtcca tgggtgcgct ctcggacctg ggccagaact tgctctacgc caactccgcc   21780
cacgccctcg acatgaccttc cgaggtcgac cccatggacg agcccaccct tctctatgtt   21840
```

```
ctgttcgaag tctttgacgt ggtccgggtc caccagccgc accgcggcgt catcgagacc    21900
gtgtacctgc gtacgccctt ctcggccggc aacgccacca cctaaagaag caagccgcag    21960
tcatcgccgc ctgcatgccg tcgggttcca ccgagcaaga gctcagggcc atcgtcagag    22020
acctgggatg cgggccctat tttttgggca ccttcgacaa gcgcttccct ggctttgtct    22080
ccccacacaa gctggcctgc gccatcgtca acacggccgg ccgcgagacc ggggcgtgc     22140 actggctggc cttcgcctgg aacccgcgct ccaaaacatg cttcctcttt gacccCttcg    22200
gcttttcgga ccagcggctc aagcaaatct acgagttcga gtacgagggc ttgctgcgtc    22260
gcagcgccat cgcctcctcg cccgaccgct gcgtcaccct cgaaaagtcc acccagaccg    22320
tgcaggggcc cgactcggcc gcctgcggtc tcttctgctg catgtttctg cacgcctttg    22380
tgcactggcc tcagagtccc atggaccgca accccaccat gaacttgctg acggggggtgc   22440 ccaactccat gctccagagc cccaggtcg agcccaccct gcgccgcaac caggagcagc     22500
tctacagctt cctggagcgc cactcgcctt acttccgccg ccacagcgca cagatcagga    22560
gggccacctc cttctgccac ttgcaagaga tgcaagaagg gtaataacga tgtacacact    22620
ttttttctca ataaatggca tcttttatt tatacaagct ctctggggta ttcatttccc      22680
accaccaccc gccgttgtcg ccatctggct ctatttagaa atcgaaaggg ttctgccggg    22740
agtcgccgtg cgccacgggc agggacacgt tgcgatactg gtagcgggtg ccccacttga    22800
actcgggcac caccaggcga ggcagctcgg ggaagttttc gctccacagg ctgcgggtca    22860
gcaccagcgc gttcatcagg tcgggcgccg agatcttgaa gtcgcagttg gggccgccgc    22920
cctgcgcgcg cgagttgcgg tacaccgggt tgcagcactg gaacaccaac agcgccgggt    22980
gcttcacgct ggccagcacg ctgcggtcgg agatcagctc ggcgtccagg tcctccgcgt    23040
tgctcagcgc gaacgggtc atcttgggca cttgccgccc caggaagggc gcgtgccccg     23100
gtttcgagtt gcagtcgcag cgcagcggga tcagcaggtg cccgtgcccg gactcggcgt    23160 tgggtacag cgccgcatg aaggcctgca tctggcggaa ggccatctgg gccttggcgc       23220
cctccgagaa gaacatgccg caggacttgc ccgagaactg gtttgcgggg cagctggcgt    23280
cgtgcaggca gcgcgcgcg tcggtgttgg cgatctgcac cacgttgcgc ccccaccggt     23340
tcttcacgat cttggccttg gacgattgct ccttcagcgc gcgctgcccg ttctcgctgg    23400
tcacatccat ctcgatcaca tgttccttgt tcaccatgct gctgccgtgc agacacttca    23460
gctcgccctc cgtctcggtg cagcggtgct gccacagcgc gcagcccgtg ggctcgaaag    23520
acttgtaggt cacctccgcg aaggactgca ggtacccctg caaaaagcgg cccatcatgg    23580
tcacgaaggt cttgttgctg ctgaaggtca gctgcagccc gcggtgctcc tcgttcagcc    23640
aggtcttgca cacggccgcc agcgcctcca cctggtcggg cagcatcttg aagttcacct    23700
tcagctcatt ctccacgtgg tacttgtcca tcagcgtgcg cgccgcctcc atgcccttct    23760
cccaggccga caccagcggc aggctcacgg ggttcttcac catcaccgtg ccgccgcct    23820 ccgccgcgct ttcgctttcc gccccgctgt tctcttcctc ttcctcctct tcctcgccgc    23880
cgcccactcg cagccccgc accacggggt cgtcttcctg caggcgctgc accttgcgct    23940
tgccgttgcg cccctgcttg atgcgcacgg gcgggttgct gaagcccacc atcaccagcg    24000
cggcctcttc ttgctcgtcc tcgctgtcca gaatgacctc cggggagggg gggttggtca    24060
tcctcagtac cgaggcacgc ttctttttct tcctgggggc gttcgccagc tccgcggctg    24120
cggccgctgc cgaggtcgaa ggccgagggc tgggcgtgcg cggcaccagc gcgtcctgcg    24180
agccgtcctc gtcctcctcg gactcgagac ggaggcgggc ccgcttcttc gggggcgcgc    24240
```

```
ggggcggcgg aggcggcggc ggcgacggag acggggacga gacatcgtcc agggtgggtg   24300
gacggcgggc cgcgccgcgt ccgcgctcgg gggtggtctc gcgctggtcc tcttcccgac   24360
tggccatctc ccactgctcc ttctcctata ggcagaaaga gatcatggag tctctcatgc   24420
gagtcgagaa ggaggaggac agcctaaccg ccccctctga gccctccacc accgccgcca   24480
ccaccgccaa tgccgccgcg gacgacgcgc caccgagac caccgccagt accaccctcc    24540
ccagcgacgc accccgctc gagaatgaag tgctgatcga gcaggacccg ggttttgtga    24600
gcggagagga ggatgaggtg gatgagaagg agaaggagga ggtcgccgcc tcagtgccaa   24660
aagaggataa aaagcaagac caggacgacg cagataagga tgagacagca gtcgggcggg   24720
ggaacggaag ccatgatgct gatgacggct acctagacgt gggagacgac gtgctgctta   24780
agcacctgca ccgccagtgc gtcatcgtct gcgacgcgct gcaggagcgc tgcgaagtgc   24840
ccctggacgt ggcggaggtc agccgcgcct acgagcggca cctcttcgcg ccgcacgtgc   24900
cccccaagcg ccgggagaac ggcacctgcg agcccaaccc gcgtctcaac ttctacccgg   24960
tcttcgcggt acccgaggtg ctggccacct accacatctt tttccaaaac tgcaagatcc   25020
ccctctcctg ccgcgccaac cgcacccgcg ccgacaaaac cctgaccctg cggcagggcg   25080
cccacatacc tgatatcgcc tctctggagg aagtgcccaa gatcttcgag ggtctcggtc   25140
gcgacgagaa acgggcggcg aacgctctgc acggagacag cgaaaacgag agtcactcgg   25200
gggtgctggt ggagctcgag ggcgacaacg cgcgcctggc cgtactcaag cgcagcatag   25260
aggtcaccca ctttgcctac ccggcgctca acctgccccc caaggtcatg agtgtggtca   25320
tgggcgagct catcatgcgc cgcgcccagc ccctggccgc ggatgcaaac ttgcaagagt   25380
cctccgagga aggcctgccc gcggtcagcg acgagcagct ggcgcgctgg ctggagaccc   25440
gcgaccccgc gcagctggag gagcggcgca agctcatgat ggccgcggtg ctggtcaccg   25500
tggagctcga gtgtctgcag cgcttcttcg cggaccccga gatgcagcgc aagctcgagg   25560
agaccctgca ctacaccttc cgccagggct acgtgcgcca ggcctgcaag atctccaacg   25620
tggagctctg caacctggtc tcctacctgg gcatcctgca cgagaaccgc ctcgggcaga   25680
acgtcctgca ctccacccct caaaggggagg cgcgccgcga ctacatccgc gactgcgcct   25740
acctcttcct ctgctacacc tggcagacgg ccatgggggt ctggcagcag tgcctggagg   25800
agcgcaacct caaggagctg gaaaagctcc tcaagcgcac cctcagggac ctctggacgg   25860
gcttcaacga gcgctcggtg gccgccgcgc tggcggacat catctttccc gagcgcctgc   25920
tcaagaccct gcagcagggc ctgcccgact tcaccagcca gagcatgctg cagaacttca   25980
ggactttcat cctggagcgc tcgggcatcc tgccggccac ttgctgcgcg ctgcccagcg   26040
acttcgtgcc catcaagtac agggagtgcc cgccgccgct ctgggccac tgctacctct    26100 tccagctggc caactacctc gcctaccact cggacctcat ggaagacgtg agcggcgagg   26160
gcctgctcga gtgccactgc cgctgcaacc tctgcacgcc caccgctct ctagtctgca    26220 acccgcagct gctcagcgag agtcagatta tcggtacctt cgagctgcag ggtccctcgc   26280
ctgacgagaa gtccgcggct ccagggctga aactcactcc ggggctgtgg acttccgcct   26340
acctacgcaa atttgtacct gaggactacc acgcccacga gatcaggttc tacgaagacc   26400
aatcccgccc gccaaggcg gagctcaccg cctgcgtcat cacccagggg cacatcctgg    26460
gccaattgca agccatcaac aaagcccgcc gagagttctt gctgaaaaag ggtcgggggg   26520
tgtacctgga ccccagtcc ggcgaggagc taaacccgct acccccgccg ccgccccagc    26580
```

```
agcgggacct tgcttcccag gatggcaccc agaaagaagc agcagccgcc gccgccgccg   26640
cagccataca tgcttctgga ggaagaggag gaggactggg acagtcaggc agaggaggtt   26700
tcggacgagg agcaggagga gatgatggaa gactgggagg aggacagcag cctagacgag   26760
gaagcttcag aggccgaaga ggtggcagac gcaacaccat cgccctcggt cgcagccccc   26820 tcgccgggc ccctgaaatc ctccgaaccc agcaccagcg ctataacctc cgctcctccg    26880
gcgccggcgc cacccgcccg cagacccaac cgtagatggg acaccacagg aaccggggtc   26940
ggtaagtcca agtgcccgcc gccgccaccg cagcagcagc agcagcagcg ccagggctac   27000
cgctcgtggc gcgggcacaa gaacgccata gtcgcctgct gcaagactg cgggggcaac    27060 atctctttcg cccgccgctt cctgctattc caccacgggg tcgcctttcc ccgcaatgtc   27120
ctgcattact accgtcatct ctacagcccc tactgcagcg gcgacccaga ggcggcagcg   27180
gcagccacag cggcgaccac cacctaggaa gatatcctcc gcgggcaaga cagcggcagc   27240
agcggccagg agaccgcgg cagcagcggc gggagcggtg ggcgcactgc gcctctcgcc    27300
caacgaaccc ctctcgaccc gggagctcag acacaggatc ttccccactt tgtatgccat   27360
cttccaacag agcagaggcc aggagcagga gctgaaaata aaaaacagat ctctgcgctc   27420
cctcacccgc agctgtctgt atcacaaaag cgaagatcag cttcggcgca cgctggagga   27480
cgcggaggca ctcttcagca aatactgcgc gctcactctt aaagactagc tccgcgccct   27540
tctcgaattt aggcgggaga aaactacgtc atcgccggcc gccgcccagc ccgcccagcc   27600
gagatgagca aagagattcc cacgccatac atgtggagct accagccgca gatgggactc   27660
gcggcgggag cggcccagga ctactccacc cgcatgaact acatgagcgc gggaccccac   27720
atgatctcac aggtcaacgg gatccgcgcc cagcgaaacc aaatactgct ggaacaggcg   27780
gccatcaccg ccacgccccg ccataatctc aacccccgaa attggccgc cgccctcgtg     27840 taccaggaaa ccccctccgc caccaccgta ctacttccgc gtgacgccca ggccgaagtc   27900
cagatgacta actcaggggc gcagctcgcg ggcggctttc gtcacggggc gcggccgctc   27960
cgaccaggta taagacacct gatgatcaga ggccgaggta tccagctcaa cgacgagtcg   28020
gtgagctctt cgctcggtct ccgtccggac ggaactttcc agctcgccgg atccggccgc   28080
tcttcgttca cgccccgcca ggcgtacctg actctgcaga cctcgtcctc ggagcccgc    28140 tccggcggca tcgaaccct ccagttcgtg gaggagttcg tgccctcggt ctacttcaac    28200
cccttctcgg gacctcccgg acgctacccc gaccagttca ttccgaactt tgacgcggtg   28260
aaggactcgg cggacggcta cgactgaatg tcaggtgtcg aggcagagca gcttcgcctg   28320
agacacctcg agcactgccg ccgccacaag tgcttcgccc gcggttctgg tgagttctgc   28380
tactttcagc tacccgagga gcataccgag gggccggcgc acggcgtccg cctgaccacc   28440
cagggcgagg ttacctgttc cctcatccgg gagtttaccc tccgtcccct gctagtggag   28500
cgggagcggg gtccctgtgt cctaactatc gcctgcaact gccctaaccc tggattacat   28560
caagatcttt gctgtcatct ctgtgctgag tttaataaac gctgagatca gaatctactg   28620
gggctcctgt cgccatcctg tgaacgccac cgtcttcacc caccccgacc aggcccaggc   28680
gaacctcacc tgcggtctgc atcggagggc caagaagtac ctcacctggt acttcaacgg   28740 caccccctttt gtggtttaca acagcttcga cggggacgga gtctccctga agaccagct    28800 ctccggtctc agctactcca tccacaagaa caccaccctc caactcttcc ctccctacct   28860
gccgggaacc tacgagtgcg tcaccggccg ctgcacccac ctcacccgcc tgatcgtaaa   28920
ccagagcttt ccgggaacag ataactccct cttccccaga acaggaggtg agctcaggaa   28980
```

```
actccccggg gaccagggcg gagacgtacc ttcgacccct gtggggttag gattttttat   29040
taccgggttg ctggctcttt taatcaaagt ttccttgaga tttgttcttt ccttctacgt   29100
gtatgaacac ctcaacctcc aataactcta cccttctt  ggaatcaggt gacttctctg   29160
aaatcgggct tggtgtgctg cttactctgt tgattttttt ccttatcata ctcagccttc   29220
tgtgcctcag gctcgccgcc tgctgcgcac acatctatat ctactgctgg ttgctcaagt   29280
gcaggggtcg ccacccaaga tgaacaggta catggtccta tcgatcctag gcctgctggc   29340
cctggcggcc tgcagcgccg ccaaaaaaga gattaccttt gaggagcccg cttgcaatgt   29400
aactttcaag cccgagggtg accaatgcac caccctcgtc aaatgcgtta ccaatcatga   29460
gaggctgcgc atcgactaca aaaacaaaac tggccagttt gcggtctata gtgtgtttac   29520
gcccggagac ccctctaact actctgtcac cgtcttccag ggcggacagt ctaagatatt   29580
caattacact ttcccttttt atgagttatg cgatgcggtc atgtacatgt caaaacagta   29640
caacctgtgg cctccctctc cccaggcgtg tgtggaaaat actgggtctt actgctgtat   29700
ggctttcgca atcactacgc tcgctctaat ctgcacggtg ctatacataa aattcaggca   29760
gaggcgaatc tttatcgatg aaaagaaaat gccttgatcg ctaacaccgg cttt ctatct   29820
gcagaatgaa tgcaatcacc tccctactaa tcaccaccac cctccttgcg attgcccatg   29880
ggttgacacg aatcgaagtg ccagtggggt ccaatgtcac catggtgggc cccgccggca   29940
attccaccct catgtgggaa aaatttgtcc gcaatcaatg ggttcatttc tgctctaacc   30000
gaatcagtat caagcccaga gccatctgcg atgggcaaaa tctaactctg atcaatgtgc   30060
aaatgatgga tgctgggtac tattacgggc agcggggaga aatcattaat tactggcgac   30120
cccacaagga ctacatgctg catgtagtcg aggcacttcc cactaccacc cccactacca   30180
cctctcccac caccaccacc actactacta ctactactac tactactact actaccacta   30240
ccgctgcccg ccatacccgc aaaagcacca tgattagcac aaagcccct cgtgctcact   30300
cccacgccgg cgggcccatc ggtgcgacct cagaaaccac cgagctttgc ttctgccaat   30360
gcactaacgc cagcgctcat gaactgttcg acctggagaa tgaggatgtc cagcagagct   30420
ccgcttgcct gacccaggag gctgtggagc ccgttgccct gaagcagatc ggtgattcaa   30480
taattgactc ttcttctttt gccactcccg aataccctcc cgattctact ttccacatca   30540
cgggtaccaa agaccctaac ctctctttct acctgatgct gctgctctgt atctctgtgg   30600
tctcttccgc gctgatgtta ctggggatgt tctgctgcct gatctgccgc agaaagagaa   30660
aagctcgctc tcagggccaa ccactgatgc ccttcccta ccccccggat tttgcagata   30720
acaagatatg agctcgctgc tgacactaac cgctttacta gcctgcgctc taaccccttgt  30780
cgcttgcgac tcgagattcc acaatgtcac agctgtggca ggagaaaatg ttactttcaa   30840
ctccacggcc gatacccagt ggtcgtggag tggctcaggt agctacttaa ctatctgcaa   30900
tagctccact tcccccggca tatcccaac caagtaccaa tgcaatgcca gcctgttcac   30960
cctcatcaac gcttccaccc tggacaatgg actctatgta ggctatgtac cctttggtgg   31020
gcaaggaaag acccacgctt acaacctgga agttcgccag cccagaacca ctacccaagc   31080
ttctcccacc accaccacca ccaccaccat caccagcagc agcagcagca gcagccacag   31140
cagcagcagc agattattga ctttggtttt ggccagctca tctgccgcta cccaggccat   31200
ctacagctct gtgcccgaaa ccactcagat ccaccgccca gaaacgacca ccgccaccac   31260
cctacacacc tccagcgatc agatgccgac caacatcacc cccttggctc ttcaaatggg   31320
```

```
acttacaagc cccactccaa aaccagtgga tgcggccgag gtctccgccc tcgtcaatga   31380
ctgggcgggg ctgggaatgt ggtggttcgc cataggcatg atggcgctct gcctgcttct   31440
gctctggctc atctgctgcc tccaccgcag gcgagccaga ccccccatct atagacccat   31500
cattgtcctg aaccccgata atgatgggat ccatagattg gatggcctga aaaacctact   31560
tttttctttt acagtatgat aaattgagac atgcctcgca ttttcttgta catgttcctt   31620
ctcccacctt ttctggggtg ttctacgctg gccgctgtgt ctcacctgga ggtagactgc   31680
ctctcaccct tcactgtcta cctgctttac ggattggtca ccctcactct catctgcagc   31740
ctaatcacag taatcatcgc cttcatccag tgcattgatt acatctgtgt gcgcctcgca   31800
tacttcagac accaccgca gtaccgagac aggaacattg cccaacttct aagactgctc   31860
taatcatgca taagactgtg atctgccttc tgatcctctg catcctgccc accctcacct   31920
cctgccagta caccacaaaa tctccgcgca aaagacatgc ctcctgccgc ttcacccaac   31980
tgtggaatat acccaaatgc tacaacgaaa agagcgagct ctccgaagct tggctgtatg   32040
gggtcatctg tgtcttagtt ttctgcagca ctgtctttgc cctcataatc tacccctact   32100
ttgatttggg atggaacgcg atcgatgcca tgaattaccc caccttttccc gcacccgaga   32160
taattccact cgcgacaagtt gtaccgcgttg tcgttaatca acgcccccca tccctcagc   32220
ccactgaaat cagctacttt aacctaacag gcggagatga ctgacgccct agatctagaa   32280
atggacggca tcagtaccga gcagcgtctc ctagagaggc gcaggcaggc ggctgagcaa   32340
gagcgcctca atcaggagct ccgagatctc gttaacctgc accagtgcaa aagaggcatc   32400
ttttgtctgg taaagcaggc caaagtcacc tacgagaaga ccggcaacag ccaccgcctc   32460
agttacaaat tgcccaccca gcgccagaag ctggtgctca tggtgggtga aatcccatc    32520
accgtcaccc agcactcggt agagaccgag gggtgtctgc actcccctg tcggggtcca    32580
gaagacctct gcaccctggt aaagaccctg tgcggtctca gagatttagt cccctttaac   32640
taatcaaaca ctggaatcaa taaaaagaat cacttactta aaatcagaca gcaggtctct   32700
gtccagttta ttcagcagca cctccttccc ctcctcccaa ctctggtact ccaaacgcct   32760
tctggcggca aacttcctcc acaccctgaa gggaatgtca gattcttgct cctgtccctc   32820
cgcacccact atcttcatgt tgttgcagat gaagcgcacc aaaacgtctg acgagagctt   32880
caaccccgtg taccctatg acacggaaag cggccctccc tccgtccctt tcctcacccc   32940
tcccttcgtg tctcccgatg gattccaaga aagtccccc ggggtcctgt ctctgaacct    33000
ggccgagccc ctggtcactt cccacggcat gctcgcccctg aaaatgggaa gtggcctctc   33060
cctggacgac gctggcaacc tcacctctca agatatcacc accgctagcc ctcccctcaa   33120
aaaaaccaag accaacctca gcctagaaac ctcatccccc ctaactgtga gcacctcagg   33180
cgccctcacc gtagcagccg ccgctcccct ggcggtggcc ggcacctccc tcaccatgca   33240
atcagaggcc cccctgacag tacaggatgc aaaaactcacc ctggccacca aggccccct    33300
gaccgtgtct gaaggcaaac tggccttgca acatcggcc ccgctgacgg ccgctgacag    33360
cagcaccctc acagtcagtg ccacaccacc ccttagcaca agcaatggca gcttgggtat   33420
tgacatgcaa gccccatttt acaccaccaa tggaaaacta ggacttaact ttggcgctcc   33480
cctgcatgtg gtagacagcc taaatgcact gactgtagtt actggccaag gtcttacgat   33540
aaacggaaca gccctacaaa ctagagtctc aggtgccctc aactatgaca catcaggaaa   33600
cctagaattg agagctgcag ggggtatgcg agttgatgca aatggtcaac ttatccttga   33660
tgtagcttac ccatttgatg cacaaaacaa tctcagcctt aggcttggac agggaccct    33720
```

```
gtttgttaac tctgcccaca acttggatgt taactacaac agaggcctct acctgttcac   33780
atctggaaat accaaaaagc tagaagttaa tatcaaaaca gccaagggtc tcatttatga   33840
tgacactgct atagcaatca atgcgggtga tgggctacag tttgactcag gctcagatac   33900
aaatccatta aaaactaaac ttggattagg actggattat gactccagca gagccataat   33960
tgctaaactg ggaactggcc taagctttga caacacaggt gccatcacag taggcaacaa   34020
aaatgatgac aagcttacct tgtgaccac accagaccca tccctaact gtagaatcta    34080
ttcagagaaa gatgctaaat tcacacttgt tttgactaaa tgcggcagtc aggtgttggc   34140
cagcgtttct gttttatctg taaaaggtag ccttgcgccc atcagtggca cagtaactag   34200
tgctcagatt gtcctcagat ttgatgaaaa tggagttcta ctaagcaatt cttcccttga   34260
ccctcaatac tggaactaca gaaaaggtga ccttacagag ggcactgcat ataccaacgc   34320
agtgggattt atgcccaacc tcacagcata cccaaaaaca cagagccaaa ctgctaaaag   34380
caacattgta agtcaggttt acttgaatgg ggacaaatcc aaacccatga ccctcaccat   34440
taccctcaat ggaactaatg aaacaggaga tgccacagta agcacttact ccatgtcatt   34500
ctcatgaac tggaatggaa gtaattacat taatgaaacg ttccaaacca actccttcac   34560
cttctcctac atcgcccaag aataaaaagc atgacgctgt tgatttgatt caatgtgttt   34620
ctgttttatt ttcaagcaca acaaaatcat tcaagtcatt cttccatctt agcttaatag   34680
acacagtagc ttaatagacc cagtagtgca agccccatt ctagcttata gatcagacag    34740
tgataattaa ccaccaccac caccatacct tttgattcag gaaatcatga tcatcacagg   34800
atcctagtct tcaggccgcc ccctccctcc caagacacag aatacacagt cctctccccc   34860
cgactggctt taaataacac catctggttg gtcacagaca tgttcttagg ggttatattc   34920
cacacggtct cctgccgcgc caggcgctcg tcggtgatgt tgataaactc tcccggcagc   34980
tcgctcaagt tcacgtcgct gtccagcggc tgaacctccg gctgacgcga taactgtgcg   35040
accggctgct ggacgaacgg aggccgcgcc tacaaggggg tagagtcata atcctcggtc   35100
aggatagggc ggtgatgcag cagcagcgag cgaaacatct gctgccgccg ccgctccgtc   35160
cggcaggaaa acaacacgcc ggtggtctcc tccgcgataa tccgcaccgc ccgcagcatc   35220
agcttcctcg ttctccgcgc gcagcacctc acccttatct cgctcaaatc ggcgcagtag   35280
gtacagcaca gcaccacgat gttattcatg atcccacagt gcagggcgct gtatccaaag   35340
ctcatgccgg gaaccaccgc ccccacgtgg ccatcgtacc acaagcgcac gtaaatcaag   35400
tgtcgacccc tcatgaacgc gctggacaca acattactt ccttgggcat gttgtaattc     35460
accacctccc ggtaccagat aaacctctgg ttgaacaggg caccttccac caccatcctg   35520
aaccaagagg ccagaacctg cccaccggct atgcactgca gggaacccgg gttggaacaa   35580
tgacaatgca gactccaagg ctcgtaaccg tggatcatcc ggctgctgaa ggcatcgatg   35640
ttggcacaac acagacacac gtgcatgcac tttctcatga ttagcagctc ttccctcgtc   35700
aggatcatat cccaaggaat aacccattct tgaatcaacg taaaacccac acagcaggga   35760
aggcctcgca cataactcac gttgtgcatg tcagcgtgt tgcattccgg aaacagcgga    35820
tgatcctcca gtatcgaggc gcgggtctcc ttctcacagg gaggtaaagg gtccctgctg   35880
tacggactgc gccgggacga ccgagatcgt gttgagcgta gtgtcatgga aagggaacg    35940
ccggacgtgg tcatacttct tgaagcagaa ccaggttcgc gcgtggcagg cctccttgcg   36000
tctgcggtct cgccgtctag ctcgctccgt gtgatagttg tagtacagcc actcccgcag   36060
```

```
agcgtcgagg cgcaccctgg cttccggatc tatgtagact ccgtcttgca ccgcggccct    36120
gataatatcc accaccgtag aataagcaac acccagccaa gcaatacact cgctctgcga    36180
gcggcagaca ggaggagcgg gcagagatgg gagaaccatg ataaaaaact tttttaaag     36240
aatattttcc aattcttcga aagtaagatc tatcaagtgg cagcgctccc ctccactggc    36300
gcggtcaaac tctacggcca agcacagac  aacggcattt ctaagatgtt ccttaatggc    36360
gtccaaaaga cacaccgctc tcaagttgca gtaaactatg aatgaaaacc catccggctg    36420
attttccaat atagacgcgc cggcagcgtc caccaaaccc agataatttt cttctctcca    36480
gcggtttacg atctgtctaa gcaaatccct tatatcaagt ccgaccatgc caaaaatctg    36540
ctcaagagcg ccctccacct tcatgtacaa gcagcgcatc atgattgcaa aaattcaggt    36600
tcttcagaga cctgtataag attcaaaatg ggaacattaa caaaaattcc tctgtcgcgc    36660
agatcccttc gcagggcaag ctgaacataa tcagacaggt ccgaacggac cagtgaggcc    36720
aaatccccac caggaaccag atccagagac cctatactga ttatgacgcg catactcggg    36780
gctatgctga ccagcgtagc gccgatgtag gcgtgctgca tgggcggcga gataaaatgc    36840
aaagtgctgg ttaaaaaatc aggcaaagcc tcgcgcaaaa aagctaacac atcataatca    36900
tgctcatgca ggtagttgca ggtaagctca ggaaccaaaa cggaataaca cacgattttc    36960
ctctcaaaca tgacttcgcg gatactgcgt aaaacaaaaa attataaata aaaaattaat    37020
taaataactt aaacattgga agcctgtctc acaacaggaa aaaccacttt aatcaacata    37080
agacgggcca cgggcatgcc ggcatagccg taaaaaaatt ggtccccgtg attaacaagt    37140
accacagaca gctccccggt catgtcgggg gtcatcatgt gagactctgt atacacgtct    37200
ggattgtgaa catcagacaa acaaagaaat cgagccacgt agcccggagg tataatcacc    37260
cgcaggcgga ggtacagcaa aacgaccccc ataggaggaa tcacaaaatt agtaggagaa    37320
aaaaatacat aaacaccaga aaaaccctgt tgctgaggca aaatagcgcc ctcccgatcc    37380
aaaacaacat aaagcgcttc cacaggagca gccataacaa agacccgagt cttaccagta    37440
aaagaaaaaa gatctctcaa cgcagcacca gcaccaacac ttcgcagtgt aaaaggccaa    37500
gtgccgagag agtatatata ggaataaaaa gtgacgtaaa cggcaaagt  ccaaaaaacg    37560
cccagaaaaa ccgcacgcga acctacgccc cgaaacgaaa gccaaaaaac actagacact    37620
cccttccggc gtcaacttcc gctttcccac gctacgtcac ttccccggt  caaacaaact    37680
acatatcccg aacttccaag tcgccacgcc caaaacaccg cctacacctc ccgcccgcc    37740
ggcccgcccc cggacccgcc tcccgccccg cgccgcccat ctcattatca tattggcttc    37800
aatccaaaat aaggtatatt attgatgatg                                      37830
```

<210> SEQ ID NO 14
<211> LENGTH: 15422
<212> TYPE: DNA
<213> ORGANISM: Pan troglodytes

<400> SEQUENCE: 14

```
tgcccgcttt ccagtcggga aacctgtcgt gccagctgca ttaatgaatc ggccaacgcg      60
cggggagagg cggtttgcgt attgggcgct agatctccca tcacatatac ctgccgttca     120
ctattattta gtgaaatgag atattatgat attttctgaa ttgtgattaa aaaggcaact     180
ttatgcccat gcaacagaaa ctataaaaaa tacagagaat gaaagaaac  agatagattt     240
tttagttctt taggcccgta gtctgcaaat ccttttatga ttttctatca aacaaaagag     300
gaaaatagac cagttgcaat ccaaacgaga gtctaataga atgaggtcga aaagtaaatc     360
```

```
gcgcgggttt gttactgata aagcaggcaa gacctaaaat gtgtaaaggg caaagtgtat    420
actttggcgt cacccettac atattttagg tctttttttta ttgtgcgtaa ctaacttgcc    480
atcttcaaac aggagggctg gaagaagcag accgctaaca cagtacataa aaaaggagac    540
atgaacgatg aacatcaaaa agtttgcaaa acaagcaaca gtattaacct ttactaccgc    600
actgctggca ggaggcgcaa ctcaagcgtt tgcgaaagaa acgaaccaaa agccatataa    660
ggaaacatac ggcatttccc atattacacg ccatgatatg ctgcaaatcc ctgaacagca    720
aaaaaatgaa aaatatcaag ttcctgaatt cgattcgtcc acaattaaaa atatctcttc    780
tgcaaaaggc ctggacgttt gggacagctg gccattacaa aacgctgacg gcactgtcgc    840
aaactatcac ggctaccaca tcgtctttgc attagccgga gatcctaaaa atgcggatga    900
cacatcgatt tacatgttct atcaaaaagt cggcgaaact tctattgaca gctgaaaaa     960 cgctggccgc gtctttaaag acagcgacaa attcgatgca aatgattcta tcctaaaaga    1020
ccaaacacaa gaatggtcag gttcagccac atttacatct gacggaaaaa tccgtttatt    1080
ctacactgat ttctccggta acattacgg caaacaaaca ctgacaactg cacaagttaa     1140
cgtatcagca tcagacagct cttttgaacat caacggtgta gaggattata atcaatctt    1200 tgacggtgac ggaaaaacgt atcaaaatgt acagcagttc atcgatgaag caactacag     1260 ctcaggcgac aaccatacgc tgagagatcc tcactacgta aagataaag gccacaaata     1320 cttagtatt gaagcaaaca ctggaactga agatggctac caaggcgaag aatctttatt    1380
taacaaagca tactatggca aaagcacatc attcttccgt caagaaagtc aaaaacttct    1440
gcaaagcgat aaaaaacgca cggctgagtt agcaaacggc gctctcggta tgattgagct    1500
aaacgatgat tacacactga aaaaagtgat gaaccgctg attgcatcta acacagtaac     1560
agatgaaatt gaacgcgcga acgtctttaa aatgaacggc aaatggtacc tgttcactga    1620
ctcccgcgga tcaaaaatga cgattgacgg cattacgtct aacgatattt acatgcttgg    1680
ttatgtttct aattctttaa ctggcccata caagccgctg aacaaaactg gccttgtgtt    1740
aaaaatggat cttgatccta cgatgtaac ctttacttac tcacacttcg ctgtacctca     1800
agcgaaagga aacaatgtcg tgattacaag ctatatgaca acagaggat tctacgcaga     1860 caaacaatca acgtttgcgc caagcttcct gctgaacatc aaaggcaaga aaacatctgt    1920
tgtcaaagac agcatccttg aacaaggaca attaacagtt aacaaataat agggataaca    1980
gggtaatgct agaagacccg agtcttacca gtaaaagaaa aagatctct caacgcagca     2040 ccagcaccaa cacttcgcag tgtaaaaggc caagtgccga gagagtatat ataggaataa    2100
aaagtgacgt aaacgggcaa agtccaaaaa acgcccagaa aaaccgcacg cgaacctacg    2160
ccccgaaacg aaagccaaaa aacactgacc actcccttcc ggcgtcaact tccgcttccc    2220
cacgctacgt cacttgcccc agtcaaacaa actacatatc ccgaacttcc aagtcgccac    2280
gcccaaaaca ccgcctacac ctccccgccc gccggcccgc cccaaacccc gcctcccgcc    2340
ccgcgccccg ccccgcgccg cccatctcat tatcatattg gcttcaatcc aaaataaggt    2400
atattattga tgatggttta aacggatcct ctagagtcga cctgcaggca tgcaagcttg    2460
agtattctat agtgtcacct aaatagcttg gcgtaatcat ggtcatagct gtttcctgtg    2520
tgaaattgtt atccgctcac aattccacac aacatacgag ccggaagcat aaagtgtaaa    2580
gcctggggtg cctaatgagt gagctaactc acattaattg cgttgcgctc actgcccgct    2640
ttccagtcgg gaaacctgtc gtgccagctg cattaatgaa tcggccaacg cgaacccctt    2700
```

```
gcggccgccc gggccgtcga ccaattctca tgtttgacag cttatcatcg aatttctgcc    2760
attcatccgc ttattatcac ttattcaggc gtagcaacca ggcgtttaag ggcaccaata    2820
actgccttaa aaaaattacg ccccgccctg ccactcatcg cagtactgtt gtaattcatt    2880
aagcattctg ccgacatgga agccatcaca aacggcatga tgaacctgaa tcgccagcgg    2940
catcagcacc ttgtcgcctt gcgtataata tttgcccatg gtgaaaacgg gggcgaagaa    3000
gttgtccata ttggccacgt ttaaatcaaa actggtgaaa ctcacccagg gattggctga    3060
gacgaaaaac atattctcaa taaacccttt agggaaatag gccaggtttt caccgtaaca    3120
cgccacatct tgcgaatata tgtgtagaaa ctgccggaaa tcgtcgtggt attcactcca    3180
gagcgatgaa aacgtttcag tttgctcatg gaaaacggtg taacaagggt gaacactatc    3240
ccatatcacc agctcaccgt ctttcattgc catacggaat tccggatgag cattcatcag    3300
gcgggcaaga atgtgaataa aggccggata aaacttgtgc ttattttttct ttacggtctt    3360 taaaaaggcc gtaatatcca gctgaacggt ctggttatag gtacattgag caactgactg    3420
aaatgcctca aaatgttctt tacgatgcca ttgggatata tcaacggtgg tatatccagt    3480
gatttttttc tccattttag cttccttagc tcctgaaaat ctcgataact caaaaaatac    3540
gcccggtagt gatcttattt cattatggtg aaagttggaa cctcttacgt gccgatcaac    3600
gtctcatttt cgccaaaagt tggcccaggg cttcccggta tcaacaggga caccaggatt    3660
tatttattct gcgaagtgat cttccgtcac aggtatttat tcgcgataag ctcatggagc    3720
ggcgtaaccg tcgcacagga aggacagaga aagcgcggat ctgggaagtg acggacagaa    3780
cggtcaggac ctggattggg gaggcggttg ccgccgctgc tgctgacggt gtgacgttct    3840
ctgttccggt cacaccacat acgttccgcc attcctatgc gatgcacatg ctgtatgccg    3900
gtataccgct gaaagttctg caaagcctga tgggacataa gtccatcagt tcaacgaagg    3960
tctacacgaa ggttttttgcg ctggatgtgg ctgcccggca ccgggtgcag tttgcgatgc    4020
cggagtctga tgcggttgcg atgctgaaac aattatcctg agaataaatg ccttggcctt    4080
tatatggaaa tgtggaactg agtggatatg ctgttttttgt ctgttaaaca gagaagctgg    4140
ctgttatcca ctgagaagcg aacgaaacag tcgggaaaat ctcccattat cgtagagatc    4200
cgcattatta atctcaggag cctgtgtagc gtttatagga agtagtgttc tgtcatgatg    4260
cctgcaagcg gtaacgaaaa cgatttgaat atgccttcag gaacaataga atcttcgtg    4320 cggtgttacg ttgaagtgga gcggattatg tcagcaatgg acagaacaac ctaatgaaca    4380
cagaaccatg atgtggtctg tccttttaca gccagtagtg ctcgccgcag tcgagcgaca    4440
gggcgaagcc ctcgagtgag cgaggaagca ccagggaaca gcacttatat attctgctta    4500
cacacgatgc ctgaaaaaac ttcccttggg gttatccact tatccacggg gatattttta    4560
taattatttt ttttatagtt tttagatctt cttttttaga gcgccttgta ggcctttatc    4620
catgctggtt ctagagaagg tgttgtgaca aattgcccctt tcagtgtgac aaatcaccct    4680
caaatgacag tcctgtctgt gacaaattgc ccttaacccct gtgacaaatt gccctcagaa    4740
gaagctgttt tttcacaaag ttatccctgc ttattgactc ttttttattt agtgtgacaa    4800
tctaaaaact tgtcacactt cacatggatc tgtcatggcg gaaacagcgg ttatcaatca    4860
caagaaacgt aaaaatagcc cgcgaatcgt ccagtcaaac gacctcactg aggcggcata    4920
tagtctctcc cggatcaaa aacgtatgct gtatctgttc gttgaccaga tcagaaaatc    4980
tgatggcacc ctacaggaac atgacggtat ctgcgagatc catgttgcta aatatgctga    5040
aatattcgga ttgacctctg cggaagccag taaggatata cggcaggcat tgaagagttt    5100
```

```
cgcggggaag gaagtggttt tttatcgccc tgaagaggat gccggcgatg aaaaaggcta   5160
tgaatctttt ccttggttta tcaaacgtgc gcacagtcca tccagagggc tttacagtgt   5220
acatatcaac ccatatctca ttcccttctt tatcgggtta cagaaccggt ttacgcagtt   5280
tcggcttagt gaaacaaaag aaatcaccaa tccgtatgcc atgcgtttat acgaatccct   5340
gtgtcagtat cgtaagccgg atggctcagg catcgtctct ctgaaaatcg actggatcat   5400
agagcgttac cagctgcctc aaagttacca gcgtatgcct gacttccgcc gccgcttcct   5460
gcaggtctgt gttaatgaga tcaacagcag aactccaatg cgcctctcat acattgagaa   5520
aaagaaaggc cgccagacga ctcatatcgt attttccttc cgcgatatca cttccatgac   5580
gacaggatag tctgagggtt atctgtcaca gatttgaggg tggttcgtca catttgttct   5640
gacctactga gggtaatttg tcacagtttt gctgtttcct tcagcctgca tggattttct   5700 catactttt gaactgtaat ttttaaggaa gccaaatttg agggcagttt gtcacagttg   5760
atttccttct ctttcccttc gtcatgtgac ctgatatcgg gggttagttc gtcatcattg   5820
atgagggttg attatcacag tttattactc tgaattggct atccgcgtgt gtacctctac   5880
ctggagtttt tcccacggtg gatatttctt cttgcgctga gcgtaagagc tatctgacag   5940
aacagttctt ctttgcttcc tcgccagttc gctcgctatg ctcggttaca cggctgcggc   6000
gagcgctagt gataataagt gactgaggta tgtgctcttc ttatctcctt ttgtagtgtt   6060
gctcttattt taaacaactt tgcggttttt tgatgacttt gcgattttgt tgttgctttg   6120
cagtaaattg caagatttaa taaaaaaacg caaagcaatg attaaaggat gttcagaatg   6180
aaactcatgg aaacacttaa ccagtgcata aacgctggtc atgaaatgac gaaggctatc   6240
gccattgcac agtttaatga tgacagcccg gaagcgagga aaataacccg cgctggagaa   6300
ataggtgaag cagcggattt agttgggtt tcttctcagg ctatcagaga tgccgagaaa   6360
gcagggcgac taccgcaccc ggatatggaa attcgaggac gggttgagca acgtgttggt   6420
tatacaattg aacaaattaa tcatatgcgt gatgtgtttg gtacgcgatt gcgacgtgct   6480
gaagacgtat ttccaccggt gatcggggtt gctgcccata aggtggcgt ttacaaaacc   6540 tcagtttctg ttcatcttgc tcaggatctg gctctgaagg ggctacgtgt tttgctcgtg   6600
gaaggtaacg accccagggg aacagcctca atgtatcacg gatgggtacc agatcttcat   6660
attcatgcag aagacactct cctgcctttc tatcttgggg aaaaggacga tgtcacttat   6720
gcaataaagc ccacttgctg gccggggctt gacattattc cttcctgtct ggctctgcac   6780
cgtattgaaa ctgagttaat gggcaaattt gatgaaggta aactgcccac cgatccacac   6840
ctgatgctcc gactggccat tgaaactgtt gctcatgact atgatgtcat agttattgac   6900
agcgcgccta acctgggtat cggcacgatt aatgtcgtat gtgctgctga tgtgctgatt   6960
gttcccacgc ctgctgagtt gtttgactac acctccgcac tgcagttttt cgatatgctt   7020
cgtgatctgc tcaagaacgt tgatcttaaa gggttcgagc tgatgtacg tatttttgctt   7080 accaaataca gcaatagtaa tggctctcag tccccgtgga tggaggagca aattcgggat   7140
gcctggggaa gcatggttct aaaaaatgtt gtacgtgaaa cggatgaagt tggtaaaggt   7200
cagatccgga tgagaactgt ttttgaacag gccattgatc aacgctcttc aactggtgcc   7260
tggagaaatg ctcttctat ttgggaacct gtctgcaatg aaattttcga tcgtctgatt   7320
aaaccacgct gggagattag ataatgaagc gtgcgcctgt tattccaaaa catacgctca   7380
atactcaacc ggttgaagat acttcgttat cgacaccagc tgccccgatg gtggattcgt   7440
```

```
taattgcgcg cgtaggagta atggctcgcg gtaatgccat tactttgcct gtatgtggtc    7500
gggatgtgaa gtttactctt gaagtgctcc ggggtgatag tgttgagaag acctctcggg    7560
tatggtcagg taatgaacgt gaccaggagc tgcttactga ggacgcactg gatgatctca    7620
tcccttcttt tctactgact ggtcaacaga caccggcgtt cggtcgaaga gtatctggtg    7680
tcatagaaat tgccgatggg agtcgccgtc gtaaagctgc tgcacttacc gaaagtgatt    7740
atcgtgttct ggttggcgag ctggatgatg agcagatggc tgcattatcc agattgggta    7800
acgattatcg cccaacaagt gcttatgaac gtggtcagcg ttatgcaagc cgattgcaga    7860
atgaatttgc tggaaatatt tctgcgctgg ctgatgcgga aaatatttca cgtaagatta    7920
ttacccgctg tatcaacacc gccaaattgc ctaaatcagt tgttgctctt ttttctcacc    7980
ccggtgaact atctgcccgg tcaggtgatg cacttcaaaa agcctttaca gataaagagg    8040
aattacttaa gcagcaggca tctaaccttc atgagcagaa aaaagctggg gtgatatttg    8100
aagctgaaga agttatcact cttttaactt ctgtgcttaa aacgtcatct gcatcaagaa    8160
ctagtttaag ctcacgacat cagtttgctc ctggagcgac agtattgtat aagggcgata    8220
aaatggtgct taacctggac aggtctcgtg ttccaactga gtgtatagag aaaattgagg    8280
ccattcttaa ggaacttgaa aagccagcac cctgatgcga ccacgtttta gtctacgttt    8340
atctgtcttt acttaatgtc ctttgttaca ggccagaaag cataactggc ctgaatattc    8400
tctctgggcc cactgttcca cttgtatcgt cggtctgata atcagactgg gaccacggtc    8460
ccactcgtat cgtcggtctg attattagtc tgggaccacg gtcccactcg tatcgtcggt    8520
ctgattatta gtctgggacc acggtcccac tcgtatcgtc ggtctgataa tcagactggg    8580
accacggtcc cactcgtatc gtcggtctga ttattagtct gggaccatgg tcccactcgt    8640
atcgtcggtc tgattattag tctgggacca cggtcccact cgtatcgtcg gtctgattat    8700
tagtctggaa ccacggtccc actcgtatcg tcggtctgat tattagtctg gaccacggt    8760 cccactcgta tcgtcggtct gattattagt ctgggaccac gatcccactc gtgttgtcgg    8820
tctgattatc ggtctgggac cacggtccca cttgtattgt cgatcagact atcagcgtga    8880
gactacgatt ccatcaatgc ctgtcaaggg caagtattga catgtcgtcg taacctgtag    8940
aacggagtaa cctcggtgtg cggttgtatg cctgctgtgg attgctgctg tgtcctgctt    9000
atccacaaca ttttgcgcac ggttatgtgg acaaaatacc tggttaccca ggccgtgccg    9060
gcacgttaac cgggctgcat ccgatgcaag tgtgtcgctg tcgacgagct cgcgagctcg    9120
gacatgaggt tgccccgtat tcagtgtcgc tgatttgtat tgtctgaagt tgtttttacg    9180
ttaagttgat gcagatcaat taatacgata cctgcgtcat aattgattat ttgacgtggt    9240
ttgatggcct ccacgcacgt tgtgatatgt agatgataat cattatcact ttacgggtcc    9300
tttccggtga tccgacaggt tacggggcgg cgacctcgcg ggttttcgct atttatgaaa    9360
attttccggt ttaaggcgtt tccgttcttc ttcgtcataa cttaatgttt ttatttaaaa    9420
taccctctga aaagaaagga aacgacaggt gctgaaagcg agcttttttgg cctctgtcgt    9480 ttcctttctc tgttttttgtc cgtggaatga acaatggaag tccgagctca tcgctaataa    9540
cttcgtatag catacattat acgaagttat attcgatgcg gccgcaaggg gttcgcgtca    9600
gcgggtgttg gcgggtgtcg gggctggctt aactatgcgg catcagagca gattgtactg    9660
agagtgcacc atatgcggtg tgaaataccg cacagatgcg taaggagaaa ataccgcatc    9720
aggcgccatt cgccattcag gctgcgcaac tgttgggaag ggcgatcggt gcgggcctct    9780
tcgctattac gccagctggc gaaagggggga tgtgctgcaa ggcgattaag ttgggtaacg    9840
```

```
ccagggtttt cccagtcacg acgttgtaaa acgacggcca gtgaattgta atacgactca    9900
ctatagggcg aattcgagct cggtacccgg ggatcctcgt ttaaaccatc atcaataata    9960
taccttattt tggattgaag ccaatatgat aatgagatgg cgggcgcggg gcggggcgcg   10020
gggcgggagg cgggtttggg ggcgggccgg cgggcgggc ggtgtggcgg aagtggactt   10080
tgtaagtgtg gcggatgtga cttgctagtg ccgggcgcgg taaaagtgac gttttccgtg   10140
cgcgacaacg cccccgggaa gtgacatttt tcccgcggtt tttaccggat gttgtagtga   10200
atttgggcgt aaccaagtaa gatttggcca ttttcgcggg aaaactgaaa cggggaagtg   10260
aaatctgatt aattttgcgt tagtcatacc gcgtaatatt tgtctagggc cgagggactt   10320
tggccgatta cgtggaggac tcgcccaggt gtttttgag gtgaatttcc gcgttccggg   10380
tcaaagtctg cgttttatta ttataggata tcccattgca tacgttgtat ccatatcata   10440
atatgtacat ttatattggc tcatgtccaa cattaccgcc atgttgacat tgattattga   10500
ctagttatta atagtaatca attacggggt cattagttca tagcccatat atggagttcc   10560
gcgttacata acttacggta aatggcccgc ctggctgacc gcccaacgac ccccgcccat   10620
tgacgtcaat aatgacgtat gttcccatag taacgccaat agggactttc cattgacgtc   10680
aatgggtgga gtatttacgg taaactgccc acttggcagt acatcaagtg tatcatatgc   10740
caagtacgcc ccctattgac gtcaatgacg gtaaatggcc cgcctggcat tatgcccagt   10800
acatgacctt atgggacttt cctacttggc agtacatcta cgtattagtc atcgctatta   10860
ccatggtgat gcggttttgg cagtacatca atgggcgtgg atagcggttt gactcacggg   10920
gatttccaag tctccacccc attgacgtca atgggagttt gttttggcac caaaatcaac   10980
gggactttcc aaaatgtcgt aacaactccg ccccattgac gcaaatgggc ggtaggcgtg   11040
tacggtggga ggtctatata agcagagctc tccctatcag tgatagagat ctccctatca   11100
gtgatagaga tcgtcgacga gctcgtttag tgaaccgtca gatcgcctgg agacgccatc   11160
cacgctgttt tgacctccat agaagacacc gggaccgatc cagcctccgc ggccgggaac   11220
ggtgcattgg aacgcggatt ccccgtgcca agagtgagat cttccgttta tctaggtacc   11280
gggccccccc tcgaggtcga cggtatcgat aagcttcacg ctgccgcaag cactcagggc   11340
gcaagggctg ctaaaggaag cggaacacgt agaaagccag tccgcagaaa cggtgctgac   11400
cccgatgaa tgtcagctac tgggctatct ggacaaggga aaacgcaagc gcaaagagaa   11460
agcaggtagc ttgcagtggg cttacatggc gatagctaga ctgggcggtt ttatggacag   11520
caagcgaacc ggaattgcca gctggggcgc cctctggtaa ggttgggaag ccctgcaaag   11580
taaactggat ggctttcttg ccgccaagga tctgatggcg cagggatca agatctaacc   11640
aggagctatt taatgcaac agttaaccag ctggtacgca aaccacgtgc tcgcaaagtt   11700
gcgaaaagca acgtgcctgc gctggaagca tgcccgcaaa acgtggcgt atgtactcgt   11760
gtatatacta ccactcctaa aaaccgaac tccgcgctgc gtaaagtatg ccgtgttcgt   11820
ctgactaacg gtttcgaagt gacttcctac atcggtggtg aaggtcacaa cctgcaggag   11880
cactccgtga tcctgatccg tggcggtcgt gttaaagacc tcccgggtgt tcgttaccac   11940
accgtacgtg gtgcgcttga ctgctccggc gttaaagacc gtaagcaggc tcgttccaag   12000
tatggcgtga agcgtcctaa ggcttaatgg tagatctgat caagagacag gatgacggtc   12060
gttccgcatg cttgaacaag atggattgca cgcaggttct ccggccgctt gggtggagag   12120
gctattcggc tatgactggg cacaacagac aatcggctgc tctgatgccg ccgtgttccg   12180
```

```
gctgtcagcg caggggcgcc cggttctttt tgtcaagacc gacctgtccg gtgccctgaa    12240
tgaactgcag gacgaggcag cgcggctatc gtggctggcc acgacgggcg ttccttgcgc    12300
agctgtgctc gacgttgtca ctgaagcggg aagggactgg ctgctattgg gcgaagtgcc    12360
ggggcaggat ctcctgtcat ctcaccttgc tcctgccgag aaagtatcca tcatggctga    12420
tgcaatgcgg cggctgcata cgcttgatcc ggctacctgc ccattcgacc accaagcgaa    12480
acatcgcatc gagcgagcac gtactcggat ggaagccggt cttgtcgatc aggatgatct    12540
ggacgaagag catcaggggc tcgcgccagc cgaactgttc gccaggctca aggcgcgcat    12600
gcccgacggc gaggatctcg tcgtgaccca tggcgatgcc tgcttgccga atatcatggt    12660
ggaaaatggc cgcttttctg gattcatcga ctgtggccgg ctgggtgtgg cggaccgcta    12720
tcaggacata gcgttggcta cccgtgatat tgctgaagag cttggcggcg aatgggctga    12780
ccgcttcctc gtgctttacg gtatcgccgc tcccgattcg cagcgcatcg ccttctatcg    12840
ccttcttgac gagttcttct gagcgggact ctggggttcg aaatgaccga ccaagcgacg    12900
cccaacctgc catcacgaga tttcgattcc accgccgcct tctatgaaag gttgggcttc    12960
ggaatcgttt tccgggacgc cggctggatg atcctccagc gcgggatct catgctggag     13020 ttcttcgccc accccgggct cgatcccctc gggggaatc agaattcagt cgacagcggc      13080
cgcgatctgc tgtgccttct agttgccagc catctgttgt tgcccctcc ccgtgccttt     13140
```

```
tgcgcaaact attaactggc gaactactta ctctagcttc ccggcaacaa ttaatagact      14640
ggatggaggc ggataaagtt gcaggaccac ttctgcgctc ggcccttccg gctggctggt      14700
ttattgctga taaatctgga gccggtgagc gtgggtctcg cggtatcatt gcagcactgg      14760
ggccagatgg taagccctcc cgtatcgtag ttatctacac gacggggagt caggcaacta      14820
tggatgaacg aaatagacag atcgctgaga taggtgcctc actgattaag cattggtaac      14880
tgtcagacca agtttactca tatatacttt agattgattt aaaatacgta tatatgtatt      14940
agtcatcgct attaccatgg ttaatgcgcc gctacagggc gcgtccattc gccattcagg      15000
ctgcgcaact gttgggaagg gcgatcgtg cgggcctctt cgctattacg ccagctggcg      15060 aaaggggat gtgctgcaag gcgattaagt tgggtaacgc cagggttttc ccagtcacga      15120
cgttgtaaaa cgacggccag tgaattgtaa tacgactcac tatagggcga attgggccct      15180
ctagatgcat gctcgagcgg ccgccagtgt gatggatatc tgcagaattc cagcacactg      15240
gcggccgtta ctagtggatc cgagctcggt accaagcttg gcgtaatcat ggtcatagct      15300
gtttcctgtg tgaaattgtt atccgctcac aattccacac aacatacgag ccggaagcat      15360
aaagtgtaaa gcctggggtg cctaatgagt gagctaactc acattaattg cgttgcgctc      15420
ac                                                                    15422
```

<210> SEQ ID NO 15
<211> LENGTH: 39535
<212> TYPE: DNA
<213> ORGANISM: Pan troglodytes
<220> FEATURE:
<221> NAME/KEY: misc_feature
<222> LOCATION: (24391)..(24393)
<223> OTHER INFORMATION: n is a, c, g, or t

<400> SEQUENCE: 15

```
catcatcaat aatataccct attttggatt gaagccaata tgataatgag atgggcggcg        60
cggggcgggg cgcggggcgg gaggcgggtt tgggggcggg ccggcgggcg gggcggtgtg       120
gcggaagtgg actttgtaag tgtggcggat gtgacttgct agtgccgggc gcggtaaaag       180
tgacgttttc cgtgcgcgac aacgcccccg ggaagtgaca ttttccccgc ggttttacc       240 ggatgttgta gtgaatttgg gcgtaaccaa gtaagatttg gccattttcg cgggaaaact       300
gaaacgggga agtgaaatct gattaatttt gcgttagtca taccgcgtaa tatttgtcta       360
gggccgaggg actttggccg attacgtgga ggactcgccc aggtgttttt tgaggtgaat       420
ttccgcgttc cgggtcaaag tctgcgtttt attattatag gatatcccat tgcatacgtt       480
gtatccatat cataatatgt acatttatat tggctcatgt ccaacattac cgccatgttg       540
acattgatta ttgactagtt attaatagta atcaattacg gggtcattag ttcatagccc       600
atatatggag ttccgcgtta cataacttac ggtaaatggc ccgcctggct gaccgcccaa       660
cgacccccgc ccattgacgt caataatgac gtatgttccc atagtaacgc caatagggac       720
tttccattga cgtcaatggg tggagtattt acggtaaact gcccacttgg cagtacatca       780
agtgtatcat atgccaagta cgccccctat tgacgtcaat gacggtaaat ggcccgcctg       840
gcattatgcc cagtacatga ccttatggga ctttcctact tggcagtaca tctacgtatt       900
agtcatcgct attaccatgg tgatgcggtt ttggcagtac atcaatgggc gtggatagcg       960
gtttgactca cggggatttc caagtctcca ccccattgac gtcaatggga gtttgttttg      1020
gcaccaaaat caacgggact ttccaaaatg tcgtaacaac tccgccccat tgacgcaaat      1080
```

```
gggcggtagg cgtgtacggt gggaggtcta tataagcaga gctctcccta tcagtgatag    1140
agatctccct atcagtgata gagatcgtcg acgagctcgt ttagtgaacc gtcagatcgc    1200
ctggagacgc catccacgct gttttgacct ccatagaaga caccgggacc gatccagcct    1260
ccgcggccgg gaacggtgca ttggaacgcg gattccccgt gccaagagtg agatcttccg    1320
tttatctagg taccgggccc ccctcgagg  tcgacggtat cgataagctt cacgctgccg    1380
caagcactca gggcgcaagg gctgctaaag gaagcggaac acgtagaaag ccagtccgca    1440
gaaacggtgc tgaccccgga tgaatgtcag ctactgggct atctggacaa gggaaaacgc    1500
aagcgcaaag agaaagcagg tagcttgcag tgggcttaca tggcgatagc tagactgggc    1560
ggttttatgg acagcaagcg aaccggaatt gccagctggg gcgccctctg gtaaggttgg    1620
gaagccctgc aaagtaaact ggatggcttt cttgccgcca aggatctgat ggcgcagggg    1680
atcaagatct aaccaggagc tatttaatgg caacagttaa ccagctggta cgcaaaccac    1740
gtgctcgcaa agttgcgaaa agcaacgtgc ctgcgctgga agcatgcccg caaaaacgtg    1800
gcgtatgtac tcgtgtatat actaccactc ctaaaaaacc gaactccgcg ctgcgtaaag    1860
tatgccgtgt tcgtctgact aacggtttcg aagtgacttc ctacatcggt ggtgaaggtc    1920
acaacctgca ggagcactcc gtgatcctga tccgtggcgg tcgtgttaaa gacctcccgg    1980
gtgttcgtta ccacaccgta cgtggtgcgc ttgactgctc cggcgttaaa gaccgtaagc    2040
aggctcgttc caagtatggc gtgaagcgtc taaggctta  atggtagatc tgatcaagag    2100
acaggatgac ggtcgtttcg catgcttgaa caagatggat tgcacgcagg ttctccggcc    2160
gcttgggtgg agaggctatt cggctatgac tgggcacaac agacaatcgg ctgctctgat    2220
gccgccgtgt tccggctgtc agcgcagggg cgcccggttc tttttgtcaa gaccgacctg    2280
tccggtgccc tgaatgaact gcaggacgag gcagcgcggc tatcgtggct ggccacgacg    2340
ggcgttcctt gcgcagctgt gctcgacgtt gtcactgaag cgggaaggga ctggctgcta    2400
ttgggcgaag tgccggggca ggatctcctg tcatctcacc ttgctcctgc cgagaaagta    2460
tccatcatgg ctgatgcaat gcggcggctg catacgcttg atccggctac ctgcccattc    2520
gaccaccaag cgaaacatcg catcgagcga gcacgtactc ggatggaagc cggtcttgtc    2580
gatcaggatg atctggacga agagcatcag gggctcgcgc cagccgaact gttcgccagg    2640
ctcaaggcgc gcatgcccga cggcgaggat ctcgtcgtga cccatggcga tgcctgcttg    2700
ccgaatatca tggtggaaaa tggccgcttt tctggattca tcgactgtgg ccggctgggt    2760
gtggcggacc gctatcagga catagcgttg gctacccgtg atattgctga agagcttggc    2820
ggcgaatggg ctgaccgctt cctcgtgctt tacggtatcg ccgctcccga ttcgcagcgc    2880
atcgccttct atcgccttct tgacgagttc ttctgagcgg gactctgggg ttcgaaatga    2940
ccgaccaagc gacgcccaac ctgccatcac gagatttcga ttccaccgcc gccttctatg    3000
aaaggttggg cttcggaatc gttttccggg acgccggctg gatgatcctc cagcgcgggg    3060
atctcatgct ggagttcttc gcccacccccg gctcgatcc  cctcgggggg aatcagaatt    3120
cagtcgacag cggccgcgat ctgctgtgcc ttctagttgc cagccatctg ttgtttgccc    3180 ctccccgtg  ccttccttga ccctggaagg tgccactccc actgtccttt cctaataaaa    3240
tgaggaaatt gcatcgcatt gtctgagtag gtgtcattct attctggggg gtggggtggg    3300
gcaggacagc aagggggagg attgggaaga caatagcagg catgctgggg atgcggtggg    3360
ctctatggcc gatcagcgat cgctgaggtg ggtgagtggg cgtggcctgg ggtggtcatg    3420
aaaatatata agttgggggt cttagggtct ctttatttgt gttgcagaga ccgccggagc    3480
```

```
catgagcggg agcagcagca gcagcagtag cagcagcgcc ttggatggca gcatcgtgag    3540
cccttatttg acgacgcgga tgccccactg ggccggggtg cgtcagaatg tgatgggctc    3600
cagcatcgac ggccgacccg tcctgcccgc aaattccgcc acgctgacct atgcgaccgt    3660
cgcggggacg ccgttggacg ccaccgccgc cgccgccgcc accgcagccg cctcggccgt    3720
gcgcagcctg gccacggact ttgcattcct gggaccactg gcgacagggg ctacttctcg    3780
ggccgctgct gccgccgttc gcgatgacaa gctgaccgcc ctgctggcgc agttggatgc    3840
gcttactcgg gaactgggtg acctttctca gcaggtcatg gccctgcgcc agcaggtctc    3900
ctccctgcaa gctggcggga atgcttctcc cacaaatgcc gtttaagata aataaaacca    3960
gactctgttt ggattaaaga aaagtagcaa gtgcattgct ctctttattt cataattttc    4020
cgcgcgcgat aggccctaga ccagcgttct cggtcgttga gggtgcggtg tatcttctcc    4080
aggacgtggt agaggtggct ctggacgttg agatacatgg gcatgagccc gtcccggggg    4140
tggaggtagc accactgcag agcttcatgc tccggggtgg tgttgtagat gatccagtcg    4200
tagcaggagc gctgggcatg gtgcctaaaa atgtccttca gcagcaggcc gatggccagg    4260
gggaggccct tggtgtaagt gtttacaaaa cggttaagtt gggaagggtg cattcgggga    4320
gagatgatgt gcatcttgga ctgtattttt agattggcga tgtttccgcc cagatccctt    4380
ctgggattca tgttgtgcag gaccaccagt acagtgtatc cggtgcactt ggggaatttg    4440
tcatgcagct tagagggaaa agcgtggaag aacttggaga cgcccttgtg gcctcccaga    4500
ttttccatgc attcgtccat gatgatggca atgggcccgc gggaggcagc ttgggcaaag    4560
atatttctgg ggtcgctgac gtcgtagttg tgttccaggg tgaggtcgtc ataggccatt    4620
tttacaaagc gcgggcggag ggtgcccgac tggggatga tggtcccctc tggccccggg    4680
gcgtagttgc cctcgcagat ctgcatttcc caggccttaa tctcggaggg gggaatcata    4740
tccacctgcg gggcgatgaa gaaaacggtt ccggagccg gggagattaa ctgggatgag    4800
agcaggtttc taagcagctg tgattttcca caaccggtgg gcccataaat aacacctata    4860
accggttgca gctggtagtt tagagagctg cagctgccgt cgtcccggag gaggggggcc    4920
acctcgttga gcatgtccct gacgcgcatg ttctccccga ccagatccgc cagaaggcgc    4980
tcgccgccca gggacagcag ctcttgcaag gaagcaaagt ttttcagcgg cttgaggccg    5040
tccgccgtgg gcatgttttt cagggtctgg ctcagcagct ccaggcggtc ccagagctcg    5100
gtgacgtgct ctacggcatc tctatccagc atatctcctc gtttcgcggg ttggggcgac    5160
tttcgctgta gggcaccaag cggtggtcgt ccagcgggc cagagtcatg tccttccatg    5220
ggcgcagggt cctcgtcagg gtggtctggg tcacggtgaa ggggtgcgct ccgggctgag    5280
cgcttgccaa ggtgcgcttg aggctggttc tgctggtgct gaagcgctgc cggtcttcgc    5340
cctgcgcgtc ggccaggtag catttgacca tggtgtcata gtccagcccc tccgcggcgt    5400
gtcccttggc gcgcagcttg cccttggagg tggcgccgca cgaggggcag agcaggctct    5460
tgagcgcgta gagcttgggg gcgaggaaga ccgattcggg ggagtaggcg tccgcgccgc    5520
agacccccgca cacggtctcg cactccacca gccaggtgag ctcggggcgc gccgggtcaa    5580
aaaccaggtt tcccccatgc tttttgatgc gtttcttacc tcgggtctcc atgaggtggt    5640
gtccccgctc ggtgacgaag aggctgtccg tgtctccgta gaccgacttg aggggtcttt    5700
tctccagggg ggtccctcgg tcttcctcgt agaggaactc ggaccactct gagacgaagg    5760
cccgcgtcca ggccaggacg aaggaggcta tgtgggaggg gtagcggtcg ttgtccacta    5820
```

```
gggggtccac cttctccaag gtgtgaagac acatgtcgcc ttcctcggcg tccaggaagg    5880
tgattggctt gtaggtgtag gccacgtgac cgggggttcc tgacgggggg gtataaaagg    5940
gggtgggggc gcgctcgtcg tcactctctt ccgcatcgct gtctgcgagg gccagctgct    6000
ggggtgagta ttccctctcg aaggcgggca tgacctccgc gctgaggttg tcagtttcca    6060
aaaacgagga ggatttgatg ttcacctgtc ccgaggtgat acctttgagg gtacccgcgt    6120
ccatctggtc agaaaacacg atcttttat tgtccagctt ggtggcgaac gacccgtaga    6180
gggcgttgga gagcagcttg gcgatggagc gcagggtctg gttcttgtcc ctgtcggcgc    6240
gctccttggc cgcgatgttg agctgcacgt actcgcgcgc gacgcagcgc cactcgggga    6300
agacggtggt gcgctcgtcg ggcaccaggc gcacgcgcca gccgcggttg tgcagggtga    6360
ccaggtccac gctggtggcg acctcgccgc gcaggcgctc gttggtccag cagagacggc    6420
cgcccttgcg cgagcagaag gggggcaggg ggtcgagctg ggtctcgtcc gggggggtccg    6480 cgtccacggt gaaaaccccg gggcgcaggc gcgcgtcgaa gtagtctatc ttgcaacctt    6540
gcatgtccag cgcctgctgc cagtcgcggg cggcgagcgc gcgctcgtag gggttgagcg    6600
gcgggcccca gggcatgggg tgggtgagtg cggaggcgta catgccgcag atgtcataga    6660
cgtagagggg ctcccgcagg accccgatgt aggtggggta gcagcggccg ccgcggatgc    6720
tggcgcgcac gtagtcatac agctcgtgcg aggggggcgag gaggtcgggg cccaggttgg    6780
tgcgggcggg gcgctccgtg cggaagacga tctgcctgaa gatggcatgc gagttggaag    6840
agatggtggg gcgctggaag acgttgaagc tggcgtcctg caggccgacg gcgtcgcgca    6900
cgaaggaggc gtaggagtcg cgcagcttgt gtaccagctc ggcggtgacc tgcacgtcga    6960
gcgcgcagta gtcgagggtc tcgcggatga tgtcatattt agcctgcccc ttctttttcc    7020
acagctcgcg gttgaggaca aactcttcgc ggtctttcca gtactcttgg atcgggaaac    7080
cgtccggttc cgaacggtaa gagcctagca tgtagaactg gttgacggcc tggtaggcgc    7140
agcagccctt ctccacgggg agggcgtagg cctgcgcggc cttgcggagc gaggtgtggg    7200
tcagggcgaa ggtgtccctg accatgactt tgaggtactg gtgcttgaag tcggagtcgt    7260
cgcagccgcc ccgctcccag agcgagaagt cggtgcgctt cttggagcgg ggggttgggca    7320 gagcgaaggt gacatcgttg aagaggattt tgcccgcgcg gggcatgaag ttgcgggtga    7380
tgcgaagggg ccccggcact tcagagcggt tgttgatgac ctgggcggcg agcacgatct    7440
cgtcgaagcc gttgatgttg tggcccacga tgtagagttc caggaagcgg ggccggccct    7500
ttacggtggg cagcttcttt agctcttcgt aggtgagctc ctcggcgag gcgaggccgt    7560 gctcggccag ggcccagtcc gcgaggtgcg ggttgtctct gaggaaggac tcccagaggt    7620
cgcgggccag gagggtctgc aggcggtccc tgaaggtcct gaactggcgg cccacgccca    7680 tttttttcggg ggtgatgcag tagaaggtga ggggtcttg ctgccagcgg tcccagtcga    7740
gctgcagggc gaggtcgcgc gcggcggtga ccaggcgctc gtcgcccccg aatttcatga    7800
ccagcatgaa gggcacgagc tgcttttccga aggcccccat ccaagtgtag gtctctacat    7860
cgtaggtgac aaagaggcgc tccgtgcgag gatgcgagcc gatcgggaag aactggatct    7920
cccgccacca gttggaggag tggctgttga tgtggtggaa gtagaagtcc cgtcgccggg    7980
ccgaacactc gtgctggctt ttgtaaaagc gagcgcagta ctggcagcgc tgcacgggct    8040
gtacctcatg cacgagatgc acctttcgcc cgcgcacgag gaagccgagg ggaaatctga    8100
gcccccgccc tggctcgcgg catggctggt gctcttctac tttggatgcg tgtccgtctc    8160
cgtctggctc ctcgagggggt gttacggtgg agcggaccac cacgccgcgc gagccgcagg    8220
```

```
tccagatatc ggcgcgcggc ggtcggagtt tgatgacgac atcgcgcagc tgggagctgt   8280
ccatggtctg gagctcccgc ggcggcggca ggtcagccgg gagttcttgc aggttcacct   8340
cgcagagtcg ggccagggcg cggggcaggt ctaggtggta cctgatctct aggggcgtgt   8400
tggtggcggc gtcgatggct tgcaggagcc cgcagccccg gggggcgacg acggtgcccc   8460
gcggggtggt ggtggtggtg gcggtgcagc tcagaagcgg tgccgcgggc gggcccccgg   8520 aggtagggg ggctccggtc ccgcgggcag gggcggcagc ggcacgtcgg cgtggagcgc   8580
gggcaggagt tggtgctgtg cccggaggtt gctggcgaag cgacgacgc ggcggttgat    8640 ctcctggatc tggcgcctct gcgtgaagac gacgggcccg gtgagcttga acctgaaaga   8700
gagttcgaca gaatcaatct cggtgtcatt gaccgcggcc tggcgcagga tctcctgcac   8760
gtctcccgag ttgtcttggt aggcgatctc ggccatgaac tgctcgatct cttcctcctg   8820
gaggtctccg cgtccggcgc gttccacggt ggccgccagg tcgttggaga tgcgcccat    8880 gagctgcgag aaggcgttga gtccgccctc gttccagact cggctgtaga ccacgccccc   8940
ctggtcatcg cgggcgcgca tgaccacctg cgcgaggttg agctccacgt gccgcgcgaa   9000
gacggcgtag ttgcgcagac gctggaagag gtagttgagg gtggtggcgg tgtgctcggc   9060
cacgaagaag ttcatgaccc agcggcgcaa cgtggattcg ttgatgtccc caaggcctc    9120 cagccgttcc atggcctcgt agaagtccac ggcgaagttg aaaaactggg agttgcgcgc   9180
cgacacggtc aactcctcct ccagaagacg gatgagctcg gcgacggtgt cgcgcacctc   9240
gcgctcgaag gctatgggga tctcttcctc cgctagcatc accacctcct cctcttcctc   9300
ctcttctggc acttccatga tggcttcctc ctcttcgggg ggtggcggcg gcggcggtgg   9360
gggagggggc gctctgcgcc ggcggcggcg caccggagg cggtcacga agcgcgcgat     9420 catctccccg cggcggcggc gcatggtctc ggtgacggcg cggccgttct cccggggcg    9480 cagttggaag acgccgccgg acatctggtg ctggggcggg tggccgtgag gcagcgagac   9540
ggcgctgacg atgcatctca acaattgctg cgtaggtacg ccgccgaggg acctgaggga   9600
gtccatatcc accggatccg aaaacctttc gaggaaggcg tctaaccagt cgcagtcgca   9660
aggtaggctg agcaccgtgg cgggcggcgg ggggtgggg gagtgtctgg cggaggtgct   9720
gctgatgatg taattgaagt aggcggactt gacacggcgg atggtcgaca ggagcaccat   9780
gtccttgggt ccggcctgct ggatgcgag gcggtcggct atgccccagg cttcgttctg    9840
gcatcggcgc aggtccttgt agtagtcttg catgagcctt ccaccggca cctcttctcc    9900 ttcctcttct gcttcttcca tgtctgcttc ggccctgggg cggcgccgcg ccccctgcc    9960 ccccatgcgc gtgaccccga accccctgag cggttggagc agggccaggt cggcgacgac  10020
gcgctcggcc aggatggcct gctgcacctg cgtgagggtc gtttggaagt catccaagtc  10080
cacgaagcgg tggtaggcgc ccgtgttgat ggtgtaggtg cagttggcca tgacggacca  10140
gttgacggtc tggtggcccg gttgcgacat ctcggtgtac ctgagtcgcg agtaggcgcg  10200
ggagtcgaag acgtagtcgt tgcaagtccg caccaggtac tggtagccca ccaggaagtg  10260
cggcggcggc tggcggtaga ggggccagcc caggtggcg ggggctccgg gggccaggtc   10320
ttccagcatg aggcggtggt aggcgtagat gtacctggac atccaggtga tacccgcggc  10380
ggtggtggag gcgcgcggga agtcgcgcac ccggttccag atgttgcgca ggggcagaaa  10440
gtgctccatg gtaggcgtgc tctgtccagt cagacgcgcg cagtcgttga tactctagac  10500
cagggaaaac gaaagccggt cagcgggcac tcttccgtgg tctggtgaat agatcgcaag  10560
```

```
ggtatcatgg cggagggcct cggttcgagc cccgggtccg ggccggacgg tccgccatga   10620
tccacgcggt taccgcccgc gtgtcgaacc caggtgtgcg acgtcagaca acggtggagt   10680
gttccttttg gcgttttttct ggccgggcgc cggcgccgcg taagagacta agccgcgaaa   10740
gcgaaagcag taagtggctc gctccccgta gccggaggga tccttgctaa gggttgcgtt   10800
gcggcgaacc ccggttcgaa tcccgtactc gggccggccg gacccgcggc taaggtgttg   10860
gattggcctc cccctcgtat aaagaccccg cttgcggatt gactccggac acggggacga   10920 gccccttttta tttttgcttt cccagatgc atccggtgtt gcgacagatg cgccccccgc   10980
cccagcagca gcaacaacac cagcaagagc ggcagcaaca gcagcgggag tcatgcaggg   11040 cccccctcacc caccctcggc ggcccggcca cctcggcgtc cgcggccgtg tctggcgcct   11100
gcggcggcgg cggcgggggg ccggctgacg accccgagga gccccgcgg cgcagggcca   11160 gacactacct ggacctggag gagggcgagg gcctggcgcg gctggggggcg ccgtctcccg   11220 agcgccaccc gcgggtgcag ctaaagcgcg actcgcgcga ggcgtacgtg cctcggcaga   11280
acctgttcag ggaccgcgcg ggcgaggagc ccgaggagat gcgggacagg aggttcagcg   11340
cggggcggga gctgcggcag gggctgaacc gcgagcggct gctgcgcgag gaggactttg   11400
agcccgacgc gcggacgggg atcagccccg cgcgcgcgca cgtggcggcc gccgacctgg   11460
tgacggcgta cgagcagacg gtgaaccagg agatcaactt ccaaaagagt ttcaacaacc   11520
acgtgcgcac gctggtggcg cgcgaggagg tgaccatcgg gctgatgcac ctgtgggact   11580
ttgtgagcgc gctggtgcag aaccccaata gcaagcctct gacggcgcag ctgttcctga   11640
tagtgcagca cagcagggac aacgaggcgt ttagggacgc gctgctgaac atcaccgagc   11700
ccgagggccg gtggctgctg gacctgatta acatcctgca gagcatagtg gtgcaggagc   11760
gcagcctgag cctggccgac aaggtggcgg ccatcaacta ctcgatgctg agcctgggca   11820 agtttttacgc gcgcaagatc taccagacgc cgtacgtgcc catagacaag gaggtgaaga   11880
tcgacggttt ttacatgcgc atggcgctga aggtgctcac cctaagcgac gacctgggcg   11940
tgtaccgcaa cgagcgcatc cacaaggccg tgagcgtgag ccggcggcgc gagctgagcg   12000
accgcgagct gatgcatagc ctgcagcggg cgctggcggg cgccggcagc ggcgacaggg   12060
aggcggagtc ctacttcgat gcggggggcgg acctgcgctg ggcgcccagc cggcgggccc   12120
tggaggccgc gggggtccgc gaggactatg acgaggacgg cgaggaggat gaggagtacg   12180
agctagagga gggcgagtac ctggactaaa ccgcgggtgg tgtttccggt agatgcaaga   12240
cccgaacgtg gtggaccccgg cgctgcgggc ggctctgcag agccagccgt ccggccttaa   12300
ctcctcagac gactggcgac aggtcatgga ccgcatcatg tcgctgacgg cgcgtaaccc   12360
ggacgcgttc cggcagcagc cgcaggccaa caggctctcc gccatcctgg aggcggtggt   12420
gcctgcgcgc tcgaaccccca cgcacgagaa ggtgctggcc atagtgaacg cgctggccga   12480
gaacagggcc atccgcccgg acgaggccgg gctggtgtac gacgcgctgc tgcagcgcgt   12540
ggcccgctac aacagcggca acgtgcagac caacctggac cggctggtgg gggacgtgcg   12600
cgaggcggtg gcgcagcgcg agcgcgcgga tcggcagggc aacctgggct ccatggtggc   12660
gctgaatgcc ttcctgagca cgcagccggc caacgtgccg cggggggcagg aagactacac   12720 caactttgtg agcgcgctgc ggctgatggt gaccgagacc ccccagagcg aggtgtacca   12780
gtcgggtccg gactacttct tccagaccag cagacagggc ctgcagacgg tgaacctgag   12840
ccaggctttc aagaacctgc gggggctgtg gggcgtgaag gcgcccaccg gcgaccgggc   12900
gacggtgtcc agcctgctga cgcccaactc gcgcctgctg ctgctgctga tcgcgccgtt   12960
```

```
cacggacagc ggcagcgtgt cccgggacac ctacctgggg cacctgctga ccctgtaccg   13020
cgaggccatc gggcaggcgc aggtggacga gcacaccttc caggagatca ccagcgttag   13080
ccgcgcgctg gggcaggagg acacgagcag cctggaggcg actctgaact acctgctgac   13140
caaccggcgg cagaagattc cctcgctgca cagcctgacc tccgaggagg agcgcatctt   13200
gcgctacgtg cagcagagcg tgagcctgaa cctgatgcgc gacggggtga cgcccagtgt   13260
ggcgctggac atgaccgcgc gcaacatgga accgggcatg tacgccgcgc accggcctta   13320
catcaaccgc ctgatggact acctgcatcg cgcggcggcc gtgaaccccg agtactttac   13380
caacgccatc ctgaacccgc actggctccc gccgccgggg ttctacagcg ggggcttcga   13440
ggtcccggag gccaacgatg gcttcctgtg gacgacatg gacgacagcg tgttctcccc   13500
gcggccgcag gcgctggcgg aagcgtccct gctgcgtccc aagaaggagg aggaggcgag   13560
tcgccgccgc ggcagcagcg gcgtggcttc tctgtccgag ctgggggcgg cagccgccgc   13620
gcgcccgggc tcctgggcg cagcccctt tccgagcctg gtggggtctc tgcacagcga   13680
gcgcaccacc cgccctcggc tgctgggcga ggacgagtac ctgaataact ccctgctgca   13740
gccggtgcgg gagaaaaacc tgcctcccgc cttccccaac aacggatag agagcctggt   13800 ggacaagatg agcagatgga agacctatgc gcaggagcac agggacgcgc ccgcgctccg   13860
gccgcccacg cggcgccagc gccacgaccg gcagcgggg ctggtgtggg atgacgagga   13920
ctccgcggac gatagcagcg tgctggacct gggagggagc ggcaacccgt tcgcgcacct   13980
gcgcccccgc ctggggagga tgttttaaaa aaaaaaaaa gcaagaagca tgatgcaaaa   14040
attaaataaa actcaccaag gccatggcga ccagcgttg gtttcttgtg ttcccttcag   14100
tatgcggcgc gcggcgatgt accaggaggg acctcctccc tcttacgaga gcgtggtggg   14160
cgcggcggcg gcggcgccct cttctcctt tgcgtcgcag ctgctggagc cgccgtacgt   14220
gcctccgcgc tacctgcggc ctacgggggg gagaaacagc atccgttact cggagctggc   14280 gccctgttc gacaccaccc gggtgtacct ggtggacaac aagtcggcgg acgtggcctc   14340
cctgaactac cagaacgacc acagcaattt tttgaccacg gtcatccaga acaatgacta   14400
cagcccgagc gaggccagca cccagaccat caatctggat gaccggtcgc actggggcgg   14460
cgacctgaaa accatcctgc acaccaacat gcccaacgtg aacgagttca tgttcaccaa   14520
taagttcaag gcgcgggtga tggtgtcgcg ctcgcacacc aaggaagacc gggtggagct   14580
gaagtacgag tgggtggagt tcgagctgcc agagggcaac tactccgaga ccatgaccat   14640
tgacctgatg aacaacgcga tcgtggagca ctatctgaaa gtgggcaggc agaacggggt   14700
cctggagagc gacatcgggg tcaagttcga caccaggaac ttccgcctgg ggctggaccc   14760
cgtgaccggg ctggttatgc ccggggtgta caccaacgag gccttccatc ccgacatcat   14820
cctgctgccc ggctgcgggg tggacttcac ttacagccgc ctgagcaacc tcctgggcat   14880
ccgcaagcgc cagcccttcc aggagggctt caggatcacc tacgaggacc tggagggggg   14940
caacatcccc gcgctcctcg atgtggaggc ctaccaggat agcttgaagg aaaatgaggc   15000
gggacaggag gataccgccc ccgccgcctc cgccgccgcc gagcagggcg aggatgctgc   15060
tgacaccgcg gccgcggacg gggcggaggc cgaccccgct atggtggtgg aggctgccga   15120
gcaggaggag gacatgaatg acagtgcggt gcgcggagac accttcgtca cccgggggga   15180
ggaaaagcaa gcggaggccg aggccgcggc cgaggaaaag caactggcgg cagcagcggc   15240
ggcggcggcg ttggccgcgg cggaggctga gtctgagggg accaagcccg ccaaggagcc   15300
```

```
cgtgattaag cccctgaccg aagatagcaa gaagcgcagt tacaacctgc tcaaggacag    15360
caccaacacc gcgtaccgca gctggtacct ggcctacaac tacggcgacc cgtcgacggg    15420
ggtgcgctcc tggaccctgc tgtgcacgcc ggacgtgacc tgcggctcgg agcaggtgta    15480
ctggtcgctg cccgacatga tgcaagaccc cgtgaccttc cgctccacgc ggcaggtcag    15540
caacttcccg gtggtgggcg ccgagctgct gcccgtgcac tccaagagct tctacaacga    15600
ccaggccgtc tactcccagc tcatccgcca gttcacctct ctgacccacg tgttcaatcg    15660
ctttcctgag aaccagattc tggcgcgccc gcccgccccc accatcacca ccgtcagtga    15720
aaacgttcct gctctcacag atcacgggac gctaccgctg cgcaacagca tcggaggagt    15780
ccagcgagtg accgttactg acgccagacg ccgcacctgc ccctacgttt acaaggcctt    15840
gggcatagtc tcgccgcgcg tccttccag ccgcactttt tgagcaacac caccatcatg    15900
tccatcctga tctcacccag caataactcc ggctggggac tgctgcgcgc gcccagcaag    15960
atgttcggag gggcgaggaa gcgttccgag cagcacccg tgcgcgtgcg cgggcacttc    16020 cgcgcccct ggggagcgca caaacgcggc cgcgcggggc gcaccaccgt ggacgacgcc    16080
atcgactcgg tggtggagca ggcgcgcaac tacaggcccg cggtctctac cgtggacgcg    16140
gccatccaga ccgtggtgcg gggcgcgcgg cggtacgcca agctgaagag ccgccggaag    16200
cgcgtggccc ccgccaccg ccgccgaccc ggggccgccg ccaaacgcgc gccgcggcc    16260 ctgcttcgcc gggccaagcg cacgggccgc cgcgccgcca tgagggccgc gcgccgcttg    16320
gccgccggca tcaccgccgc caccatggcc ccccgtaccc gaagacgcgc ggccgccgcc    16380
gccgccgccg ccatcagtga catggccagc aggcgccggg gcaacgtgta ctgggtgcgc    16440
gactcggtga ccggcacgcg cgtgcccgtg cgcttccgcc ccccgcggac ttgagatgat    16500
gtgaaaaaac aacactgagt ctcctgctgt tgtgtgtatc ccagcggcgg cggcggcgcg    16560
cgcagcgtca tgtccaagcg caaaatcaaa gaagagatgc tccaggtcgt cgcgccggag    16620
atctatgggc ccccgaagaa ggaagagcag gattcgaagc cccgcaagat aaagcgggtc    16680
aaaaagaaaa agaaagatga tggcgatgcc gatggggagg tggagttcct gcgcgccacg    16740
gcgcccaggc gcccggtgca gtggaagggc cggcgcgtaa agcgcgtcct gcgccccggc    16800
accgcggtgg tcttcacgcc cggcgagcgc tccacccgga cttcaagcg cgtctatgac    16860 gaggtgtacg gcgacgaaga cctgctggag caggccaacg agcgcttcgg agagtttgct    16920
tacgggaagc gtcagcggcc gctggggaag gaggacctgc tggcgctgcc gctggaccag    16980
ggcaacccca cccccagtct gaagcccgtg accctgcagc aggtgctgcc gagcagcgca    17040
ccctccgagg cgaagcgggg tctgaagcgc gagggcggcg acctggcgcc caccgtgcag    17100
ctcatggtgc ccaagcggca gaggctggag gatgtgctgg agaaaatgaa agtagacccc    17160
ggtctgcagc cggacatcag ggtccgtccc atcaagcagg tggcgccggg cctcggcgtg    17220
cagaccgtgg acgtggtcat ccccaccggc aactccccg ccgccaccac cactaccgct    17280
gcctccacgg acatggagac acagaccgat cccgccgcag ccgccgccac cgccgccgcc    17340
gcgacctcct cggcggaggt gcagacggac ccctggctgc cgccggcgat gtcagctccc    17400
cgcgcgcgtc gcgggcgcag gaagtacggc gccgccaacg cgctcctgcc cgagtacgcc    17460
ttgcatcctt ccatcgcgcc caccccggc taccgaggct ataccaccg cccgcgaaga    17520 gccaagggtt ccaccccgcc tccccgccga cgcgccgccg ccaccacccg ccgccgcgc    17580 cgcagacgcc agcccgcact ggctccagtc tccgtgagga gagtgcgcg cgacggacac    17640 accctggtgc tgcccagggc gcgctaccac cccagcatcg tttaaaagcc tgttgtggtt    17700
```

```
cttgcagata tggccctcac ttgccgcctc cgtttcccgg tgccgggata ccgaggagga   17760
agatcgcgcc gcaggagggg tctggccggc cgcggcctga gcggaggcag ccgccgcgcg   17820
caccggcggc gacgcgccac cagccgacgc atgcgcggcg gggtgctgcc cctgttaatc   17880
cccctgatcg ccgcggcgat cggcgccgtg cccgggatcg cctccgtggc cttgcaggcg   17940
tcccagaggc attgacagac ttgcaaactt gcaaatatgg aaaaaaaccc caataaaaaa   18000
gtctagactc tcacgctcgc ttggtcctgt gactattttg tagaatggaa gacatcaact   18060
ttgcgtcgct ggccccgcgt cacggctcgc gcccgttcct gggacactgg aacgatatcg   18120
gcaccagcaa catgagcggt ggcgccttca gttggggctc tctgtggagc ggcattaaaa   18180
gtatcgggtc tgccgttaaa aattacggct cccgggcctg gaacagcagc acgggccaga   18240
tgttgagaga caagttgaaa gagcagaact tccagcagaa ggtggtggag ggcctggcct   18300
ccggcatcaa cggggtggtg gacctggcca accaggccgt gcagaataag atcaacagca   18360
gactggaccc ccggccgccg gtggaggagg tgccgccggc gctggagacg tgtgtccccg   18420
atgggcgtgg cgagaagcgc ccgcggcccg atagggaaga gaccactctg gtcacgcaga   18480
ccgatgagcc gccccgtat gaggaggccc tgaagcaagg tctgcccacc acgcggccca   18540
tcgcgcccat ggccaccggg gtggtgggcc gccacacccc cgccacgctg gacttgcctc   18600
cgcccgccga tgtgccgcag cagcagcaga aggcggcaca gccgggcccg cccgtgaccg   18660
cctcccgttc ctccgccggt cctctgcgcc gcgcggccag cggcccccgc gggggggtcg   18720
cgaggcacgg caactggcag agcacgctga acagcatcgt gggtctgggg gtgcggtccg   18780
tgaagcgccg ccgatgctac tgaatagctt agctaacgtg ttgtatgtgt gtatgcgccc   18840
tatgtcgccg ccagaggagc tgctgagtcg ccgccgttcg cgcgcccacc accaccaccg   18900
ccactccgcc cctcaagatg gcgaccccat cgatgatgcc gcagtggtcg tacatgcaca   18960
tctcgggcca ggacgcctcg gagtacctga gccccgggct ggtgcagttc gcccgcgcca   19020
ccgagagcta cttcagcctg agtaacaagt ttaggaaccc cacggtggcg cccacgcacg   19080
atgtgaccac cgaccggtct cagcgcctga cgctgcggtt cattcccgtg gaccgcgagg   19140
acaccgcgta ctcgtacaag gcgcggttca ccctggccgt gggcgacaac cgcgtgctgg   19200
acatggcctc cacctacttt gacatccgcg gggtgctgga ccggggcccc actttcaagc   19260
cttactctgg caccgcctac aactccctgg cccccaaggg cgctcccaac tcctgcgagt   19320
gggagcaatt agaagaagcc caggccgctg tggaagacga agaattagaa gatgaagacg   19380
aggaaccaca ggatgaggca cctgtgaaaa aaacccatgt atacgctcag gctcccttt    19440 ctggagaaga aattactaaa aacggtttgc aaatagggtc agataacaca gaagcccagt   19500
ctaagcccat atatgcagat cctacattcc agcctgaacc ccaaatcggg gaatcccagt   19560
ggaatgaggc agatgctaca gttgccggcg gtagagtgct aaagaaatcc actcccatga   19620
agccatgcta tggttcctat gcaagaccca caaactccaa tggaggtcaa ggtgtgctgg   19680
tggctgatga agggggggtt cttcaatcta agttgaatt gcaatttttt tcaaatacta    19740
ctactcttaa tcagcgggag ggtaacgata caaaaccaaa agtggtgctg tatagcgaag   19800
atgtgcacat ggaaactcca gacacccaca tttcttacaa gccacaaaaa agcgatgaca   19860
attcaaaaat catgctgggt cagcagtcca tgcccaacag acctaattac atcggcttca   19920
gagacaactt tatcggcctc atgtattaca atagcactgg caacatggga gtgcttcag    19980 gtcaggcctc tcagttgaat gcagtggtgg acttgcaaga cagaaacaca gaactgtcct   20040
```

```
accagctctt gcttgattcc atgggtgaca gaaccagata cttttccatg tggaatcagg   20100
cagtggacag ttatgaccca gatgtcagaa ttattgaaaa tcatggaact gaagacgagc   20160
tccccaacta ttgtttccct ctgggcggca taggggtaac tgacacttac caggccatta   20220
aaaccaatgg caatggtcaa gaaacccaa cctgggaaaa agatacagag tttgcagacc    20280
gcaatgaaat aggggtggga aacaatttcg ctatggagat caacctcagt gccaacctgt   20340
ggagaaactt cctgtactcc aacgtggcgc tgtacctgcc agacaagctt aagtacaacc   20400
cctccaatgt ggacatctct gacaacccca acacctacga ttacatgaac aagcgagtgg   20460
tggccccggg gctggtggac tgctacatca acctgggcgc gcgctggtcg ctggactaca   20520
tggacaacgt caacccctc aaccaccacc gcaatgcggg cctgcgctac cgctccatgc    20580
tcctgggcaa cgggcgctac gtgcccttcc acatccaggt gccccagaag ttctttgcca   20640
tcaagaacct cctcctcctg ccgggctcct acacctacga gtggaacttc aggaaggatg   20700
tcaacatggt cctccagagc tctctgggta cgatctcag ggtggacggg gccagcatca    20760
agttcgagag catctgcctc tacgccacct tcttccccat ggcccacaac acggcctcca   20820
cgctcgaggc catgctcagg aacgacacca cgaccagtc cttcaatgac tacctctccg    20880
ccgccaacat gctctacccc ataccgcca acgccaccaa cgtccccatc tccatcccct    20940
cgcgcaactg gcggccttc cgcggctggg ccttcacccg cctcaagacc aaggagaccc    21000
cctccctggg ctcgggattc gacccctact acacctactc gggctccatt ccctacctgg   21060
acggcacctt ctacctcaac cacactttca gaaggtctc ggtcaccttc gactcctcgg    21120
tcagctggcc gggcaacgac cgtctgctca cccccaacga gttcgaaatc aagcgctcgg   21180
tcgacgggga gggctacaac gtggcccagt gcaacatgac caaggactgg ttcctggtcc   21240
agatgctggc caactacaac atcggctacc agggcttcta catcccagag agctacaagg   21300
acaggatgta ctccttcttc aggaacttcc agcccatgag ccggcaggtg gtggaccaga   21360
ccaagtacaa ggactaccag gaggtgggca tcatccacca gcacaacaac tcgggcttcg   21420
tgggctacct cgccccccacc atgcgcgagg acaggcctta ccccgccaac ttcccctacc   21480
cgctcatagg caagaccgcg gtcgacagca tcacccagaa aaagttcctc tgcgatcgca   21540
ccctctggcg catcccctc tccagcaact tcatgtccat gggtgcgctc tcggacctgg    21600
gccagaactt gctctacgcc aactccgccc acgcctcga catgaccttc gaggtcgacc    21660
ccatggacga gccccacctt ctctatgttc tgttcgaagt ctttgacgtg gtccgggtcc   21720
accagccgca ccgcggcgtc atcgagaccg tgtacctgcg tacgcccttc tcggccggca   21780
acgccaccac ctaaagaagc aagccgcagt catcgccgcc tgcatgccgt cgggttccac   21840
cgagcaagag ctcagggcca tcgtcagaga cctgggatgc gggccctatt ttttgggcac   21900
tttcgacaag cgcttccctg gctttgtctc cccacacaag ctggcctgcg ccatcgtcaa   21960
cacggccggc cgcgagaccg ggggcgtgca ctggctggcc ttcgcctgga acccgcgctc   22020
caaaacatgc ttcctctttg accccttcgg cttttcggac cagcggctca agcaaatcta   22080
cgagttcgag tacgagggct tgctgcgtcg cagcgccatc gcctcctcgc ccgaccgctg   22140
cgtcacccta gaaaagtcca cccagaccgt gcagggcccc gactcggccg cctgcggtct   22200
cttctgctgc atgtttctgc acgcctttgt gcactggcct cagagtccca tggaccgcaa   22260
ccccaccatg aacttgctga cgggggtgcc caactccatg ctccagagcc ccaggtcga   22320
gcccaccctc cgccgcaacc aggagcagct ctacagcttc ctggagcgcc actcgcccta   22380
cttccgccgc cacagcgcac agatcaggag ggccacctcc ttctgccact gcaagagat   22440
```

```
gcaagaaggg taataacgat gtacacactt ttttctcaat aaatggcatt tttttattta    22500
tacaagctct ctggggtatt catttcccac caccaccacc acccgccgtt gtcgccatct    22560
ggctctattt agaaatcgaa agggttctgc cgggagtcgc cgtgcgccac gggcagggac    22620
acgttgcgat actggtagcg ggtgccccac ttgaactcgg gcaccaccag gcgaggcagc    22680
tcggggaagt tttcgctcca caggctgcgg gtcagcacca gcgcgttcat caggtcgggc    22740
gccgagatct tgaagtcgca gttggggccg ccgccctgcg cgcgcgagtt gcggtacacc    22800
gggttgcagc actggaacac caacagcgcc gggtgcttca cgctagccag cacgctgcgg    22860
tcggagatca gctcggcgtc caggtcctcc gcgttgctca gcgcgaacgg ggtcatcttg    22920
ggcacttgcc tccccaggaa gggcgcgtgc cccggtttcg agttgcagtc gcagcgcagc    22980
gggatcagca ggtgcccatg cccggactcg gcgttgggt  acagcgcgcg catgaaggcc    23040
tgcatctggc ggaaggccat ctgggccttg gcgccctccg agaagaacat gccgcaggac    23100
ttgcccgaga actggtttgc ggggcagctg gcgtcgtgca ggcagcagcg cgcgtcggtg    23160
ttggcgatct gcaccacgtt gcgcccccac cggttcttca cgatcttggc cttggacgat    23220
tgctccttca gcgcgcgctg cccgttctcg ctggtcacat ccatctcgat cacatgttcc    23280
ttgttcacca tgctgctgcc gtgcaggcac ttcagctcgc cctccgtctc ggtgcagcgg    23340
tgctgccaca gcgcgcagcc cgtgggctcg aaagacttgt aggtcacctc cgcgaaggac    23400
tgcaggtacc cctgcaaaaa gcggcccatc atggtcacga aggtcttgtt gctgctgaag    23460
gtcagctgca gcccgcggtg ctcctcgttc agccaggtct tgcacacggc cgccagcgcc    23520
tccacctggt cgggcagcat cttgaagttc accttcagct cattctccac gtggtacttg    23580
tccatcagcg tgcgcgccgc ctccatgccc ttctcccagg ccgacaccag cggcaggctc    23640
acggggttct tcaccatcac cgtggccgcc gcctccgccg cgctttcgct ttccgccccg    23700
ctgttctctt cctcttcctc ctcttcctcg ccgccgccca ctcgcagccc ccgcaccacg    23760
gggtcgtctt cctgcaggcg ctgcaccttg cgcttgccgt tgcgcccctg cttgatgcgc    23820
acgggcgggt tgctgaagcc caccatcacc agcgcggcct cttcttgctc gtcctcgctg    23880
tccagaatga cctccgggga gggggggttg gtcatcctca gtaccgaggc acgcttcttt    23940
ttcttcctgg gggcgttcgc cagctccgcg gctgcggccg ctgccgaggt cgaaggccga    24000
gggctgggcg tgcgcggcac cagcgcgtcc tgcgagccgt cctcgtcctc ctcggactcg    24060
agacggaggc gggcccgctt cttcgggggc gcgcggggcg gcggaggcgg cggcggcgac    24120
ggagacgggg acgagacatc gtccagggtg ggtggacggc gggccgcgcc gcgtccgcgc    24180 tcggggggtgg tctcgcgctg gtcctcttcc cgactggcca tctcccactg ctccttctcc    24240
tataggcaga aagagatcat ggagtctctc atgcgagtcg agaaggagga ggacagccta    24300 accgcccct  ctgagccctc caccaccgcc gccaccaccg ccaatgccgc cgcggacgac    24360
gcgcccaccg agaccaccgc cagtaccacc nnnctcccca gcgacgcacc cccgctcgag    24420
aatgaagtgc tgatcgagca ggacccgggt tttgtgagcg gagaggagga tgaggtggat    24480
gagaaggaga aggaggaggt cgccgcctca gtgccaaaag aggataaaaa gcaagaccag    24540
gacgacgcag ataaggatga gacagcagtc gggcggggga acggaagcca tgatgctgat    24600
gacggctacc tagacgtggg agacgacgtg ctgcttaagc acctgcaccg ccagtgcgtc    24660
atcgtctgcg acgcgctgca ggagcggtgc gaagtgcccc tggacgtggc ggaggtcagc    24720
cgcgcctacg agcggcacct cttcgcgccg cacgtgcccc ccaagcgccg ggagaacggc    24780
```

```
acctgcgagc ccaacccgcg tctcaacttc tacccggtct tcgcggtacc cgaggtgctg    24840
gccacctacc acatcttttt ccaaaactgc aagatccccc tctcctgccg cgctaaccgc    24900
acccgcgccg acaaaaccct gaccctgcgg cagggcgccc atacctga tattgcctct     24960
ctggaggaag tgcccaagat cttcgagggt ctcggtcgcg acgagaaacg ggcggcgaac    25020
gctctgcacg gagacagcga aaacgagagt cactcggggg tgctggtgga gctcgagggc    25080
gacaacgcgc gcctggccgt actcaagcgc agcatagagg tcacccactt tgcctacccg    25140
gcgctcaacc tgccccccaa ggtcatgagt gtggtcatgg gcgagctcat catgcgccgc    25200
gcccagcccc tggccgcgga tgcaaacttg caagagtcct cagaggaagg cctgcccgcg    25260
gtcagcgacg agcagctggc gcgctggctg gagacccgcg accccgcgca gctggaggag    25320
cggcgcaagc tcatgatggc cgcggtgctg gtcaccgtgg agctcgagtg tctgcagcgc    25380
ttcttcgcgg accccgagat gcagcgcaag ctcgaggaga ccctgcacta caccttccgc    25440
cagggctacg tgcgccaggc ctgcaagatc tccaacgtgg agctctgcaa cctggtctcc    25500
tacctgggca tcctgcacga gaaccgcctc gggcagaacg tcctgcactc caccctcaaa    25560
ggggaggcgc ccgcgacta catccgcgac tgccgcctac tcttcctctg ctacacctgg    25620
cagacggcca tgggggtctg gcagcagtgc ctggaggagc gcaacctcaa ggagctggaa    25680
aagctcctca agcgcaccct cagggacctc tggacgggct tcaacgagcg ctcggtggcc    25740
gccgcgctgg cggacatcat cttccccgag cgcctgctca agaccctgca gcagggcctg    25800
cccgacttca ccagccagag catgctgcag aacttcagga cttttcatcct ggagcgctcg    25860
ggcatcctgc cggccacttg ctgcgcgctg cccagcgact tcgtgcccat caagtacagg    25920
gagtgcccgc cgccgctctg gggccactgc tacctcttcc agctggccaa ctacctcgcc    25980
taccactcgg acctcatgga agacgtgagc ggcgagggcc tgctcgagtg ccactgccgc    26040
tgcaacctct gcacgcccca ccgctctcta gtctgcaacc cgcagctgct cagcgagagt    26100
cagattatcg gtaccttcga gctgcagggt ccctcgcctg acgagaagtc cgcggctccg    26160
gggctgaaac tcactccggg gctgtggact tccgcctacc tacgcaaatt tgtacctgag    26220
gactaccacg cccacgagat caggttctac gaagaccaat cccgcccgcc caaggcggag    26280
ctcaccgcct gcgtcatcac ccaggggcac atcctgggcc aattgcaagc catcaacaaa    26340
gcccgccgag agttcttgct gaaaaagggt cgggggtgt acctggaccc ccagtccggc    26400
gaggagctaa acccgctacc cccgccgccg ccccagcagc gggaccttgc ttcccaggat    26460
ggcacccaga aagaagcagc agccgccgcc gcagccatac atgcttctgg aggaagagga    26520
ggaggactgg gacagtcagg cagaggagat gatggaagac tgggaggagg acagcagcct    26580
agacgaggaa gcttcagagg ccgaagaggt ggcagacgca acaccatcac cctcggtcgc    26640
agccccctcg ccggggcccc tgaaatcctc cgaacccagc accagcgcta aacctccgc     26700
tcctccggcg ccggcgccac ccgcccgcag acccaaccgt agatgggaca ccacaggaac    26760
cggggtcggt aagtccaagt gcccgccgcc gccaccgcag cagcagcagc agcagcgcca    26820
gggctaccgc tcgtggcgcg ggcacaagaa cgccatagtc gcctgcttgc aagactgcgg    26880
gggcaacatc tctttcgccc gccgcttcct gctattccac cacggggtcg cctttccccg    26940
caatgtcctg cattactacc gtcatctcta cagcccctac tgcagcggcg acccagaggc    27000
ggcagcggca gccacagcgg cgaccaccac ctaggaagat atcctccgcg ggcaagacag    27060
cggcagcagc ggccaggaga cccgcggcag cagcggcggg agcggtgggc gcactgccgc    27120
tctcgcccaa cgaacccctc tcgacccggg agctcagaca caggatcttc cccactttgt    27180
```

```
atgccatctt ccaacagagc agaggccagg agcaggagct gaaaataaaa aacagatctc   27240
tgcgctccct cacccgcagc tgtctgtatc acaaaagcga agatcagctt cggcgcacgc   27300
tggaggacgc ggaggcactc ttcagcaaat actgcgcgct cactcttaaa gactagctcc   27360
gcgcccttct cgaatttagg cgggagaaaa ctacgtcatc gccggccgcc gcccagcccg   27420
cccagccgag atgagcaaag agattcccac gccatacatg tggagctacc agccgcagat   27480
gggactcgcg gcgggagcgg cccaggacta ctccacccgc atgaactaca tgagcgcggg   27540
accccacatg atctcacagg tcaacgggat ccgcgcccag cgaaaccaaa tactgctgga   27600
acaggcggcc atcaccgcca cgccccgcca taatctcaac ccccgaaatt ggcccgccgc   27660
cctagtgtac caggaaaccc cctccgccac caccgtacta cttccgcgtg acgcccaggc   27720
cgaagtccag atgactaact caggggcgca gctcgcgggc ggcttttcgtc acggggcgcg   27780
gccgctccga ccaggtataa gacacctgat gatcagaggc cgaggtatcc agctcaacga   27840
cgagtcggtg agctcttcgc tcggtctccg tccggacgga actttccagc tcgccggatc   27900
cggtcgctct tcgttcacgc cccgccaggc gtacctgact ctgcagacct cgtcctcgga   27960
gccccgctcc ggcggcatcg gaaccctcca gttcgtggag gagttcgtgc cctcggtcta   28020
cttcaacccc ttctcgggac ctcccggacg ctaccccgac cagttcattc gaactttga    28080
cgcggtgaag gactcggcgg acggctacga ctgaatgtca ggtgccgagg cagagcagct   28140
tcgcctgaga cacctcgagc actgccgccg ccacaagtgc ttcgcccgcg gttccggtga   28200
gttctgctac tttcagctac ccgaggagca taccgagggg ccggcgcacg gcgtccgcct   28260
gaccacccag ggcgaggtta cctgttccct catccgggag ttcaccctcc gtccctgct    28320
agtggagcgg gagcggggtc cctgtgtcct aactatcgcc tgcaactgcc ctaaccctgg   28380
attacatcaa gatctttgct gtcatctctg tgctgagttt aataaacgct gagatcagaa   28440
tctactgggg ctcctgtcgc catcctgtga acgccaccgt cttcacccac cccgaccagg   28500
cccaggcgaa cctcacctgc ggtctgcatc ggaggtccaa gaagtacctc acctggtact   28560
tcaacggcac ccccttgtg gtttacaaca gcttcgacgg ggacggagtc tccctgaaag   28620
accagctctc cggtctcagc tactccatcc acaagaacac caccctccaa ctcttccctc   28680
cctacctgcc gggaacctac gagtgcgtca ccggccgctg cacccacctc acccgcctga   28740
tcgtaaacca gagcttccg ggaacagata actccctctt ccccagaaca ggaggtgagc   28800
tcaggaaact ccccggggac cagggcggag acgtaccttc gaccccttgtg gggttaggat   28860
tttttattac cggggttgctg gctcttttaa tcaaagcttc cttgagattt gttctttcct   28920
tctacgtgta tgaacacctc agcctccaat aactctaccc tttcttcggg atcaggtgac   28980
ttttctgaaa tcgggcttgg tgtgctgctt actctgttga tttttttcct tatcatactc   29040
agccttctgt gcctcaggct cgccgcctgc tgcgcacaca tctatatcta ctgctggttg   29100
ctcaagtgca ggggtcgcca cccaagatga acagtacat ggtcctatcg atcctaggcc    29160
tgctggccct ggcggcctgc agcgccgcca aaaagagat taccttgag gagcccgctt     29220
gcaatgtaac tttcaagccc gagggtgacc aatgcaccac cctcgtcaaa tgcgttacca   29280
atcatgagaa gctgcgcatc gactacaaaa acaaactgg ccggtttgcg gtctatagtg    29340
tgtttacgcc cggagacccc tctaactact ctgtcaccgt cttccagggc ggacagtcta   29400
agatattcaa ttacacttc ccttttatg agttgtgcga tgcggtcatg tacatgtcaa     29460
aacagtacaa cctgtggcct ccctctcccc aggcgtgtgt ggaaaatact gggtcttact   29520
```

```
gctgtatggc tttggcaatc actacgctcg ctctaatctg cacggtgcta tatataaaat  29580
tcaggcagag gcgaatcttt atcgatgaaa agaaaatgcc ttgatcgcta acaccggctt  29640
tctatctgca gaatgaatgc aatcacctcc ctactaatca ccaccaccct ccttgcgatt  29700
gcccatgggt tgacacgaat cgaagtgcca gtggggtcca atgtcaccat ggtgggcccc  29760
gccggcaatt ccaccctcat gtgggaaaaa tttgtccgca atcaatgggt tcatttctgc  29820
tctaaccgaa tcagtatcaa gcccagagcc atctgcgatg ggcaaaatct aactctgatc  29880
aatgtgcaaa tgatggatgc tgggtactat tacgggcagc ggggagaaat cattaattac  29940
tggcgacccc acaaggacta catgctgcat gtagtcgagg cacttcccac taccacccc   30000 actaccacct ctcccaccac cactaccact actactacta ctactaccac taccgctgcc  30060
cgccataccc gcaaaagcac catgattagc acaaagcccc ctcgtgctca ctcccacgcc  30120
ggcgggccca tcggtgcgac ctcagaaacc accgagcttt gcttctgcca atgcactaac  30180
gccagcgctc atgaactgtt cgacctggag aatgaggatg cccagcagag ctccgcttgc  30240
ctgacccagg aggctgtgga gcccgttgcc ctgaagcaga tcggtgattc aataattgac  30300
tcttcttctt ttgccactcc cgaatacccct cccgattcta cttttccacat cacgggtacc  30360 aaagacccta acctctcttt ctacctgatg ctgctgctct gtatctctgt ggtctcttcc  30420
gcgctgatgt tactggggat gttctgctgc ctgatctgcc gcagaaagag aaaagctcgc  30480
tctcagggcc aaccactgat gcccttcccc tacccccgg attttgcaga taacaagata  30540
tgagctcgct gctgacacta accgctttac tagcctgcgc tctaacccctt gtcgcttgcg  30600 actcgagatt ccacaatgtc acagctgtgg caggagaaaa tgttactttc aactccacgg  30660
ccgataccca gtggtcgtgg agtggctcag gtagctactt aactatctgc aatagctcca  30720
cttcccccag catatcccca accaagtacc aatgcaatgc cagcctgttc accctcatca  30780
acgcttccac cctggacaat ggactctatg taggctatgt acccttttggt gggcaaggaa  30840 agacccacgc ttcaaacctg gaagttcgcc agcccagaac cactacccaa gctwcymcca  30900
ycaccagcac cagcagcagc agccacagca gcagcagcag attattgact ttggttttgg  30960
ccagctcatc tgccgctacc caggccatct acagctctgt gcccgaaacc actcagaccc  31020
accgcccaga aacgaccacc gccaccaccc tacacacctc cagcgatcag atgccgacca  31080
acatcacccc cttggctctt caaatgggac ttacaagccc cactccaaaa ccagtggatg  31140
cggccgaggt ctccgccctc gtcaatgact gggcggggct gggaatgtgg tggttcgcca  31200
taggcatgat ggcgctctgc ctgcttctgc tctggctcat ctgctgcctc caccgcaggc  31260
gagccagacc ccccatctat agacccatca ttgtcctgaa cccgataat gatgggatcc  31320 atagattgga tggcctgaaa aacctacttt tttcttttac agtatgataa attgagacat  31380
gcctcgcatt ttcttgtaca tgttccttct cccaccttt ctgggtgtt ctacgctggc  31440 cgctgtgtct cacctggagg tagactgcct ctcaccctttc actgtctacc tgctttacgg  31500
attggtcacc ctcactctca tctgcagcct aatcacagta atcatcgcct tcatccagtg  31560
cattgattac atctgtgtgc gcctcgcata cttcagacac caccccgcagt accgagacag  31620 gaacattgcc caacttctaa gactgctcta atcatgcata agactgtgat ctgccttctg  31680
atcctctgca tcctgcccac cctcacctcc tgccagtaca ccacaaaatc tccgcgcaaa  31740
agacatgcct cctgccgctt cacccaactg tggaatatac ccaaatgcta caacgaaaag  31800
agcgagctct ccgaagcttg gctgtatggg gtcatctgtg tcttagtttt ctgcagcact  31860
gtctttgccc tcatgatcta cccctacttt gatttgggat ggaacgcgat cgatgccatg  31920
```

```
aattacccca cctttcccgc acccgagata attccactgc gacaagttgt acccgttgtc   31980
gttaatcaac gccccccatc ccctacgccc actgaaatca gctactttaa cctaacaggc   32040
ggagatgact gacgccctag atctagaaat ggacggcatc agtaccgagc agcgtctcct   32100
agagaggcgc aggcaggcgg ctgagcaaga gcgcctcaat caggagctcc gagatctcgt   32160
taacctgcac cagtgcaaaa gaggcatctt ttgtctggta aagcaggcca aagtcaccta   32220
cgagaagacc ggcaacagcc accgcctcag ttacaaattg cccacccagc gccagaagct   32280
ggtgctcatg gtgggtgaga atcccatcac cgtcacccag cactcggtag agaccgaggg   32340
gtgtctgcac tcccccctgtc ggggtccaga agacctctgc accctggtaa agaccctgtg   32400
cggtctcaga gatttagtcc cctttaacta atcaaacact ggaatcaata aaagaatca   32460
cttacttaaa atcagacagc aggtctctgt ccagtttatt cagcagcacc tccttcccct   32520
cctcccaact ctggtactcc aaacgccttc tggcggcaaa cttcctccac accctgaagg   32580
gaatgtcaga ttcttgctcc tgtccctccg cacccactat cttcatgttg ttgcagatga   32640
agcgcaccaa aacgtctgac gagagcttca accccgtgta cccctatgac acggaaagcg   32700
gccctccctc cgtcccttc ctcacccctc ccttcgtgtc tcccgatgga ttccaagaaa   32760
gtccccccgg ggtcctgtct ctgaacctgg ccgagcccct ggtcacttcc cacggcatgc   32820
tcgccctgaa aatgggaagt ggcctctccc tggacgacgc tggcaacctc acctctcaag   32880
atatccaccac cgctagccct cccctcaaaa aaaccaagac caacctcagc ctagaaacct   32940
catcccccct aactgtgagc acctcaggcg ccctcaccgt agcagccgcc gctcccctgg   33000
cggtggccgg cacctccctc accatgcaat cagaggcccc cctgacagta caggatgcaa   33060
aactcacccct ggccaccaaa ggccccctga ccgtgtctga aggcaaactg gccttgcaaa   33120
catcggcccc gctgacggcc gctgacagca gcaccctcac cgttagcgcc acaccaccaa   33180
ttaatgtaag cagtggaagt ttaggcttag acatggaaga ccctatgtat actcacaatg   33240
gaaaactggg aataagaatt gggggtccac taagagtagt agacagcttg catacactca   33300
ctgtagttac cggaaatgga ctaactgtag ataacaatgc cctccaaact aaagttacgg   33360
gcgccctagg ttatgacaca tcaggaaatc tacaattaag agctgcagga ggtatgcgaa   33420
ttgacgcaaa tggccaactt atccttaatg tggcataccc atttgatgct cagaacaatc   33480
tcagccttag acttggtcag ggacccctgt atataaacac agaccacaac ctggatttga   33540
attgcaacag aggtctaacc acaactacca ccaacaacac aaaaaaactt gagactaaaa   33600
ttagctcagg cttagactat gacaccaatg gtgctgtcat tattaaactt ggcactggtc   33660
taagcttcga caacacaggc gccctaactg tgggaaacac tggtgatgat aaactgactc   33720
tgtggacgac cccagacca tctccaaatt gcagaattca ctcagacaaa gactgcaagt   33780
ttactctagt cctaactaag tgtggaagcc aaatcctggc ctctgtcgcc gccctagcgg   33840
tatcaggaaa tctggcttcg ataacaggca ccgttgccag cgttaccatc tttctcagat   33900
ttgatcagaa tggagtgctt atggaaaact cctcgctaga caggcagtac tggaacttca   33960
gaaatggcaa ctcaactaac gctgccccct acaccaatgc agttgggttc atgccaaacc   34020
tcgcagcata ccccaaaacg caaagccaga ctgctaaaaa caacattgta agtcaggttt   34080
acttgaatgg agacaaatcc aaacccatga cccttaccat caccctcaat ggaactaatg   34140
aatccagtga aactagccag gtgagtcact actccatgtc atttacatgg gcttgggaaa   34200
gtgggcaata tgccactgaa acctttgcca ccaactcctt caccttttct tacattgctg   34260
```

```
aacaataaaa agcatgacac tgatgttcat ttctgattct tattttatta ttttcaaaca    34320
caacaaaatc attcaagtca ttcttccatc ttagcttaat agacacagta gcttaataga    34380
cccagtagtg caaagcccca ttctagctta tagatcagac agtgataatt aaccaccacc    34440
accaccatac cttttgattc aggaaatcat gatcatcaca ggatcctagt cttcaggccg    34500 cccctccct cccaagacac agaatacaca gtcctctccc cccgactggc tttaaataac     34560
accatctggt tggtcacaga catgttctta ggggttatat tccacacggt ctcctgccgc    34620
gccaggcgct cgtcggtgat gttgataaac tctcccggca gctcgctcaa gttcacgtcg    34680
ctgtccagcg gctgaacctc cggctgacgc gataactgtg cgaccggctg ctggacaaac    34740
ggaggccgcg cctacaaggg ggtagagtca taatcctcgg tcaggatagg gcggtgatgc    34800
agcagcagcg agcgaaacat ctgctgccgc cgccgctccg tccggcagga aaacaacacg    34860
ccggtggtct cctccgcgat aatccgcacc gcccgcagca tcagcttcct cgttctccgc    34920
gcgcagcacc tcaccctgat ctcgctcaag tcggcgcagt aggtacagca cagcaccacg    34980
atgttattca tgatcccaca gtgcagggcg ctgtatccaa agctcatgcc gggaaccacc    35040
gcccccacgt ggccatcgta ccacaagcgc acgtaaatta agtgtcgacc cctcatgaac    35100
gtgctggaca caaacattac ttccttgggc atgttgtaat tcaccacctc ccggtaccag    35160
ataaacctct ggttaaacag ggcaccttcc accaccatcc tgaaccaaga ggccagaacc    35220
tgcccaccgg ctatgcactg cagggaaccc gggttggaac aatgacaatg cagactccaa    35280
ggctcgtaac cgtggatcat ccggctgctg aaggcatcga tgttggcaca acacagacac    35340
acgtgcatgc actttctcat gattagcagc tcttccctcg tcaggatcat atcccaagga    35400 ataaccatt cttgaatcaa cgtaaaaccc acacagcagg aaggcctcg cacataactc      35460 acgttgtgca tggtcagcgt gttgcattcc ggaaacagcg gatgatcctc cagtatcgag    35520
gcgcgggtct ccttctcaca gggaggtaaa gggtccctgc tgtacggact gcgccgggac    35580
gaccgagatc gtgttgagcg tagtgtcatg gaaaagggaa cgccggacgt ggtcatactt    35640
cttgaagcag aaccaggttc gcgcgtggca ggcctccttg cgtctgcggt ctcgccgtct    35700
agctcgctcc gtgtgatagt tgtagtacag ccactcccgc agagcgtcga ggcgcaccct    35760
ggcttccgga tctatgtaga ctccgtcttg caccgcggcc ctgataatat ccaccaccgt    35820
agaataagca cacccagcc aagcaataca ctcgctctgc gagcggcaga caggaggagc     35880
gggcagagat gggagaacca tgataaaaaa cttttttaa agaatatttt ccaattcttc     35940
gaaagtaaga tctatcaagt ggcagcgctc ccctccactg gcgcggtcaa actctacggc    36000
caaagcacag acaacggcat ttctaagatg ttccttaatg gcgtccaaaa gacacaccgc    36060
tctcaagtcg cagtaaacta tgaatgaaaa cccatccggc tgattttcca atatagacgc    36120
gccggcggcg tccaccaaac ccagataatt ttcttctctc cagcggttta gaatctgtct    36180
aagcaaatcc cttatatcaa gtccggccat gccaaaaatc tgctcaagag cgccctccac    36240
cttcatgacc aagcagcgca tcatgattgc aaaaattcag gttcttcaga gacctgtata    36300
agattcaaaa tggaacatt aacaaaaatt cctctgtcgc gcagatccct tcgcagggca     36360
agctgaacat aatcagacag gtctgaacgg accagtgagg ccaaatcccc accaggaacc    36420
agatccagag accctatact gattatgacg cgcatactcg gggctatgct gaccagcgta    36480
gcgccgatgt aggcgtgctg catgggcggc gagataaaat gcaaagtgct ggttaaaaaa    36540
tcaggcaaag cctcgcgcaa aaaagctaac acatcataat catgctcatg caggtagttg    36600
caggtaagct caggaaccaa aacggaataa cacacgattt tcctctcaaa catgacttcg    36660
```

```
cggatactgc gtaaaacaaa aattataaat aaaaaattaa ttaacttaaa cattggaagc   36720
ctgtctcaca acaggaaaaa ccactttaat caacataaga cgggccacgg gcatgccggc   36780
atagccgtaa aaaaattggt ccccgtgatt aacaagtacc acagacagct ccccggtcat   36840
gtcgggggtc atcatgtgag actctgtata cacgtctgga ttgtgaacat cagacaaaca   36900
aagaaatcga gccacgtagc ccggaggtat aatcacccgc aggcggaggt acagcaaaac   36960 gaccccccata ggaggaatca caaaattagt aggagaaaaa aatacataaa caccagaaaa   37020
accctgttgc tgaggcaaaa tagcgccctc ccgatccaaa acaacataaa gcgcttccac   37080
aggagcagcc ataacaaaga cccgagtctt accagtaaaa agaaaaaaga tctctcaacg   37140
cagcaccagc accaacactt cgcagtgtaa aaggccaagt gccgagagag tatatatagg   37200
aataaaaagt gacgtaaacg ggcaaagtcc aaaaaacgcc cagaaaaacc gcacgcgaac   37260
ctacgccccg aaacgaaagc caaaaaacac tagacactcc cttccggcgt caacttccgc   37320
tttcccacgc tacgtcactt gccccagtca acaaactac atatcccgaa cttccaagtc   37380
gccacgccca aaacaccgcc tacacctccc cgcccgccgg cccgccccca aacccgcctc   37440 ccgcccgcg ccccgccccg cgccgcccat ctcattatca tattggcttc aatccaaaat   37500
aaggtatatt attgatgatg gtttaaacgg atccaattct tgaagacgaa agggcctcgt   37560
gatacgccta ttttataggt taatgtcat gataataatg gtttcttaga cgtcaggtgg   37620
cacttttcgg ggaaatgtgc gcggaacccc tatttgttta tttttctaaa tacattcaaa   37680
tatgtatccg ctcatgagac aataaccctg ataaatgctt caataatatt gaaaaggaa   37740 gagtatgagt attcaacatt tccgtgtcgc ccttattccc ttttttgcgg cattttgcct   37800
tcctgttttt gctcacccag aaacgctggt gaaagtaaaa gatgctgaag atcagttggg   37860
tgcacgagtg ggttacatcg aactggatct caacagcggt aagatccttg agagttttcg   37920
ccccgaagaa cgttttccaa tgatgagcac ttttaaagtt ctgctatgtg gcgcggtatt   37980
atcccgtgtt gacgccgggc aagagcaact cggtcgccgc atacactatt ctcagaatga   38040
cttggttgag tactcaccag tcacagaaaa gcatcttacg gatggcatga cagtaagaga   38100
attatgcagt gctgccataa ccatgagtga taacactgcg gccaacttac ttctgacaac   38160
gatcggagga ccgaaggagc taaccgcttt tttgcacaac atgggggatc atgtaactcg   38220
ccttgatcgt tgggaaccgg agctgaatga agccatacca aacgacgagc gtgacaccac   38280
gatgcctgta gcaatggcaa caacgttgcg caaactatta actggcgaac tacttactct   38340
agcttcccgg caacaattaa tagactggat ggaggcggat aaagttgcag gaccacttct   38400
gcgctcggcc cttccggctg gctggtttat tgctgataaa tctggagccg gtgagcgtgg   38460
gtctcgcggt atcattgcag cactggggcc agatggtaag ccctcccgta tcgtagttat   38520
ctacacgacg gggagtcagg caactatgga tgaacgaaat agacagatcg ctgagatagg   38580
tgcctcactg attaagcatt ggtaactgtc agaccaagtt tactcatata ctttagat   38640 tgatttaaaa ggatctaggt gaagatcctt tttgataatc tcatgaccaa atcccttaa   38700 cgtgagtttt cgttccactg agcgtcagac cccgtagaaa agatcaaagg atcttcttga   38760 gatcctttt ttctgcgcgt aatctgctgc ttgcaaacaa aaaaaccacc gctaccagcg   38820
gtggtttgtt tgccggatca agagctacca actctttttc cgaaggtaac tggcttcagc   38880
agagcgcaga taccaaatac tgtccttcta gtgtagccgt agttaggcca ccacttcaag   38940
aactctgtag caccgcctac atacctcgct ctgctaatcc tgttaccagt ggctgctgcc   39000
```

```
agtggcgata agtcgtgtct taccgggttg gactcaagac gatagttacc ggataaggcg    39060
cagcggtcgg gctgaacggg gggttcgtgc acacagccca gcttggagcg aacgacctac    39120
accgaactga gatacctaca gcgtgagcta tgagaaagcg ccacgcttcc cgaagggaga    39180
aaggcggaca ggtatccggt aagcggcagg gtcggaacag gagagcgcac gagggagctt    39240 ccaggqggaa acgcctggta tctttatagt cctgtcgggt ttcgccacct ctgacttgag    39300
cgtcgatttt tgtgatgctc gtcagggggg cggagcctat ggaaaaacgc cagcaacgcg    39360
gcctttttac ggttcctggc cttttgctgg ccttgaagct gtccctgatg gtcgtcatct    39420
acctgcctgg acagcatggc ctgcaacgcg gcatcccga tgccgccgga agcgagaaga    39480
atcataatgg ggaaggccat ccagcctcgc gtcgcagatc cgaattcgtt taaac         39535

<210> SEQ ID NO 16
<211> LENGTH: 1500
<212> TYPE: DNA
<213> ORGANISM: Human immunodeficiency virus

<400> SEQUENCE: 16
atgggtgcta gggcttctgt gctgtctggt ggtgagctgg acaagtggga aagatcagg      60 ctgaggcctg gtggcaagaa gaagtacaag ctaaagcaca ttgtgtgggc ctccagggag    120
ctggagaggt ttgctgtgaa ccctggcctg ctggagacct ctgaggggtg caggcagatc    180
ctgggccagc tccagccctc cctgcaaaca ggctctgagg agctgaggtc cctgtacaac    240
acagtggcta ccctgtactg tgtgcaccag aagattgatg tgaaggacac caaggaggcc    300
ctggagaaga ttgaggagga gcagaacaag tccaagaaga aggcccagca ggctgctgct    360
ggcacaggca actccagcca ggtgtcccag aactacccca ttgtgcagaa cctccagggc    420
cagatggtgc accaggccat ctccccccgg accctgaatg cctgggtgaa ggtggtggag    480
gagaaggcct tctccccctga ggtgatcccc atgttctctg ccctgtctga gggtgccacc    540 cccccaggacc tgaacaccat gctgaacaca gtgggggggcc atcaggctgc catgcagatg    600
ctgaaggaga ccatcaatga ggaggctgct gagtgggaca ggctgcatcc tgtgcacgct    660 ggcccccattg cccccggcca gatgagggag cccagggggc tgacattgc tggcaccacc    720 tccaccctcc aggagcagat tggctggatg accaacaacc cccccatccc tgtgggggaa    780
atctacaaga ggtggatcat cctgggcctg aacaagattg tgaggatgta ctcccccacc    840
tccatcctgg acatcaggca gggccccaag gagcccttca gggactatgt ggacaggttc    900
tacaagaccc tgagggctga gcaggcctcc caggaggtga gaactggat gacagagacc    960 ctgctggtgc agaatgccaa ccctgactgc aagaccatcc tgaaggccct gggccctgct    1020
gccaccctgg aggagatgat gacagcctgc caggggggtgg ggggcctgg tcacaaggcc    1080 agggtgctgg ctgaggccat gtcccaggtg accaactccg ccaccatcat gatgcagagg    1140
ggcaacttca ggaaccagag gaagacagtg aagtgcttca ctgtggcaa ggtgggccac    1200 attgccaaga actgtagggc ccccaggaag aagggctgct ggaagtgtgg caaggagggc    1260
caccagatga aggactgcaa tgagaggcag gccaacttcc tgggcaaaat ctggccctcc    1320
cacaagggca ggcctggcaa cttcctccag tccaggcctg agcccacagc ccctcccgag    1380
gagtccttca ggtttgggga ggagaagacc cccccagcc agaagcagga gcccattgac    1440
aaggagctgt accccctggc ctccctgagg tccctgtttg caacgaccc ctcctcccag    1500

<210> SEQ ID NO 17
<211> LENGTH: 39240
```

```
<212> TYPE: DNA
<213> ORGANISM: Pan troglodytes
<220> FEATURE:
<221> NAME/KEY: misc_feature
<222> LOCATION: (24096)..(24098)
<223> OTHER INFORMATION: n is a, c, g, or t

<400> SEQUENCE: 17
```

| | | | | | |
|---|---|---|---|---|---|
| catcatcaat | aatatacctt | attttggatt | gaagccaata | tgataatgag | atgggcggcg | 60 |
| cggggcgggg | cgcggggcgg | gaggcgggtt | tggggcggg | ccggcgggcg | gggcggtgtg | 120 |
| gcggaagtgg | actttgtaag | tgtggcggat | gtgacttgct | agtgccgggc | gcggtaaaag | 180 |
| tgacgttttc | cgtgcgcgac | aacgcccccg | ggaagtgaca | ttttccccgc | ggttttacc | 240 |
| ggatgttgta | gtgaatttgg | gcgtaaccaa | gtaagatttg | gccattttcg | cgggaaaact | 300 |
| gaaacgggga | agtgaaatct | gattaatttt | gcgttagtca | taccgcgtaa | tatttgtcta | 360 |
| gggccgaggg | actttggccg | attacgtgga | ggactcgccc | aggtgttttt | tgaggtgaat | 420 |
| ttccgcgttc | cgggtcaaag | tctgcgtttt | attattatag | gatatcccat | tgcatacgtt | 480 |
| gtatccatat | cataatatgt | acatttatat | tggctcatgt | ccaacattac | cgccatgttg | 540 |
| acattgatta | ttgactagtt | attaatagta | atcaattacg | gggtcattag | ttcatagccc | 600 |
| atatatggag | ttccgcgtta | cataacttac | ggtaaatggc | ccgcctggct | gaccgcccaa | 660 |
| cgacccccgc | ccattgacgt | caataatgac | gtatgttccc | atagtaacgc | caatagggac | 720 |
| tttccattga | cgtcaatggg | tggagtattt | acggtaaact | gcccacttgg | cagtacatca | 780 |
| agtgtatcat | atgccaagta | cgccccctat | tgacgtcaat | gacggtaaat | ggcccgcctg | 840 |
| gcattatgcc | cagtacatga | ccttatggga | ctttcctact | tggcagtaca | tctacgtatt | 900 |
| agtcatcgct | attaccatgg | tgatgcggtt | ttggcagtac | atcaatgggc | gtggatagcg | 960 |
| gtttgactca | cggggatttc | caagtctcca | ccccattgac | gtcaatggga | gtttgttttg | 1020 |
| gcaccaaaat | caacgggact | ttccaaaatg | tcgtaacaac | tccgccccat | tgacgcaaat | 1080 |
| gggcggtagg | cgtgtacggt | gggaggtcta | tataagcaga | gctctcccta | tcagtgatag | 1140 |
| agatctccct | atcagtgata | gagatcgtcg | acgagctcgt | ttagtgaacc | gtcagatcgc | 1200 |
| ctggagacgc | catccacgct | gttttgacct | ccatagaaga | caccgggacc | gatccagcct | 1260 |
| ccgcggccgg | gaacggtgca | ttggaacgcg | gattccccgt | gccaagagtg | agatctacca | 1320 |
| tgggtgctag | ggcttctgtg | ctgtctggtg | gtgagctgga | caagtgggag | aagatcaggc | 1380 |
| tgaggcctgg | tggcaagaag | aagtacaagc | taaagcacat | tgtgtgggcc | tccagggagc | 1440 |
| tggagaggtt | tgctgtgaac | cctggcctgc | tggagacctc | tgaggggtgc | aggcagatcc | 1500 |
| tgggccagct | ccagccctcc | ctgcaaacag | gctctgagga | gctgaggtcc | ctgtacaaca | 1560 |
| cagtggctac | cctgtactgt | gtgcaccaga | agattgatgt | gaaggacacc | aaggaggccc | 1620 |
| tggagaagat | tgaggaggag | cagaacaagt | ccaagaagaa | ggcccagcag | gctgctgctg | 1680 |
| gcacaggcaa | ctccagccag | gtgtcccaga | actaccccat | tgtgcagaac | ctccagggcc | 1740 |
| agatggtgca | ccaggccatc | tccccccgga | ccctgaatgc | ctgggtgaag | gtggtggagg | 1800 |
| agaaggcctt | ctcccctgag | gtgatcccca | tgttctctgc | cctgtctgag | ggtgccaccc | 1860 |
| cccaggacct | gaacaccatg | ctgaacacag | tgggggcca | tcaggctgcc | atgcagatgc | 1920 |
| tgaaggagac | catcaatgag | gaggctgctg | agtgggacag | gctgcatcct | gtgcacgctg | 1980 |
| gccccattgc | ccccggccag | atgagggagc | caggggctc | tgacattgct | ggcaccacct | 2040 |
| ccaccctcca | ggagcagatt | ggctggatga | ccaacaaccc | cccatccct | gtggggaaa | 2100 |

```
tctacaagag gtggatcatc ctgggcctga acaagattgt gaggatgtac tccccacct      2160
ccatcctgga catcaggcag ggccccaagg agcccttcag ggactatgtg acaggttct      2220
acaagaccct gagggctgag caggcctccc aggaggtgaa gaactggatg acagagaccc    2280
tgctggtgca gaatgccaac cctgactgca agaccatcct gaaggccctg ggccctgctg    2340
ccaccctgga ggagatgatg acagcctgcc aggggtgggg gggccctggt cacaaggcca    2400
gggtgctggc tgaggccatg tcccaggtga ccaactccgc caccatcatg atgcagaggg    2460
gcaacttcag gaaccagagg aagacagtga agtgcttcaa ctgtggcaag gtgggccaca    2520
ttgccaagaa ctgtagggcc cccaggaaga agggctgctg gaagtgtggc aaggagggcc    2580
accagatgaa ggactgcaat gagaggcagg ccaacttcct gggcaaaatc tggccctccc    2640
acaagggcag gcctggcaac ttcctccagt ccaggcctga gcccacagcc cctcccgagg    2700
agtccttcag gtttggggag gagaagacca ccccagcca aagcaggag cccattgaca     2760
aggagctgta cccctggcc tcctgaggt ccctgtttgg caacgacccc tcctcccagt      2820
aaaataaagc ccgggcagat ctgatctgct gtgccttcta gttgccagcc atctgttgtt    2880
tgccctccc ccgtgccttc cttgaccctg gaaggtgcca ctcccactgt cctttcctaa     2940
taaaatgagg aaattgcatc gcattgtctg agtaggtgtc attctattct gggggtggg     3000
gtggggcagc acagcaaggg ggaggattgg gaagacaata gcaggcatgc tggggatgcg    3060
gtgggctcta tggccgatca gcgatcgctg aggtgggtga gtgggcgtgg cctggggtgg    3120
tcatgaaaat atataagttg ggggtcttag ggtctcttta tttgtgttgc agagaccgcc    3180
ggagccatga gcgggagcag cagcagcagc agtagcagca gcgccttgga tggcagcatc    3240
gtgagcccctt atttgacgac gcggatgccc cactgggccg gggtgcgtca gaatgtgatg    3300
ggctccagca tcgacggccg acccgtcctg cccgcaaatt ccgccacgct gacctatgcg    3360
accgtcgcgg ggacgccgtt ggacgccacc gccgcgccg ccgccaccgc agccgcctcg     3420
gccgtgcgca gcctggccac ggactttgca ttcctgggac cactggcgac aggggctact    3480
tctcgggccg ctgctgccgc cgttcgcgat gacaagctga ccgccctgct ggcgcagttg    3540
gatgcgctta ctcgggaact gggtgacctt tctcagcagg tcatggccct cgccagcag    3600
gtctcctccc tgcaagctgg cgggaatgct tctcccacaa atgccgttta agataaataa    3660
aaccagactc tgtttggatt aaagaaaagt agcaagtgca ttgctctctt tatttcataa    3720
ttttccgcgc gcgataggcc ctagaccagc gttctcggtc gttgagggtg cggtgtatct    3780
tctccaggac gtggtagagg tggctctgga cgttgagata catgggcatg agcccgtccc    3840
gggggtggag gtagcaccac tgcagagctt catgctccgg ggtggtgttg tagatgatcc    3900
agtcgtagca ggacgctgg gcatggtgcc taaaaatgtc cttcagcagc aggccgatgg    3960
ccaggggag gcccttggtg taagtgttta caaaacggtt aagttgggaa gggtgcattc    4020
ggggagagat gatgtgcatc ttggactgta ttttagatt ggcgatgttt ccgcccagat    4080
ccccttctggg attcatgttg tgcaggacca ccagtacagt gtatccggtg cacttgggga    4140
atttgtcatg cagcttagag ggaaaagcgt ggaagaactt ggagacgccc ttgtggcctc    4200
ccagattttc catgcattcg tccatgatga tggcaatggg cccgcgggag gcagcttggg    4260
caaagatatt tctggggtcg ctgacgtcgt agttgtgttc cagggtgagg tcgtcatagg    4320
ccatttttac aaagcgcggg cggagggtgc ccgactgggg gatgatggtc ccctctggcc    4380
ccggggcgta gttgccctcg cagatctgca tttcccaggc cttaatctcg gagggggaa    4440
tcatatccac ctgcggggcg atgaagaaaa cggtttccgg agccggggag attaactggg    4500
```

```
atgagagcag gtttctaagc agctgtgatt ttccacaacc ggtgggccca taaataacac    4560
ctataaccgg ttgcagctgg tagtttagag agctgcagct gccgtcgtcc cggaggaggg    4620
gggccacctc gttgagcatg tccctgacgc gcatgttctc cccgaccaga tccgccagaa    4680
ggcgctcgcc gcccagggac agcagctctt gcaaggaagc aaagtttttc agcggcttga    4740
ggccgtccgc cgtgggcatg tttttcaggg tctggctcag cagctccagg cggtcccaga    4800
gctcggtgac gtgctctacg gcatctctat ccagcatatc tcctcgtttc gcgggttggg    4860
gcgactttcg ctgtagggca ccaagcggtg gtcgtccagc ggggccagag tcatgtcctt    4920
ccatgggcgc agggtcctcg tcaggtggt ctgggtcacg gtgaaggggt gcgctccggg     4980
ctgagcgctt gccaaggtgc gcttgaggct ggttctgctg gtgctgaagc gctgccggtc    5040
ttcgccctgc gcgtcggcca ggtagcattt gaccatggtg tcatagtcca gcccctccgc    5100
ggcgtgtccc ttggcgcgca gcttgccctt ggaggtggcg ccgcacgagg ggcagagcag    5160
gctcttgagc gcgtagagct ggggcgag aagaccgat tcgggggagt aggcgtccgc       5220
gccgcagacc ccgcacacgg tctcgcactc caccagccag gtgagctcgg ggcgcgccgg    5280
gtcaaaaacc aggtttcccc catgcttttt gatgcgtttc ttacctcggg tctccatgag    5340
gtggtgtccc cgctcggtga cgaagaggct gtccgtgtct ccgtagaccg acttgagggg    5400
tcttttctcc aggggggtcc ctcggtcttc ctcgtagagg aactcggacc actctgagac    5460
gaaggcccgc gtccaggcca ggacgaagga ggctatgtgg gaggggtagc ggtcgttgtc    5520
cactaggggg tccaccttct ccaaggtgtg aagacacatg tcgccttcct cggcgtccag    5580
gaaggtgatt ggcttgtagg tgtaggccac gtgaccgggg gttcctgacg gggggtata     5640 aaaggggggtg ggggcgcgct cgtcgtcact ctcttccgca tcgctgtctg cgagggccag   5700
ctgctggggt gagtattccc tctcgaaggc gggcatgacc tccgcgctga ggttgtcagt    5760
ttccaaaaac gaggaggatt tgatgttcac ctgtcccgag gtgataccttt tgagggtacc   5820 cgcgtccatc tggtcagaaa acacgatctt tttattgtcc agcttggtgg cgaacgaccc    5880
gtagagggcg ttggagagca gcttggcgat ggagcgcagg gtctggttct tgtccctgtc    5940
ggcgcgctcc ttggccgcga tgttgagctg cacgtactcg cgcgcgacgc agcgccactc    6000
ggggaagacg gtggtgcgct cgtcgggcac caggcgcacg cgccagccgc ggttgtgcag    6060
ggtgaccagg tccacgctgg tggcgacctc gccgcgcagg cgctcgttgg tccagcagag    6120
acggccgccc ttgcgcgagc agaagggggg cagggggtcg agctgggtct cgtccggggg   6180
gtccgcgtcc acggtgaaaa ccccggggcg caggcgcgcg tcgaagtagt ctatcttgca    6240
accttgcatg tccagcgcct gctgccagtc gcgggcggcg agcgcgcgct cgtagggggtt   6300 gagcggcggc cccagggca tgggtgggt gagtgcggag gcgtacatgc gcagatgtc      6360 atagacgtag aggggctccc gcaggacccc gatgtaggtg gggtagcagc ggccgccgcg    6420
gatgctggcg cgcacgtagt catacagctc gtgcgagggg gcgaggaggt cggggcccag    6480
gttggtgcgg gcggggcgct ccgtgcggaa gacgatctgc ctgaagatgg catgcgagtt    6540
ggaagagatg gtgggggcgct ggaagacgtt gaagctggcg tcctgcaggc cgacggcgtc   6600
gcgcacgaag gaggcgtagg agtcgcgcag cttgtgtacc agctcggcgg tgacctgcac    6660
gtcgagcgcg cagtagtcga gggtctcgcg gatgatgtca tatttagcct gccccttctt    6720
tttccacagc tcgcggttga ggacaaactc ttcgcggtct ttccagtact cttggatcgg    6780
gaaaccgtcc ggttccgaac ggtaagagcc tagcatgtag aactggttga cggcctggta    6840
```

```
ggcgcagcag cccttctcca cggggagggc gtaggcctgc gcggccttgc ggagcgaggt    6900
gtgggtcagg gcgaaggtgt ccctgaccat gactttgagg tactggtgct tgaagtcgga    6960
gtcgtcgcag ccgccccgct cccagagcga gaagtcggtg cgcttcttgg agcggggtt     7020 gggcagagcg aaggtgacat cgttgaagag gattttgccc gcgcggggca tgaagttgcg    7080
ggtgatgcgg aagggccccg gcacttcaga gcggttgttg atgacctggg cggcgagcac    7140
gatctcgtcg aagccgttga tgttgtggcc cacgatgtag agttccagga agcggggccg    7200 gcccttacg gtgggcagct tctttagctc ttcgtaggtg agctcctcgg gcgaggcgag      7260
gccgtgctcg gccagggccc agtccgcgag gtgcgggttg tctctgagga aggactccca    7320
gaggtcgcgg gccaggaggg tctgcaggcg gtccctgaag gtcctgaact ggcggcccac    7380 ggccatttt tcgggggtga tgcagtagaa ggtgagggg tcttgctgcc agcggtccca      7440
gtcgagctgc agggcgaggt cgcgcgcggc ggtgaccagg cgctcgtcgc cccgaattt      7500 catgaccagc atgaagggca cgagctgctt tccgaaggcc cccatccaag tgtaggtctc    7560
tacatcgtag gtgacaaaga ggcgctccgt gcgaggatgc gagccgatcg ggaagaactg    7620
gatctcccgc caccagttgg aggagtggct gttgatgtgg tggaagtaga agtcccgtcg    7680
ccgggccgaa cactcgtgct ggcttttgta aaagcgagcg cagtactggc agcgctgcac    7740
gggctgtacc tcatgcacga gatgcacctt tcgcccgcgc acgaggaagc cgaggggaaa    7800
tctgagcccc ccgcctggct cgcggcatgg ctggtgctct tctactttgg atgcgtgtcc    7860
gtctccgtct ggctcctcga ggggtgttac ggtggagcgg accaccacgc cgcgcgagcc    7920
gcaggtccag atatcggcgc gcggcggtcg gagtttgatg acgacatcgc gcagctggga    7980
gctgtccatg gtctggagct cccgcggcgg cggcaggtca gccgggagtt cttgcaggtt    8040
cacctcgcag agtcgggcca gggcgcgggg caggtctagg tggtacctga tctctagggg    8100
cgtgttggtg gcggcgtcga tggcttgcag gagcccgcag ccccgggggg cgacgacggt    8160
gccccgcggg gtggtggtgg tggtggcggt gcagctcaga agcggtgccg cgggcggcc      8220 cccggaggta gggggggctc cggtcccgcg ggcaggggcg gcagcggcac gtcggcgtgg    8280
agcgcgggca ggagttggtg ctgtgcccgg aggttgctgg cgaaggcgac gacgcggcg      8340 ttgatctcct ggatctggcg cctctgcgtg aagacgacgg gcccggtgag cttgaacctg    8400
aaagagagtt cgacagaatc aatctcggtg tcattgaccg cggcctggcg caggatctcc    8460
tgcacgtctc ccgagttgtc ttggtaggcg atctcggcca tgaactgctc gatctcttcc    8520
tcctggaggt ctccgcgtcc ggcgcgttcc acggtggccg ccaggtcgtt ggagatgcgc    8580
cccatgagct gcgagaaggc gttgagtccg ccctcgttcc agactcggct gtagaccacg    8640
cccccctggt catcgcgggc gcgcatgacc acctgcgcga ggttgagctc cacgtgccgc    8700
gcgaagacgg cgtagttgcg cagacgctgg aagaggtagt tgagggtggt ggcggtgtgc    8760
tcggccacga agaagttcat gacccagcgg cgcaacgtgg attcgttgat gtcccccaag    8820
gcctccagcc gttccatggc ctcgtagaag tccacgcgca agttgaaaaa ctgggagttg    8880
cgcgccgaca cggtcaactc ctcctccaga agacggatga gctcggcgac ggtgtcgcgc    8940
acctcgcgct cgaaggctat ggggatctct tcctccgcta gcatcaccac ctcctcctct    9000
tcctcctctt ctggcacttc catgatggct tcctcctctt cggggggtgg cggcggcggc    9060
ggtgggggag gggcgcgtct gcgccggcgg cggcgcaccg ggaggcggtc cacgaagcgc    9120
gcgatcatct ccccgcggcg gcggcgcatg gtctcggtga cggcgcggcc gttctcccgg    9180
gggcgcagtt ggaagacgcc gccggacatc tggtgctggg gcgggtggcc gtgaggcagc    9240
```

```
gagacggcgc tgacgatgca tctcaacaat tgctgcgtag gtacgccgcc gagggacctg    9300
agggagtcca tatccaccgg atccgaaaac ctttcgagga aggcgtctaa ccagtcgcag    9360
tcgcaaggta ggctgagcac cgtggcgggc ggcgggggt gggggagtg tctggcggag      9420 gtgctgctga tgatgtaatt gaagtaggcg gacttgacac ggcggatggt cgacaggagc    9480
accatgtcct tgggtccggc ctgctggatg cggaggcggt cggctatgcc ccaggcttcg    9540
ttctggcatc ggcgcaggtc cttgtagtag tcttgcatga gcctttccac cggcacctct    9600
tctccttcct cttctgcttc ttccatgtct gcttcggccc tggggcggcg ccgcgccccc    9660 ctgccccca tgcgcgtgac cccgaaccc ctgagcggtt ggagcagggc caggtcggcg      9720
acgacgcgct cggccaggat ggcctgctgc acctgcgtga gggtggtttg gaagtcatcc    9780
aagtccacga agcggtggta ggcgcccgtg ttgatggtgt aggtgcagtt ggccatgacg    9840
gaccagttga cggtctggtg gcccggttgc gacatctcgg tgtacctgag tcgcgagtag    9900
gcgcgggagt cgaagacgta gtcgttgcaa gtccgcacca ggtactggta gcccaccagg    9960
aagtgcggcg gcggctggcg gtagaggggc cagcgcaggg tggcggggc tccggggcc    10020 aggtcttcca gcatgaggcg gtggtaggcg tagatgtacc tggacatcca ggtgataccc    10080
gcggcggtgg tggaggcgcg cgggaagtcg cgcacccggt tccagatgtt gcgcaggggc    10140
agaaagtgct ccatggtagg cgtgctctgt ccagtcagac gcgcgcagtc gttgatactc    10200
tagaccaggg aaaacgaaag ccggtcagcg ggcactcttc cgtggtctgg tgaatagatc    10260
gcaagggtat catggcggag ggcctcggtt cgagccccgg gtccgggccg acggtccgc    10320 catgatccac gcggttaccg cccgcgtgtc gaacccaggt gtgcgacgtc agacaacggt    10380
ggagtgttcc ttttggcgtt tttctggccg ggcgccggcg ccgcgtaaga gactaagccg    10440
cgaaagcgaa agcagtaagt ggctcgctcc ccgtagccgg agggatcctt gctaagggtt    10500
gcgttgcggc gaaccccggt tcgaatcccg tactcgggcc ggccggaccc gcggctaagg    10560
tgttggattg gcctccccct cgtataaaga ccccgcttgc ggattgactc cggacacggg    10620
gacgagcccc ttttattttt gctttcccca gatgcatccg tgttgcgac agatgcgccc    10680 cccgccccag cagcagcaac aacaccagca agagcggcag caacagcagc gggagtcatg    10740
cagggccccc tcacccaccc tcggcggccc ggccacctcg gcgtccgcgg ccgtgtctgg    10800
cgcctgcggc ggcggcggcg gggggccggc tgacgacccc gaggagcccc gcggcgcag    10860 ggccagacac tacctggacc tggaggaggg cgagggcctg gcgcggctgg gggcgccgtc    10920
tcccgagcgc caccgcgggg tgcagctaaa gcgcgactcg cgcgaggcgt acgtgcctcg    10980
gcagaacctg ttcagggacc gcgcgggcga ggagcccgag gagatgcggg acaggaggtt    11040
cagcgcgggg cgggagctgc ggcaggggct gaaccgcgag cggctgctgc gcgaggagga    11100
ctttgagccc gacgcgcgga cgggatcag ccccgcgcgc gcgcacgtgg cggccgccga    11160
cctggtgacg gcgtacgagc agacggtgaa ccaggagatc aacttccaaa agagtttcaa    11220
caaccacgtg cgcacgctgg tggcgcgcga ggaggtgacc atcgggctga tgcacctgtg    11280
ggactttgtg agcgcgctgg tgcagaaccc caatagcaag cctctgacgg cgcagctgtt    11340
cctgatagtg cagcacagca gggacaacga ggcgtttagg gacgcgctgc tgaacatcac    11400
cgagcccgag ggccggtggc tgctggacct gattaacatc ctgcagagca tagtggtgca    11460
ggagcgcagc ctgagcctgg ccgacaaggt ggcggccatc aactactcga tgctgagcct    11520
gggcaagttt tacgcgcgca agatctacca gacgccgtac gtgcccatag acaaggaggt    11580
```

```
gaagatcgac ggtttttaca tgcgcatggc gctgaaggtg ctcaccctaa gcgacgacct    11640
gggcgtgtac cgcaacgagc gcatccacaa ggccgtgagc gtgagccggc ggcgcgagct    11700
gagcgaccgc gagctgatgc atagcctgca gcgggcgctg gcgggcgccg gcagcggcga    11760
cagggaggcg gagtcctact tcgatgcggg ggcggacctg cgctgggcgc ccagccggcg    11820
ggccctggag gccgcggggg tccgcgagga ctatgacgag gacggcgagg aggatgagga    11880
gtacgagcta gaggagggcg agtacctgga ctaaaccgcg ggtggtgttt ccggtagatg    11940
caagacccga acgtggtgga cccggcgctg cgggcggctc tgcagagcca gccgtccggc    12000
cttaactcct cagacgactg cgacaggtc atggaccgca tcatgtcgct gacggcgcgt     12060
aacccggacg cgttccggca gcagccgcag gccaacaggc tctccgccat cctggaggcg    12120
gtggtgcctg cgcgctcgaa ccccacgcac gagaaggtgc tggccatagt gaacgcgctg    12180
gccgagaaca gggccatccg cccggacgag gccgggctgg tgtacgacgc gctgctgcag    12240
cgcgtggccc gctacaacag cggcaacgtg cagaccaacc tggaccggct ggtggggggac   12300 gtgcgcgagg cggtggcgca gcgcgagcgc gcggatcggc agggcaacct gggctccatg    12360
gtggcgctga atgccttcct gagcacgcag ccggccaacg tgccgcgggg gcaggaagac    12420
tacaccaact ttgtgagcgc gctgcggctg atggtgaccg agaccccca gagcgaggtg     12480 taccagtcgg gtccggacta cttcttccag accagcagac agggcctgca gacggtgaac    12540
ctgagccagg ctttcaagaa cctgcggggg ctgtggggcg tgaaggcgcc caccggcgac    12600
cgggcgacgg tgtccagcct gctgacgccc aactcgcgcc tgctgctgct gctgatcgcg    12660
ccgttcacgg acagcggcag cgtgtcccgg gacacctacc tgggggcacct gctgaccctg   12720 taccgcgagg ccatcgggca ggcgcaggtg gacgagcaca ccttccagga gatcaccagc    12780
gttagccgcg cgctggggca ggaggacacg agcagcctgg aggcgactct gaactacctg    12840
ctgaccaacc ggcggcagaa gattccctcg ctgcacagcc tgacctccga ggaggagcgc    12900
atcttgcgct acgtgcagca gagcgtgagc ctgaacctga tgcgcgacgg ggtgacgccc    12960
agtgtggcgc tggacatgac cgcgcgcaac atggaaccgg gcatgtacgc cgcgcaccgg    13020
ccttacatca accgcctgat ggactacctg catcgcgcgg cggccgtgaa ccccgagtac    13080
tttaccaacg ccatcctgaa cccgcactgg ctcccgccgc ccgggttcta cagcggggggc   13140 ttcgaggtcc cggaggccaa cgatggcttc ctgtgggacg acatggacga cagcgtgttc    13200
tccccgcggc cgcaggcgct ggcggaagcg tccctgctgc gtcccaagaa ggaggaggag    13260
gcgagtcgcc gccgcggcag cagcggccgtg gcttctctgt ccgagctggg ggcggcagcc   13320
gccgcgcgcc ccgggtccct gggcggcagc ccctttccga gcctggtggg gtctctgcac    13380
agcgagcgca ccacccgccc tcggctgctg ggcgaggacg agtacctgaa taactccctg    13440
ctgcagccgg tgcgggagaa aaacctgcct cccgccttcc ccaacaacgg gatagagagc    13500
ctggtggaca agatgagcag atggaagacc tatgcgcagg agcacaggga cgcgcccgcg    13560
ctccggccgc ccacgcggcg ccagcgccac gaccggcagc gggggctggt gtgggatgac    13620
gaggactccg cggacgatag cagcgtgctg gacctgggag ggagcggcaa cccgttcgcg    13680
cacctgcgcc ccgcctggg gaggatgttt taaaaaaaaa aaaagcaag aagcatgatg      13740 caaaaattaa ataaaactca ccaaggccat ggcgaccgag cgttggtttc ttgtgttccc    13800
ttcagtatgc ggcgcgcggc gatgtaccag gagggacctc ctccctctta cgagagcgtg    13860
gtgggcgcgg cggcggcggc gccctcttct ccctttgcgt cgcagctgct ggagccgccg    13920
tacgtgcctc cgcgctacct gcggcctacg ggggggagaa acagcatccg ttactcggag    13980
```

```
ctggcgcccc tgttcgacac cacccgggtg tacctggtgg acaacaagtc ggcggacgtg    14040
gcctccctga actaccagaa cgaccacagc aattttttga ccacggtcat ccagaacaat    14100
gactacagcc cgagcgaggc cagcacccag accatcaatc tggatgaccg gtcgcactgg    14160
ggcggcgacc tgaaaaccat cctgcacacc aacatgccca acgtgaacga gttcatgttc    14220
accaataagt tcaaggcgcg ggtgatggtg tcgcgctcgc acaccaagga agaccgggtg    14280
gagctgaagt acgagtgggt ggagttcgag ctgccagagg gcaactactc cgagaccatg    14340
accattgacc tgatgaacaa cgcgatcgtg gagcactatc tgaaagtggg caggcagaac    14400
ggggtcctgg agagcgacat cggggtcaag ttcgacacca ggaacttccg cctggggctg    14460
gaccccgtga ccgggctggt tatgcccggg gtgtacacca acgaggcctt ccatcccgac    14520
atcatcctgc tgcccggctg cggggtggac ttcacttaca gccgcctgag caacctcctg    14580
ggcatccgca gcggcagcc cttccaggag ggcttcagga tcacctacga ggacctggag    14640
gggggcaaca tccccgcgct cctcgatgtg gaggcctacc aggatagctt gaaggaaaat    14700
gaggcgggac aggaggatac cgcccccgcc gcctccgccg ccgccgagca gggcgaggat    14760
gctgctgaca ccgcggccgc ggacggggcg gaggccgacc ccgctatggt ggtggaggct    14820
gccgagcagg aggaggacat gaatgacagt gcggtgcgcg gagacaccct cgtcacccgg    14880
ggggaggaaa agcaagcgga ggccgaggcc gcggccgagg aaaagcaact ggcggcagca    14940
gcggcggcgg cggcgttggc cgcggcggag gctgagtctg aggggaccaa gcccgccaag    15000
gagcccgtga ttaagcccct gaccgaagat agcaagaagc gcagttacaa cctgctcaag    15060
gacagcacca acaccgcgta ccgcagctgg tacctggcct acaactacgg cgacccgtcg    15120 acggggtgc gctcctggac cctgctgtgc acgccggacg tgacctgcgg ctcggagcag    15180
gtgtactggt cgctgcccga catgatgcaa gaccccgtga ccttccgctc cacgcggcag    15240
gtcagcaact ccccggtggt gggcgccgag ctgctgcccg tgcactccaa gagcttctac    15300
aacgaccagg ccgtctactc ccagctcatc cgccagttca cctctctgac ccacgtgttc    15360
aatcgctttc ctgagaacca gattctggcg cgcccgcccg ccccaccat caccaccgtc    15420 agtgaaaacg ttcctgctct cacagatcac gggacgctac cgctgcgcaa cagcatcgga    15480
ggagtccagc gagtgaccgt tactgacgcc agacgccgca cctgccccta cgtttacaag    15540
gccttgggca tagtctcgcc gcgcgtcctt tccagccgca cttttttgagc aacaccacca    15600 tcatgtccat cctgatctca cccagcaata actccggctg gggactgctg cgcgcgccca    15660
gcaagatgtt cggaggggcg aggaagcgtt ccgagcagca cccgtgcgc gtgcgcgggc    15720 acttccgcgc ccctggggga gcgcacaaac gcggccgcgc ggggcgcacc accgtggacg    15780
acgccatcga ctcggtggtg gagcaggcgc gcaactacag gccgcggtc tctaccgtgg    15840 acgcggccat ccagaccgtg gtgcggggcg cggcggta cgccaagctg aagagccgcc    15900
ggaagcgcgt ggcccgccgc caccgccgcc gacccgggc cgccgccaaa cgcgccgccg    15960
cggccctgct tcgccgggcc aagcgcacgg gccgccgcgc cgccatgagg gccgcgcgcc    16020
gcttggccgc cggcatcacc gccgccacca tggccccccg tacccgaaga cgcgcggccg    16080
ccgccgccgc cgccgccatc agtgacatgg ccagcaggcg ccggggcaac gtgtactggg    16140
tgcgcgactc ggtgaccggc acgcgcgtgc ccgtgcgctt ccgccccccg cggacttgag    16200
atgatgtgaa aaacaacac tgagtctcct gctgttgtgt gtatcccagc ggcggcggc    16260 gcgcgcgcag cgtcatgtcc aagcgcaaaa tcaaagaaga gatgctccag gtcgtcgcgc    16320
```

```
cggagatcta tgggcccccg aagaaggaag agcaggattc gaagcccccgc aagataaagc    16380 gggtcaaaaa gaaaaagaaa gatgatggcg atgccgatgg ggaggtggag ttcctgcgcg    16440
ccacggcgcc caggcgcccg gtgcagtgga agggccggcg cgtaaagcgc gtcctgcgcc    16500
ccggcaccgc ggtggtcttc acgcccggcg agcgctccac ccggactttc aagcgcgtct    16560
atgacgaggt gtacggcgac gaagacctgc tggagcaggc caacgagcgc ttcggagagt    16620
ttgcttacgg gaagcgtcag cggccgctgg ggaaggagga cctgctggcg ctgccgctgg    16680
accagggcaa ccccaccccc agtctgaagc ccgtgaccct gcagcaggtg ctgccgagca    16740
gcgcaccctc cgaggcgaag cggggtctga agcgcgaggg cggcgacctg cgcccaccg    16800 tgcagctcat ggtgcccaag cggcagaggc tggaggatgt gctggagaaa atgaaagtag    16860
accccggtct gcagccggac atcagggtcc gtcccatcaa gcaggtggcg ccgggcctcg    16920
gcgtgcagac cgtggacgtg gtcatcccca ccggcaactc ccccgccgcc accaccacta    16980
ccgctgcctc cacggacatg gagacacaga ccgatcccgc cgcagccgcc gccaccgccg    17040
ccgccgcgac ctcctcggcg gaggtgcaga cggacccctg gctgccgccg gcgatgtcag    17100
ctccccgcgc gcgtcgcggg cgcaggaagt acggcgccgc caacgcgctc ctgcccgagt    17160
acgccttgca tccttccatc gcgcccaccc ccggctaccg aggctatacc taccgcccgc    17220
gaagagccaa gggttccacc cgccgtcccc gccgacgcgc cgccgccacc acccgccgcc    17280
gccgccgcag acgccagccc gcactggctc cagtctccgt gaggagagtg gcgcgcgacg    17340
gacacaccct ggtgctgccc agggcgcgct accaccccag catcgtttaa aagcctgttg    17400
tggttcttgc agatatggcc ctcacttgcc gcctccgttt cccggtgccg ggataccgag    17460
gaggaagatc gcgccgcagg aggggtctgg ccggccgcgg cctgagcgga ggcagccgcc    17520
gcgcgcaccg gcggcgacgc gccaccagcc gacgcatgcg cggcggggtg ctgcccctgt    17580
taatccccct gatcgccgcg gcgatcggcg ccgtgcccgg gatcgcctcc gtggccttgc    17640
aggcgtccca gaggcattga cagacttgca aacttgcaaa tatggaaaaa accccccaata    17700 aaaaagtcta gactctcacg ctcgcttggt cctgtgacta ttttgtagaa tggaagacat    17760
caactttgcg tcgctggccc cgcgtcacgg ctcgcgcccg ttcctgggac actggaacga    17820
tatcggcacc agcaacatga gcggtggcgc cttcagttgg ggctctctgt ggagcggcat    17880
taaaagtatc gggtctgccg ttaaaaatta cggctcccgg gcctggaaca gcagcacggg    17940
ccagatgttg agagacaagt tgaaagagca gaacttccag cagaaggtgg tggagggcct    18000
ggcctccggc atcaacgggg tggtggacct ggccaaccag gccgtgcaga ataagatcaa    18060
cagcagactg gaccccggc cgccggtgga ggaggtgccg ccggcgctgg agacggtgtc    18120
ccccgatggg cgtggcgaga gcgcccgcg gcccgatagg gaagagacca ctctggtcac    18180
gcagaccgat gagccgcccc cgtatgagga ggccctgaag caaggtctgc ccaccacgcg    18240
gcccatcgcg cccatggcca ccggggtggt gggccgccac acccccgcca cgctggactt    18300
gcctccgccc gccgatgtgc cgcagcagca gcagaaggcg gcacagccgg gccgccgt    18360 gaccgcctcc cgttcctccg ccggtcctct gcgccgcgcg gccagcggcc ccgcggggg    18420 ggtcgcgagg cacggcaact ggcagagcac gctgaacagc atcgtgggtc tggggggtgcg    18480 gtccgtgaag cgccgccgat gctactgaat agcttagcta acgtgttgta tgtgtgtatg    18540
cgccctatgt cgccgccaga ggagctgctg agtcgccgcc gttcgcgcgc ccaccaccac    18600
caccgccact ccgcccctca agatggcgac ccctcgatg atgccgcagt ggtcgtacat    18660
gcacatctcg ggccaggacg cctcggagta cctgagccccc gggctggtgc agttcgcccg    18720
```

```
cgccaccgag agctacttca gcctgagtaa caagtttagg aaccccacgg tggcgcccac   18780
gcacgatgtg accaccgacc ggtctcagcg cctgacgctg cggttcattc ccgtggaccg   18840
cgaggacacc gcgtactcgt acaaggcgcg gttcaccctg gccgtgggcg acaaccgcgt   18900
gctggacatg gcctccacct actttgacat ccgcggggtg ctggaccggg cccccacttt   18960
caagccttac tctggcaccg cctacaactc cctggccccc aagggcgctc ccaactcctg   19020
cgagtgggag caattagaag aagcccaggc cgctgtggaa gacgaagaat tagaagatga   19080
agacgaggaa ccacaggatg aggcacctgt gaaaaaaacc catgtatacg ctcaggctcc   19140
cctttctgga gaagaaatta ctaaaaacgg tttgcaaata gggtcagata acacagaagc   19200
ccagtctaag cccatatatg cagatcctac attccagcct gaaccccaaa tcggggaatc   19260
ccagtggaat gaggcagatg ctacagttgc cggcggtaga gtgctaaaga aatccactcc   19320
catgaagcca tgctatggtt cctatgcaag acccacaaac tccaatggag gtcaaggtgt   19380
gctggtggct gatgataagg gggttcttca atctaaagtt gaattgcaat ttttttcaaa   19440
tactactact cttaatcagc gggagggtaa cgatacaaaa ccaaaagtgg tgctgtatag   19500
cgaagatgtg cacatggaaa ctccagacac ccacatttct tacaagccca caaaaagcga   19560
tgacaattca aaaatcatgc tgggtcagca gtccatgccc aacagaccta attacatcgg   19620
cttcagagac aactttatcg gcctcatgta ttacaatagc actggcaaca tgggagtgct   19680
tgcaggtcag gcctctcagt tgaatgcagt ggtggacttg caagacagaa acacagaact   19740
gtcctaccag ctcttgcttg attccatggg tgacagaacc agatacttt ccatgtggaa   19800 tcaggcagtg gacagttatg acccagatgt cagaattatt gaaaatcatg gaactgaaga   19860
cgagctcccc aactattgtt tccctctggg cggcataggg gtaactgaca cttaccaggc   19920
cattaaaacc aatggcaatg gtcaagaaaa cccaacctgg gaaaaagata cagagtttgc   19980
agaccgcaat gaaatagggg tgggaaacaa tttcgctatg gagatcaacc tcagtgccaa   20040
cctgtggaga aacttcctgt actccaacgt ggcgctgtac ctgccagaca agcttaagta   20100 caaccctcc aatgtggaca tctctgacaa ccccaagcac tacgattaca tgaacaagcg   20160
agtggtggcc ccggggctgg tggactgcta catcaacctg ggcgcgcgct ggtcgctgga   20220
ctacatggac aacgtcaacc ccttcaacca ccaccgcaat gcgggcctgc gctaccgctc   20280
catgctcctg ggcaacgggc gctacgtgcc cttccacatc caggtgcccc agaagttctt   20340
tgccatcaag aacctcctcc tcctgccggg ctcctacacc tacgagtgga acttcaggaa   20400
ggatgtcaac atggtcctcc agagctctct gggtaacgat ctcagggtgg acggggccag   20460
catcaagttc gagagcatct gcctctacgc caccttcttc cccatggccc acaacacggc   20520
ctccacgctc gaggccatgc tcaggaacga caccaacgac cagtccttca atgactacct   20580
ctccgccgcc aacatgctct accccatacc cgccaacgcc accaacgtcc ccatctccat   20640
cccctcgcgc aactgggcgg ccttccgcgc ctgggccttc acccgcctca gaccaagga    20700 gacccctcc ctgggctcgg gattcgaccc ctactacacc tactcgggct ccattcccta   20760
cctggacggc accttctacc tcaaccacac tttcaagaag gtctcggtca ccttcgactc   20820
ctcggtcagc tggccgggca acgaccgtct gctcaccccc aacagagttcg aaatcaagcg   20880 ctcggtcgac ggggagggct acaacgtggc ccagtgcaac atgaccaagg actggttcct   20940
ggtccagatg ctgccaact acaacatcgg ctaccagggc ttctacatcc agagagcta    21000 caaggacagg atgtactcct tcttcaggaa cttccagccc atgagccggc aggtggtgga   21060
```

```
ccagaccaag tacaaggact accaggaggt gggcatcatc caccagcaca acaactcggg   21120
cttcgtgggc tacctcgccc ccaccatgcg cagggacag gcctacccg ccaacttccc    21180
ctaccgctc ataggcaaga ccgcggtcga cagcatcacc cagaaaaagt tcctctgcga   21240
tcgcaccctc tggcgcatcc ccttctccag caacttcatg tccatgggtg cgctctcgga  21300
cctgggccag aacttgctct acgccaactc cgcccacgcc ctcgacatga ccttcgaggt  21360
cgacccatg gacgagccca cccttctcta tgttctgttc gaagtctttg acgtggtccg   21420
ggtccaccag ccgcaccgcg gcgtcatcga gaccgtgtac ctgcgtacgc ccttctcggc  21480
cggcaacgcc accacctaaa gaagcaagcc gcagtcatcg ccgcctgcat gccgtcgggt  21540
tccaccgagc aagagctcag ggccatcgtc agagacctgg gatgcgggcc ctatttttg   21600
ggcactttcg acaagcgctt ccctggcttt gtctccccac acaagctggc ctgcgccatc  21660
gtcaacacgg ccggccgcga accgggggc gtgcactggc tggccttcgc ctggaacccg   21720
cgctccaaaa catgcttcct ctttgacccc ttcggctttt cggaccagcg gctcaagcaa  21780
atctacgagt tcgagtacga gggcttgctg cgtcgcagcg ccatcgcctc ctcgcccgac  21840
cgctgcgtca ccctcgaaaa gtccacccag accgtgcagg ggcccgactc ggccgcctgc  21900
ggtctcttct gctgcatgtt tctgcacgcc tttgtgcact ggcctcagag tcccatggac  21960
cgcaaccca ccatgaactt gctgacgggg gtgcccaact ccatgctcca gagcccccag   22020
gtcgagccca ccctgcgccg caaccaggag cagctctaca gcttcctgga cgccactcg   22080
ccctacttcc gccgccacag cgcacagatc aggagggcca cctccttctg ccacttgcaa  22140
gagatgcaag aagggtaata acgatgtaca cactttttc tcaataaatg gcattttttt   22200
atttatacaa gctctctggg gtattcattt cccaccacca ccaccacccg ccgttgtcgc  22260
catctggctc tatttagaaa tcgaaagggt tctgccggga gtcgccgtgc gccacgggca  22320
gggacacgtt gcgatactgg tagcgggtgc cccacttgaa ctcgggcacc accaggcgag  22380
gcagctcggg gaagttttcg ctccacaggc tgcgggtcag caccagcgcg ttcatcaggt  22440
cgggcgccga gatcttgaag tcgcagttgg ggccgccgcc ctgcgcgcgc gagttgcggt  22500
acaccgggtt gcagcactgg aacaccaaca gcgccgggtg cttcacgcta gccagcacgc  22560
tgccggtcgga gatcagctcg gcgtccaggt cctccgcgtt gctcagcgcg aacggggtca  22620
tcttgggcac ttgcctcccc aggaagggcg cgtgccccgg tttcgagttg cagtcgcagc  22680
gcagcgggat cagcaggtgc ccatgcccgg actcggcgtt ggggtacagc gcgcgcatga  22740
aggcctgcat ctggcggaag gccatctggg ccttggcgcc ctccgagaag aacatgccgc  22800
aggacttgcc cgagaactgg tttgcggggc agctggcgtc gtgcaggcag cagcgcgcgt  22860
cggtgttggc gatctgcacc acgttgcgcc cccaccggtt cttcacgatc ttggccttgg  22920
acgattgctc cttcagcgcg cgctgcccgt tctcgctggt cacatccatc tcgatcacat  22980
gttccttgtt caccatgctg ctgccgtgca ggcacttcag ctcgccctcc gtctcggtgc  23040
agcggtgctg ccacagcgcg cagcccgtgg gctcgaaaga cttgtaggtc acctccgcga  23100
aggactgcag gtaccctgc aaaaagcggc ccatcatggt cacgaaggtc ttgttgctgc    23160
tgaaggtcag ctgcagcccg cggtgctcct cgttcagcca ggtcttgcac acggccgcca  23220
gcgcctccac ctggtcgggc agcatcttga agttcacctt cagctcattc tccacgtggt  23280
acttgtccat cagcgtgcgc gccgcctcca tgcccttctc ccaggccgac accagcggca  23340
ggctcacggg gttcttcacc atcaccgtgg ccgccgcctc cgccgcgctt cgctttccg   23400
ccccgctgtt ctcttcctct tcctcctctt cctgccgcc gcccactcgc agcccccgca   23460
```

```
ccacgggtc gtcttcctgc aggcgctgca ccttgcgctt gccgttgcgc ccctgcttga      23520
tgcgcacggg cgggttgctg aagcccacca tcaccagcgc ggcctcttct tgctcgtcct      23580
cgctgtccag aatgacctcc ggggaggggg ggttggtcat cctcagtacc gaggcacgct      23640
tcttttctt cctgggggcg ttcgccagct ccgcggctgc ggccgctgcc gaggtcgaag      23700
gccgagggct gggcgtgcgc ggcaccagcg cgtcctgcga gccgtcctcg tcctcctcgg      23760
actcgagacg gaggcgggcc cgcttcttcg ggggcgcgcg gggcggcgga ggcggcggcc      23820
gcgacggaga cggggacgag acatcgtcca gggtgggtgg acggcgggcc gcgccgcgtc      23880
cgcgctcggg ggtggtctcg cgctggtcct cttcccgact ggccatctcc cactgctcct      23940
tctcctatag gcagaaagag atcatggagt ctctcatgcg agtcgagaag gaggaggaca      24000
gcctaaccgc cccctctgag ccctccacca ccgccgccac caccgccaat gccgccgcgg      24060
acgacgcgcc caccgagacc accgccagta ccaccnnnct ccccagcgac gcaccccgc       24120
tcgagaatga agtgctgatc gagcaggacc cgggttttgt gagcggagag gaggatgagg      24180
tggatgagaa ggagaaggag gaggtcgccg cctcagtgcc aaaagaggat aaaaagcaag      24240
accaggacga cgcagataag gatgagacag cagtcgggcg ggggaacgga agccatgatg      24300
ctgatgacgg ctacctagac gtgggagacg acgtgctgct taagcacctg caccgccagt      24360
gcgtcatcgt ctgcgacgcg ctgcaggagc ggtgcgaagt gccctggac gtggcggagg       24420
tcagccgcgc ctacgagcgg cacctcttcg cgccgcacgt gccccccaag cgccgggaga      24480
acggcacctg cgagcccaac ccgcgtctca acttctaccc ggtcttcgcg gtacccgagg      24540
tgctggccac ctaccacatc tttttccaaa actgcaagat ccccctctcc tgccgcgcta      24600
accgcacccg cgccgacaaa accctgaccc tgcggcaggg cgcccacata cctgatattg      24660
cctctctgga ggaagtgccc aagatcttcg agggtctcgg tcgcgacgag aaacgggcgg      24720
cgaacgctct gcacggagac agcgaaaacg agagtcactc gggggtgctg gtggagctcg      24780
agggcgacaa cgcgcgcctg gccgtactca agcgcagcat agaggtcacc cactttgcct      24840
acccggcgct caacctgccc cccaaggtca tgagtgtggt catgggcgag ctcatcatgc      24900
gccgcgccca gcccctggcc gcggatgcaa acttgcaaga gtcctcagag gaaggcctgc      24960
ccgcggtcag cgacgagcag ctggcgcgct ggctggagac ccgcgacccc gcgcagctgg      25020
aggagcggcg caagctcatg atggccgcgg tgctggtcac cgtggagctc gagtgtctgc      25080
agcgcttctt cgcggacccc gagatgcagc gcaagctcga ggagaccctg cactacacct      25140
tccgccaggg ctacgtgcgc caggcctgca agatctccaa cgtggagctc tgcaacctgg      25200
tctcctacct gggcatcctg cacgagaacc gcctcgggca gaacgtcctg cactccaccc      25260
tcaaagggga ggcgcgccgc gactacatcc gcgactgcgc ctacctcttc ctctgctaca      25320
cctggcagac ggccatgggg gtctggcagc agtgcctgga ggagcgcaac ctcaaggagc      25380
tggaaaagct cctcaagcgc accctcaggg accctctgga gggcttcaac gagcgctcgg      25440
tggccgccgc gctggcggac atcatcttcc ccgagcgcct gctcaagacc ctgcagcagg      25500
gcctgcccga cttcaccagc cagagcatgc tgcagaactt caggactttc atcctggagc      25560
gctcgggcat cctgccggcc acttgctgcg cgctgcccag cgacttcgtg cccatcaagt      25620
acagggagtg cccgccgccg ctctggggcc actgctacct cttccagctg gccaactacc      25680
tcgcctacca ctcggacctc atggaagacg tgagcggcga gggcctgctc gagtgccact      25740
gccgctgcaa cctctgcacg ccccaccgct ctctagtctg caacccgcag ctgctcagcg      25800
```

```
agagtcagat tatcggtacc ttcgagctgc agggtccctc gcctgacgag aagtccgcgg   25860
ctccggggct gaaactcact ccggggctgt ggacttccgc ctaccacgc  aaatttgtac   25920
ctgaggacta ccacgcccac gagatcaggt tctacgaaga ccaatcccgc ccgcccaagg   25980
cggagctcac cgcctgcgtc atcacccagg ggcacatcct gggccaattg caagccatca   26040
acaaagcccg ccgagagttc ttgctgaaaa agggtcgggg ggtgtacctg gaccccagt    26100
ccggcgagga gctaaacccg ctaccccgc  cgccgcccca gcagcgggac cttgcttccc    26160
aggatggcac ccagaaagaa gcagcagccg ccgccgcagc catacatgct tctggaggaa   26220
gaggaggagg actgggacag tcaggcagag gagatgatgg aagactggga ggaggacagc   26280
agcctagacg aggaagcttc agaggccgaa gaggtggcag acgcaacacc atcaccctcg   26340
gtcgcagccc cctcgccggg gcccctgaaa tcctccgaac ccagcaccag cgctataacc   26400
tccgctcctc cggcgccggc gccacccgcc cgcagaccca accgtagatg ggacaccaca   26460
ggaaccgggg tcggtaagtc caagtgcccg ccgccgccac cgcagcagca gcagcagcag   26520
cgccagggct accgctcgtg gcgcgggcac aagaacgcca tagtcgcctg cttgcaagac   26580
tgcgggggca acatctcttt cgcccgccgc ttcctgctat tccaccacgg ggtcgccttt   26640
ccccgcaatg tcctgcatta ctaccgtcat ctctacagcc cctactgcag cggcgaccca   26700
gaggcggcag cggcagccac agcggcgacc accacctagg aagatatcct ccgcgggcaa   26760
gacagcggca gcagcggcca ggagaccgc  ggcagcagcg gcgggagcgg tgggcgcact   26820
gcgcctctcg cccaacgaac ccctctcgac ccgggagctc agacacagga tcttccccac   26880
tttgtatgcc atcttccaac agagcagagg ccaggagcag gagctgaaaa taaaaaacag   26940
atctctgcgc tccctcaccc gcagctgtct gtatcacaaa agcgaagatc agcttcggcg   27000
cacgctggag gacgcggagg cactcttcag caaatactgc gcgctcactc ttaaagacta   27060
gctccgcgcc cttctcgaat ttaggcggga gaaaactacg tcatcgccgg ccgccgccca   27120
gcccgcccag ccgagatgag caaagagatt cccacgccat acatgtggag ctaccagccg   27180
cagatgggac tcgcggcggg agcggcccag gactactcca cccgcatgaa ctacatgagc   27240
gcgggacccc acatgatctc acaggtcaac gggatccgcg cccagcgaaa ccaaatactg   27300
ctggaacagg cggccatcac cgccacgccc cgccataatc tcaaccccg  aaattggccc   27360
gccgccctag tgtaccagga aacccctcc  gccaccaccg tactacttcc gcgtgacgcc   27420
caggccgaag tccagatgac taactcaggg gcgcagctcg cgggcggctt tcgtcacggg   27480
gcgcggccgc tccgaccagg tataagacac ctgatgatca gaggccgagg tatccagctc   27540
aacgacgagt cggtgagctc ttcgctcggt ctccgtccgg acggaacttt ccagctcgcc   27600
ggatccggtc gctcttcgtt cacgcccgc  caggcgtacc tgactctgca gacctcgtcc   27660
tcggagcccc gctccggcgg catcggaacc ctccagttcg tggaggagtt cgtgccctcg   27720
gtctacttca cccccttctc gggacctccc ggacgctacc ccgaccagtt cattccgaac   27780
tttgacgcgg tgaaggactc ggcggacggc tacgactgaa tgtcaggtgc cgaggcagag   27840
cagcttcgcc tgagacacct cgagcactgc cgccgccaca agtgcttcgc ccgcggttcc   27900
ggtgagttct gctactttca gctacccgag gagcataccg aggggccggc gcacggcgtc   27960
cgcctgacca cccagggcga ggttacctgt tccctcatcc gggagttcac cctccgtccc   28020
ctgctagtgg agcgggagcg gggtccctgt gtcctaacta tcgcctgcaa ctgccctaac   28080
cctggattac atcaagatct ttgctgtcat ctctgtgctg agtttaataa acgctgagat   28140
cagaatctac tggggctcct gtcgccatcc tgtgaacgcc accgtcttca cccaccccga   28200
```

```
ccaggcccag gcgaacctca cctgcggtct gcatcggagg tccaagaagt acctcacctg  28260
gtacttcaac ggcacccct  ttgtggttta caacagcttc gacggggacg gagtctccct  28320
gaaagaccag ctctccggtc tcagctactc catccacaag aacaccaccc tccaactctt  28380
ccctccctac ctgccgggaa cctacgagtg cgtcaccggc cgctgcaccc acctcacccg  28440
cctgatcgta aaccagagct ttccgggaac agataactcc ctcttcccca gaacaggagg  28500
tgagctcagg aaactccccg gggaccaggg cggagacgta ccttcgaccc ttgtggggtt  28560
aggatttttt attaccgggt tgctggctct tttaatcaaa gcttccttga gatttgttct  28620
ttccttctac gtgtatgaac acctcagcct ccaataactc taccctttct tcgggatcag  28680
gtgacttttc tgaaatcggg cttggtgtgc tgcttactct gttgattttt ttccttatca  28740
tactcagcct tctgtgcctc aggctcgccg cctgctgcgc acacatctat atctactgct  28800
ggttgctcaa gtgcaggggt cgccacccaa gatgaacagg tacatggtcc tatcgatcct  28860
aggcctgctg gccctggcgg cctgcagcgc cgccaaaaaa gagattacct ttgaggagcc  28920
cgcttgcaat gtaactttca gcccgaggg  tgaccaatgc accaccctcg tcaaatgcgt  28980
taccaatcat gagaagctgc gcatcgacta caaaaacaaa actggccggt ttgcggtcta  29040
tagtgtgttt acgcccggag acccctctaa ctactctgtc accgtcttcc agggcggaca  29100
gtctaagata ttcaattaca ctttcccttt ttatgagttg tgcgatgcgg tcatgtacat  29160
gtcaaaacag tacaacctgt ggcctccctc tccccaggcg tgtgtggaaa atactgggtc  29220
ttactgctgt atggctttgg caatcactac gctcgctcta atctgcacgg tgctatatat  29280
aaaattcagg cagaggcgaa tctttatcga tgaaaagaaa atgccttgat cgctaacacc  29340
ggctttctat ctgcagaatg aatgcaatca cctccctact aatcaccacc accctccttg  29400
cgattgccca tgggttgaca cgaatcgaag tgccagtggg gtccaatgtc accatggtgg  29460
gccccgccgg caattccacc ctcatgtggg aaaaatttgt ccgcaatcaa tgggttcatt  29520
tctgctctaa ccgaatcagt atcaagccca gagccatctg cgatgggcaa aatctaactc  29580
tgatcaatgt gcaaatgatg gatgctgggt actattacgg gcagcgggga gaaatcatta  29640
attactggcg accccacaag gactacatgc tgcatgtagt cgaggcactt cccactacca  29700
cccccactac cacctctccc accaccacta ccactactac tactactact accactaccg  29760
ctgcccgcca tacccgcaaa agcaccatga ttagcacaaa gcccctcgt  gctcactccc  29820 acgccggcgg gcccatcggt gcgacctcag aaaccaccga gctttgcttc tgccaatgca  29880
ctaacgccag cgctcatgaa ctgttcgacc tggagaatga ggatgcccag cagagctccg  29940
cttgcctgac ccaggaggct gtggagcccg ttgccctgaa gcagatcggt gattcaataa  30000
ttgactcttc ttcttttgcc actcccgaat accctcccga ttctactttc cacatcacgg  30060
gtaccaaaga ccctaacctc tctttctacc tgatgctgct gctctgtatc tctgtggtct  30120
cttccgcgct gatgttactg gggatgttct gctgcctgat ctgccgcaga aagagaaaag  30180
ctcgctctca gggccaacca ctgatgccct tcccctaccc ccggatttt  gcagataaca  30240 agatatgagc tcgctgctga cactaaccgc tttactagcc tgccgctctaa cccttgtcgc  30300 ttgcgactcg agattccaca atgtcacagc tgtggcagga gaaaatgtta ctttcaactc  30360
cacggccgat acccagtggt cgtggagtgg ctcaggtagc tacttaacta tctgcaatag  30420
ctccacttcc cccagcatat ccccaaccaa gtaccaatgc aatgccagcc tgttcaccct  30480
catcaacgct tccacccctgg acaatggact ctatgtaggc tatgtaccct ttggtgggca  30540
```

```
aggaaagacc cacgcttaca acctggaagt tcgccagccc agaaccacta cccaagctwc   30600
ymccaycacc agcaccagca gcagcagcca cagcagcagc agcagattat tgactttggt   30660
tttggccagc tcatctgccg ctacccaggc catctacagc tctgtgcccg aaaccactca   30720
gacccaccgc ccagaaacga ccaccgccac caccctacac acctccagcg atcagatgcc   30780
gaccaacatc acccccttgg ctcttcaaat gggacttaca agccccactc caaaaccagt   30840
ggatgcggcc gaggtctccg ccctcgtcaa tgactgggcg gggctgggaa tgtggtggtt   30900
cgccataggc atgatggcgc tctgcctgct tctgctctgg ctcatctgct gcctccaccg   30960
caggcgagcc agaccccca tctatagacc catcattgtc ctgaacccg ataatgatgg   31020 gatccataga ttggatggcc tgaaaaacct actttttct tttacagtat gataaattga   31080
gacatgcctc gcattttctt gtacatgttc cttctcccac cttttctggg gtgttctacg   31140
ctggccgctg tgtctcacct ggaggtagac tgcctctcac ccttcactgt ctacctgctt   31200
tacggattgg tcaccctcac tctcatctgc agcctaatca cagtaatcat cgccttcatc   31260
cagtgcattg attacatctg tgtgcgcctc gcatacttca gacaccaccc gcagtaccga   31320
gacaggaaca ttgcccaact tctaagactg ctctaatcat gcataagact gtgatctgcc   31380
ttctgatcct ctgcatcctg cccacccctca cctcctgcca gtacaccaca aaatctccgc   31440
gcaaaagaca tgcctcctgc cgcttcaccc aactgtggaa tatacccaaa tgctacaacg   31500
aaaagagcga gctctccgaa gcttggctgt atggggtcat ctgtgtctta gttttctgca   31560
gcactgtctt tgccctcatg atctaccccct actttgattt gggatggaac gcgatcgatg   31620
ccatgaatta ccccacccttt cccgcacccg agataattcc actgcgacaa gttgtacccg   31680
ttgtcgttaa tcaacgcccc ccatccccta cgcccactga aatcagctac tttaacctaa   31740
caggcggaga tgactgacgc cctagatcta gaaatggacg gcatcagtac cgagcagcgt   31800
ctcctagaga ggcgcaggca ggcggctgag caagagcgcc tcaatcagga gctccgagat   31860
ctcgttaacc tgcaccagtg caaaagaggc atcttttgtc tggtaaagca ggccaaagtc   31920
acctacgaga agaccggcaa cagccaccgc ctcagttaca aattgcccac ccagcgccag   31980
aagctggtgc tcatggtggg tgagaatccc atcaccgtca cccagcactc ggtagagacc   32040 gagggggtgtc tgcactcccc ctgtcgggt ccagaagacc tctgcaccct ggtaaagacc   32100
ctgtgcggtc tcagagattt agtcccctt aactaatcaa acactggaat caataaaaag   32160
aatcacttac ttaaaatcag acagcaggtc tctgtccagt ttattcagca gcacctcctt   32220 ccctcctcc caactctggt actccaaacg ccttctggcg gcaaacttcc tccacaccct   32280
gaagggaatg tcagattctt gctcctgtcc ctccgcaccc actatcttca tgttgttgca   32340
gatgaagcgc accaaaacgt ctgacgagag cttcaaccc gtgtaccct atgcacgga   32400 aagcggccct ccctccgtcc ctttcctcac ccctcccttc gtgtctcccg atggattcca   32460
agaaagtccc cccggggtcc tgtctctgaa cctggccgag ccctggtca cttcccacgg   32520 catgctcgcc ctgaaaatgg gaagtggcct ctccctggac gacgctggca acctcacctc   32580
tcaagatatc accaccgcta gccctcccct caaaaaaacc aagaccaacc tcagcctaga   32640
aacctcatcc cccctaactg tgagcaccte aggcgccctc accgtagcag ccgccgctcc   32700
cctggcggtg gccggcacct ccctcaccat gcaatcagag gcccccctga cagtacagga   32760
tgcaaaactc accctggcca ccaaaggccc cctgaccgtg tctgaaggca aactggcctt   32820
gcaaacatcg gccccgctga cggccgctga cagcagcacc ctcaccgtta gcgccacacc   32880
accaattaat gtaagcagtg gaagtttagg cttagacatg gaagacccta tgtatactca   32940
```

```
caatggaaaa ctgggaataa gaattgggggg tccactaaga gtagtagaca gcttgcatac   33000
actcactgta gttaccggaa atggactaac tgtagataac aatgccctcc aaactaaagt   33060
tacgggcgcc ctaggttatg acacatcagg aaatctacaa ttaagagctg caggaggtat   33120
gcgaattgac gcaaatggcc aacttatcct taatgtggca tacccatttg atgctcagaa   33180
caatctcagc cttagacttg gtcagggacc cctgtatata aacacagacc acaacctgga   33240
tttgaattgc aacagaggtc taaccacaac taccaccaac aacacaaaaa aacttgagac   33300
taaaattagc tcaggcttag actatgacac caatggtgct gtcattatta aacttggcac   33360
tggtctaagc ttcgacaaca caggcgccct aactgtggga aacactggtg atgataaact   33420
gactctgtgg acgacccag acccatctcc aaattgcaga attcactcag acaaagactg   33480
caagtttact ctagtcctaa ctaagtgtgg aagccaaatc ctggcctctg tcgccgccct   33540
agcggtatca ggaaatctgg cttcgataac aggcaccgtt gccagcgtta ccatctttct   33600
cagatttgat cagaatggag tgcttatgga aaactcctcg ctagacaggc agtactggaa   33660
cttcagaaat ggcaactcaa ctaacgctgc ccctacacc aatgcagttg ggttcatgcc   33720
aaacctcgca gcataccca aaacgcaaag ccagactgct aaaaacaaca ttgtaagtca   33780
ggtttacttg aatggagaca aatccaaacc catgacctt accatcaccc tcaatggaac   33840
taatgaatcc agtgaaacta gccaggtgag tcactactcc atgtcattta catgggcttg   33900
ggaaagtggg caatatgcca ctgaaacctt tgccaccaac tccttcacct tttcttacat   33960
tgctgaacaa taaaaagcat gacactgatg ttcatttctg attcttattt tattattttc   34020
aaacacaaca aaatcattca agtcattctt ccatcttagc ttaatagaca cagtagctta   34080
atagacccag tagtgcaaag ccccattcta gcttatagat cagacagtga taattaacca   34140
ccaccaccac catacctttt gattcaggaa atcatgatca tcacaggatc ctagtcttca   34200
ggccgccccc tccctcccaa gacacagaat acacagtcct ctcccccga ctggctttaa   34260 ataacaccat ctggttggtc acagacatgt tcttaggggt tatattccac acggtctcct   34320
gccgcgccag gcgctcgtcg gtgatgttga taaactctcc cggcagctcg ctcaagttca   34380
cgtcgctgtc cagcggctga acctccggct gacgcgataa ctgtgcgacc ggctgctgga   34440
caaacggagg ccgcgcctac aaggggtag agtcataatc ctcggtcagg atagggcggt   34500
gatgcagcag cagcgagcga acatctgct gccgccgccg ctccgtccgg caggaaaaca   34560
acacgccggt ggtctcctcc gcgataatcc gcaccgcccg cagcatcagc ttcctcgttc   34620
tccgcgcgca gcacctcacc ctgatctcgc tcaagtcggc gcagtaggta cagcacagca   34680
ccacgatgtt attcatgatc ccacagtgca gggcgctgta tccaaagctc atgccgggaa   34740
ccaccgcccc cacgtggcca tcgtaccaca agcgcacgta aattaagtgt cgacccctca   34800
tgaacgtgct ggacacaaac attacttcct tgggcatgtt gtaattcacc acctcccggt   34860
accagataaa cctctggtta aacagggcac cttccaccac catcctgaac caagaggcca   34920
gaacctgccc accggctatg cactgcaggg aacccgggtt ggaacaatga caatgcagac   34980
tccaaggctc gtaaccgtgg atcatccggc tgctgaaggc atcgatgttg gcacaacaca   35040
gacacacgtg catgcacttt ctcatgatta gcagctcttc cctcgtcagg atcatatccc   35100
aaggaataac ccattcttga atcaacgtaa aacccacaca gcagggaagg cctcgcacat   35160
aactcacgtt gtgcatggtc agcgtgttgc attccgaaaa cagcgatga tcctccagta   35220 tcgaggcgcg ggtctccttc tcacagggag gtaaagggtc cctgctgtac ggactgcgcc   35280
```

```
gggacgaccg agatcgtgtt gagcgtagtg tcatggaaaa gggaacgccg gacgtggtca    35340
tacttcttga agcagaacca ggttcgcgcg tggcaggcct ccttgcgtct gcggtctcgc    35400
cgtctagctc gctccgtgtg atagttgtag tacagccact cccgcagagc gtcgaggcgc    35460
accctggctt ccggatctat gtagactccg tcttgcaccg cggccctgat aatatccacc    35520
accgtagaat aagcaacacc cagccaagca atacactcgc tctgcgagcg gcagacagga    35580
ggagcgggca gagatgggag aaccatgata aaaaactttt tttaaagaat attttccaat    35640
tcttcgaaag taagatctat caagtggcag cgctcccctc cactggcgcg gtcaaactct    35700
acggccaaag cacagacaac ggcatttcta agatgttcct taatggcgtc aaaagacac     35760
accgctctca agtcgcagta aactatgaat gaaaacccat ccggctgatt ttccaatata    35820
gacgcgccgg cggcgtccac caaacccaga taatttttctt ctctccagcg gtttagaatc   35880
tgtctaagca aatcccttat atcaagtccg gccatgccaa aaatctgctc aagagcgccc    35940
tccaccttca tgaccaagca gcgcatcatg attgcaaaaa ttcaggttct tcagagacct    36000
gtataagatt caaaatggga acattaacaa aaattcctct gtcgcgcaga tcccttcgca    36060
gggcaagctg aacataatca gacaggtctg aacggaccag tgaggccaaa tccccaccag    36120
gaaccagatc cagagaccct atactgatta tgacgcgcat actcggggct atgctgacca    36180
gcgtagcgcc gatgtaggcg tgctgcatgg gcggcgagat aaaatgcaaa gtgctggtta    36240
aaaaatcagg caaagcctcg cgcaaaaaag ctaacacatc ataatcatgc tcatgcaggt    36300
agttgcaggt aagctcagga accaaaacgg aataacacac gattttcctc tcaaacatga    36360
cttcgcggat actgcgtaaa acaaaaatta taaataaaaa attaattaac ttaaacattg    36420
gaagcctgtc tcacaacagg aaaaaccact ttaatcaaca taagacgggc cacgggcatg    36480
ccggcatagc cgtaaaaaaa ttggtccccg tgattaacaa gtaccacaga cagctccccg    36540
gtcatgtcgg gggtcatcat gtgagactct gtatacacgt ctggattgtg aacatcagac    36600
aaacaaagaa atcgagccac gtagcccgga ggtataatca cccgcaggcg gaggtacagc    36660
aaaacgaccc ccataggagg aatcacaaaa ttagtaggag aaaaaaatac ataaacacca    36720
gaaaaaccct gttgctgagg caaaatagcg ccctcccgat ccaaacaac ataaagcgct     36780
tccacaggag cagccataac aaagacccga gtcttaccag taaaaagaaa aaagatctct    36840
caacgcagca ccagcaccaa cacttcgcag tgtaaaaggc caagtgccga gagagtatat    36900
ataggaataa aaagtgacgt aaacgggcaa agtccaaaaa acgcccagaa aaaccgcacg    36960
cgaacctacg ccccgaaacg aaagccaaaa aacactagac actcccttcc ggcgtcaact    37020
tccgctttcc cacgctacgt cacttgcccc agtcaaacaa actacatatc ccgaacttcc    37080
aagtcgccac gcccaaaaca ccgcctacac ctccccgccc gccggccgc cccaaaccc      37140
gcctcccgcc ccgcgccccg ccccgcgccg cccatctcat tatcatattg gcttcaatcc    37200
aaaataaggt atattattga tgatggttta aacggatcca attcttgaag acgaaagggc    37260
ctcgtgatac gcctattttt ataggttaat gtcatgataa taatgggttc ttagacgtca    37320
ggtggcactt ttcggggaaa tgtgcgcgga accccctattt gtttattttt ctaaatacat   37380
tcaaatatgt atccgctcat gagacaataa ccctgataaa tgcttcaata atattgaaaa    37440
aggaagagta tgagtattca acatttccgt gtcgccctta ttccctttttt gcggcatttt   37500
tgccttcctg ttttttgctca cccagaaacg ctggtgaaag taaaagatgc tgaagatcag    37560
ttgggtgcac gagtgggtta catcgaactg gatctcaaca gcggtaagat ccttgagagt    37620
tttcgccccg aagaacgttt tccaatgatg agcactttta aagttctgct atgtggcgcg    37680
```

```
gtattatccc gtgttgacgc cgggcaagag caactcggtc gccgcataca ctattctcag   37740
aatgacttgg ttgagtactc accagtcaca gaaaagcatc ttacggatgg catgacagta   37800
agagaattat gcagtgctgc cataaccatg agtgataaca ctgcggccaa cttacttctg   37860
acaacgatcg gaggaccgaa ggagctaacc gcttttttgc acaacatggg ggatcatgta   37920
actcgccttg atcgttggga accggagctg aatgaagcca taccaaacga cgagcgtgac   37980
accacgatgc ctgtagcaat ggcaacaacg ttgcgcaaac tattaactgg cgaactactt   38040
actctagctt cccggcaaca attaatagac tggatggagg cggataaagt tgcaggacca   38100
cttctgcgct cggcccttcc ggctggctgg tttattgctg ataaatctgg agccggtgag   38160
cgtgggtctc gcggtatcat tgcagcactg gggccagatg gtaagccctc ccgtatcgta   38220
gttatctaca cgacggggag tcaggcaact atggatgaac gaaatagaca gatcgctgag   38280
ataggtgcct cactgattaa gcattggtaa ctgtcagacc aagtttactc atatatactt   38340
tagattgatt taaaaggatc taggtgaaga tcctttttga taatctcatg accaaaatcc   38400
cttaacgtga gttttcgttc cactgagcgt cagaccccgt agaaaagatc aaaggatctt   38460
cttgagatcc ttttttctg cgcgtaatct gctgcttgca acaaaaaaa ccaccgctac   38520 cagcggtggt ttgtttgccg gatcaagagc taccaactct ttttccgaag gtaactggct   38580
tcagcagagc gcagatacca aatactgtcc ttctagtgta gccgtagtta ggccaccact   38640
tcaagaactc tgtagcaccg cctacatacc tcgctctgct aatcctgtta ccagtggctg   38700
ctgccagtgg cgataagtcg tgtcttaccg ggttggactc aagacgatag ttaccggata   38760
aggcgcagcg gtcgggctga acggggggtt cgtgcacaca gcccagcttg gagcgaacga   38820
cctacaccga actgagatac ctacagcgtg agctatgaga aagcgccacg cttcccgaag   38880
ggagaaaggc ggacaggtat ccggtaagcg gcagggtcgg aacaggagag cgcacgaggg   38940
agcttccagg gggaaacgcc tggtatcttt atagtcctgt cgggtttcgc cacctctgac   39000
ttgagcgtcg atttttgtga tgctcgtcag ggggcggag cctatggaaa aacgccagca   39060
acgcggcctt tttacggttc ctggcctttt gctggccttg aagctgtccc tgatggtcgt   39120
catctacctg cctggacagc atggcctgca acgcgggcat cccgatgccg ccggaagcga   39180
gaagaatcat aatggggaag gccatccagc ctcgcgtcgc agatccgaat tcgtttaaac   39240
```

<210> SEQ ID NO 18
<211> LENGTH: 33
<212> TYPE: DNA
<213> ORGANISM: Pan troglodytes

<400> SEQUENCE: 18
atacggacta gtggagaagt actcgcctac atg                                  33

<210> SEQ ID NO 19
<211> LENGTH: 36
<212> TYPE: DNA
<213> ORGANISM: Pan troglodytes

<400> SEQUENCE: 19
atacggaaga tctaagactt caggaaatat gactac                               36

<210> SEQ ID NO 20
<211> LENGTH: 45
<212> TYPE: DNA
<213> ORGANISM: Pan troglodytes

<400> SEQUENCE: 20
attcagtgta caggcgcgcc aaagcatgac actgatgttc atttc    45

<210> SEQ ID NO 21
<211> LENGTH: 35
<212> TYPE: DNA
<213> ORGANISM: Pan troglodytes

<400> SEQUENCE: 21
actaggacta gttataagct agaatggggc tttgc    35

<210> SEQ ID NO 22
<211> LENGTH: 37740
<212> TYPE: DNA
<213> ORGANISM: Pan troglodytes
<220> FEATURE:
<221> NAME/KEY: misc_feature
<222> LOCATION: (24391)..(24393)
<223> OTHER INFORMATION: n is a, c, g, or t

<400> SEQUENCE: 22

| | | | | | |
|---|---|---|---|---|---|
| catcatcaat | aatataccttt | attttggatt | gaagccaata | tgataatgag | atgggcggcg | 60 |
| cggggcgggg | cgcggggcgg | gaggcgggtt | tgggggcggg | ccggcgggcg | gggcggtgtg | 120 |
| gcggaagtgg | actttgtaag | tgtggcggat | gtgacttgct | agtgccgggc | gcggtaaaag | 180 |
| tgacgttttc | cgtgcgcgac | aacgcccccg | ggaagtgaca | ttttttcccgc | ggttttttacc | 240 |
| ggatgttgta | gtgaatttgg | gcgtaaccaa | gtaagatttg | gccattttcg | cgggaaaact | 300 |
| gaaacgggga | agtgaaatct | gattaatttt | gcgttagtca | taccgcgtaa | tatttgtcta | 360 |
| gggccgaggg | actttggccg | attacgtgga | ggactcgccc | aggtgttttt | tgaggtgaat | 420 |
| ttccgcgttc | cgggtcaaag | tctgcgtttt | attattatag | gatatcccat | tgcatacgtt | 480 |
| gtatccatat | cataatatgt | acatttatat | tggctcatgt | ccaacattac | cgccatgttg | 540 |
| acattgatta | ttgactagtt | attaatagta | atcaattacg | gggtcattag | ttcatagccc | 600 |
| atatatggag | ttccgcgtta | cataacttac | ggtaaatggc | ccgcctggct | gaccgcccaa | 660 |
| cgacccccgc | ccattgacgt | caataatgac | gtatgttccc | atagtaacgc | caatagggac | 720 |
| tttccattga | cgtcaatggg | tggagtattt | acggtaaact | gcccacttgg | cagtacatca | 780 |
| agtgtatcat | atgccaagta | cgccccctat | tgacgtcaat | gacggtaaat | ggcccgcctg | 840 |
| gcattatgcc | cagtacatga | ccttatggga | ctttcctact | tggcagtaca | tctacgtatt | 900 |
| agtcatcgct | attaccatgg | tgatgcggtt | ttggcagtac | atcaatgggc | gtggatagcg | 960 |
| gtttgactca | cggggatttc | caagtctcca | ccccattgac | gtcaatggga | gtttgttttg | 1020 |
| gcaccaaaat | caacgggact | ttccaaaatg | tcgtaacaac | tccgccccat | tgacgcaaat | 1080 |
| gggcggtagg | cgtgtacggt | gggaggtcta | tataagcaga | gctctcccta | tcagtgatag | 1140 |
| agatctccct | atcagtgata | gagatcgtcg | acgagctcgt | ttagtgaacc | gtcagatcgc | 1200 |
| ctggagacgc | catccacgct | gttttgacct | ccatagaaga | caccgggacc | gatccagcct | 1260 |
| ccgcggccgg | gaacggtgca | ttggaacgcg | gattccccgt | gccaagagtg | agatcttccg | 1320 |
| tttatctagg | taccgggccc | ccctcgagg | tcgacggtat | cgataagctt | cacgctgccg | 1380 |
| caagcactca | gggcgcaagg | gctgctaaag | gaagcggaac | acgtagaaag | ccagtccgca | 1440 |
| gaaacggtgc | tgaccccgga | tgaatgtcag | ctactgggct | atctggacaa | gggaaaacgc | 1500 |
| aagcgcaaag | agaaagcagg | tagcttgcag | tgggcttaca | tggcgatagc | tagactgggc | 1560 |
| ggttttatgg | acagcaagcg | aaccggaatt | gccagctggg | gcgccctctg | gtaaggttgg | 1620 |

-continued

```
gaagccctgc aaagtaaact ggatggcttt cttgccgcca aggatctgat ggcgcagggg    1680
atcaagatct aaccaggagc tatttaatgg caacagttaa ccagctggta cgcaaaccac    1740
gtgctcgcaa agttgcgaaa agcaacgtgc ctgcgctgga agcatgcccg caaaaacgtg    1800
gcgtatgtac tcgtgtatat actaccactc ctaaaaaacc gaactccgcg ctgcgtaaag    1860
tatgccgtgt tcgtctgact aacggtttcg aagtgacttc ctacatcggt ggtgaaggtc    1920
acaacctgca ggagcactcc gtgatcctga tccgtggcgg tcgtgttaaa gacctcccgg    1980
gtgttcgtta ccacaccgta cgtggtgcgc ttgactgctc cggcgttaaa gaccgtaagc    2040
aggctcgttc caagtatggc gtgaagcgtc ctaaggctta atggtagatc tgatcaagag    2100
acaggatgac ggtcgtttcg catgcttgaa caagatggat tgcacgcagg ttctccggcc    2160
gcttgggtgg agaggctatt cggctatgac tgggcacaac agacaatcgg ctgctctgat    2220
gccgccgtgt tccggctgtc agcgcagggg cgcccggttc tttttgtcaa gaccgacctg    2280
tccggtgccc tgaatgaact gcaggacgag gcagcgcggc tatcgtggct ggccacgacg    2340
ggcgttcctt gcgcagctgt gctcgacgtt gtcactgaag cgggaaggga ctggctgcta    2400
ttgggcgaag tgccggggca ggatctcctg tcatctcacc ttgctcctgc cgagaaagta    2460
tccatcatgg ctgatgcaat gcggcggctg catacgcttg atccggctac ctgcccattc    2520
gaccaccaag cgaaacatcg catcgagcga gcacgtactc ggatggaagc cggtcttgtc    2580
gatcaggatg atctggacga agagcatcag gggctcgcgc cagccgaact gttcgccagg    2640
ctcaaggcgc gcatgcccga cggcgaggat ctcgtcgtga cccatggcga tgcctgcttg    2700
ccgaatatca tggtggaaaa tggccgcttt tctggattca tcgactgtgg ccggctgggt    2760
gtggcggacc gctatcagga catagcgttg gctacccgtg atattgctga agagcttggc    2820
ggcgaatggg ctgaccgctt cctcgtgctt tacggtatcg ccgctcccga ttcgcagcgc    2880
atcgccttct atcgccttct tgacgagttc ttctgagcgg gactctgggg ttcgaaatga    2940
ccgaccaagc gacgcccaac ctgccatcac gagatttcga ttccaccgcc gccttctatg    3000
aaaggttggg cttcggaatc gttttccggg acgccggctg gatgatcctc cagcgcgggg    3060
atctcatgct ggagttcttc gcccaccccg ggctcgatcc cctcgggggg aatcagaatt    3120
cagtcgacag cggccgcgat ctgctgtgcc ttctagttgc cagccatctg ttgtttgccc    3180
ctcccccgtg ccttccttga ccctggaagg tgccactccc actgtccttt cctaataaaa    3240
tgaggaaatt gcatcgcatt gtctgagtag gtgtcattct attctggggg gtggggtggg    3300
gcaggacagc aagggggagg attgggaaga caatagcagg catgctgggg atgcggtggg    3360
ctctatggcc gatcagcgat cgctgaggtg ggtgagtggg cgtggcctgg ggtggtcatg    3420
aaaatatata agttggggt cttagggtct ctttatttgt gttgcagaga ccgccggagc    3480
catgagcggg agcagcagca gcagcagtag cagcagcgcc ttggatggca gcatcgtgag    3540
cccttatttg acgacgcgga tgccccactg ggccggggtg cgtcagaatg tgatgggctc    3600
cagcatcgac ggccgacccg tcctgcccgc aaattccgcc acgctgacct atgcgaccgt    3660
cgcggggacg ccgttggacg ccaccgccgc cgccgccgcc accgcagccg cctcggccgt    3720
gcgcagcctg gccacggact ttgcattcct gggaccactg gcgacagggg ctacttctcg    3780
ggccgctgct gccgccgttc gcgatgacaa gctgaccgcc ctgctggcgc agttggatgc    3840
gcttactcgg gaactgggtg accttttctca gcaggtcatg gccctgcgcc agcaggtctc    3900 ctcccctgcaa gctggcggga atgcttctcc cacaaatgcc gtttaagata aataaaacca    3960
```

```
gactctgttt ggattaaaga aaagtagcaa gtgcattgct ctctttattt cataattttc    4020
cgcgcgcgat aggccctaga ccagcgttct cggtcgttga gggtgcggtg tatcttctcc    4080
aggacgtggt agaggtggct ctggacgttg agatacatgg gcatgagccc gtcccggggg    4140
tggaggtagc accactgcag agcttcatgc tccggggtgg tgttgtagat gatccagtcg    4200
tagcaggagc gctgggcatg gtgcctaaaa atgtccttca gcagcaggcc gatggccagg    4260
gggaggccct tggtgtaagt gtttacaaaa cggttaagtt gggaagggtg cattcgggga    4320
gagatgatgt gcatcttgga ctgtattttt agattggcga tgtttccgcc cagatccctt    4380
ctgggattca tgttgtgcag gaccaccagt acagtgtatc cggtgcactt ggggaatttg    4440
tcatgcagct tagagggaaa agcgtggaag aacttggaga cgcccttgtg gcctcccaga    4500
ttttccatgc attcgtccat gatgatggca atgggcccgc ggaggcagc ttggcaaag     4560
atatttctgg ggtcgctgac gtcgtagttg tgttccaggg tgaggtcgtc ataggccatt    4620
tttacaaagc gcgggcggag ggtgcccgac tggggatga tggtcccctc tggccccggg     4680
gcgtagttgc cctcgcagat ctgcatttcc caggccttaa tctcgagggg gggaatcata    4740
tccacctgcg gggcgatgaa gaaaacggtt tccggagccg gggagattaa ctgggatgag    4800
agcaggtttc taagcagctg tgattttcca caaccggtgg gcccataaat aacacctata    4860
accggttgca gctggtagtt tagagagctg cagctgccgt cgtcccggag gagggggcc     4920
acctcgttga gcatgtccct gacgcgcatg ttctccccga ccagatccgc cagaaggcgc    4980
tcgccgccca gggacagcag ctcttgcaag gaagcaaagt ttttcagcgg cttgaggccg    5040
tccgccgtgg gcatgttttt cagggtctgg ctcagcagct ccaggcggtc ccagagctcg    5100
gtgacgtgct ctacggcatc tctatccagc atatctcctc gtttcgcggg ttggggcgac    5160
tttcgctgta gggcaccaag cggtggtcgt ccagcgggc cagagtcatg tccttccatg     5220
ggcgcagggt cctcgtcagg gtggtctggg tcacggtgaa ggggtgcgct ccgggctgag    5280
cgcttgccaa ggtgcgcttg aggctggttc tgctggtgct gaagcgctgc cggtcttcgc    5340
cctgcgcgtc ggccaggtag catttgacca tggtgtcata gtccagcccc tccgcggcgt    5400
gtcccttggc gcgcagcttg cccttggagg tggcgccgca cgaggggcag agcaggctct    5460
tgagcgcgta gagcttgggg gcgaggaaga ccgattcggg ggagtaggcg tccgcgccgc    5520
agaccccgca cacggtctcg cactccacca gccaggtgag ctcggggcgc gccgggtcaa    5580
aaaccaggtt tccccatgc tttttgatgc gtttcttacc tcgggtctcc atgaggtggt     5640
gtccccgctc ggtgacgaag aggctgtccg tgtctccgta gaccgacttg aggggtcttt    5700
tctccagggg ggtccctcgg tcttcctcgt agaggaactc ggaccactct gagacgaagg    5760
cccgcgtcca ggccaggacg aaggaggcta tgtgggaggg gtagcggtcg ttgtccacta    5820
ggggggtccac cttctccaag gtgtgaagac acatgtcgcc ttcctcggcg tccaggaagg    5880
tgattggctt gtaggtgtag gccacgtgac cggggggttcc tgacgggggg gtataaaagg    5940
gggtgggggc gcgctcgtcg tcactctctt ccgcatcgct gtctgcgagg gccagctgct    6000
ggggtgagta ttccctctcg aaggcgggca tgacctccgc gctgaggttg tcagtttcca    6060
aaaacgagga ggatttgatg ttcacctgtc ccgaggtgat acctttgagg gtacccgcgt    6120
ccatctggtc agaaaacacg atctttttat tgtccagctt ggtggcgaac gacccgtaga    6180
gggcgttgga gagcagcttg gcgatggagc gcagggtctg gttcttgtcc ctgtcggcgc    6240
gctccttggc cgcgatgttg agctgcacgt actcgcgcgc gacgcagcgc cactcgggga    6300
agacggtggt gcgctcgtcg ggcaccaggc gcacgcgcca gccgcggttg tgcagggtga    6360
```

```
ccaggtccac gctggtggcg acctcgccgc gcaggcgctc gttggtccag cagagacggc    6420
cgcccttgcg cgagcagaag gggggcaggg ggtcgagctg ggtctcgtcc gggggggtccg   6480 cgtccacggt gaaaaccccg gggcgcaggc gcgcgtcgaa gtagtctatc ttgcaacctt    6540
gcatgtccag cgcctgctgc cagtcgcggg cggcgagcgc gcgctcgtag gggttgagcg    6600
gcgggcccca gggcatgggg tgggtgagtg cggaggcgta catgccgcag atgtcatgaga  6660 cgtagagggg ctcccgcagg accccgatgt aggtggggta gcagcggccg ccgcggatgc    6720
tggcgcgcac gtagtcatac agctcgtgcg aggggggcgag gaggtcgggg cccaggttgg   6780
tgcgggcggc gcgctccgtg cggaagacga tctgcctgaa gatggcatgc gagttggaag    6840
agatggtggg gcgctggaag acgttgaagc tggcgtcctg caggccgacg gcgtcgcgca    6900
cgaaggaggc gtaggagtcg cgcagcttgt gtaccagctc ggcggtgacc tgcacgtcga    6960
gcgcgcagta gtcgagggtc tcgcggatga tgtcatattt agcctgcccc ttcttttttcc   7020 acagctcgcg gttgaggaca aactcttcgc ggtctttcca gtactcttgg atcgggaaac    7080
cgtccggttc cgaacggtaa gagcctagca tgtagaactg gttgacggcc tggtaggcgc    7140
agcagcccct tctccacgggg agggcgtagg cctgcgcggc cttgcggagc gaggtgtggg   7200
tcagggcgaa ggtgtccctg accatgactt tgaggtactg gtgcttgaag tcggagtcgt    7260
cgcagccgcc ccgctcccag agcgagaagt cggtgcgctt cttggagcgg ggggttgggca   7320 gagcgaaggt gacatcgttg aagaggattt tgcccgcgcg gggcatgaag ttgcgggtga    7380
tgcggaaggg ccccggcact tcagagcggt tgttgatgac ctgggcggcg agcacgatct    7440
cgtcgaagcc gttgatgttg tggcccacga tgtagagttc caggaagcgg ggccggccct    7500
ttacggtggg cagcttcttt agctcttcgt aggtgagctc ctcgggcgag gcgaggccgt    7560
gctcggccag ggcccagtcc gcgaggtgcg ggttgtctct gaggaaggac tcccagaggt    7620
cgcgggccag gagggtctgc aggcggtccc tgaaggtcct gaactggcgg cccacggcca    7680
ttttttcggg ggtgatgcag tagaaggtga ggggtcttg ctgccagcgg tcccagtcga     7740
gctgcagggc gaggtcgcgc gcggcggtga ccaggcgctc gtcgccccg aatttcatga     7800 ccagcatgaa gggcacgagc tgcttttccga aggcccccat ccaagtgtag gtctctacat   7860
cgtaggtgac aaagaggcgc tccgtgcgag gatgcgagcc gatcgggaag aactggatct    7920
cccgccacca gttggaggag tggctgttga tgtggtggaa gtagaagtcc cgtcgccggg    7980
ccgaacactc gtgctggctt ttgtaaaagc gagcgcagta ctggcagcgc tgcacgggct    8040
gtacctcatg cacgagatgc accttttcgcc cgcgcacgag gaagccgagg ggaaatctga   8100
gccccccgcc tggctcgcgg catggctggt gctcttctac tttggatgcg tgtccgtctc    8160
cgtctggctc ctcgaggggt gttacggtgg agcggaccac cacgccgcgc gagccgcagg    8220
tccagatatc ggcgcgcggc ggtcggagtt tgatgacgac atcgcgcagc tgggagctgt    8280
ccatggtctg gagctcccgc ggcggcggca ggtcagccgg gagttcttgc aggttcacct    8340
cgcagagtcg ggccagggcg cggggcaggt ctaggtggta cctgatctct aggggcgtgt    8400
tggtggcggc gtcgatggct tgcaggagcc cgcagccccg gggggcgacg acggtgcccc    8460
gcggggtggt ggtggtggtg gcggtgcagc tcagaagcgg tgccgcgggc gggccccgg    8520 aggtaggggg ggctccggtc ccgcgggcag gggcggcagc ggcacgtcgg cgtggagcgc    8580
gggcaggagt tggtgctgtg cccggaggtt gctggcgaag gcgacgacgc ggcggttgat    8640
ctcctggatc tggcgcctct gcgtgaagac gacgggcccg gtgagcttga acctgaaaga    8700
```

```
gagttcgaca gaatcaatct cggtgtcatt gaccgcggcc tggcgcagga tctcctgcac    8760
gtctcccgag ttgtcttggt aggcgatctc ggccatgaac tgctcgatct cttcctcctg    8820
gaggtctccg cgtccggcgc gttccacggt ggccgccagg tcgttggaga tgcgcccat    8880
gagctgcgaa aaggcgttga gtccgccctc gttccagact cggctgtaga ccacgccccc    8940
ctggtcatcg cgggcgcgca tgaccacctg cgcgaggttg agctccacgt gccgcgcgaa    9000
gacggcgtag ttgcgcagac gctggaagag gtagttgagg gtggtggcgg tgtgctcggc    9060
cacgaagaag ttcatgaccc agcggcgcaa cgtggattcg ttgatgtccc caaggcctc    9120
cagccgttcc atggcctcgt agaagtccac ggcgaagttg aaaaactggg agttgcgcgc    9180
cgacacggtc aactcctcct ccagaagacg gatgagctcg gcgacggtgt cgcgcacctc    9240
gcgctcgaag gctatgggga tctcttcctc cgctagcatc accacctcct cctcttcctc    9300
ctcttctggc acttccatga tggcttcctc ctcttcgggg ggtggcggcg gcggcggtgg    9360
gggaggggc gctctgcgcc ggcggcggcg caccgggagg cggtccacga agcgcgcgat    9420
catctccccg cggcggcggc gcatggtctc ggtgacggcg cggccgttct cccggggggcg    9480
cagttggaag acgccgccgg acatctggtg ctggggcggg tggccgtgag gcagcgagac    9540
ggcgctgacg atgcatctca acaattgctg cgtaggtacg ccgccgaggg acctgaggga    9600
gtccatatcc accggatccg aaaacctttc gaggaaggcg tctaaccagt cgcagtcgca    9660
aggtaggctg agcaccgtgg cgggcggcgg ggggtggggg gagtgtctgg cggaggtgct    9720
gctgatgatg taattgaagt aggcggactt gacacggcgg atggtcgaca ggagcaccat    9780
gtccttgggt ccggcctgct ggatgcgag gcggtcggct atgccccagg cttcgttctg    9840
gcatcggcgc aggtccttgt agtagtcttg catgagcctt ccaccggca cctcttctcc    9900
ttcctcttct gcttcttcca tgtctgcttc ggccctgggg cggcgccgcg ccccctgcc    9960
ccccatgcgc gtgaccccga acccctgag cggttggagc agggccaggt cggcgacgac   10020
gcgctcggcc aggatggcct gctgcacctg cgtgagggtg gtttggaagt catccaagtc   10080
cacgaagcgg tggtaggcgc ccgtgttgat ggtgtaggtg cagttggcca tgacggacca   10140
gttgacggtc tggtggcccg gttgcgcat ctcggtgtac ctgagtcgcg agtaggcgcg   10200
ggagtcgaag acgtagtcgt tgcaagtccg caccaggtac tggtagccca ccaggaagtg   10260
cggcggcggc tggcgtaga ggggccagcc caggtggcg ggggctccgg gggccaggtc   10320
ttccagcatg aggcggtggt aggcgtagat gtacctggac atccaggtga tacccgcggc   10380
ggtggtggag gcgcgcggga agtcgcgcac ccggttccag atgttgcgca ggggcagaaa   10440
gtgctccatg gtaggcgtgc tctgtccagt cagacgcgcg cagtcgttga tactctagac   10500
cagggaaaac gaaagccggt cagcgggcac tcttccgtgg tctggtgaat agatcgcaag   10560
ggtatcatgg cggagggcct cggttcgagc cccgggtccg ggccggacgg tccgccatga   10620
tccacgcggt taccgcccgc gtgtcgaacc caggtgtgcg acgtcagaca acggtggagt   10680
gttccttttg gcgttttct ggccgggcgc cggcgccgcg taagagacta agccgcgaaa   10740
gcgaaagcag taagtggctc gctccccgta gccggaggga tccttgctaa gggttgcgtt   10800
gcggcgaacc ccggttcgaa tcccgtactc gggccggccg gacccgcggc taaggtgttg   10860
gattggcctc cccctcgtat aaagaccccg cttgcggatt gactccggac acggggacga   10920
gccccttta ttttgcttt ccccagatgc atccggtgtt gcgacagatg cgcccccgc   10980
cccagcagca gcaacaacac cagcaagagc ggcagcaaca gcagcgggag tcatgcaggg   11040
ccccctcacc caccctcggc ggcccggcca cctcggcgtc cgcggccgtg tctggcgcct   11100
```

```
gcggcggcgg cggcgggggg ccggctgacg accccgagga gccccgcgg cgcagggcca    11160 gacactacct ggacctggag gagggcgagg gcctggcgcg gctggggcg ccgtctcccg    11220 agcgccaccc gcgggtgcag ctaaagcgcg actcgcgcga ggcgtacgtg cctcggcaga    11280
acctgttcag ggaccgcgcg ggcgaggagc ccgaggagat gcgggacagg aggttcagcg    11340
cggggcggga gctgcggcag gggctgaacc gcgagcggct gctgcgcgag gaggactttg    11400
agcccgacgc gcggacgggg atcagcccg cgcgcgcgca cgtggcggcc gccgacctgg    11460
tgacggcgta cgagcagacg gtgaaccagg agatcaactt ccaaaagagt ttcaacaacc    11520
acgtgcgcac gctggtggcg cgcgaggagg tgaccatcgg gctgatgcac ctgtgggact    11580
ttgtgagcgc gctggtgcag aaccccaata gcaagcctct gacggcgcag ctgttcctga    11640
tagtgcagca cagcagggac aacgaggcgt ttagggacgc gctgctgaac atcaccgagc    11700
ccgagggccg gtggctgctg gacctgatta acatcctgca gagcatagtg gtgcaggagc    11760
gcagcctgag cctggccgac aaggtggcgg ccatcaacta ctcgatgctg agcctgggca    11820
agttttacgc gcgcaagatc taccagacgc cgtacgtgcc catagacaag gaggtgaaga    11880
tcgacggttt ttacatgcgc atggcgctga aggtgctcac cctaagcgac gacctgggcg    11940
tgtaccgcaa cgagcgcatc cacaaggccg tgagcgtgag ccggcggcgc gagctgagcg    12000
accgcgagct gatgcatagc ctgcagcggg cgctggcggg cgccggcagc ggcgacaggg    12060
aggcggagtc ctacttcgat gcgggggcgg acctgcgctg ggcgcccagc cggcgggccc    12120
tggaggccgc gggggtccgc gaggactatg acgaggacgg cgaggaggat gaggagtacg    12180
agctagagga gggcgagtac ctggactaaa ccgcgggtgg tgtttccggt agatgcaaga    12240
cccgaacgtg gtggacccgg cgctgcgggc ggctctgcag agccagccgt ccggccttaa    12300
ctcctcagac gactggcgac aggtcatgga ccgcatcatg tcgctgacgg cgcgtaaccc    12360
ggacgcgttc cggcagcagc cgcaggccaa caggctctcc gccatcctgg aggcggtggt    12420
gcctgcgcgc tcgaaccccca cgcacgagaa ggtgctggcc atagtgaacg cgctggccga    12480
gaacagggcc atccgcccgg acgaggccgg gctggtgtac gacgcgctgc tgcagcgcgt    12540
ggcccgctac aacagcggca acgtgcagac caacctggac cggctggtgg gggacgtgcg    12600
cgaggcggtg cgcagcgcg agcgcgcgga tcggcagggc aacctgggct ccatggtggc    12660
gctgaatgcc ttcctgagca cgcagccggc caacgtgccg cggggcagg aagactacac    12720 caactttgtg agcgcgctgc ggctgatggt gaccgagacc ccccagagcg aggtgtacca    12780
gtcgggtccg gactacttct tccagaccag cagacagggc ctgcagacgg tgaacctgag    12840
ccaggctttc aagaacctgc gggggctgtg gggcgtgaag gcgcccaccg gcgaccgggc    12900
gacggtgtcc agcctgctga cgcccaactc gcgcctgctg ctgctgctga tcgcgccgtt    12960
cacggacagc ggcagcgtgt cccgggacac ctacctgggg cacctgctga ccctgtaccg    13020
cgaggccatc gggcaggcgc aggtggacga gcacaccttc caggagatca ccagcgttag    13080
ccgcgcgctg gggcaggagg acacgagcag cctggaggcg actctgaact acctgctgac    13140
caaccggcgg cagaagattc cctcgctgca cagcctgacc tccgaggagg agcgcatctt    13200
gcgctacgtg cagcagagcg tgagcctgaa cctgatgcgc gacggggtga cgcccagtgt    13260
ggcgctggac atgaccgcgc gcaacatgga accgggcatg tacgccgcgc accggcctta    13320
catcaaccgc ctgatggact acctgcatcg gcgcggcggc gtgaacccg agtactttac    13380 caacgccatc ctgaacccgc actggctccc gccgcccggg ttctacagcg ggggcttcga    13440
```

```
ggtcccggag gccaacgatg gcttcctgtg ggacgacatg gacgacagcg tgttctcccc    13500
gcggccgcag gcgctggcgg aagcgtccct gctgcgtccc aagaaggagg aggaggcgag    13560
tcgccgccgc ggcagcagcg gcgtggcttc tctgtccgag ctgggggcgg cagccgccgc    13620
gcgcccgggc tccctgggcg gcagcccctt tccgagcctg gtggggtctc tgcacagcga    13680
gcgcaccacc cgccctcggc tgctgggcga ggacgagtac ctgaataact ccctgctgca    13740
gccggtgcgg gagaaaaacc tgcctcccgc cttccccaac aacgggatag agagcctggt    13800
ggacaagatg agcagatgga agacctatgc gcaggagcac agggacgcgc ccgcgctccg    13860
gccgcccacg cggcgccagc gccacgaccg gcagcggggg ctggtgtggg atgacgagga    13920
ctccgcggac gatagcagcg tgctggacct gggagggagc ggcaacccgt tcgcgcacct    13980
gcgcccccgc ctggggagga tgttttaaaa aaaaaaaaaa gcaagaagca tgatgcaaaa    14040
attaaataaa actcaccaag gccatggcga ccgagcgttg gtttcttgtg ttcccttcag    14100
tatgcggcgc gcggcgatgt accaggaggg acctcctccc tcttacgaga gcgtggtggg    14160
cgcggcggcg gcggcgccct cttctcccct tgcgtcgcag ctgctggagc cgccgtacgt    14220
gcctccgcgc tacctgcggc ctacgggggg gagaaacagc atccgttact cggagctggc    14280
gcccctgttc gacaccaccc gggtgtacct ggtggacaac aagtcggcgg acgtggcctc    14340
cctgaactac cagaacgacc acagcaattt tttgaccacg gtcatccaga acaatgacta    14400
cagcccgagc gaggccagca cccagaccat caatctggat gaccggtcgc actggggcgg    14460
cgacctgaaa accatcctgc acaccaacat gcccaacgtg aacgagttca tgttcaccaa    14520
taagttcaag gcgcggggtga tggtgtcgcg ctcgcacacc aaggaagacc gggtggagct    14580
gaagtacgag tgggtggagt tcgagctgcc agagggcaac tactccgaga ccatgaccat    14640
tgacctgatg aacaacgcga tcgtggagca ctatctgaaa gtgggcaggc agaacggggt    14700
cctggagagc gacatcgggg tcaagttcga caccaggaac ttccgcctgg ggctggaccc    14760
cgtgaccggg ctggttatgc ccggggtgta caccaacgag gccttccatc ccgacatcat    14820
cctgctgccc ggctgcgggg tggacttcac ttacagccgc ctgagcaacc tcctgggcat    14880
ccgcaagcgc cagcccttcc aggagggctt caggatcacc tacgaggacc tggaggggg    14940 caacatcccc gcgctcctcg atgtggaggc ctaccaggat agcttgaagg aaaatgaggc    15000
gggacaggag gataccgccc ccgccgcctc cgccgccgcc gagcagggcg aggatgctgc    15060
tgacaccgcg gccgcggacg gggcggaggc cgaccccgct atggtggtgg aggctgccga    15120
gcaggaggag gacatgaatg acagtgcggt gcgcggagac accttcgtca cccgggggga    15180
ggaaaagcaa gcggaggccg aggccgcggc cgaggaaaag caactggcgg cagcagcggc    15240 ggcggcggc ttggccgcgg cggaggctga gtctgagggg accaagcccg ccaaggagcc    15300
cgtgattaag cccctgaccg aagatagcaa gaagcgcagt tacaacctgc tcaaggacag    15360
caccaacacc gcgtaccgca gctggtacct ggcctacaac tacggcgacc cgtcgacggg    15420
ggtgcgctcc tggaccctgc tgtgcacgcc ggacgtgacc tgcggctcgg agcaggtgta    15480
ctggtcgctg cccgacatga tgcaagaccc cgtgaccttc cgctccacgc ggcaggtcag    15540
caacttcccg gtggtgggcg ccgagctgct gcccgtgcac tccaagagct tctacaacga    15600
ccaggccgtc tactcccagc tcatccgcca gttcacctct ctgacccacg tgttcaatcg    15660 cttttcctgag aaccagattc tggcgcgccc gccgcccccc accatcacca ccgtcagtga    15720
aaacgttcct gctctcacag atcacggac gctaccgctg cgcaacagca tcggaggagt    15780
ccagcgagtg accgttactg acgccagacg ccgcacctgc ccctacgttt acaaggcctt    15840
```

```
gggcatagtc tcgccgcgcg tcctttccag ccgcactttt tgagcaacac caccatcatg   15900
tccatcctga tctcacccag caataactcc ggctggggac tgctgcgcgc gcccagcaag   15960
atgttcggag gggcgaggaa gcgttccgag cagcaccccg tgcgcgtgcg cgggcacttc   16020 cgcgcccct  ggggagcgca caaacgcggc cgcgcggggc gcaccaccgt ggacgacgcc   16080
atcgactcgg tggtggagca ggcgcgcaac tacaggcccg cggtctctac cgtggacgcg   16140
gccatccaga ccgtggtgcg gggcgcgcgg cggtacgcca agctgaagag ccgccggaag   16200
cgcgtggccc gccgccaccg ccgccgaccc ggggccgccg ccaaacgcgc cgccgcggcc   16260
ctgcttcgcc gggccaagcg cacgggccgc cgcgccgcca tgagggccgc gcgccgcttg   16320
gccgccggca tcaccgccgc caccatggcc ccccgtaccc gaagacgcgc ggccgccgcc   16380
gccgccgccg ccatcagtga catggccagc aggcgccggg gcaacgtgta ctgggtgcgc   16440
gactcggtga ccggcacgcg cgtgcccgtg cgcttccgcc ccccgcggac ttgagatgat   16500
gtgaaaaaac aacactgagt ctcctgctgt tgtgtgtatc ccagcggcgg cggcggcgcg   16560
cgcagcgtca tgtccaagcg caaaatcaaa gaagagatgc tccaggtcgt cgcgccggag   16620
atctatgggc ccccgaagaa ggaagagcag gattcgaagc cccgcaagat aaagcgggtc   16680
aaaaagaaaa agaaagatga tggcgatgcc gatggggagg tggagttcct gcgcgccacg   16740
gcgcccaggc gccggtgca  gtggaagggc cggcgcgtaa agcgcgtcct gcgcccccggc   16800 accgcggtgg tcttcacgcc cggcgagcgc tccacccgga ctttcaagcg cgtctatgac   16860
gaggtgtacg gcgacgaaga cctgctggag caggccaacg agcgcttcgg agagtttgct   16920
tacgggaagc gtcagcggcc gctggggaag gaggacctgc tggcgctgcc gctggaccag   16980
ggcaacccca cccccagtct gaagcccgtg accctgcagc aggtgctgcc gagcagcgca   17040
ccctccgagg cgaagcgggg tctgaagcgc gagggcggcg acctggcgcc caccgtgcag   17100
ctcatggtgc ccaagcggca gaggctggag gatgtgctgg agaaaatgaa agtagacccc   17160
ggtctgcagc cggacatcag ggtccgtccc atcaagcagg tggcgccggg cctcggcgtg   17220
cagaccgtgg acgtggtcat ccccaccggc aactcccccg ccgccaccac cactaccgct   17280
gcctccacgg acatggagac acagaccgat cccgccgcag ccgccgccac cgccgccgcc   17340
gcgacctcct cggcggaggt gcagacggac ccctggctgc cgccggcgat gtcagctccc   17400
cgcgcgcgtc gcgggcgcag gaagtacggc gccgccaacg cgctcctgcc cgagtacgcc   17460
ttgcatcctt ccatcgcgcc caccccggc  taccgaggct ataccttaccg cccgcgaaga   17520 gccaagggtt ccaccgccg  tccccgccga cgcgccgccg ccaccacccg ccgccgccgc   17580
cgcagacgcc agcccgcact ggctccagtc tccgtgagga gagtggcgcg cgacggacac   17640
accctggtgc tgcccagggc gcgctaccac cccagcatcg tttaaaagcc tgttgtggtt   17700
cttgcagata tggccctcac ttgccgcctc cgtttcccgg tgccgggata ccgaggagga   17760
agatcgcgcc gcaggagggg tctgccggcc cgcggcctga gcggaggcag ccgccgcgcg   17820
caccggcggc gacgcgccac cagccgacgc atgcgcggcg gggtgctgcc cctgttaatc   17880 ccctgatcg  ccgcggcgat cggcgccgtg cccgggatcg cctccgtggc cttgcaggcg   17940
tcccagaggc attgacagac ttgcaaactt gcaaatatgg aaaaaaaccc caataaaaaa   18000
gtctagactc tcacgctcgc ttggtcctgt gactattttg tagaatggaa gacatcaact   18060
ttgcgtcgct ggccccgcgt cacggctcgc gcccgttcct gggacactgg aacgatatcg   18120
gcaccagcaa catgagcggt ggcgccttca gttgggcctc tctgtggagc ggcattaaaa   18180
```

```
gtatcgggtc tgccgttaaa aattacggct cccgggcctg aacagcagc acgggccaga    18240 tgttgagaga caagttgaaa gagcagaact tccagcagaa ggtggtggag ggcctggcct    18300
ccggcatcaa cggggtggtg gacctggcca accaggccgt gcagaataag atcaacagca    18360
gactggaccc ccggccgccg gtggaggagg tgccgccggc gctggagacg gtgtccccg     18420 atgggcgtgg cgagaagcgc ccgcggcccg atagggaaga gaccactctg gtcacgcaga    18480
ccgatgagcc gccccccgtat gaggaggccc tgaagcaagg tctgcccacc acgcgggcca   18540
tcgcgcccat ggccaccggg gtggtgggcc gccacacccc cgccacgctg gacttgcctc    18600
cgcccgccga tgtgccgcag cagcagcaga aggcggcaca gccgggcccg cccgtgaccg    18660
cctcccgttc ctccgccggt cctctgcgcc gcgcggccag cggcccccgc gggggggtcg    18720
cgaggcacgg caactggcag agcacgctga acagcatcgt gggtctgggg gtgcggtccg    18780
tgaagcgccg ccgatgctac tgaatagctt agctaacgtg ttgtatgtgt gtatgcgccc    18840
tatgtcgccg ccagaggagc tgctgagtcg ccgccgttcg cgcgcccacc accaccaccg    18900
ccactccgcc cctcaagatg gcgaccccat cgatgatgcc gcagtggtcg tacatgcaca    18960
tctcgggcca ggacgcctcg gagtacctga gccccgggct ggtgcagttc gcccgcgcca    19020
ccgagagcta cttcagcctg agtaacaagt ttaggaaccc cacggtggcg cccacgcacg    19080
atgtgaccac cgaccggtct cagcgcctga cgctgcggtt cattcccgtg gaccgcgagg    19140
acaccgcgta ctcgtacaag gcgcggttca ccctggccgt gggcgacaac cgcgtgctgg    19200
acatggcctc cacctacttt gacatccgcg gggtgctgga ccggggcccc actttcaagc    19260
cttactctgg caccgcctac aactccctgg ccccaagggg cgctcccaac tcctgcgagt    19320
gggagcaatt agaagaagcc caggccgctg tggaagacga agaattagaa gatgaagacg    19380
aggaaccaca ggatgaggca cctgtgaaaa aacccatgt atacgctcag gctccccttt    19440
ctggagaaga aattactaaa aacggtttgc aaatagggtc agataacaca gaagcccagt    19500
ctaagcccat atatgcagat cctacattcc agcctgaacc ccaaatcggg gaatcccagt    19560
ggaatgaggc agatgctaca gttgccggcg gtagagtgct aaagaaatcc actcccatga    19620
agccatgcta tggttcctat gcaagaccca caaactccaa tggaggtcaa ggtgtgctgg    19680
tggctgatga taagggggtt cttcaatcta aagttgaatt gcaattttt tcaaatacta     19740 ctactcttaa tcagcgggag ggtaacgata caaaaccaaa agtggtgctg tatagcgaag    19800
atgtgcacat ggaaactcca gacacccaca tttcttacaa gcccacaaaa agcgatgaca    19860
attcaaaaat catgctgggt cagcagtcca tgcccaacag acctaattac atcggcttca    19920
gagacaactt tatcggcctc atgtattaca atagcactgg caacatggga gtgcttgcag    19980
gtcaggcctc tcagttgaat gcagtggtgg acttgcaaga cagaaacaca gaactgtcct    20040
accagctctt gcttgattcc atgggtgaca gaaccagata cttttccatg tggaatcagg    20100
cagtggacag ttatgaccca gatgtcagaa ttattgaaaa tcatggaact gaagacgagc    20160
tccccaacta ttgtttccct ctgggcggca taggggtaac tgacacttac caggccatta    20220
aaaccaatgg caatggtcaa gaaaaccca cctgggaaaa agatacagag tttgcagacc    20280
gcaatgaaat aggggtggga aacaatttcg ctatggagat caacctcagt gccaacctgt    20340
ggagaaactt cctgtactcc aacgtggcgc tgtacctgcc agacaagctt aagtacaacc    20400
cctccaatgt ggacatctct gacaaccccca cacctacga ttacatgaac aagcgagtgg    20460
tggcccccgg gctggtggac tgctacatca acctgggcgc gcgctggtcg ctggactaca    20520
tggacaacgt caacccttc aaccaccacc gcaatgcggg cctgcgctac cgctccatgc    20580
```

```
tcctgggcaa cgggcgctac gtgcccttcc acatccaggt gccccagaag ttctttgcca   20640
tcaagaacct cctcctcctg ccgggctcct acacctacga gtggaacttc aggaaggatg   20700
tcaacatggt cctccagagc tctctgggta acgatctcag ggtggacggg gccagcatca   20760
agttcgagag catctgcctc tacgccacct tcttccccat ggcccacaac acggcctcca   20820
cgctcgaggc catgctcagg aacgacacca cgaccagtc cttcaatgac tacctctccg   20880
ccgccaacat gctctacccc ataccccgcca acgccaccaa cgtccccatc tccatcccct   20940
cgcgcaactg gcgggccttc cgcggctggg ccttcacccg cctcaagacc aaggagaccc   21000
cctccctggg ctcgggattc gacccctact acacctactc gggctccatt ccctacctgg   21060
acggcacctt ctacctcaac cacactttca agaaggtctc ggtcaccttc gactcctcgg   21120
tcagctggcc gggcaacgac cgtctgctca ccccaacga gttcgaaatc aagcgctcgg   21180
tcgacgggga gggctacaac gtggcccagt gcaacatgac caaggactgg ttcctggtcc   21240
agatgctggc caactacaac atcggctacc agggcttcta catcccagag agctacaagg   21300
acaggatgta ctccttcttc aggaacttcc agcccatgag ccggcaggtg gtggaccaga   21360
ccaagtacaa ggactaccag gaggtgggca tcatccacca gcacaacaac tcgggcttcg   21420
tgggctacct cgcccccacc atgcgcgagg acaggcctta ccccgccaac ttcccctacc   21480
cgctcatagg caagaccgcg gtcgacagca tcacccagaa aaagttcctc tgcgatcgca   21540
ccctctggcg catccccttc tccagcaact tcatgtccat gggtgcgctc tcggacctgg   21600
gccagaactt gctctacgcc aactccgccc acgccctcga catgaccttc gaggtcgacc   21660
ccatggacga gcccacccctt ctctatgttc tgttcgaagt ctttgacgtg gtcccgggtcc   21720 accagccgca ccgcgcgtc atcgagaccg tgtacctgcg tacgcccttc tcggccggca   21780
acgccaccac ctaaagaagc aagccgcagt catcgccgcc tgcatgccgt cgggttccac   21840
cgagcaagag ctcagggcca tcgtcagaga cctgggatgc gggccctatt ttttgggcac   21900
tttcgacaag cgcttccctg ctttgtctc cccacacaag ctggcctgcg ccatcgtcaa   21960 cacgccggc cgcgagaccg ggggcgtgca ctggctggcc ttcgcctgga acccgcgctc   22020
caaaacatgc ttcctctttg accccttcgg cttttcggac cagcggctca gcaaatcta   22080 cgagttcgag tacgagggct tgctgcgtcg cagcgccatc gcctcctcgc ccgaccgctg   22140 cgtcacccte gaaaagtcca cccagaccgt gcagggccc gactcggccg cctgcggtct   22200
cttctgctgc atgttttctgc acgcctttgt gcactggcct cagagtccca tggaccgcaa   22260
ccccaccatg aacttgctga cggggggtgcc caactccatg ctccagagcc cccaggtcga   22320
gcccaccctg cgccgcaacc aggagcagct ctacagcttc ctggagcgcc actcgcccta   22380
cttccgccgc cacagcgcac agatcaggag gccaccctcc ttctgccact tgcaagagat   22440
gcaagaaggg taataacgat gtacacactt ttttctcaat aaatggcatt ttttttattta   22500 tacaagctct ctggggtatt catttcccac caccaccacc cccgccgtt gtcgccatct   22560 ggctctattt agaaatcgaa agggttctgc cgggagtcgc cgtgcgccac gggcagggac   22620
acgttgcgat actggtagcg ggtgccccac ttgaactcgg gcaccaccag gcgaggcagc   22680
tcggggaagt tttcgctcca caggctgcgg gtcagcacca gcgcgttcat caggtcggc   22740 gccgagatct tgaagtcgca gttggggccg ccgccctgcg cgcgcgagtt gcggtacacc   22800
gggttgcagc actggaacac caacagcgcc gggtgcttca cgctagccag cacgctgcgg   22860
tcggagatca gctcggcgtc caggtcctcc gcgttgctca gcgcgaacgg ggtcatcttg   22920
```

```
ggcacttgcc tcccccaggaa gggcgcgtgc cccggtttcg agttgcagtc gcagcgcagc    22980
gggatcagca ggtgcccatg cccggactcg gcgttggggt acagcgcgcg catgaaggcc    23040
tgcatctggc ggaaggccat ctgggccttg gcgccctccg agaagaacat gccgcaggac    23100
ttgcccgaga actggtttgc ggggcagctg cgtcgtgca ggcagcagcg cgcgtcggtg     23160
ttggcgatct gcaccacgtt gcgccccac cggttcttca cgatcttggc cttggacgat     23220
tgctccttca gcgcgcgctg cccgttctcg ctggtcacat ccatctcgat cacatgttcc    23280
ttgttcacca tgctgctgcc gtgcaggcac ttcagctcgc cctccgtctc ggtgcagcgg    23340
tgctgccaca gcgcgcagcc cgtgggctcg aaagacttgt aggtcacctc cgcgaaggac    23400
tgcaggtacc cctgcaaaaa gcggcccatc atggtcacga aggtcttgtt gctgctgaag    23460
gtcagctgca gcccgcggtg ctcctcgttc agccaggtct tgcacacggc cgccagcgcc    23520
tccacctggt cgggcagcat cttgaagttc accttcagct cattctccac gtggtacttg    23580
tccatcagcg tgcgcgccgc ctccatgccc ttctcccagg ccgacaccag cggcaggctc    23640
acggggttct tcaccatcac cgtggccgcc gcctccgccg cgctttcgct ttccgccccg    23700
ctgttctctt cctcttcctc ctcttcctcg ccgccgccca ctcgcagccc ccgcaccacg    23760
gggtcgtctt cctgcaggcg ctgcaccttg cgcttgccgt tgcgcccctg cttgatcgcg    23820
acgggcgggt tgctgaagcc caccatcacc agcgcggcct cttcttgctc gtcctcgctg    23880
tccagaatga cctccgggga ggggggggttg gtcatcctca gtaccgaggc acgcttcttt    23940
ttcttcctgg gggcgttcgc cagctccgcg gctgcggccg ctgccgaggt cgaaggccga    24000
gggctgggcg tgcgcggcac cagcgcgtcc tgcgagccgt cctcgtcctc ctcggactcg    24060
agacggaggc gggcccgctt cttcggggc gcgcggggcg gcggaggcgg cggcggcgac     24120
ggagacgggg acgagacatc gtccagggtg ggtggacggc gggccgcgcc gcgtccgcgc    24180 tcggggggtgg tctcgcgctg gtcctcttcc cgactggcca tctcccactg ctccttctcc    24240
tataggcaga aagagatcat ggagtctctc atgcgagtcg agaaggagga ggacagccta    24300
accgccccct ctgagccctc caccaccgcc gccaccaccg ccaatgccgc cgcggacgac    24360
gcgcccaccg agaccaccgc cagtaccacc nnnctcccca gcgacgcacc cccgctcgag    24420
aatgaagtgc tgatcgagca ggacccgggt tttgtgagcg agaggagga tgaggtggat    24480 gagaaggaga aggaggaggt cgccgcctca gtgccaaaag aggataaaaa gcaagaccag    24540
gacgacgcag ataaggatga gacagcagtc gggcggggga acggaagcca tgatgctgat    24600
gacggctacc tagacgtggg agacgacgtg ctgcttaagc acctgcaccg ccagtgcgtc    24660
atcgtctgcg acgcgctgca ggagcggtgc gaagtgcccc tggacgtggc ggaggtcagc    24720
cgcgcctacg agcggcacct cttcgcgccg cacgtgcccc ccaagcgccg ggagaacggc    24780
acctgcgagc ccaacccgcg tctcaacttc tacccggtct tcgcggtacc cgaggtgctg    24840
gccacctacc acatcttttt ccaaaactgc aagatccccc tctcctgccg cgctaaccgc    24900
acccgcgccg acaaaaccct gaccctgcgg cagggcgccc acatacctga tattgcctct    24960
ctggaggaag tgcccaagat cttcgagggt ctcggtcgcg acgagaaacg ggcggcgaac    25020
gctctgcacg gagacagcga aaacgagagt cactcggggg tgctggtgga gctcgagggc    25080
gacaacgcgc gcctggccgt actcaagcgc agcatagagg tcacccactt tgcctacccg    25140
gcgctcaacc tgccccccaa ggtcatgagt gtggtcatgg gcgagctcat catgcgccgc    25200
gcccagcccc tggccgcgga tgcaaacttg caagagtcct cagaggaagg cctgcccgcg    25260
gtcagcgacg agcagctggc gcgctggctg gagacccgcg acccccgcgca gctggaggag    25320
```

```
cggcgcaagc tcatgatggc cgcggtgctg gtcaccgtgg agctcgagtg tctgcagcgc    25380
ttcttcgcgg accccgagat gcagcgcaag ctcgaggaga ccctgcacta caccttccgc    25440
cagggctacg tgcgccaggc ctgcaagatc tccaacgtgg agctctgcaa cctggtctcc    25500
tacctgggca tcctgcacga gaaccgcctc gggcagaacg tcctgcactc cacccctcaaa   25560 ggggaggcgc gccgcgacta catccgcgac tgcgcctacc tcttcctctg ctacacctgg    25620
cagacggcca tggggtgtctg gcagcagtgc ctggaggagc gcaacctcaa ggagctggaa   25680
aagctcctca agcgcaccct cagggacctc tggacgggct tcaacgagcg ctcggtggcc    25740
gccgcgctgg cggacatcat cttccccgag cgcctgctca agaccctgca gcagggcctg    25800
cccgacttca ccagccagag catgctgcag aacttcagga ctttcatcct ggagcgctcg    25860
ggcatcctgc cggccacttg ctgcgcgctg cccagcgact tcgtgcccat caagtacagg    25920
gagtgcccgc cgccgctctg gggccactgc tacctcttcc agctggccaa ctacctcgcc    25980
taccactcgg acctcatgga agacgtgagc ggcgagggcc tgctcgagtg ccactgccgc    26040
tgcaacctct gcacgcccca ccgctctcta gtctgcaacc cgcagctgct cagcgagagt    26100
cagattatcg gtaccttcga gctgcagggt ccctcgcctg acgagaagtc cgcggctccg    26160
gggctgaaac tcactccggg gctgtggact tccgcctacc tacgcaaatt tgtacctgag    26220
gactaccacg cccacgagat caggttctac gaagaccaat cccgcccgcc caaggcggag    26280
ctcaccgcct gcgtcatcac ccaggggcac atcctgggcc aattgcaagc catcaacaaa    26340
gcccgccgag agttcttgct gaaaaagggt cgggggggtgt acctggaccc ccagtccggc    26400
gaggagctaa accgctaccc ccgccgccg ccccagcagc gggaccttgc ttcccaggat    26460
ggcacccaga aagaagcagc agccgccgcc gcagccatac atgcttctgg aggaagagga    26520
ggaggactgg gacagtcagg cagaggagat gatggaagac tgggaggagg acagcagcct    26580
agacgaggaa gcttcagagg ccgaagaggt ggcagacgca acaccatcac cctcggtcgc    26640
agccccctcg ccggggcccc tgaaatcctc cgaacccagc accagcgcta taacctccgc    26700
tcctccggcg ccggcgccac ccgcccgcag acccaaccgt agatgggaca ccacaggaac    26760
cggggtcggt aagtccaagt gcccgccgcc gccaccgcag cagcagcagc agcagcgcca    26820
gggctaccgc tcgtggcgcg ggcacaagaa cgccatagtc gcctgcttgc aagactgcgg    26880
gggcaacatc tctttcgccc gccgcttcct gctattccac cacggggtcg cctttccccg    26940
caatgtcctg cattactacc gtcatctcta cagcccctac tgcagcggcg acccagaggc    27000
ggcagcggca gccacagcgg cgaccaccac ctaggaagat atcctccgcg ggcaagacag    27060
cggcagcagc ggccaggaga cccgcggcag cagcggcggg agcggtgggc gcactgcgcc    27120
tctcgcccaa cgaaccctc tcgacccggg agctcagaca caggatcttc cccactttgt    27180
atgccatctt ccaacagagc agaggccagg agcaggagct gaaaataaaa aacagatctc    27240
tgcgctccct cacccgcagc tgtctgtatc acaaaagcga agatcagctt cggcgcacgc    27300
tggaggacgc ggaggcactc ttcagcaaat actgcgcgct cactcttaaa gactagctcc    27360
gcgcccttct cgaatttagg cgggagaaaa ctacgtcatc gccggccgcc gcccagcccg    27420
cccagccgag atgagcaaag agattccac gccatacatg tggagctacc agccgcagat    27480
gggactcgcg gcgggagcgg cccaggacta ctccacccgc atgaactaca tgagcgcggg    27540
accccacatg atctcacagg tcaacgggat ccgcgcccag cgaaaccaaa tactgctgga    27600
acaggcggcc atcaccgcca cgcccgccaa taatctcaac ccccgaaatt ggcccgccgc    27660
```

```
cctagtgtac caggaaaccc cctccgccac caccgtacta cttccgcgtg acgcccaggc   27720
cgaagtccag atgactaact caggggcgca gctcgcgggc ggctttcgtc acggggcgcg   27780
gccgctccga ccaggtataa gacacctgat gatcagaggc cgaggtatcc agctcaacga   27840
cgagtcggtg agctcttcgc tcggtctccg tccggacgga actttccagc tcgccggatc   27900
cggtcgctct tcgttcacgc cccgccaggc gtacctgact ctgcagacct cgtcctcgga   27960
gccccgctcc ggcggcatcg gaaccctcca gttcgtggag gagttcgtgc cctcggtcta   28020 cttcaaccccc ttctcgggac ctcccggacg ctaccccgac cagttcattc cgaactttga   28080
cgcggtgaag gactcggcgg acggctacga ctgaatgtca ggtgccgagg cagagcagct   28140
tcgcctgaga cacctcgagc actgccgccg ccacaagtgc ttcgcccgcg gttccggtga   28200
gttctgctac tttcagctac ccgaggagca taccgagggg ccggcgcacg gcgtccgcct   28260
gaccacccag ggcgaggtta cctgttccct catccgggag ttcaccctcc gtccctgct   28320 agtggagcgg gagcggggtc cctgtgtcct aactatcgcc tgcaactgcc ctaaccctgg   28380
attacatcaa gatctttgct gtcatctctg tgctgagttt aataaacgct gagatcagaa   28440
tctactgggg ctcctgtcgc catcctgtga acgccaccgt cttcacccac cccgaccagg   28500
cccaggcgaa cctcacctgc ggtctgcatc ggaggtccaa gaagtacctc acctggtact   28560
tcaacggcac ccccttttgtg gtttacaaca gcttcgacgg ggacggagtc tccctgaaag   28620
accagctctc cggtctcagc tactccatcc acaagaacac caccctccaa ctcttccctc   28680
cctacctgcc gggaacctac gagtgcgtca ccggccgctg caccacctc acccgcctga   28740 tcgtaaacca gagcttttcg ggaacagata actccctctt ccccagaaca ggaggtgagc   28800
tcaggaaact ccccggggac cagggcggag acgtaccttc gacccttgtg gggttaggat   28860
tttttattac cgggttgctg gctcttttaa tcaaagcttc cttgagattt gttctttcct   28920
tctacgtgta tgaacacctc agcctccaat aactctaccc tttcttcggg atcaggtgac   28980
ttttctgaaa tcgggcttgg tgtgctgctt actctgttga tttttttcct tatcatactc   29040
agccttctgt gcctcaggct cgccgcctgc tgcgcacaca tctatatcta ctgctggttg   29100
ctcaagtgca ggggtcgcca cccaagatga acaggtacat ggtcctatcg atcctaggcc   29160
tgctggccct ggcggcctgc agcgccgcca aaaagagat taccttttgag gagcccgctt   29220 gcaatgtaac tttcaagccc gagggtgacc aatgcaccac cctcgtcaaa tgcgttacca   29280
atcatgagaa gctgcgcatc gactacaaaa acaaaactgg ccggtttgcg gtctatagtg   29340
tgtttacgcc cggagacccc tctaactact ctgtcaccgt cttccagggc ggacagtcta   29400
agatattcaa ttacactttc cctttttatg agttgtgcga tgcggtcatg tacatgtcaa   29460
aacagtacaa cctgtggcct ccctctcccc aggcgtgtgt ggaaaatact gggtcttact   29520
gctgtatggc tttggcaatc actacgctcg ctctaatctg cacggtgcta tatataaaat   29580
tcaggcagag gcgaatcttt atcgatgaaa agaaaatgcc ttgatcgcta acaccggctt   29640
tctatctgca gaatgaatgc aatcacctcc ctactaatca ccaccaccct ccttgcgatt   29700
gcccatgggt tgacacgaat cgaagtgcca gtggggtcca atgtcaccat ggtgggcccc   29760
gccggcaatt ccaccctcat gtgggaaaaa tttgtccgca atcaatgggt tcatttctgc   29820
tctaaccgaa tcagtatcaa gcccagagcc atctgcgatg gcaaaatct aactctgatc   29880 aatgtgcaaa tgatggatgc tgggtactat tacgggcagc ggggagaaat cattaattac   29940
tggcgacccc acaaggacta catgctgcat gtagtcgagg cacttccac taccacccc   30000 actaccacct ctcccaccac cactaccact actactacta ctactaccac taccgctgcc   30060
```

```
cgccataccc gcaaaagcac catgattagc acaaagcccc ctcgtgctca ctcccacgcc    30120
ggcgggccca tcggtgcgac ctcagaaacc accgagcttt gcttctgcca atgcactaac    30180
gccagcgctc atgaactgtt cgacctggag aatgaggatg cccagcagag ctccgcttgc    30240
ctgacccagg aggctgtgga gcccgttgcc ctgaagcaga tcggtgattc aataattgac    30300
tcttcttctt ttgccactcc cgaataccct cccgattcta cttccacat cacgggtacc     30360 aaagacccta acctctcttt ctacctgatg ctgctgctct gtatctctgt ggtctcttcc    30420
gcgctgatgt tactggggat gttctgctgc ctgatctgcc gcagaaagag aaaagctcgc    30480
tctcagggcc aaccactgat gcccttcccc tacccccgg attttgcaga taacaagata     30540
tgagctcgct gctgacacta accgctttac tagcctgcgc tctaacccct gtcgcttgcg    30600
actcgagatt ccacaatgtc acagctgtgg caggagaaaa tgttactttc aactccacgg    30660 ccgatacccca gtggtcgtgg agtggctcag gtagctactt aactatctgc aatagctcca   30720
cttcccccag catatcccca accaagtacc aatgcaatgc cagcctgttc accctcatca    30780
acgcttccac cctggacaat ggactctatg taggctatgt acccttTggt gggcaaggaa    30840
agacccacgc ttacaacctg gaagttcgcc agcccagaac cactacccaa gctwcymcca    30900
ycaccagcac cagcagcagc agccacagca gcagcagcag attattgact ttggttttgg    30960
ccagctcatc tgccgctacc caggccatct acagctctgt gcccgaaacc actcagaccc    31020
accgcccaga aacgaccacc gccaccaccc tacacacctc cagcgatcag atgccgacca    31080 acatcaccccc cttggctctt caaatgggac ttacaagccc cactccaaaa ccagtggatg   31140
cggccgaggt ctccgccctc gtcaatgact gggcggggct gggaatgtgg tggttcgcca    31200
taggcatgat ggcgctctgc ctgcttctgc tctggctcat ctgctgcctc caccgcaggc    31260
gagccagacc ccccatctat agacccatca ttgtcctgaa cccgataat gatgggatcc     31320 atagattgga tggcctgaaa aacctacttt tttctttTtac agtatgataa attgagacat    31380
gcctcgcatt ttcttgtaca tgttccttct cccaccTttt ctggggtgtt ctacgctggc    31440
cgctgtgtct cacctggagg tagactgcct ctcaccctTc actgtctacc tgctttacgg    31500
attggtcacc ctcactctca tctgcagcct aatcacagta atcatcgcct tcatccagtg    31560
cattgattac atctgtgtgc gcctcgcata cttcagacac caccgcagt accgagacag    31620 gaacattgcc caacttctaa gactgctcta atcatgcata agactgtgat ctgccttctg    31680
atcctctgca tcctgcccac cctcacctcc tgccagtaca ccacaaaatc tccgcgcaaa    31740
agacatgcct cctgccgctt cacccaactg tggaatatac ccaaatgcta caacgaaaag    31800
agcgagctct ccgaagcttg gctgtatggg gtcatctgtg tcttagtttt ctgcagcact    31860
gtctttgccc tcatgatcta cccctacttt gatttgggat ggaacgcgat cgatgccatg    31920
aattacccca ccttcccgc acccgagata attccactgc gacaagttgt acccgttgtc     31980
gttaatcaac gccccccatc ccctacgccc actgaaatca gctactttaa cctaacaggc    32040
ggagatgact gacgccctag atctagaaat ggacggcatc agtaccgagc agcgtctcct    32100
agagaggcgc aggcaggcgg ctgagcaaga gcgcctcaat caggagctcc gagatctcgt    32160
taacctgcac cagtgcaaaa gaggcatctt ttgtctggta aagcaggcca aagtcaccta    32220
cgagaagacc ggcaacagcc accgcctcag ttacaaattg cccacccagc gccagaagct    32280
ggtgctcatg gtgggtgaga atcccatcac cgtcacccag cactcggtag agaccgaggg    32340
gtgtctgcac tccccctgtc ggggtccaga agacctctgc accctggtaa agaccctgtg    32400
```

```
cggtctcaga gatttagtcc cctttaacta atcaaacact ggaatcaata aaagaatca      32460 cttacttaaa atcagacagc aggtctctgt ccagtttatt cagcagcacc tccttcccct      32520
cctcccaact ctggtactcc aaacgccttc tggcggcaaa cttcctccac accctgaagg      32580
gaatgtcaga ttcttgctcc tgtccctccg cacccactat cttcatgttg ttgcagatga      32640
agcgcaccaa aacgtctgac gagagcttca accccgtgta cccctatgac acggaaagcg      32700
gccctccctc cgtcccttc ctcacccctc ccttcgtgtc tcccgatgga ttccaagaaa      32760 gtcccccgg ggtcctgtct ctgaacctgg ccgagcccct ggtcacttcc cacggcatgc      32820
tcgccctgaa aatgggaagt ggcctctccc tggacgacgc tggcaacctc acctctcaag      32880
atatcaccac cgctagccct cccctcaaaa aaaccaagac caacctcagc ctagaaacct      32940 catccccct aactgtgagc acctcaggcg ccctcaccgt agcagccgcc gctcccctgg      33000
cggtggccgg cacctcccctc accatgcaat cagaggcccc cctgacagta caggatgcaa      33060
aactcaccct ggccaccaaa ggccccctga ccgtgtctga aggcaaactg gccttgcaaa      33120
catcggcccc gctgacggcc gctgacagca gcaccctcac cgttagcgcc acccaccaa      33180 ttaatgtaag cagtggaagt ttaggcttag acatggaaga ccctatgtat actcacaatg      33240
gaaaactggg aataagaatt gggggtccac taagagtagt agacagcttg catacactca      33300
ctgtagttac cggaaatgga ctaactgtag ataacaatgc cctccaaact aaagttacgg      33360 gcgcccctagg ttatgacaca tcaggaaatc tacaattaag agctgcagga ggtatgcgaa      33420
ttgacgcaaa tggccaactt atccttaatg tggcataccc atttgatgct cagaacaatc      33480
tcagccttag acttggtcag ggaccccctgt atataaacac agaccacaac ctggatttga      33540
attgcaacag aggtctaacc acaactacca ccaacaacac aaaaaaactt gagactaaaa      33600
ttagctcagg cttagactat gacaccaatg gtgctgtcat tattaaactt ggcactggtc      33660
taagcttcga caacacaggc gccctaactg tgggaaacac tggtgatgat aaactgactc      33720
tgtggacgac cccagaccca tctccaaatt gcagaattca ctcagacaaa gactgcaagt      33780
ttactctagt cctaactaag tgtggaagcc aaatcctggc ctctgtcgcc gccctagcgg      33840
tatcaggaaa tctggcttcg ataacaggca ccgttgccag cgttaccatc tttctcagat      33900
ttgatcagaa tggagtgctt atggaaaact cctcgctaga caggcagtac tggaacttca      33960
gaaatggcaa ctcaactaac gctgcccct acaccaatgc agttgggttc atgccaaacc      34020
tcgcagcata ccccaaaacg caaagccaga ctgctaaaaa caacattgta agtcaggttt      34080
acttgaatgg agacaaatcc aaacccatga cccttaccat caccctcaat ggaactaatg      34140
aatccagtga aactagccag gtgagtcact actccatgtc atttacatgg gcttgggaaa      34200
gtgggcaata tgccactgaa accttttgcca ccaactcctt cacctttttct tacattgctg      34260 aacaataaaa agcatgacac tgatgttcat ttctgattct tattttatta ttttcaaaca      34320
caacaaaatc attcaagtca ttcttccatc ttagcttaat agacacagta gcttaataga      34380
cccagtagtg caaagcccca ttctagctta taactagtgg agaagtactc gcctacatgg      34440
gggtagagtc ataatcgtgc atcaggatag ggcggtggtg ctgcagcagc gcgcgaataa      34500
actgctgccg ccgccgctcc gtcctgcagg aatacaacat ggcagtggtc tcctcagcga      34560
tgattcgcac cgcccgcagc ataaggcgcc ttgtcctccg ggcacagcag cgcaccctga      34620
tctcacttaa atcagcacag taactgcagc acagcaccac aatattgttc aaaatcccac      34680
agtgcaaggc gctgtatcca aagctcatgg cggggaccac agaacccacg tggccatcat      34740
accacaagcg caggtagatt aagtggcgac ccctcataaa cacgctggac ataaacatta      34800
```

```
cctcttttgg catgttgtaa ttcaccacct cccggtacca tataaacctc tgattaaaca   34860
tggcgccatc caccaccatc ctaaaccagc tggccaaaac ctgcccgccg gctatacact   34920
gcagggaacc gggactggaa caatgacagt ggagagccca ggactcgtaa ccatggatca   34980
tcatgctcgt catgatatca atgttggcac aacacaggca cacgtgcata cacttcctca   35040
ggattacaag ctcctcccgc gttagaacca tatcccaggg aacaacccat tcctgaatca   35100
gcgtaaatcc cacactgcag gaagacctc gcacgtaact cacgttgtgc attgtcaaag    35160
tgttacattc gggcagcagc ggatgatcct ccagtatggt agcgcgggtt tctgtctcaa   35220
aaggaggtag acgatcccta ctgtacggag tgcgccgaga caaccgagat cgtgttggtc   35280
gtagtgtcat gccaaatgga acgccggacg tagtcatatt tcctgaagtc ttagatctct   35340
caacgcagca ccagcaccaa cacttcgcag tgtaaaaggc caagtgccga gagagtatat   35400
ataggaataa aaagtgacgt aaacgggcaa agtccaaaaa acgcccagaa aaaccgcacg   35460
cgaacctacg ccccgaaacg aaagccaaaa aacactagac actcccttcc ggcgtcaact   35520
tccgctttcc cacgctacgt cacttgcccc agtcaaacaa actacatatc ccgaacttcc   35580
aagtcgccac gcccaaaaca ccgcctacac ctcccogccc gccggccccgc ccccaaaccc   35640 gcctcccgcc ccgcgccccg ccccgcgccg cccatctcat tatcatattg gcttcaatcc   35700
aaaataaggt atattattga tgatggttta aacggatcca attcttgaag acgaaagggc   35760
ctcgtgatac gccattttt ataggttaat gtcatgataa taatggtttc ttagacgtca    35820
ggtggcactt tcggggaaa tgtgcgcgga acccctattt gtttatttt ctaaatacat     35880 tcaaatatgt atccgctcat gagacaataa ccctgataaa tgcttcaata atattgaaaa   35940
aggaagagta tgagtattca acatttccgt gtcgccctta ttccctttt tgcggcattt    36000 tgccttcctg ttttgctca cccagaaacg ctggtgaaag taaaagatgc tgaagatcag    36060
ttgggtgcac gagtgggtta catcgaactg gatctcaaca gcggtaagat ccttgagagt   36120
tttcgccccg aagaacgttt tccaatgatg agcactttta aagttctgct atgtggcgcg   36180
gtattatccc gtgttgacgc cgggcaagag caactcggtc gccgcataca ctattctcag   36240
aatgacttgg ttgagtactc accagtcaca gaaaagcatc ttacgatgg catgacagta    36300 agagaattat gcagtgctgc cataaccatg agtgataaca ctgcggccaa cttacttctg   36360
acaacgatcg gaggaccgaa ggagctaacc gcttttttgc acaacatggg ggatcatgta   36420
actcgccttg atcgttggga accggagctg aatgaagcca taccaaacga cgagcgtgac   36480
accacgatgc ctgtagcaat ggcaacaacg ttgcgcaaac tattaactgg cgaactactt   36540
actctagctt cccggcaaca attaatagac tggatggagg cggataaagt tgcaggacca   36600
cttctgcgct cggcccttcc ggctggctgg tttattgctg ataaatctgg agccggtgag   36660
cgtgggtctc gcggtatcat tgcagcactg gggccagatg gtaagccctc ccgtatcgta   36720
gttatctaca cgacggggag tcaggcaact atggatgaac gaaatagaca gatcgctgag   36780
ataggtgcct cactgattaa gcattggtaa ctgtcagacc aagtttactc atatatactt   36840
tagattgatt taaaaggatc taggtgaaga tcctttttga taatctcatg accaaaatcc   36900
cttaacgtga gttttcgttc cactgagcgt cagaccccgt agaaaagatc aaaggatctt   36960
cttgagatcc tttttttctg cgcgtaatct gctgcttgca acaaaaaaa ccaccgctac    37020 cagcggtggt ttgtttgccg gatcaagagc taccaactct ttttccgaag gtaactggct   37080
tcagcagagc gcagatacca aatactgtcc ttctagtgta gccgtagtta ggccaccact   37140
```

```
tcaagaactc tgtagcaccg cctacatacc tcgctctgct aatcctgtta ccagtggctg    37200
ctgccagtgg cgataagtcg tgtcttaccg ggttggactc aagacgatag ttaccggata    37260
aggcgcagcg gtcgggctga acggggggtt cgtgcacaca gcccagcttg gagcgaacga    37320
cctacaccga actgagatac ctacagcgtg agctatgaga aagcgccacg cttcccgaag    37380
ggagaaaggc ggacaggtat ccggtaagcg gcagggtcgg aacaggagag cgcacgaggg    37440
agcttccagg gggaaacgcc tggtatcttt atagtcctgt cgggtttcgc cacctctgac    37500
ttgagcgtcg attttttgtga tgctcgtcag ggggcggag cctatggaaa aacgccagca    37560
acgcggcctt tttacggttc ctggcctttt gctggcttg aagctgtccc tgatggtcgt    37620
catctacctg cctggacagc atggcctgca acgcgggcat cccgatgccg ccggaagcga    37680
gaagaatcat aatggggaag gccatccagc ctcgcgtcgc agatccgaat tcgtttaaac    37740

<210> SEQ ID NO 23
<211> LENGTH: 1572
<212> TYPE: DNA
<213> ORGANISM: Rabies virus

<400> SEQUENCE: 23
atggtgcctc aagccctgct gttcgtgccc ctgctggtct tctccctctg ctttggcaag      60
ttccccatct acaccatccc tgacaagctc ggcccctggt cccccattga catacatcac     120
ctcagctgcc ccaacaacct ggtggtggag atgagggct gcacaaacct gagcggcttc     180
tcctatatgg aactcaaggt gggctatatc tccgccatca aggtcaatgg attcacatgc     240
accggcgtcg tgacagaggc tgaaacatac accaactttg tgggctacgt caccaccaca     300
ttcaagagga agcacttcag gcccaccccct gacgcttgca gggctgccta caattggaag     360
atggctggcg acccccaggta tgaggagtcc ctgcacaatc cctaccccga ctaccattgg     420
ctcaggacag tcaagaccac caaggagtcc ctggtcatta tctcccctag cgtggccgac     480
ctagacccgt atgacaaaag cctgcactcc agggtcttcc ctagcggcaa atgctccggc     540
attacagtga gctccaccta ctgcagcaca aaccacgact acaccatctg gatgcctgag     600
aatcctaggc tcggcaccct ctgtgacata tttacaaata gcaggggcaa gagggcttcc     660
aaaggcagca aaacctgcgg cttttgtcgac gaaagaggcc tgtacaagtc cctcaagggc     720
gcttgtaaac tcaagctgtg cggagtgctg gactcagac tcatggacgg cacatggggtg     780 gccatgcaga ccagcgatga gaccaagtgg tgcccccccg atcagctggt gaatctgcac     840
gacttcaggt ccgacgaaat tgagcacctc gtggtcgagg agctggtgaa gaagagagaa     900
gagtgcctgg atgctctgga gtccatcatg accaccaaat ccgtgtcctt cagaaggctg     960
agccacctca ggaagctggt ccccggcttt ggcaaggcct acacaatttt caataagaca    1020
ctgatggagg ccgatgctca ctacaaatcc gtgaggacct ggaacgagat catccccctcc    1080 aaaggctgcc tgagggtggg aggaagatgc caccccacg tcaacggcgt cttcttcaac    1140
ggcattatcc tcggacccga tgccatgtc ctgatccctg aaatgcaaag ctccctgctg    1200
cagcagcaca tggaactcct ggagagctcc gtcatccccc tgatgcaccc tctcgctgac    1260
cccagcaccg tgtttaaaga cggcgatgag gccgaggact tcgtggaagt gcatctgcct    1320
gatgtgcata agcaagtcag cggcgtcgat ctgggcctgc taattggggg caagtatgtc    1380
ctgctctccg ccggagctct gattgccctg atgctgatca tcttcctgat gacctgctgc    1440
agaagagtca cagacctga gagcacccaa agatccctcg gcggaaccgg aaggaaggtc    1500
agcgtgacca gccagtccgg caaagtgatt tcctcctggg agagctataa aagcggcgga    1560
```

-continued gagaccaggc tg                                                                  1572

<210> SEQ ID NO 24
<211> LENGTH: 37536
<212> TYPE: DNA
<213> ORGANISM: Pan troglodytes
<220> FEATURE:
<221> NAME/KEY: misc_feature
<222> LOCATION: (24187)..(24189)
<223> OTHER INFORMATION: n is a, c, g, or t

<400> SEQUENCE: 24

| | | | | | |
|---|---|---|---|---|---|
| catcatcaat | aatatacctt | attttggatt | gaagccaata | tgataatgag | atgggcggcg | 60 |
| cggggcgggg | cgcggggcgg | gaggcgggtt | tggggcggg | ccggcgggcg | ggcggtgtg | 120 |
| gcggaagtgg | actttgtaag | tgtggcggat | gtgacttgct | agtgccgggc | gcggtaaaag | 180 |
| tgacgttttc | cgtgcgcgac | aacgccccg | ggaagtgaca | ttttccccgc | ggttttacc | 240 |
| ggatgttgta | gtgaatttgg | gcgtaaccaa | gtaagatttg | gccattttcg | cgggaaaact | 300 |
| gaaacgggga | agtgaaatct | gattaatttt | gcgttagtca | taccgcgtaa | tatttgtcta | 360 |
| gggccgaggg | actttggccg | attacgtgga | ggactcgccc | aggtgttttt | tgaggtgaat | 420 |
| ttccgcgttc | cgggtcaaag | tctgcgtttt | attattatag | gatatcccat | tgcatacgtt | 480 |
| gtatccatat | cataatatgt | acatttatat | tggctcatgt | ccaacattac | cgccatgttg | 540 |
| acattgatta | ttgactagtt | attaatagta | atcaattacg | gggtcattag | ttcatagccc | 600 |
| atatatggag | ttccgcgtta | cataacttac | ggtaaatggc | ccgcctggct | gaccgcccaa | 660 |
| cgaccccgc | ccattgacgt | caataatgac | gtatgttccc | atagtaacgc | caatagggac | 720 |
| tttccattga | cgtcaatggg | tggagtattt | acggtaaact | gcccacttgg | cagtacatca | 780 |
| agtgtatcat | atgccaagta | cgccccctat | tgacgtcaat | gacggtaaat | ggcccgcctg | 840 |
| gcattatgcc | cagtacatga | ccttatggga | ctttcctact | tggcagtaca | tctacgtatt | 900 |
| agtcatcgct | attaccatgg | tgatgcggtt | ttggcagtac | atcaatgggc | gtggatagcg | 960 |
| gtttgactca | cggggatttc | caagtctcca | ccccattgac | gtcaatggga | gtttgttttg | 1020 |
| gaaccaaaat | caacgggact | ttccaaaatg | tcgtaacaac | tccgccccat | tgacgcaaat | 1080 |
| gggcggtagg | cgtgtacggt | gggaggtcta | tataagcaga | gctctcccta | tcagtgatag | 1140 |
| agatctccct | atcagtgata | gagatcgtcg | acgagctcgt | ttagtgaacc | gtcagatcgc | 1200 |
| ctggagacgc | catccacgct | gttttgacct | ccatagaaga | caccgggacc | gatccagcct | 1260 |
| ccgcggccgg | gaacggtgca | ttggaacgcg | gattccccgt | gccaagagtg | agatcttccg | 1320 |
| tttatctagg | taccagatat | cgccaccatg | gtgcctcaag | ccctgctgtt | cgtgcccctg | 1380 |
| ctggtcttct | ccctctgctt | tggcaagttc | cccatctaca | ccatccctga | caagctcggc | 1440 |
| ccctggtccc | ccattgacat | acatcacctc | agctgcccca | acaacctggt | ggtggaggat | 1500 |
| gagggctgca | caaacctgag | cggcttctcc | tatatggaac | tcaaggtggg | ctatatctcc | 1560 |
| gccatcaagg | tcaatggatt | cacatgcacc | ggcgtcgtga | cagaggctga | aacatacacc | 1620 |
| aactttgtgg | gctacgtcac | caccacattc | aagaggaagc | acttcaggcc | cacccctgac | 1680 |
| gcttgcaggg | ctgcctacaa | ttggaagatg | gctggcgacc | caggtatga | ggagtccctg | 1740 |
| cacaatccct | accccgacta | ccattggctc | aggacagtca | agaccaccaa | ggagtccctg | 1800 |
| gtcattatct | ccctagcgt | ggccgaccta | gaccccgtatg | acaaaagcct | gcactccagg | 1860 |
| gtcttcccta | gcggcaaatg | ctccggcatt | acagtgagct | ccacctactg | cagcacaaac | 1920 |

```
cacgactaca ccatctggat gcctgagaat cctaggctcg gcacctcctg tgacatattt   1980
acaaatagca ggggcaagag ggcttccaaa ggcagcaaaa cctgcggctt tgtcgacgaa   2040
agaggcctgt acaagtccct caagggcgct tgtaaactca agctgtgcgg agtgctggga   2100
ctcagactca tggacggcac atgggtggcc atgcagacca gcgatgagac caagtggtgc   2160
cccccccgatc agctggtgaa tctgcacgac ttcaggtccg acgaaattga gcacctcgtg   2220
gtcgaggagc tggtgaagaa gagagaagag tgcctggatg ctctggagtc catcatgacc   2280
accaaatccg tgtccttcag aaggctgagc cacctcagga agctggtccc cggcttttggc  2340
aaggcctaca caattttcaa taagacactg atggaggccg atgctcacta caaatccgtg   2400
aggacctgga acgagatcat cccctccaaa ggctgcctga gggtgggagg aagatgccac   2460
ccccacgtca acggcgtctt cttcaacggc attatcctcg acccgatgg ccatgtcctg    2520
atccctgaaa tgcaaagctc cctgctgcag cagcacatgg aactcctgga gagctccgtc   2580
atcccccctga tgcaccctct cgctgacccc agcaccgtgt ttaaagacgg cgatgaggcc   2640
gaggacttcg tggaagtgca tctgcctgat gtgcataagc aagtcagcgg cgtcgatctg   2700
ggcctgccta attggggcaa gtatgtcctg ctctccgccg gagctctgat tgccctgatg   2760
ctgatcatct tcctgatgac ctgctgcaga gagtcaaca gacctgagag cacccaaaga    2820
tccctcggcg gaaccggaag gaaggtcagc gtgaccagcc agtccggcaa agtgatttcc   2880
tcctgggaga gctataaaag cggcggagag accaggctgt gatgagcggc gcgatctgc    2940
tgtgccttct agttgccagc catctgttgt ttgcccctcc cccgtgcctt ccttgaccct   3000
ggaaggtgcc actcccactg tccttttccta ataaaatgag gaaattgcat cgcattgtct  3060
gagtaggtgt cattctattc tgggggtgg ggtggggcag gacagcaagg gggaggattg    3120
ggaagacaat agcaggcatg ctgggatgc ggtgggctct atggccgatc agcgatcgct    3180
gaggtgggtg agtgggcgtg gcctggggtg gtcatgaaaa tatataagtt ggggggtctta  3240
gggtctcttt atttgtgttg cagagaccgc cggagccatg agcgggagca gcagcagcag   3300
cagtagcagc agcgccttgg atggcagcat cgtgagccct tatttgacga cgcggatgcc   3360
ccactgggcc ggggtgcgtc agaatgtgat gggctccagc atcgacggcc gacccgtcct   3420
gcccgcaaat tccgccacgc tgacctatgc gaccgtcgcg gggacgccgt tggacgccac   3480
cgccgccgcc gccgccaccg cagccgcctc ggccgtgcgc agcctggcca cggactttgc   3540
attcctggga ccactggcga caggggctac ttctcgggcc gctgctgccg ccgttcgcga   3600
tgacaagctg accgccctgc tggcgcagtt ggatgcgctt actcgggaac tgggtgacct   3660
ttctcagcag gtcatggccc tgcgccagca ggtctcctcc ctgcaagctg gcgggaatgc   3720
ttctcccaca aatgccgttt aagataaata aaaccagact ctgtttggat taagaaaag    3780
tagcaagtgc attgctctct ttatttcata attttccgcg cgcgataggc cctagaccag   3840
cgttctcggt cgttgagggt gcggtgtatc ttctccagga cgtggtagag gtggctctgg   3900
acgttgagat acatgggcat gagcccgtcc cggggtgga ggtagcacca ctgcagagct    3960
tcatgctccg gggtggtgtt gtagatgatc cagtcgtagc aggagcgctg ggcatggtgc   4020
ctaaaaatgt ccttcagcag caggccgatg gccaggggga ggcccttggt gtaagtgttt   4080
acaaaacggt taagttggga agggtgcatt cggggagaga tgatgtgcat cttggactgt   4140
attttttagat tggcgatgtt tccgcccaga tcccttctgg gattcatgtt gtgcaggacc   4200
accagtacag tgtatccggt gcacttgggg aatttgtcat gcagcttaga gggaaaagcg   4260
tggaagaact tggagacgcc cttgtggcct cccagatttt ccatgcattc gtccatgatg   4320
```

```
atggcaatgg gcccgcggga ggcagcttgg gcaaagatat ttctggggtc gctgacgtcg    4380
tagttgtgtt ccagggtgag gtcgtcatag gccatttta caaagcgcgg gcggagggtg    4440
cccgactggg ggatgatggt cccctctggc cccggggcgt agttgccctc gcagatctgc    4500
atttcccagg ccttaatctc ggagggggga atcatatcca cctgcggggc gatgaagaaa    4560
acggtttccg gagccgggga gattaactgg gatgagagca ggtttctaag cagctgtgat    4620
tttccacaac cggtgggccc ataaataaca cctataaccg gttgcagctg gtagtttaga    4680
gagctgcagc tgccgtcgtc ccggaggagg ggggccacct cgttgagcat gtccctgacg    4740
cgcatgttct ccccgaccag atccgccaga aggcgctcgc cgcccaggga cagcagctct    4800
tgcaaggaag caaagttttt cagcggcttg aggccgtccg ccgtgggcat gttttttcagg   4860 gtctggctca gcagctccag gcggtcccag agctcggtga cgtgctctac ggcatctcta    4920
tccagcatat ctcctcgttt cgcgggttgg ggcgactttc gctgtagggc accaagcggt    4980
ggtcgtccag cggggccaga gtcatgtcct tccatgggcg cagggtcctc gtcagggtgg    5040
tctgggtcac ggtgaagggg tgcgctccgg gctgagcgct tgccaaggtg cgcttgaggc    5100
tggttctgct ggtgctgaag cgctgccggt cttcgccctg cgcgtcggcc aggtagcatt    5160
tgaccatggt gtcatagtcc agcccctccg cggcgtgtcc cttggcgcgc agcttgccct    5220
tggaggtggc gccgcacgag gggcagagca ggctcttgag cgcgtagagc ttggggcga    5280 ggaagaccga ttcgggggag taggcgtccg cgccgcagac cccgcacacg gtctcgcact    5340
ccaccagcca ggtgagctcg gggcgcgccg ggtcaaaaac caggtttccc ccatgctttt    5400
tgatgcgttt cttacctcgg gtctccatga ggtggtgtcc ccgctcggtg acgaagaggc    5460
tgtccgtgtc tccgtagacc gacttgaggg gtcttttctc caggggggtc cctcggtctt    5520
cctcgtagag gaactcggac cactctgaga cgaaggcccg cgtccaggcc aggacgaagg    5580
aggctatgtg ggaggggtag cggtcgttgt ccactagggg gtccaccttc tccaaggtgt    5640
gaagacacat gtcgccttcc tcggcgtcca ggaaggtgat tggcttgtag gtgtaggcca    5700
cgtgaccggg ggttcctgac gggggggtat aaaaggggt gggggcgcgc tcgtcgtcac    5760
tctcttccgc atcgctgtct gcgagggcca gctgctgggg tgagtattcc ctctcgaagg    5820
cgggcatgac ctccgcgctg aggttgtcag tttccaaaaa cgaggaggat ttgatgttca    5880
cctgtcccga ggtgatacct ttgagggtac ccgcgtccat ctggtcagaa aacacgatct    5940
ttttattgtc cagcttggtg gcgaacgacc cgtagagggc gttggagagc agcttggcga    6000
tggagcgcag ggtctggttc ttgtccctgt cggcgcgctc cttggccgcg atgttgagct    6060
gcacgtactc gcgcgcgacg cagcgccact cggggaagac ggtggtgcgc tcgtcgggca    6120
ccaggcgcac gcgccagccg cggttgtgca gggtgaccag gtccacgctg gtggcgacct    6180
cgccgcgcag gcgctcgttg gtccagcaga gacggccgcc cttgcgcgag cagaagggg    6240 gcaggggtc gagctgggtc tcgtccgggg ggtccgcgtc cacggtgaaa accccggggc    6300
gcaggcgcgc gtcgaagtag tctatcttgc aaccttgcat gtccagcgcc tgctgccagt    6360
cgcgggcggc gagcgcgcgc tcgtaggggt tgagcggcgg gccccagggc atggggtggg    6420
tgagtgcgga ggcgtacatg ccgcagatgt catagacgta gaggggctcc cgcaggaccc    6480
cgatgtaggt ggggtagcag cggccgccgc ggatgctggc gcgcacgtag tcatacagct    6540
cgtgcgaggg ggcgaggagg tcgggcccca ggttggtgcg ggcggggcgc tccgtgcgga    6600
agacgatctg cctgaagatg gcatgcgagt tggaagagat ggtggggcgc tggaagacgt    6660
```

```
tgaagctggc gtcctgcagg ccgacggcgt cgcgcacgaa ggaggcgtag gagtcgcgca    6720
gcttgtgtac cagctcggcg gtgacctgca cgtcgagcgc gcagtagtcg agggtctcgc    6780
ggatgatgtc atatttagcc tgccccttct ttttccacag ctcgcggttg aggacaaact    6840
cttcgcggtc tttccagtac tcttggatcg ggaaaccgtc cggttccgaa cggtaagagc    6900
ctagcatgta gaactggttg acggcctggt aggcgcagca gcccttctcc acggggaggg    6960
cgtaggcctg cgcggccttg cggagcgagg tgtgggtcag ggcgaaggtg tccctgacca    7020
tgactttgag gtactggtgc ttgaagtcgg agtcgtcgca gccgccccgc tcccagagcg    7080
agaagtcggt gcgcttcttg gagcgggggt tgggcagagc gaaggtgaca tcgttgaaga    7140
ggattttgcc cgcgcggggc atgaagttgc gggtgatgcg gaagggcccc ggcacttcag    7200
agcggttgtt gatgacctgg gcggcgagca cgatctcgtc gaagccgttg atgttgtggc    7260
ccacgatgta gagttccagg aagcggggcc ggccctttac ggtgggcagc ttctttagct    7320
cttcgtaggt gagctcctcg ggcgaggcga ggccgtgctc ggccagggcc cagtccgcga    7380
ggtgcgggtt gtctctgagg aaggactccc agaggtcgcg ggccaggagg gtctgcaggc    7440
ggtccctgaa ggtcctgaac tggcggccca cggccatttt tcgggggtg atgcagtaga    7500 aggtgagggg gtcttgctgc cagcggtccc agtcgagctg cagggcgagg tcgcgcgcgg    7560
cggtgaccag gcgctcgtcg cccccgaatt tcatgaccag catgaagggc acgagctgct    7620
ttccgaaggc ccccatccaa gtgtaggtct ctacatcgta ggtgacaaag aggcgctccg    7680
tgcgaggatg cgagccgatc gggaagaact ggatctcccg ccaccagttg gaggagtggc    7740
tgttgatgtg gtggaagtag aagtcccgtc gccgggccga acactcgtgc tggctttgt    7800 aaaagcgagc gcagtactgg cagcgctgca cgggctgtac ctcatgcacg agatgcacct    7860
ttcgcccgcg cacgaggaag ccgaggggaa atctgagccc cccgcctggc tcgcggcatg    7920
gctggtgctc ttctactttg gatgcgtgtc cgtctccgtc tggctcctcg aggggtgtta    7980
cggtggagcg gaccaccacg ccgcgcgagc cgcaggtcca gatatcggcg cgcggcggtc    8040
ggagtttgat gacgacatcg cgcagctggg agctgtccat ggtctggagc tcccgcggcg    8100
gcggcaggtc agccgggagt tcttgcaggt tcacctcgca gagtcgggcc agggcgcggg    8160
gcaggtctag gtggtacctg atctctaggg gcgtgttggt ggcggcgtcg atggcttgca    8220
ggagcccgca gccccggggg gcgacgacgg tgccccgcgg ggtggtggtg gtggtggcgg    8280
tgcagctcag aagcggtgcc gcgggcgggc cccggaggt aggggggct ccggtcccgc     8340 gggcagggga gcagcggca cgtcggcgtg gagcgcgggc aggagttggt gctgtgcccg    8400
gaggttgctg gcgaaggcga cgacgcggcg gttgatctcc tggatctggc gcctctgcgt    8460
gaagacgacg ggcccggtga gcttgaacct gaaagagagt tcgacagaat caatctcggt    8520
gtcattgacc gcggcctggc gcaggatctc ctgcacgtct cccgagttgt cttggtaggc    8580
gatctcggcc atgaactgct cgatctcttc ctccctggagg tctccgcgtc cggcgcgttc    8640
cacggtggcc gccaggtcgt tggagatgcg ccccatgagc tgcgagaagg cgttgagtcc    8700
gccctcgttc cagactcggc tgtagaccac gccccctgg tcatcgcggg cgcgcatgac     8760
cacctgcgca aggttgagct ccacgtgccg cgcgaagacg gcgtagttgc gcagacgctg    8820
gaagaggtag ttgagggtgg tggcggtgtg ctcggccacg aagaagttca tgacccagcg    8880
gcgcaacgtg gattcgttga tgtccccaa ggcctccagc cgttccatgg cctcgtagaa     8940
gtccacggcg aagttgaaaa actgggagtt gcgcgccgac acggtcaact cctcctccag    9000
aagacggatg agctcggcga cggtgtcgcg cacctcgcgc tcgaaggcta tggggatctc    9060
```

```
ttcctccgct agcatcacca cctcctcctc ttcctcctct tctggcactt ccatgatggc   9120
ttcctcctct tcggggggtg gcggcggcgg cggtggggga gggggcgctc tgcgccggcg   9180
gcggcgcacc gggaggcggt ccacgaagcg cgcgatcatc tccccgcggc ggcggcgcat   9240
ggtctcggtg acgcgcggc cgttctcccg ggggcgcagt tggaagacgc cgccggacat    9300
ctggtgctgg ggcgggtggc cgtgaggcag cgagacggcg ctgacgatgc atctcaacaa   9360
ttgctgcgta ggtacgccgc cgagggacct gagggagtcc atatccaccg gatccgaaaa   9420
cctttcgagg aaggcgtcta accagtcgca gtcgcaaggt aggctgagca ccgtggcggg   9480
cggcgggggg tggggggagt gtctggcgga ggtgctgctg atgatgtaat tgaagtaggc   9540
ggacttgaca cggcggatgg tcgacaggag caccatgtcc ttgggtccgg cctgctggat   9600
gcggaggcgg tcggctatgc cccaggcttc gttctggcat cggcgcaggt ccttgtagta   9660
gtcttgcatg agccttttcca ccggcacctc ttctccttcc tcttctgctt cttccatgtc   9720
tgcttcggcc ctggggcggc gccgcgcccc cctgccccc atgcgcgtga ccccgaaccc    9780
cctgagcggt tggagcaggg ccaggtcggc gacgacgcgc tcggccagga tggcctgctg   9840
cacctgcgtg agggtggttt ggaagtcatc caagtccacg aagcggtggt aggcgcccgt   9900
gttgatggtg taggtgcagt tggccatgac ggaccagttg acggtctggt ggcccggttg   9960
cgacatctcg gtgtacctga gtcgcgagta ggcgcgggag tcgaagacgt agtcgttgca  10020
agtccgcacc aggtactggt agcccaccag gaagtgcggc ggcggctggc ggtagagggg  10080
ccagcgcagg gtggcggggg ctccggggc caggtcttcc agcatgaggc ggtggtaggc   10140
gtagatgtac ctggacatcc aggtgatacc cgcggcggtg gtggaggcgc gcgggaagtc  10200
gcgcacccgg ttccagatgt tgcgcagggg cagaaagtgc tccatggtag gcgtgctctg  10260
tccagtcaga cgcgcgcagt cgttgatact ctagaccagg aaaacgaaa gccggtcagc   10320 gggcactctt ccgtggtctg gtgaatagat cgcaagggta tcatggcgga gggcctcggt  10380
tcgagccccg ggtccgggcc ggacggtccg ccatgatcca cgcggttacc gcccgcgtgt  10440
cgaacccagg tgtgcgacgt cagacaacgg tggagtgttc cttttggcgt ttttctggcc  10500
gggcgccggc gccgcgtaag agactaagcc gcgaaagcga aagcagtaag tggctcgctc  10560
cccgtagccg gagggatcct tgctaagggt tgcgttgcgg cgaacccggg ttcgaatccc   10620
gtactcgggc cggccggacc cgcggctaag gtgttggatt ggcctccccc tcgtataaag  10680
accccgcttg cggattgact ccggacacgg ggacgagccc cttttatttt tgctttcccc  10740
agatgcatcc ggtgttgcga cagatgcgcc ccccgcccca gcagcagcaa caacaccagc  10800
aagagcggca gcaacagcag cgggagtcat gcagggcccc ctcacccacc ctcggcggcc  10860
cggccacctc ggcgtccgcg gccgtgtctg gcgcctgcgg cggcggcggc gggggccggg  10920
ctgacgaccc cgaggagccc ccgcggcgca gggccagaca ctacctggac ctggaggagg  10980
gcgagggcct ggcgcggctg ggggcgccgt ctcccgagcg ccaccgcggg gtgcagctaa  11040
agcgcgactc gcgcgaggcg tacgtgcctc ggcagaacct gttcagggac cgcgcgggcg  11100
aggagcccga ggagatgcgg gacaggaggt tcagcgcggg gcgggagctg cggcagggc   11160 tgaaccgcga gcggctgctg cgcgaggagg actttgagcc cgacgcgcgg acgggatca   11220 gccccgcgcg cgcgcacgtg gcggccgccg acctggtgac ggcgtacgag cagacggtga  11280
accaggagat caacttccaa aagagtttca acaaccacgt gcgcacgctg gtggcgcgcg  11340
aggaggtgac catcggggctg atgcacctgt gggactttgt gagcgcgctg gtgcagaacc  11400
```

```
ccaatagcaa gcctctgacg gcgcagctgt tcctgatagt gcagcacagc agggacaacg  11460
aggcgtttag ggacgcgctg ctgaacatca ccgagcccga gggccggtgg ctgctggacc  11520
tgattaacat cctgcagagc atagtggtgc aggagcgcag cctgagcctg gccgacaagg  11580
tggcggccat caactactcg atgctgagcc tgggcaagtt ttacgcgcgc aagatctacc  11640
agacgccgta cgtgcccata gacaaggagg tgaagatcga cggttttttac atgcgcatgg  11700 cgctgaaggt gctcacccta agcgacgacc tgggcgtgta ccgcaacgag cgcatccaca  11760
aggccgtgag cgtgagccgg cggcgcgagc tgagcgaccg cgagctgatg catagcctgc  11820
agcgggcgct ggcgggcgcc ggcagcgcg acagggaggc ggagtcctac ttcgatgcgg  11880
gggcggacct gcgctgggcg cccagccggc gggccctgga ggccgcgggg gtccgcgagg  11940
actatgacga ggacggcgag gaggatgagg agtacgagct agaggagggc gagtacctgg  12000
actaaaccgc gggtggtgtt tccggtagat gcaagacccg aacgtggtgg acccggcgct  12060
gcgggcggct ctgcagagcc agccgtccgg ccttaactcc tcagacgact ggcgacaggt  12120 catgaccgc atcatgtcgc tgacggcgcg taacccggac gcgttccggc agcagccgca  12180
ggccaacagg ctctccgcca tcctggaggc ggtggtgcct gcgcgctcga accccacgca  12240
cgagaaggtg ctggccatag tgaacgcgct ggccgagaac agggccatcc gcccggacga  12300
ggccgggctg gtgtacgacg cgctgctgca gcgcgtggcc cgctacaaca gcggcaacgt  12360
gcagaccaac ctggaccggc tggtgggggga cgtgcgcgag gcggtggcgc agcgcgagcg  12420
cgcggatcgg cagggcaacc tgggctccat ggtggcgctg aatgccttcc tgagcacgca  12480 gccgccaac gtgccgcggg ggcaggaaga ctacaccaac tttgtgagcg cgctgcggct  12540
gatggtgacc gagaccccc agagcgaggt gtaccagtcg ggtccggact acttcttcca  12600
gaccagcaga cagggcctgc agacggtgaa cctgagccag gctttcaaga acctgcgggg  12660
gctgtggggc gtgaaggcgc ccaccggcga ccgggcgacg gtgtccagcc tgctgacgcc  12720
caactcgcgc ctgctgctgc tgctgatcgc gccgttcacg gacagcggca gcgtgtcccg  12780
ggacacctac ctggggcacc tgctgaccct gtaccgcgag gccatcgggc aggcgcaggt  12840
ggacgagcac accttccagg agatcaccag cgttagccgc gcgctggggc aggaggacac  12900
gagcagcctg gaggcgactc tgaactacct gctgaccaac cggcggcaga agattccctc  12960
gctgcacagc ctgacctccg aggaggagcg catcttgcgc tacgtgcagc agagcgtgag  13020
cctgaacctg atgcgcgacg gggtgacgcc cagtgtggcg ctggacatga ccgcgcgcaa  13080
catggaaccg ggcatgtacg ccgcgcaccg gccttacatc aaccgcctga tggactacct  13140
gcatcgcgcg gcggccgtga accccgagta ctttaccaac gccatcctga cccgcactg  13200 gctcccgccg ccggggttct acagcggggg cttcgaggtc ccggaggcca acgatggctt  13260
cctgtgggac gacatggacg acagcgtgtt ctccccgcgg ccgcaggcgc tggcggaagc  13320
gtccctgctg cgtcccaaga aggaggagga ggcgagtcgc cgccgcggca gcagcggcgt  13380
ggcttctctg tccgagctgg gggcggcagc cgccgcgcgc cccgggtccc tgggcggcag  13440
cccctttccg agcctggtgg ggtctctgca cagcgagcgc accacccgcc ctcggctgct  13500
gggcgaggac gagtacctga ataactccct gctgcagccg gtgcgggaga aaaacctgcc  13560
tcccgccttc cccaacaacg ggatagagag cctggtggac aagatgagca gatggaagac  13620
ctatgcgcag gagcacaggg acgcccgc gctccggccg cccacgcggc gccagcgcca  13680
cgaccggcag cgggggctgg tgtgggatga cgaggactcc gcggacgata gcagcgtgct  13740
ggacctggga gggagcggca acccgttcgc gcacctgcgc cccgcctgg ggaggatgtt  13800
```

```
ttaaaaaaaa aaaaaagcaa gaagcatgat gcaaaaatta aataaaactc accaaggcca   13860
tggcgaccga gcgttggttt cttgtgttcc cttcagtatg cggcgcgcgg cgatgtacca   13920
ggagggacct cctccctctt acgagagcgt ggtgggcgcg gcggcggcgg cgccctcttc   13980 tcccttttgcg tcgcagctgc tggagccgcc gtacgtgcct ccgcgctacc tgcggcctac   14040 ggggggggaga aacagcatcc gttactcgga gctggcgccc ctgttcgaca ccacccgggt   14100
gtacctggtg gacaacaagt cggcggacgt ggcctccctg aactaccaga acgaccacag   14160
caattttttg accacggtca tccagaacaa tgactacagc ccgagcgagg ccagcaccca   14220
gaccatcaat ctggatgacc ggtcgcactg gggcggcgac ctgaaaacca tcctgcacac   14280
caacatgccc aacgtgaacg agttcatgtt caccaataag ttcaaggcgc gggtgatggt   14340
gtcgcgctcg cacaccaagg aagacccggg ggagctgaag tacgagtggg tggagttcga   14400
gctgccagag ggcaactact ccgagaccat gaccattgac ctgatgaaca cgcgatcgt    14460 ggagcactat ctgaaagtgg gcaggcagaa cggggtcctg gagagcgaca tcggggtcaa   14520
gttcgacacc aggaacttcc gcctgggggct ggaccccgtg accgggctgg ttatgcccgg   14580
ggtgtacacc aacgaggcct tccatcccga catcatcctg ctgcccggct gcggggtgga   14640
cttcacttac agccgcctga gcaacctcct gggcatccgc aagcggcagc ccttccagga   14700
gggcttcagg atcacctacg aggacctgga gggggcaac atccccgcgc tcctcgatgt    14760
ggaggcctac caggatagct tgaaggaaaa tgaggcggga caggaggata ccgccccgc    14820 cgcctccgcc gccgccgagc agggcgagga tgctgctgac accgcggccg cggacggggc   14880
ggaggccgac cccgctatgg tggtggaggc tgccgagcag gaggaggaca tgaatgacag   14940
tgcggtgcgc ggagacacct tcgtcacccg gggggaggaa aagcaagcgg aggccgaggc   15000
cgcggccgag gaaaagcaac tggcggcagc agcggcggcg gcggcgttgg ccgcggcgga   15060
ggctgagtct gagggggacca gcccgccaa ggagcccgtg attaagcccc tgaccgaaga    15120
tagcaagaag cgcagttaca acctgctcaa ggacagcacc aacaccgcgt accgcagctg   15180
gtacctggcc tacaactacg cgacccgtc gacggggtg cgctcctgga ccctgctgtg     15240
cacgccggac gtgacctgcg gctcggagca ggtgtactgg tcgctgcccg acatgatgca   15300
agaccccgtg accttccgct ccacgcggca ggtcagcaac ttcccggtgg tgggcgccga   15360
gctgctgccc gtgcactcca agagcttcta caacgaccag gccgtctact cccagctcat   15420
ccgccagttc acctctctga cccacgtgtt caatcgcttt cctgagaacc agattctggc   15480
gcgcccgccc gcccccacca tcaccaccgt cagtgaaaac gttcctgctc tcacagatca   15540
cgggacgcta ccgctgcgca acagcatcgg aggagtccag cgagtgaccg ttactgacgc   15600
cagacgccgc acctgcccct acgtttacaa ggccttgggc atagtctcgc gcgcgtcct    15660 ttccagccgc acttttgag caacaccacc atcatgtcca tcctgatctc acccagcaat    15720
aactccggct ggggactgct gcgcgcgccc agcaagatgt tcggagggggc gaggaagcgt   15780 tccgagcagc accccgtgcg cgtgcgcggg cacttccgcg cccctgggg agcgcacaaa    15840 cgcggccgcg cggggcgcac caccgtggac gacgccatcg actcggtggt ggagcaggcg   15900
cgcaactaca ggcccgcggt ctctaccgtg acgcggcca tccagaccgt ggtgcggggc    15960
gcgcggcggt acgccaagct gaagagccgc cggaagcgcg tggcccgccg ccaccgccgc   16020
cgacccgggg ccgccgccaa acgcgccgcc gcggccctgc ttcgccgggc caagcgcacg   16080
ggccgccgcg ccgccatgag ggccgcgcgc cgcttggccg ccggcatcac cgccgccacc   16140
```

```
atggcccccc gtacccgaag acgcgcggcc gccgccgccg ccgccgccat cagtgacatg    16200
gccagcaggc gccggggcaa cgtgtactgg gtgcgcgact cggtgaccgg cacgcgcgtg    16260
cccgtgcgct tccgcccccc gcggacttga gatgatgtga aaaacaaca ctgagtctcc    16320 tgctgttgtg tgtatcccag cggcggcggc ggcgcgcgca cgtcatgtc caagcgcaaa    16380 atcaaagaag agatgctcca ggtcgtcgcg ccggagatct atgggccccc gaagaaggaa    16440
gagcaggatt cgaagccccg caagataaag cgggtcaaaa agaaaaagaa agatgatggc    16500
gatgccgatg gggaggtgga gttcctgcgc gccacggcgc ccaggcgccc ggtgcagtgg    16560
aagggccggc gcgtaaagcg cgtcctgcgc cccggcaccg cggtggtctt cacgcccggc    16620
gagcgctcca cccggacttt caagcgcgtc tatgacgagg tgtacggcga cgaagacctg    16680
ctggagcagg ccaacgagcg cttcggagag tttgcttacg ggaagcgtca gcggccgctg    16740
gggaaggagg acctgctggc gctgccgctg gaccagggca cccccacccc cagtctgaag    16800
cccgtgaccc tgcagcaggt gctgccgagc agcgcaccct ccgaggcgaa gcggggtctg    16860
aagcgcgagg gcggcgacct ggcgcccacc gtgcagctca tggtgcccaa gcggcagagg    16920
ctggaggatg tgctggagaa aatgaaagta gaccccggtc tgcagccgga catcagggtc    16980
cgtcccatca gcaggtggc gccgggcctc ggcgtgcaga ccgtggacgt ggtcatcccc    17040
accggcaact cccccgccgc caccaccact accgctgcct ccacggacat ggagacacag    17100
accgatcccg ccgcagccgc cgccaccgcc gccgccgcga cctcctcggc ggaggtgcag    17160
acggacccct ggctgccgcc ggcgatgtca gctccccgcg cgcgtcgcgg gcgcaggaag    17220 tacgcgccc ccaacgcgct cctgcccgag tacgccttgc atccttccat cgcgcccacc    17280
cccggctacc gaggctatac ctaccgcccg cgaagagcca agggttccac ccgccgtccc    17340
cgccgacgcg ccgccgccac cacccgccgc cgccgccgca gacgccagcc cgcactggct    17400
ccagtctccg tgaggagagt ggcgcgcgac ggacacaccc tggtgctgcc cagggcgcgc    17460
taccacccca gcatcgttta aaagcctgtt gtggttcttg cagatatggc cctcacttgc    17520
cgcctccgtt tcccggtgcc gggataccga ggaggaagat cgcgccgcag gaggggtctg    17580 gccgccgcg gcctgagcgg aggcagccgc cgcgcgcacc ggcggcgacg cgccaccagc    17640
cgacgcatgc gcggcggggt gctgcccctg ttaatccccc tgatcgccgc ggcgatcggc    17700
gccgtgcccg ggatcgcctc cgtggccttg caggcgtccc agaggcattg acagacttgc    17760
aaacttgcaa atatggaaaa aaaccccaat aaaaagtct agactctcac gctcgcttgg    17820
tcctgtgact atttttgtaga atggaagaca tcaactttgc gtcgctggcc ccgcgtcacg    17880
gctcgcgccc gttcctggga cactggaacg atatcggcac cagcaacatg agcggtggcg    17940
ccttcagttg gggctctctg tggagcggca ttaaaagtat cgggtctgcc gttaaaaatt    18000
acggctcccg ggcctggaac agcagcacgg gccagatgtt gagagacaag ttgaaagagc    18060
agaacttcca gcagaaggtg gtggagggcc tggcctccgg catcaacggg gtggtggacc    18120
tggccaacca ggccgtgcag aataagatca acagcagact ggaccccggg ccgcggtgg    18180 aggaggtgcc gccggcgctg agacggtgt ccccgatgg gcgtggcgag aagcgcccgc    18240
ggcccgatag ggaagagacc actctggtca cgcagaccga tgagccgccc ccgtatgagg    18300
aggccctgaa gcaaggtctg cccaccacgc ggcccatcgc gcccatggcc accggggtgg    18360
tgggccgcca cacccccgcc acgctggact gcctccgcc cgccgatgtg ccgcagcagc    18420
agcagaaggc ggcacagccg ggcccgcccg tgaccgcctc ccgttcctcc gccggtcctc    18480
tgcgccgcgc ggccagcggc ccccgcgggg gggtcgcgag gcacggcaac tggcagagca    18540
```

```
cgctgaacag catcgtgggt ctggggtgc ggtccgtgaa gcgccgccga tgctactgaa    18600
tagcttagct aacgtgttgt atgtgtgtat gcgccctatg tcgccgccag aggagctgct    18660
gagtcgccgc cgttcgcgcg cccaccacca ccaccgccac tccgcccctc aagatggcga    18720
ccccatcgat gatgccgcag tggtcgtaca tgcacatctc gggccaggac gcctcggagt    18780
acctgagccc cgggctggtg cagttcgccc gcgccaccga gagctacttc agcctgagta    18840
acaagtttag gaaccccacg gtggcgccca cgcacgatgt gaccaccgac cggtctcagc    18900
gcctgacgct gcggttcatt cccgtggacc gcgaggacac cgcgtactcg tacaaggcgc    18960
ggttcaccct ggccgtgggc gacaaccgcg tgctggacat ggcctccacc tactttgaca    19020
tccgcggggt gctggaccgg ggccccactt tcaagcctta ctctggcacc gcctacaact    19080
ccctggcccc caagggcgct cccaactcct gcgagtggga gcaattagaa gaagcccagg    19140
ccgctgtgga agacgaagaa ttagaagatg aagacgagga accacaggat gaggcacctg    19200
tgaaaaaaac ccatgtatac gctcaggctc cctttctgg agaagaaatt actaaaaacg    19260
gtttgcaaat agggtcagat aacacagaag cccagtctaa gcccatatat gcagatccta    19320
cattccagcc tgaaccccaa atcggggaat cccagtggaa tgaggcagat gctacagttg    19380
ccggcggtag agtgctaaag aaatccactc ccatgaagcc atgctatggt tcctatgcaa    19440
gacccacaaa ctccaatgga ggtcaaggtg tgctggtggc tgatgataag ggggttcttc    19500
aatctaaagt tgaattgcaa ttttttttcaa atactactac tcttaatcag cgggagggta    19560
acgatacaaa accaaaagtg gtgctgtata gcgaagatgt gcacatggaa actccagaca    19620
cccacatttc ttacaagccc acaaaaagcg atgacaattc aaaaatcatg ctgggtcagc    19680
agtccatgcc caacagacct aattacatcg gcttcagaga caactttatc ggcctcatgt    19740
attacaatag cactggcaac atgggagtgc ttgcaggtca ggcctctcag ttgaatgcag    19800
tggtggactt gcaagacaga aacacagaac tgtcctacca gctcttgctt gattccatgg    19860
gtgacagaac cagatacttt tccatgtgga atcaggcagt ggacagttat gacccagatg    19920
tcagaattat tgaaaatcat ggaactgaag acgagctccc caactattgt ttccctctgg    19980
gcggcatagg ggtaactgac acttaccagg ccattaaaac caatggcaat ggtcaagaaa    20040
acccaacctg ggaaaaagat acagagtttg cagaccgcaa tgaaataggg gtgggaaaca    20100
atttcgctat ggagatcaac ctcagtgcca acctgtggag aaacttcctg tactccaacg    20160
tggcgctgta cctgccagac aagcttaagt acaacccctc caatgtggac atctctgaca    20220
accccaacac ctacgattac atgaacaagc gagtggtggc cccggggctg gtggactgct    20280
acatcaacct gggcgcgcgc tggtcgctgg actacatgga caacgtcaac cccttcaacc    20340
accaccgcaa tgcgggcctg cgctaccgct ccatgctcct gggcaacggg cgctacgtgc    20400
ccttccacat ccaggtgccc cagaagttct ttgccatcaa gaacctcctc ctcctgccgg    20460
gctcctacac ctacgagtgg aacttcagga aggatgtcaa catggtcctc cagagctctc    20520
tgggtaacga tctcagggtg gacggggcca gcatcaagtt cgagagcatc tgcctctacg    20580
ccaccttctt ccccatggcc cacaaacacg cctccacgct cgaggccatg ctcaggaacg    20640
acaccaacga ccagtccttc aatgactacc tctccgccgc caacatgctc tacccccata    20700
ccgccaacgc caccaacgtc cccatctcca tccctcgcg caactgggcg ccttccgcg    20760 gctgggcctt caccccgcctc aagaccaagg agacccctc cctgggctcg ggattcgacc    20820
cctactacac ctactcgggc tccattccct acctggacgg caccttctac ctcaaccaca    20880
```

```
ctttcaagaa ggtctcggtc accttcgact cctcggtcag ctggccgggc aacgaccgtc   20940
tgctcacccc caacgagttc gaaatcaagc gctcggtcga cggggagggc tacaacgtgg   21000
cccagtgcaa catgaccaag gactggttcc tggtccagat gctggccaac tacaacatcg   21060
gctaccaggg cttctacatc ccagagagct acaaggacag gatgtactcc ttcttcagga   21120
acttccagcc catgagccgg caggtggtgg accagaccaa gtacaaggac taccaggagg   21180
tgggcatcat ccaccagcac aacaactcgg gcttcgtggg ctacctcgcc cccaccatgc   21240
gcgagggaca ggcctacccc gccaacttcc cctacccgct cataggcaag accgcggtcg   21300
acagcatcac ccagaaaaag ttcctctgcg atcgcaccct ctggcgcatc cccttctcca   21360
gcaacttcat gtccatgggt gcgctctcgg acctgggcca gaacttgctc tacgccaact   21420
ccgcccacgc cctcgacatg accttcgagg tcgaccccat ggacgagccc acccttctct   21480
atgttctgtt cgaagtcttt gacgtggtcc gggtccacca gccgcaccgc ggcgtcatcg   21540
agaccgtgta cctgcgtacg cccttctcgg ccggcaacgc caccacctaa agaagcaagc   21600
cgcagtcatc gccgcctgca tgccgtcggg ttccaccgag caagagctca gggccatcgt   21660
cagagacctg ggatgcgggc cctattttt gggcactttc gacaagcgct tccctggctt   21720
tgtctcccca cacaagctgg cctgcgccat cgtcaacacg gccggccgcg agaccggggg   21780
cgtgcactgg ctggccttcg cctggaaccc gcgctccaaa acatgcttcc tctttgaccc   21840
cttcggcttt tcggaccagc ggctcaagca aatctacgag ttcgagtacg agggcttgct   21900
gcgtcgcagc gccatcgcct cctcgcccga ccgctgcgtc accctcgaaa agtccaccca   21960
gaccgtgcag gggcccgact cggccgcctg cggtctcttc tgctgcatgt ttctgcacgc   22020
ctttgtgcac tggcctcaga gtcccatgga ccgcaacccc accatgaact gctgacgggc   22080
ggtgcccaac tccatgctcc agagccccca ggtcgagccc accctgcgcc gcaaccagga   22140
gcagctctac agcttcctgg agcgccactc gccctacttc cgccgccaca cgcacacagat   22200 caggagggcc acctccttct gccacttgca agagatgcaa gaagggtaat aacgatgtac   22260 acacttttt ctcaataaat ggcatttttt tatttataca agctctctgg ggtattcatt   22320
tcccaccacc accaccaccc gccgttgtcg ccatctggct ctatttagaa atcgaaaggg   22380
ttctgccggg agtcgccgtg cgccacgggc agggacacgt tgcgatactg gtagcgggtg   22440
ccccacttga actcgggcac caccaggcga ggcagctcgg ggaagttttc gctccacagg   22500
ctgcgggtca gcaccagcgc gttcatcagg tcggcgccg agatcttgaa gtcgcagttg   22560
gggccgccgc cctgcgcgcg cgagttgcgg tacaccgggt tgcagcactg gaacaccaac   22620
agcgccgggt gcttcacgct agccagcacg ctgcggtcgg agatcagctc ggcgtccagg   22680
tcctccgcgt tgctcagcgc gaacgggtgc atcttgggca cttgcctccc caggaagggc   22740
gcgtgccccg gtttcgagtt gcagtcgcag cgcagcggga tcagcaggtg cccatgcccg   22800
gactcggcgt tgggggtacag cgcgcgcatg aaggcctgca tctggcggaa ggccatctgg   22860
gccttggcgc cctccgagaa gaacatgccg caggacttgc ccgagaactg gtttgcgggg   22920
cagctggcgt cgtgcaggca gcagcgcgcg tcggtgttgg cgatctgcac cacgttgcgc   22980
ccccaccggt tcttcacgat cttggccttg gacgattgct ccttcagcgc gcgctgcccg   23040
ttctcgctgg tcacatccat ctcgatcaca tgttccttgt tcaccatgct gctgccgtgc   23100
aggcacttca gctcgccctc cgtctcggtg cagcggtgct gccacagcgc gcagcccgtg   23160
ggctcgaaag acttgtaggt cacctccgcg aaggactgca ggtaccctg caaaaagcgg   23220 cccatcatgg tcacgaaggt cttgttgctg ctgaaggtca gctgcagccc gcggtgctcc   23280
```

```
tcgttcagcc aggtcttgca cacggccgcc agcgcctcca cctggtcggg cagcatcttg   23340
aagttcacct tcagctcatt ctccacgtgg tacttgtcca tcagcgtgcg cgccgcctcc   23400
atgcccttct cccaggccga caccagcggc aggctcacgg ggttcttcac catcaccgtg   23460
gccgccgcct ccgccgcgct ttcgctttcc gccccgctgt tctcttcctc ttcctcctct   23520
tcctcgccgc cgcccactcg cagccccgc accacggggt cgtcttcctg caggcgctgc   23580
accttgcgct tgccgttgcg cccctgcttg atgcgcacgg gcgggttgct gaagcccacc   23640
atcaccagcg cggcctcttc ttgctcgtcc tcgctgtcca gaatgacctc cggggagggg   23700
gggttggtca tcctcagtac cgaggcacgc ttcttttct tcctgggggc gttcgccagc   23760
tccgcggctg cggccgctgc cgaggtcgaa ggccgagggc tgggcgtgcg cggcaccagc   23820
gcgtcctgcg agccgtcctc gtcctcctcg gactcgagac ggaggcgggc ccgcttcttc   23880
gggggcgcgc ggggcggcgg aggcggcggc ggcgacggag acggggacga gacatcgtcc   23940
agggtgggtg gacggcgggc cgcgccgcgt ccgcgctcgg gggtggtctc gcgctggtcc   24000
tcttcccgac tggccatctc ccactgctcc ttctcctata ggcagaaaga gatcatggag   24060
tctctcatgc gagtcgagaa ggaggaggac agcctaaccg ccccctctga gccctccacc   24120
accgccgcca ccaccgccaa tgccgccgcg gacgacgcgc ccaccgagac caccgccagt   24180
accaccnnnc tccccagcga cgcacccccg ctcgagaatg aagtgctgat cgagcaggac   24240
ccgggttttg tgagcggaga ggaggatgag gtggatgaga aggagaagga ggaggtcgcc   24300
gcctcagtgc caaaagagga taaaaagcaa gaccaggacg acgcagataa ggatgagaca   24360
gcagtcgggc gggggaacgg aagccatgat gctgatgacg gctacctaga cgtgggagac   24420
gacgtgctgc ttaagcacct gcaccgccag tgcgtcatcg tctgcgacgc gctgcaggag   24480
cggtgcgaag tgcccctgga cgtggcggag gtcagccgcg cctacgagcg gcacctcttc   24540
gcgccgcacg tgcccccaa gcgcggcag aacggcacct gcgagcccaa cccgcgtctc   24600
aacttctacc cggtcttcgc ggtacccgag gtgctggcca cctaccacat cttttttccaa   24660 aactgcaaga tccccctctc ctgccgcgct aaccgcaccc gcgccgacaa aaccctgacc   24720
ctgcggcagg gcgcccacat acctgatatt gcctctctgg aggaagtgcc caagatcttc   24780
gagggtctcg gtcgcgacga gaaacgggcg gcgaacgctc tgcacggaga cagcgaaaac   24840
gagagtcact cggggggtgct ggtggagctc gagggcgaca acgcgcgcct ggccgtactc   24900
aagcgcagca tagaggtcac ccactttgcc tacccggcgc tcaacctgcc ccccaaggtc   24960
atgagtgtgg tcatgggcga gctcatcatg cgccgcgccc agccctggc cgcggatgca   25020 aacttgcaag agtcctcaga ggaaggcctg cccgcggtca gcgacgagca gctggcgcgc   25080
tggctggaga cccgcgaccc cgcgcagctg gaggagcggc gcaagctcat gatggccgcg   25140
gtgctggtca ccgtggagct cgagtgtctg cagcgcttct tcgcggaccc cgagatgcag   25200
cgcaagctcg aggagaccct gcactacacc ttccgccagg gctacgtgcg ccaggcctgc   25260
aagatctcca acgtggagct ctgcaacctg gtctcctacc tgggcatcct gcacgagaac   25320
cgcctcgggc agaacgtcct gcactccacc ctcaaagggg aggcgcgccc cgactacatc   25380
cgcgactgcg cctacctctt cctctgctac acctggcaga cggccatggg ggtctggcag   25440
cagtgcctgg aggagcgcaa cctcaaggag ctggaaaagc tcctcaagcg cacccctcagg   25500 gacctctgga cgggcttcaa cgagcgctcg gtggccgccg cgctggcgga catcatcttc   25560
cccgagcgcc tgctcaagac cctgcagcag ggcctgcccg acttcaccag ccagagcatg   25620
```

```
ctgcagaact tcaggacttt catcctggag cgctcgggca tcctgccggc cacttgctgc    25680
gcgctgccca gcgacttcgt gcccatcaag tacagggagt gcccgccgcc gctctggggc    25740
cactgctacc tcttccagct ggccaactac ctcgcctacc actcggacct catggaagac    25800
gtgagcggcg agggcctgct cgagtgccac tgccgctgca acctctgcac gccccaccgc    25860
tctctagtct gcaacccgca gctgctcagc gagagtcaga ttatcggtac cttcgagctg    25920
cagggtccct cgcctgacga aagtccgcg gctccggggc tgaaactcac tccggggctg    25980
tggacttccg cctacctacg caaatttgta cctgaggact accacgccca cgagatcagg    26040
ttctacgaag accaatcccg cccgcccaag gcggagctca ccgcctgcgt catcacccag    26100
gggcacatcc tgggccaatt gcaagccatc aacaaagccc gccgagagtt cttgctgaaa    26160
aagggtcggg gggtgtacct ggaccccag tccggcgagg agctaaaccc gctaccccg    26220
ccgccgcccc agcagcggga ccttgcttcc caggatggca cccagaaaga agcagcagcc    26280
gccgccgcag ccatacatgc ttctggagga agaggaggag gactgggaca gtcaggcaga    26340
ggagatgatg gaagactggg aggaggacag cagcctagac gaggaagctt cagaggccga    26400
agaggtggca gacgcaacac catcacccct ggtcgcagcc ccctcgccgg ggcccctgaa    26460
atcctccgaa cccagcacca gcgctataac ctccgctcct ccggcgccgg cgccaccgc    26520
ccgcagaccc aaccgtagat gggacaccac aggaaccggg gtcggtaagt ccaagtgccc    26580
gccgccgcca ccgcagcagc agcagcagca gcgccagggc taccgctcgt ggcgcgggca    26640
caagaacgcc atagtcgcct gcttgcaaga ctgcggggc aacatctctt cgcccgccg    26700
cttcctgcta ttccaccacg gggtcgcctt tccccgcaat gtcctgcatt actaccgtca    26760
tctctacagc ccctactgca gcggcgaccc agaggcggca gcggcagcca cagcggcgac    26820
caccacctag gaagatatcc tccgcgggca agacagcggc agcagcggcc aggagacccg    26880
cggcagcagc ggcgggagcg gtgggcgcac tgcgcctctc gcccaacgaa ccctctcga    26940
cccgggagct cagacacagg atcttcccca ctttgtatgc catcttccaa cagagcagag    27000
gccaggagca ggagctgaaa ataaaaaaca gatctctgcg ctccctcacc cgcagctgtc    27060
tgtatcacaa aagcgaagat cagcttcggc gcacgctgga ggacgcggag gcactcttca    27120
gcaaatactg cgcgctcact cttaaagact agctccgcgc ccttctcgaa tttaggcggg    27180
agaaaactac gtcatcgccg gccgccgccc agcccgccca gccgagatga gcaaagagat    27240
tcccacgcca tacatgtgga gctaccagcc gcagatggga ctcgcggcgg gagcggccca    27300
ggactactcc acccgcatga actacatgag gcgggaccc cacatgatct cacaggtcaa    27360
cgggatccgc gcccagcgaa accaaatact gctggaacag gcggccatca ccgccacgcc    27420
ccgccataat ctcaacccc gaaattggcc cgccgcccta gtgtaccagg aaaccccctc    27480
cgccaccacc gtactacttc gcgtgacgc ccaggccgaa gtccagatga ctaactcagg    27540
ggcgcagctc gcgggcggct ttcgtcacgg ggcgcggccg ctccgaccag gtataagaca    27600
cctgatgatc agaggccgag gtatccagct caacgacgag tcggtgagct cttcgctcgg    27660
tctccgtccg gacggaactt ccagctcgc cggatccggt cgctcttcgt tcacgccccg    27720
ccaggcgtac ctgactctgc agacctcgtc ctcggagccc cgctcggcg gcatcggaac    27780
cctccagttc gtggaggagt tcgtgccctc ggtctacttc aaccccttct cgggacctcc    27840
cggacgctac cccgaccagt tcattccgaa cttgacgcg gtgaaggact cggcggacgg    27900
ctacgactga atgtcaggtg ccgaggcaga gcagcttcgc ctgagacacc tcgagcactg    27960
ccgccgccac aagtgcttcg cccgcggttc cggtgagttc tgctactttc agctacccga    28020
```

```
ggagcatacc gaggggccgg cgcacggcgt ccgcctgacc acccagggcg aggttacctg   28080
ttccctcatc cgggagttca ccctccgtcc cctgctagtg gagcgggagc ggggtccctg   28140
tgtcctaact atcgcctgca actgccctaa ccctggatta catcaagatc tttgctgtca   28200
tctctgtgct gagtttaata aacgctgaga tcagaatcta ctggggctcc tgtcgccatc   28260
ctgtgaacgc caccgtcttc acccaccccg accaggccca ggcgaacctc acctgcggtc   28320
tgcatcggag gtccaagaag tacctcacct ggtacttcaa cggcaccccc tttgtggttt   28380
acaacagctt cgacggggac ggagtctccc tgaaagacca gctctccggt ctcagctact   28440
ccatccacaa gaacaccacc ctccaactct tccctcccta cctgccggga acctacgagt   28500
gcgtcaccgg ccgctgcacc cacctcaccc gcctgatcgt aaaccagagc tttccgggaa   28560
cagataactc cctcttcccc agaacaggag gtgagctcag gaaactcccc ggggaccagg   28620
gcggagacgt accttcgacc cttgtggggt taggattttt tattaccggg ttgctggctc   28680 tttaatcaa agcttccttg agatttgttc tttccttcta cgtgtatgaa cacctcagcc   28740
tccaataact ctaccctttc ttcgggatca ggtgactttt ctgaaatcgg gcttggtgtg   28800
ctgcttactc tgttgatttt tttccttatc atactcagcc ttctgtgcct caggctcgcc   28860
gcctgctgcg cacacatcta tatctactgc tggttgctca agtgcagggg tcgccaccca   28920
agatgaacag gtacatggtc ctatcgatcc taggcctgct ggccctggcg gcctgcagcg   28980
ccgccaaaaa agagattacc tttgaggagc ccgcttgcaa tgtaactttc aagcccgagg   29040
gtgaccaatg caccaccctc gtcaaatgcg ttaccaatca tgagaagctg cgcatcgact   29100
acaaaaacaa aactggccgg tttgcggtct atagtgtgtt tacgcccgga gacccctcta   29160
actactctgt caccgtcttc cagggcggac agtctaagat attcaattac actttccctt   29220
tttatgagtt gtgcgatgcg gtcatgtaca tgtcaaaaca gtacaacctg tggcctccct   29280
ctccccaggc gtgtgtggaa aatactgggt cttactgctg tatggctttg gcaatcacta   29340
cgctcgctct aatctgcacg gtgctatata taaaattcag gcagaggcga atctttatcg   29400
atgaaaagaa aatgccttga tcgctaacac cggctttcta tctgcagaat gaatgcaatc   29460
acctccctac taatcaccac caccctcctt gcgattgccc atgggttgac acgaatcgaa   29520
gtgccagtgg ggtccaatgt caccatggtg ggccccgccg gcaattccac cctcatgtgg   29580
gaaaaatttg tccgcaatca atgggttcat ttctgctcta accgaatcag tatcaagccc   29640
agagccatct gcgatgggca aaatctaact ctgatcaatg tgcaaatgat ggatgctggg   29700
tactattacg ggcagcgggg agaaatcatt aattactggc gaccccacaa ggactacatg   29760
ctgcatgtag tcgaggcact tcccactacc accccacta ccacctctcc caccaccact   29820
accactacta ctactactac taccactacc gctgccgcc ataccgcaa aagcaccatg   29880 attagcacaa agcccctcg tgctcactcc cacgccggcg ggcccatcgg tgcgacctca   29940
gaaaccaccg agctttgctt ctgccaatgc actaacgcca gcgctcatga actgttcgac   30000
ctggagaatg aggatgccca gcagagctcc gcttgcctga cccaggaggc tgtggagccc   30060
gttgccctga agcagatcgg tgattcaata attgactctt cttcttttgc cactcccgaa   30120
taccctcccg attctacttt ccacatcacg ggtaccaaag accctaacct ctctttctac   30180
ctgatgctgc tgctctgtat ctctgtggtc tcttccgcgc tgatgttact ggggatgttc   30240
tgctgcctga tctgccgcag aaagagaaaa gctcgctctc agggccaacc actgatgccc   30300
ttcccctacc ccccggattt tgcagataac aagatatgag ctcgctgctg acactaaccg   30360
```

```
ctttactagc ctgcgctcta acccttgtcg cttgcgactc gagattccac aatgtcacag   30420
ctgtggcagg agaaaatgtt actttcaact ccacggccga tacccagtgg tcgtggagtg   30480
gctcaggtag ctacttaact atctgcaata gctccacttc ccccagcata tccccaacca   30540
agtaccaatg caatgccagc ctgttcaccc tcatcaacgc ttccaccctg acaatggac    30600
tctatgtagg ctatgtaccc tttggtgggc aaggaaagac ccacgcttac aacctggaag   30660
ttcgccagcc cagaaccact acccaagctw cymccaycac cagcaccagc agcagcagcc   30720
acagcagcag cagcagatta ttgactttgg ttttggccag ctcatctgcc gctacccagg   30780
ccatctacag ctctgtgccc gaaaccactc agacccaccg cccagaaacg accaccgcca   30840
ccaccctaca cacctccagc gatcagatgc cgaccaacat caccccttg gctcttcaaa    30900
tgggacttac aagccccact ccaaaaccag tggatgcggc cgaggtctcc gccctcgtca   30960
atgactgggc ggggctggga atgtggtggt tcgccatagg catgatggcg ctctgcctgc   31020
ttctgctctg gctcatctgc tgcctccacc gcaggcgagc cagaccccc atctatagac     31080
ccatcattgt cctgaacccc gataatgatg ggatccatag attggatggc ctgaaaaacc   31140
tactttttc ttttacagta tgataaattg agacatgcct cgcattttct tgtacatgtt    31200
ccttctccca ccttttctgg ggtgttctac gctggccgct gtgtctcacc tggaggtaga   31260
ctgcctctca cccttcactg tctacctgct ttacggattg gtcaccctca ctctcatctg   31320
cagcctaatc acagtaatca tcgccttcat ccagtgcatt gattacatct gtgtgcgcct   31380
cgcatacttc agacaccacc cgcagtaccg agacaggaac attgcccaac ttctaagact   31440
gctctaatca tgcataagac tgtgatctgc cttctgatcc tctgcatcct gcccaccctc   31500
acctcctgcc agtacaccac aaaatctccg cgcaaaagac atgcctcctg ccgcttcacc   31560
caactgtgga atatacccaa atgctacaac gaaaagagcg agctctccga agcttggctg   31620
tatggggtca tctgtgtctt agttttctgc agcactgtct ttgccctcat gatctacccc   31680
tactttgatt tgggatggaa cgcgatcgat gccatgaatt accccacctt tcccgcaccc   31740
gagataattc cactgcgaca agttgtaccc gttgtcgtta atcaacgccc ccatcccct    31800
acgcccactg aaatcagcta ctttaaccta acaggcggag atgactgacg ccctagatct   31860
agaaatggac ggcatcagta ccgagcagcg tctcctagag aggcgcaggc aggcggctga   31920
gcaagagcgc ctcaatcagg agctccgaga tctcgttaac ctgcaccagt gcaaaagagg   31980
catcttttgt ctggtaaagc aggccaaagt cacctacgag aagaccggca acagccaccg   32040
cctcagttac aaaattgccca cccagcgcca gaagctggtg ctcatggtgg gtgagaatcc   32100
catcaccgtc acccagcact cggtagagac cgaggggtgt ctgcactccc cctgtcgggg   32160
tccagaagac ctctgcaccc tggtaaagac cctgtgcggt ctcagagatt tagtcccctt   32220
taactaatca aacactggaa tcaataaaaa gaatcactta cttaaaatca dacagcaggt   32280
ctctgtccag tttattcagc agcacctcct tcccctcctc ccaactctgg tactccaaac   32340
gccttctggg ggcaaacttc ctccacaccc tgaagggaat gtcagattct tgctcctgtc   32400
cctccgcacc cactatcttc atgttgttgc agatgaagcg caccaaaacg tctgacgaga   32460
gcttcaaccc cgtgtaccccc tatgacacgg aaagcggccc tccctccgtc cctttcctca   32520
cccctccctt cgtgtctccc gatggattcc aagaaagtcc ccccggggtc ctgtctctga   32580
acctggccga gccctggtc acttcccacg gcatgctcgc cctgaaaatg ggaagtggcc   32640
tctccctgga cgacgctggc aacctcacct ctcaagatat caccaccgct agccctcccc   32700
tcaaaaaaac caagaccaac ctcagcctag aaacctcatc ccccctaact gtgagcacct   32760
```

```
caggcgccct caccgtagca gccgccgctc ccctggcggt ggccggcacc tccctcacca    32820
tgcaatcaga ggccccccctg acagtacagg atgcaaaact caccctggcc accaaaggcc   32880
ccctgaccgt gtctgaaggc aaactggcct tgcaaacatc ggccccgctg acggccgctg    32940
acagcagcac cctcaccgtt agcgccacac caccaattaa tgtaagcagt ggaagtttag    33000
gcttagacat ggaagaccct atgtatactc acaatggaaa actgggaata agaattgggg    33060
gtccactaag agtagtagac agcttgcata cactcactgt agttaccgga aatggactaa    33120
ctgtagataa caatgccctc caaactaaag ttacgggcgc cctaggttat gacacatcag    33180
gaaatctaca attaagagct gcaggaggta tgcgaattga cgcaaatggc caacttatcc    33240
ttaatgtggc atacccattt gatgctcaga acaatctcag ccttagactt ggtcagggac    33300
ccctgtatat aaacacagac cacaacctgg atttgaattg caacagaggt ctaaccacaa    33360
ctaccaccaa caacacaaaa aaacttgaga ctaaaattag ctcaggctta gactatgaca    33420
ccaatggtgc tgtcattatt aaacttggca ctggtctaag cttcgacaac acaggcgccc    33480
taactgtggg aaacactggt gatgataaac tgactctgtg gacgaccccca gacccatctc    33540 caaattgcag aattcactca gacaaagact gcaagtttac tctagtccta actaagtgtg    33600
gaagccaaat cctggcctct gtcgccgccc tagcggtatc aggaaatctg gcttcgataa    33660
caggcaccgt tgccagcgtt accatctttc tcagatttga tcagaatgga gtgcttatgg    33720
aaaactcctc gctagacagg cagtactgga acttcagaaa tggcaactca actaacgctg    33780 cccctacac caatgcagtt gggttcatgc caaacctcgc agcataccccc aaaacgcaaa    33840 gccagactgc taaaaacaac attgtaagtc aggtttactt gaatggagac aaatccaaac    33900 ccatgacccct taccatcacc ctcaatggaa ctaatgaatc cagtgaaact agccaggtga    33960
gtcactactc catgtcattt acatgggctt gggaaagtgg gcaatatgcc actgaaaccct   34020 ttgccaccaa ctccttcacc ttttcttaca ttgctgaaca ataaaaagca tgacactgat    34080
gttcatttct gattcttatt ttattatttt caaacacaac aaaatcattc aagtcattct    34140
tccatcttag cttaatagac acagtagctt aatagaccca gtagtgcaaa gccccattct    34200
agcttataac tagtggagaa gtactcgcct acatgggggt agagtcataa tcgtgcatca    34260
ggatagggcg gtggtgctgc agcagcgcgc gaataaactg ctgccgccgc cgctccgtcc    34320
tgcaggaata caacatggca gtggtctcct cagcgatgat tcgcaccgcc cgcagcataa    34380
ggcgccttgt cctccgggca cagcagcgca ccctgatctc acttaaatca gcacagtaac    34440
tgcagcacag caccacaata ttgttcaaaa tcccacagtg caaggcgctg tatccaaagc    34500
tcatggcggg gaccacagaa cccacgtggc catcatacca caagcgcagg tagattaagt    34560
ggcgacccct cataaacacg ctggacataa acattacctc ttttggcatg ttgtaattca    34620
ccacctcccg gtaccatata aacctctgat taaacatggc gccatccacc accatcctaa    34680
accagctggc caaaacctgc ccgccggcta tacactgcag ggaaccggga ctggaacaat    34740
gacagtggag agcccaggac tcgtaaccat ggatcatcat gctcgtcatg atatcaatgt    34800
tggcacaaca caggcacacg tgcatacact tcctcaggat tacaagctcc tcccgcgtta    34860
gaaccatatc ccagggaaca acccattcct gaatcagcgt aaatcccaca ctgcaggaa    34920 gacctcgcac gtaactcacg ttgtgcattg tcaaagtgtt acattcgggc agcagcggat    34980
gatcctccag tatggtagcg cgggtttctg tctcaaaagg aggtagacga tccctactgt    35040
acggagtgcg ccgagacaac cgagatcgtg ttggtcgtag tgtcatgcca aatggaacgc    35100
```

```
cggacgtagt catatttcct gaagtcttag atctctcaac gcagcaccag caccaacact    35160
tcgcagtgta aaaggccaag tgccgagaga gtatatatag gaataaaaag tgacgtaaac    35220
gggcaaagtc caaaaaacgc ccagaaaaac cgcacgcgaa cctacgcccc gaaacgaaag    35280
ccaaaaaaca ctagacactc ccttccggcg tcaacttccg ctttcccacg ctacgtcact    35340
tgccccagtc aaacaaacta catatcccga acttccaagt cgccacgccc aaaacaccgc    35400
ctacacctcc ccgcccgccg gcccgccccc aaacccgcct cccgcccgc gcccgcccc    35460 gcgccgccca tctcattatc atattggctt caatccaaaa taaggtatat tattgatgat    35520
ggtttaaacg gatccaattc ttgaagacga aagggcctcg tgatacgcct attttatag    35580 gttaatgtca tgataataat ggtttcttag acgtcaggtg gcacttttcg gggaaatgtg    35640
cgcggaaccc ctatttgttt attttttctaa atacattcaa atatgtatcc gctcatgaga    35700
caataaccct gataaatgct tcaataatat tgaaaaagga gagtatgag tattcaacat    35760 ttccgtgtcg cccttattcc cttttttgcg cattttgcc ttcctgtttt tgctcaccca    35820
gaaacgctgg tgaaagtaaa agatgctgaa gatcagttgg gtgcacgagt gggttacatc    35880
gaactggatc tcaacagcgg taagatcctt gagagttttc gccccgaaga acgttttcca    35940
atgatgagca cttttaaagt tctgctatgt ggcgcggtat tatcccgtgt tgacgccggg    36000
caagagcaac tcggtcgccg catacactat tctcagaatg acttggttga gtactcacca    36060
gtcacagaaa agcatcttac ggatggcatg acagtaagag aattatgcag tgctgccata    36120
accatgagtg ataacactgc ggccaactta cttctgacaa cgatcggagg accgaaggag    36180
ctaaccgctt ttttgcacaa catggggat catgtaactc gccttgatcg ttgggaaccg    36240
gagctgaatg aagccatacc aaacgacgag cgtgacacca cgatgcctgt agcaatggca    36300
acaacgttgc gcaaactatt aactggcgaa ctacttactc tagcttcccg gcaacaatta    36360
atagactgga tggaggcgga taaagttgca ggaccacttc tgcgctcggc ccttccggct    36420
ggctggttta ttgctgataa atctggagcc ggtgagcgtg gtctcgcgg tatcattgca    36480 gcactggggc cagatggtaa gccctcccgt atcgtagtta tctacacgac ggggagtcag    36540
gcaactatgg atgaacgaaa tagacagatc gctgagatag gtgcctcact gattaagcat    36600
tggtaactgt cagaccaagt ttactcatat atactttaga ttgatttaaa aggatctagg    36660
tgaagatcct ttttgataat ctcatgacca aaatccctta acgtgagttt tcgttccact    36720
gagcgtcaga ccccgtagaa aagatcaaag gatcttcttg agatcctttt tttctgcgcg    36780
taatctgctg cttgcaaaca aaaaaaccac cgctaccagc ggtggtttgt ttgccggatc    36840
aagagctacc aactcttttt ccgaaggtaa ctggcttcag cagagcgcag ataccaaata    36900
ctgtccttct agtgtagccg tagttaggcc accacttcaa gaactctgta gcaccgccta    36960
catacctcgc tctgctaatc ctgttaccag tggctgctgc cagtggcgat aagtcgtgtc    37020
ttaccgggtt ggactcaaga cgatagttac cggataaggc gcagcggtcg ggctgaacgg    37080
ggggttcgtg cacacagccc agcttggagc gaacgaccta ccgaactg agatacctac    37140 agcgtgagct atgagaaagc gccacgcttc ccgaagggag aaaggcggac aggtatccgg    37200
taagcggcag ggtcggaaca ggagagcgca cgagggagct tccaggggga aacgcctggt    37260
atctttatag tcctgtcggg tttcgccacc tctgacttga gcgtcgattt tgtgatgct    37320 cgtcaggggg gcggagccta tggaaaaacg ccagcaacgc ggcctttta cggttcctgg    37380 ccttttgctg gccttgaagc tgtccctgat ggtcgtcatc tacctgcctg acagcatgg    37440 cctgcaacgc gggcatcccg atgccgccgg aagcgagaag aatcataatg gggaaggcca    37500
```

```
tccagcctcg cgtcgcagat ccgaattcgt ttaaac                              37536
```

<210> SEQ ID NO 25
<211> LENGTH: 29
<212> TYPE: DNA
<213> ORGANISM: Human cytomegalovirus

<400> SEQUENCE: 25

```
catctacgta ttagtcatcg ctattacca                                      29
```

<210> SEQ ID NO 26
<211> LENGTH: 21
<212> TYPE: DNA
<213> ORGANISM: Human cytomegalovirus

<400> SEQUENCE: 26

```
gacttggaaa tccccgtgag t                                              21
```

<210> SEQ ID NO 27
<211> LENGTH: 543
<212> TYPE: PRT
<213> ORGANISM: Pan troglodytes

<400> SEQUENCE: 27

| | | | | | | | | | | | | | | |
|---|---|---|---|---|---|---|---|---|---|---|---|---|---|---|
| Met | Lys | Arg | Thr | Lys | Thr | Ser | Asp | Glu | Ser | Phe | Asn | Pro | Val | Tyr | Pro |
| 1 | | | | 5 | | | | | 10 | | | | | 15 | |
| Tyr | Asp | Thr | Glu | Ser | Gly | Pro | Pro | Ser | Val | Pro | Phe | Leu | Thr | Pro | Pro |
| | | | 20 | | | | | 25 | | | | | 30 | | |
| Phe | Val | Ser | Pro | Asp | Gly | Phe | Gln | Glu | Ser | Pro | Pro | Gly | Val | Leu | Ser |
| | | 35 | | | | | 40 | | | | | 45 | | | |
| Leu | Asn | Leu | Ala | Glu | Pro | Leu | Val | Thr | Ser | His | Gly | Met | Leu | Ala | Leu |
| | 50 | | | | | 55 | | | | | 60 | | | | |
| Lys | Met | Gly | Ser | Gly | Leu | Ser | Leu | Asp | Asp | Ala | Gly | Asn | Leu | Thr | Ser |
| 65 | | | | | 70 | | | | | 75 | | | | | 80 |
| Gln | Asp | Ile | Thr | Thr | Ala | Ser | Pro | Pro | Leu | Lys | Lys | Thr | Lys | Thr | Asn |
| | | | | 85 | | | | | 90 | | | | | 95 | |
| Leu | Ser | Leu | Glu | Thr | Ser | Ser | Pro | Leu | Thr | Val | Ser | Thr | Ser | Gly | Ala |
| | | | 100 | | | | | 105 | | | | | 110 | | |
| Leu | Thr | Val | Ala | Ala | Ala | Pro | Leu | Ala | Val | Ala | Gly | Thr | Ser | Leu |
| | | 115 | | | | | 120 | | | | | 125 | | | |
| Thr | Met | Gln | Ser | Glu | Ala | Pro | Leu | Thr | Val | Gln | Asp | Ala | Lys | Leu | Thr |
| | 130 | | | | | 135 | | | | | 140 | | | | |
| Leu | Ala | Thr | Lys | Gly | Pro | Leu | Thr | Val | Ser | Glu | Gly | Lys | Leu | Ala | Leu |
| 145 | | | | | 150 | | | | | 155 | | | | | 160 |
| Gln | Thr | Ser | Ala | Pro | Leu | Thr | Ala | Ala | Asp | Ser | Ser | Thr | Leu | Thr | Val |
| | | | | 165 | | | | | 170 | | | | | 175 | |
| Ser | Ala | Thr | Pro | Pro | Ile | Asn | Val | Ser | Ser | Gly | Ser | Leu | Gly | Leu | Asp |
| | | | 180 | | | | | 185 | | | | | 190 | | |
| Met | Glu | Asp | Pro | Met | Tyr | Thr | His | Asp | Gly | Lys | Leu | Gly | Ile | Arg | Ile |
| | | 195 | | | | | 200 | | | | | 205 | | | |
| Gly | Gly | Pro | Leu | Arg | Val | Val | Asp | Ser | Leu | His | Thr | Leu | Thr | Val | Val |
| | 210 | | | | | 215 | | | | | 220 | | | | |
| Thr | Gly | Asn | Gly | Leu | Thr | Val | Asp | Asn | Asn | Ala | Leu | Gln | Thr | Arg | Val |
| 225 | | | | | 230 | | | | | 235 | | | | | 240 |
| Thr | Gly | Ala | Leu | Gly | Tyr | Asp | Thr | Ser | Gly | Asn | Leu | Gln | Leu | Arg | Ala |
| | | | | 245 | | | | | 250 | | | | | 255 | |

```
Ala Gly Gly Met Arg Ile Asp Ala Asn Gly Gln Leu Ile Leu Asn Val
            260                 265                 270

Ala Tyr Pro Phe Asp Ala Gln Asn Asn Leu Ser Leu Arg Leu Gly Gln
        275                 280                 285

Gly Pro Leu Tyr Ile Asn Thr Asp His Asn Leu Asp Leu Asn Cys Asn
    290                 295                 300

Arg Gly Leu Thr Thr Thr Thr Asn Asn Thr Lys Lys Leu Glu Thr
305                 310                 315                 320

Lys Ile Ser Ser Gly Leu Asp Tyr Asp Thr Asn Gly Ala Val Ile Ile
                325                 330                 335

Lys Leu Gly Thr Gly Leu Ser Phe Asp Asn Thr Gly Ala Leu Thr Val
            340                 345                 350

Gly Asn Thr Gly Asp Asp Lys Leu Thr Leu Trp Thr Thr Pro Asp Pro
        355                 360                 365

Ser Pro Asn Cys Arg Ile His Ser Asp Lys Asp Cys Lys Phe Thr Leu
    370                 375                 380

Val Leu Thr Lys Cys Gly Ser Gln Ile Leu Ala Ser Val Ala Ala Leu
385                 390                 395                 400

Ala Val Ser Gly Asn Leu Ala Ser Ile Thr Gly Thr Val Ala Ser Val
                405                 410                 415

Thr Ile Phe Leu Arg Phe Asp Gln Asn Gly Val Leu Met Glu Asn Ser
            420                 425                 430

Ser Leu Asp Arg Gln Tyr Trp Asn Phe Arg Asn Gly Asn Ser Thr Asn
        435                 440                 445

Ala Ala Pro Tyr Thr Asn Ala Val Gly Phe Met Pro Asn Leu Ala Ala
    450                 455                 460

Tyr Pro Lys Thr Gln Ser Gln Thr Ala Lys Asn Asn Ile Val Ser Gln
465                 470                 475                 480

Val Tyr Leu Asn Gly Asp Lys Ser Lys Pro Met Thr Leu Thr Ile Thr
                485                 490                 495

Leu Asn Gly Thr Asn Glu Ser Ser Glu Thr Ser Gln Val Ser His Tyr
            500                 505                 510

Ser Met Ser Phe Thr Trp Ala Trp Glu Ser Gly Gln Tyr Ala Thr Glu
        515                 520                 525

Thr Phe Ala Thr Asn Ser Phe Thr Phe Ser Tyr Ile Ala Glu Gln
    530                 535                 540

<210> SEQ ID NO 28
<211> LENGTH: 542
<212> TYPE: PRT
<213> ORGANISM: Pan paniscus

<400> SEQUENCE: 28

Met Lys Arg Ala Lys Thr Ser Asp Glu Thr Phe Asn Pro Val Tyr Pro
1               5                   10                  15

Tyr Asp Thr Glu Asn Gly Pro Pro Ser Val Pro Phe Leu Thr Pro Pro
            20                  25                  30

Phe Val Ser Pro Asp Gly Phe Gln Glu Ser Pro Pro Gly Val Leu Ser
        35                  40                  45

Leu Arg Leu Ser Glu Pro Leu Val Thr Ser His Gly Met Leu Ala Leu
    50                  55                  60

Lys Met Gly Asn Gly Leu Ser Leu Asp Asp Ala Gly Asn Leu Thr Ser
65                  70                  75                  80

Gln Asp Val Thr Thr Val Thr Pro Pro Leu Lys Lys Thr Lys Thr Asn
                85                  90                  95
```

```
Leu Ser Leu Gln Thr Ser Ala Pro Leu Thr Val Ser Ser Gly Ser Leu
            100                 105                 110

Thr Val Ala Ala Ala Pro Leu Ala Val Ala Gly Thr Ser Leu Thr
        115                 120                 125

Met Gln Ser Gln Ala Pro Leu Thr Val Gln Asp Ala Lys Leu Gly Leu
    130                 135                 140

Ala Thr Gln Gly Pro Leu Thr Val Ser Glu Gly Lys Leu Thr Leu Gln
145                 150                 155                 160

Thr Ser Ala Pro Leu Thr Ala Ala Asp Ser Ser Thr Leu Thr Val Gly
                165                 170                 175

Thr Thr Pro Pro Ile Ser Val Ser Gly Ser Leu Gly Leu Asp Met
            180                 185                 190

Glu Asp Pro Met Tyr Thr His Asp Gly Lys Leu Gly Ile Arg Ile Gly
            195                 200                 205

Gly Pro Leu Gln Val Val Asp Ser Leu His Thr Leu Thr Val Val Thr
        210                 215                 220

Gly Asn Gly Ile Thr Val Ala Asn Asn Ala Leu Gln Thr Lys Val Ala
225                 230                 235                 240

Gly Ala Leu Gly Tyr Asp Ser Ser Gly Asn Leu Glu Leu Arg Ala Ala
                245                 250                 255

Gly Gly Met Arg Ile Asn Thr Gly Gln Leu Ile Leu Asp Val Ala
            260                 265                 270

Tyr Pro Phe Asp Ala Gln Asn Asn Leu Ser Leu Arg Leu Gly Gln Gly
            275                 280                 285

Pro Leu Tyr Val Asn Thr Asn His Asn Leu Asp Leu Asn Cys Asn Arg
        290                 295                 300

Gly Leu Thr Thr Thr Thr Ser Ser Asn Thr Thr Lys Leu Glu Thr Lys
305                 310                 315                 320

Ile Asp Ser Gly Leu Asp Tyr Asn Ala Asn Gly Ala Ile Ile Ala Lys
                325                 330                 335

Leu Gly Thr Gly Leu Thr Phe Asp Asn Thr Gly Ala Ile Thr Val Gly
            340                 345                 350

Asn Thr Gly Asp Asp Lys Leu Thr Leu Trp Thr Thr Pro Asp Pro Ser
        355                 360                 365

Pro Asn Cys Arg Ile His Ala Asp Lys Asp Cys Lys Phe Thr Leu Val
        370                 375                 380

Leu Thr Lys Cys Gly Ser Gln Ile Leu Ala Ser Val Ala Ala Leu Ala
385                 390                 395                 400

Val Ser Gly Asn Leu Ser Ser Met Thr Gly Thr Val Ser Ser Val Thr
                405                 410                 415

Ile Phe Leu Arg Phe Asp Gln Asn Gly Val Leu Met Glu Asn Ser Ser
            420                 425                 430

Leu Asp Lys Glu Tyr Trp Asn Phe Arg Asn Gly Asn Ser Thr Asn Ala
        435                 440                 445

Thr Pro Tyr Thr Asn Ala Val Gly Phe Met Pro Asn Leu Ser Ala Tyr
        450                 455                 460

Pro Lys Thr Gln Ser Gln Thr Ala Lys Asn Asn Ile Val Ser Glu Val
465                 470                 475                 480

Tyr Leu His Gly Asp Lys Ser Lys Pro Met Ile Leu Thr Ile Thr Leu
                485                 490                 495

Asn Gly Thr Asn Glu Ser Ser Glu Thr Ser Gln Val Ser His Tyr Ser
            500                 505                 510
```

```
Met Ser Phe Thr Trp Ser Trp Asp Ser Gly Lys Tyr Ala Thr Glu Thr
            515                 520                 525

Phe Ala Thr Asn Ser Phe Thr Phe Ser Tyr Ile Ala Glu Gln
            530                 535                 540

<210> SEQ ID NO 29
<211> LENGTH: 543
<212> TYPE: PRT
<213> ORGANISM: Pan troglodytes

<400> SEQUENCE: 29

Met Lys Arg Thr Lys Thr Ser Asp Glu Ser Phe Asn Pro Val Tyr Pro
1               5                   10                  15

Tyr Asp Thr Glu Ser Gly Pro Pro Ser Val Pro Phe Leu Thr Pro Pro
            20                  25                  30

Phe Val Ser Pro Asp Gly Phe Gln Glu Ser Pro Pro Gly Val Leu Ser
        35                  40                  45

Leu Asn Leu Ala Glu Pro Leu Val Thr Ser His Gly Met Leu Ala Leu
    50                  55                  60

Lys Met Gly Ser Gly Leu Ser Leu Asp Asp Ala Gly Asn Leu Thr Ser
65                  70                  75                  80

Gln Asp Ile Thr Ser Thr Thr Pro Pro Leu Lys Lys Thr Lys Thr Asn
                85                  90                  95

Leu Ser Leu Glu Thr Ser Ser Pro Leu Thr Val Ser Thr Ser Gly Ala
            100                 105                 110

Leu Thr Val Ala Ala Ala Ala Pro Leu Ala Val Ala Gly Thr Ser Leu
        115                 120                 125

Thr Met Gln Ser Glu Ala Pro Leu Ala Val Gln Asp Ala Lys Leu Thr
    130                 135                 140

Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Thr Leu Thr Val
                165                 170                 175

Ser Ser Thr Pro Pro Ile Ser Val Ser Ser Gly Ser Leu Gly Leu Asp
            180                 185                 190

Met Glu Asp Pro Met Tyr Thr His Asp Gly Lys Leu Gly Ile Arg Ile
        195                 200                 205

Gly Gly Pro Leu Arg Val Val Asp Ser Leu His Thr Leu Thr Val Val
    210                 215                 220

Thr Gly Asn Gly Leu Thr Val Asp Asn Asn Ala Leu Gln Thr Arg Val
225                 230                 235                 240

Thr Gly Ala Leu Gly Tyr Asp Thr Ser Gly Asn Leu Gln Leu Arg Ala
                245                 250                 255

Ala Gly Gly Met Arg Ile Asp Ala Asn Gly Gln Leu Ile Leu Asp Val
            260                 265                 270

Ala Tyr Pro Phe Asp Ala Gln Asn Asn Leu Ser Leu Arg Leu Gly Gln
        275                 280                 285

Gly Pro Leu Tyr Val Asn Thr Asp His Asn Leu Asp Leu Asn Cys Asn
    290                 295                 300

Arg Gly Leu Thr Thr Thr Thr Asn Asn Thr Lys Lys Leu Glu Thr
305                 310                 315                 320

Lys Ile Ser Ser Gly Leu Asp Tyr Asp Thr Asn Gly Ala Val Ile Ile
                325                 330                 335

Lys Leu Gly Thr Gly Leu Ser Phe Asp Asn Thr Gly Ala Leu Thr Val
            340                 345                 350
```

```
Gly Asn Thr Gly Asp Asp Lys Leu Thr Leu Trp Thr Thr Pro Asp Pro
            355                 360                 365

Ser Pro Asn Cys Arg Ile His Ser Asp Lys Asp Cys Lys Phe Thr Leu
    370                 375                 380

Val Leu Thr Lys Cys Gly Ser Gln Ile Leu Ala Ser Val Ala Ala Leu
385                 390                 395                 400

Ala Val Ser Gly Asn Leu Ala Ser Ile Thr Gly Thr Val Ala Ser Val
                405                 410                 415

Thr Ile Phe Leu Arg Phe Asp Gln Asn Gly Val Leu Met Glu Asn Ser
            420                 425                 430

Ser Leu Asp Lys Gln Tyr Trp Asn Phe Arg Asn Gly Asn Ser Thr Asn
        435                 440                 445

Ala Ala Pro Tyr Thr Asn Ala Val Gly Phe Met Pro Asn Leu Ala Ala
    450                 455                 460

Tyr Pro Lys Thr Gln Ser Gln Thr Ala Lys Asn Asn Ile Val Ser Gln
465                 470                 475                 480

Val Tyr Leu Asn Gly Asp Lys Ser Lys Pro Met Thr Leu Thr Ile Thr
                485                 490                 495

Leu Asn Gly Thr Asn Glu Ser Ser Glu Thr Ser Gln Val Ser His Tyr
            500                 505                 510

Ser Met Ser Phe Thr Trp Ala Trp Glu Ser Gly Gln Tyr Ala Thr Glu
        515                 520                 525

Thr Phe Ala Thr Asn Ser Phe Thr Phe Ser Tyr Ile Ala Glu Gln
    530                 535                 540

<210> SEQ ID NO 30
<211> LENGTH: 543
<212> TYPE: PRT
<213> ORGANISM: Pan troglodytes

<400> SEQUENCE: 30

Met Lys Arg Thr Lys Thr Ser Asp Lys Ser Phe Asn Pro Val Tyr Pro
1               5                   10                  15

Tyr Asp Thr Glu Asn Gly Pro Pro Ser Val Pro Phe Leu Thr Pro Pro
            20                  25                  30

Phe Val Ser Pro Asp Gly Phe Gln Glu Ser Pro Pro Gly Val Leu Ser
        35                  40                  45

Leu Asn Leu Ala Glu Pro Leu Val Thr Ser His Gly Met Leu Ala Leu
    50                  55                  60

Lys Met Gly Ser Gly Leu Ser Leu Asp Asp Ala Gly Asn Leu Thr Ser
65                  70                  75                  80

Gln Asp Val Thr Thr Thr Thr Pro Pro Leu Lys Lys Thr Lys Thr Asn
                85                  90                  95

Leu Ser Leu Glu Thr Ser Ala Pro Leu Thr Val Ser Thr Ser Gly Ala
            100                 105                 110

Leu Thr Leu Ala Ala Ala Ala Pro Leu Ala Val Ala Gly Thr Ser Leu
        115                 120                 125

Thr Met Gln Ser Glu Ala Pro Leu Thr Val Gln Asp Ala Lys Leu Thr
    130                 135                 140

Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Thr Leu Thr Val
                165                 170                 175

Ser Ala Thr Pro Pro Ile Ser Val Ser Ser Gly Ser Leu Gly Leu Asp
```

```
            180                 185                 190
Met Glu Asp Pro Met Tyr Thr His Asp Gly Lys Leu Gly Ile Arg Ile
            195                 200                 205

Gly Gly Pro Leu Arg Val Val Asp Ser Leu His Thr Leu Thr Val Val
            210                 215                 220

Thr Gly Asn Gly Ile Ala Val Asp Asn Asn Ala Leu Gln Thr Arg Val
225                 230                 235                 240

Thr Gly Ala Leu Gly Tyr Asp Thr Ser Gly Asn Leu Gln Leu Arg Ala
                245                 250                 255

Ala Gly Gly Met Arg Ile Asp Ala Asn Gly Gln Leu Ile Leu Asp Val
                260                 265                 270

Ala Tyr Pro Phe Asp Ala Gln Asn Asn Leu Ser Leu Arg Leu Gly Gln
            275                 280                 285

Gly Pro Leu Tyr Val Asn Thr Asp His Asn Leu Asp Leu Asn Cys Asn
            290                 295                 300

Arg Gly Leu Thr Thr Thr Thr Asn Thr Lys Lys Leu Glu Thr
305                 310                 315                 320

Lys Ile Gly Ser Gly Leu Asp Tyr Asp Thr Asn Gly Ala Val Ile Ile
                325                 330                 335

Lys Leu Gly Thr Gly Val Ser Phe Asp Ser Thr Gly Ala Leu Ser Val
                340                 345                 350

Gly Asn Thr Gly Asp Asp Lys Leu Thr Leu Trp Thr Thr Pro Asp Pro
            355                 360                 365

Ser Pro Asn Cys Arg Ile His Ser Asp Lys Asp Cys Lys Phe Thr Leu
370                 375                 380

Val Leu Thr Lys Cys Gly Ser Gln Ile Leu Ala Ser Val Ala Ala Leu
385                 390                 395                 400

Ala Val Ser Gly Asn Leu Ala Ser Ile Thr Gly Thr Val Ser Ser Val
                405                 410                 415

Thr Ile Phe Leu Arg Phe Asp Gln Asn Gly Val Leu Met Glu Asn Ser
            420                 425                 430

Ser Leu Asp Lys Gln Tyr Trp Asn Phe Arg Asn Gly Asn Ser Thr Asn
            435                 440                 445

Ala Thr Pro Tyr Thr Asn Ala Val Gly Phe Met Pro Asn Leu Ala Ala
            450                 455                 460

Tyr Pro Lys Thr Gln Ser Gln Thr Ala Lys Asn Asn Ile Val Ser Gln
465                 470                 475                 480

Val Tyr Leu Asn Gly Asp Lys Ser Lys Pro Met Thr Leu Thr Ile Thr
                485                 490                 495

Leu Asn Gly Thr Asn Glu Ser Ser Glu Thr Ser Gln Val Ser His Tyr
            500                 505                 510

Ser Met Ser Phe Thr Trp Ala Trp Glu Ser Gly Gln Tyr Ala Thr Glu
            515                 520                 525

Thr Phe Ala Thr Asn Ser Phe Thr Phe Ser Tyr Ile Ala Glu Gln
            530                 535                 540

<210> SEQ ID NO 31
<211> LENGTH: 543
<212> TYPE: PRT
<213> ORGANISM: Pan troglodytes

<400> SEQUENCE: 31

Met Lys Arg Thr Lys Thr Ser Asp Glu Ser Phe Asn Pro Val Tyr Pro
1               5                   10                  15
```

```
Tyr Asp Thr Glu Asn Gly Pro Pro Ser Val Pro Phe Leu Thr Pro Pro
                 20                  25                  30

Phe Val Ser Pro Asp Gly Phe Gln Glu Ser Pro Pro Gly Val Leu Ser
             35                  40                  45

Leu Asn Leu Ala Glu Pro Leu Val Thr Ser His Gly Met Leu Ala Leu
 50                      55                  60

Lys Met Gly Ser Gly Leu Ser Leu Asp Asp Ala Gly Asn Leu Thr Ser
 65                  70                  75                  80

Gln Asp Val Thr Thr Thr Thr Pro Pro Leu Lys Lys Thr Lys Thr Asn
                 85                  90                  95

Leu Ser Leu Glu Thr Ser Ala Pro Leu Thr Val Ser Thr Ser Gly Ala
             100                 105                 110

Leu Thr Leu Ala Ala Ala Ala Pro Leu Ala Val Ala Gly Thr Ser Leu
             115                 120                 125

Thr Met Gln Ser Glu Ala Pro Leu Thr Val Gln Asp Ala Lys Leu Thr
             130                 135                 140

Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Thr Leu Thr Val
                 165                 170                 175

Ser Ala Thr Pro Pro Ile Asn Val Ser Ser Gly Ser Leu Gly Leu Asp
             180                 185                 190

Met Glu Asn Pro Met Tyr Thr His Asp Gly Lys Leu Gly Ile Arg Ile
             195                 200                 205

Gly Gly Pro Leu Arg Val Val Asp Ser Leu His Thr Leu Thr Val Val
210                 215                 220

Thr Gly Asn Gly Ile Ala Val Asp Asn Asn Ala Leu Gln Thr Arg Val
225                 230                 235                 240

Thr Gly Ala Leu Gly Tyr Asp Thr Ser Gly Asn Leu Gln Leu Arg Ala
                 245                 250                 255

Ala Gly Gly Met Arg Ile Asp Ala Asn Gly Gln Leu Ile Leu Asp Val
             260                 265                 270

Ala Tyr Pro Phe Asp Ala Gln Asn Asn Leu Ser Leu Arg Leu Gly Gln
             275                 280                 285

Gly Pro Leu Tyr Val Asn Thr Asp His Asn Leu Asp Leu Asn Cys Asn
             290                 295                 300

Arg Gly Leu Thr Thr Thr Thr Asn Asn Thr Lys Lys Leu Glu Thr
305                 310                 315                 320

Lys Ile Gly Ser Gly Leu Asp Tyr Asp Thr Asn Gly Ala Val Ile Ile
             325                 330                 335

Lys Leu Gly Thr Gly Val Ser Phe Asp Ser Thr Gly Ala Leu Ser Val
             340                 345                 350

Gly Asn Thr Gly Asp Asp Lys Leu Thr Leu Trp Thr Thr Pro Asp Pro
             355                 360                 365

Ser Pro Asn Cys Arg Ile His Ser Asp Lys Asp Cys Lys Phe Thr Leu
             370                 375                 380

Val Leu Thr Lys Cys Gly Ser Gln Ile Leu Ala Ser Val Ala Ala Leu
385                 390                 395                 400

Ala Val Ser Gly Asn Leu Ala Ser Ile Thr Gly Thr Val Ser Ser Val
                 405                 410                 415

Thr Ile Phe Leu Arg Phe Asp Gln Asn Gly Val Leu Met Glu Asn Ser
             420                 425                 430

Ser Leu Asp Lys Gln Tyr Trp Asn Phe Arg Asn Gly Asn Ser Thr Asn
```

-continued

```
              435                 440                 445
Ala Thr Pro Tyr Thr Asn Ala Val Gly Phe Met Pro Asn Leu Ala Ala
    450                 455                 460

Tyr Pro Lys Thr Gln Ser Gln Thr Ala Lys Asn Asn Ile Val Ser Gln
465                 470                 475                 480

Val Tyr Leu Asn Gly Asp Lys Ser Lys Pro Met Ile Leu Thr Ile Thr
                485                 490                 495

Leu Asn Gly Thr Asn Glu Ser Ser Glu Thr Ser Gln Val Ser His Tyr
            500                 505                 510

Ser Met Ser Phe Thr Trp Ala Trp Glu Ser Gly Gln Tyr Ala Thr Glu
            515                 520                 525

Thr Phe Ala Thr Asn Ser Phe Thr Phe Ser Tyr Ile Ala Glu Gln
    530                 535                 540

<210> SEQ ID NO 32
<211> LENGTH: 578
<212> TYPE: PRT
<213> ORGANISM: Pan troglodytes

<400> SEQUENCE: 32

Met Lys Arg Thr Lys Thr Ser Asp Glu Ser Phe Asn Pro Val Tyr Pro
1               5                  10                  15

Tyr Asp Thr Glu Asn Gly Pro Pro Ser Val Pro Phe Leu Thr Pro Pro
            20                  25                  30

Phe Val Ser Pro Asp Gly Phe Gln Glu Ser Pro Pro Gly Val Leu Ser
        35                  40                  45

Leu Asn Leu Ala Glu Pro Leu Val Thr Ser His Gly Met Leu Ala Leu
    50                  55                  60

Lys Met Gly Ser Gly Leu Ser Leu Asp Asp Ala Gly Asn Leu Thr Ser
65                  70                  75                  80

Gln Asp Val Thr Thr Thr Thr Pro Pro Leu Lys Lys Thr Lys Thr Asn
                85                  90                  95

Leu Ser Leu Glu Thr Ser Ala Pro Leu Thr Val Ser Thr Ser Gly Ala
            100                 105                 110

Leu Thr Leu Ala Ala Ala Val Pro Leu Ala Val Ala Gly Thr Ser Leu
        115                 120                 125

Thr Met Gln Ser Glu Ala Pro Leu Thr Val Gln Asp Ala Lys Leu Thr
    130                 135                 140

Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Thr Leu Thr Ile
                165                 170                 175

Ser Ala Thr Pro Pro Leu Ser Thr Ser Asn Gly Ser Leu Gly Ile Asp
            180                 185                 190

Met Gln Ala Pro Ile Tyr Thr Thr Asn Gly Lys Leu Gly Leu Asn Phe
        195                 200                 205

Gly Ala Pro Leu His Val Val Asp Ser Leu Asn Ala Leu Thr Val Val
    210                 215                 220

Thr Gly Gln Gly Leu Thr Ile Asn Gly Thr Ala Leu Gln Thr Arg Val
225                 230                 235                 240

Ser Gly Ala Leu Asn Tyr Asp Ser Ser Gly Asn Leu Glu Leu Arg Ala
                245                 250                 255

Ala Gly Gly Met Arg Val Asp Ala Asn Gly Lys Leu Ile Leu Asp Val
            260                 265                 270
```

Ala Tyr Pro Phe Asp Ala Gln Asn Asn Leu Ser Leu Arg Leu Gly Gln
            275                 280                 285

Gly Pro Leu Phe Val Asn Ser Ala His Asn Leu Asp Val Asn Tyr Asn
290                 295                 300

Arg Gly Leu Tyr Leu Phe Thr Ser Gly Asn Thr Lys Leu Glu Val
305                 310                 315                 320

Asn Ile Lys Thr Ala Lys Gly Leu Ile Tyr Asp Asp Thr Ala Ile Ala
                325                 330                 335

Ile Asn Pro Gly Asp Gly Leu Glu Phe Gly Ser Gly Ser Asp Thr Asn
            340                 345                 350

Pro Leu Lys Thr Lys Leu Gly Leu Gly Leu Glu Tyr Asp Ser Ser Arg
            355                 360                 365

Ala Ile Ile Ala Lys Leu Gly Thr Gly Leu Ser Phe Asp Asn Thr Gly
370                 375                 380

Ala Ile Thr Val Gly Asn Lys Asn Asp Asp Lys Leu Thr Leu Trp Thr
385                 390                 395                 400

Thr Pro Asp Pro Ser Pro Asn Cys Arg Ile Tyr Ser Glu Lys Asp Ala
                405                 410                 415

Lys Phe Thr Leu Val Leu Thr Lys Cys Gly Ser Gln Val Leu Ala Ser
                420                 425                 430

Val Ser Val Leu Ser Val Lys Gly Ser Leu Ala Pro Ile Ser Gly Thr
            435                 440                 445

Val Thr Ser Ala Gln Ile Ile Leu Arg Phe Asp Glu Asn Gly Val Leu
            450                 455                 460

Leu Ser Asn Ser Ser Leu Asp Pro Gln Tyr Trp Asn Tyr Arg Lys Gly
465                 470                 475                 480

Asp Leu Thr Glu Gly Thr Ala Tyr Thr Asn Ala Val Gly Phe Met Pro
                485                 490                 495

Asn Leu Thr Ala Tyr Pro Lys Thr Gln Ser Gln Thr Ala Lys Ser Asn
                500                 505                 510

Ile Val Ser Gln Val Tyr Leu Asn Gly Asp Lys Ser Lys Pro Met Ile
            515                 520                 525

Leu Thr Ile Thr Leu Asn Gly Thr Asn Glu Thr Gly Asp Ala Thr Val
530                 535                 540

Ser Thr Tyr Ser Met Ser Phe Ser Trp Asn Trp Asn Gly Ser Asn Tyr
545                 550                 555                 560

Ile Asn Glu Thr Phe Gln Thr Asn Ser Phe Thr Phe Ser Tyr Ile Ala
                565                 570                 575

Gln Glu

<210> SEQ ID NO 33
<211> LENGTH: 578
<212> TYPE: PRT
<213> ORGANISM: Pan troglodytes

<400> SEQUENCE: 33

Met Lys Arg Thr Lys Thr Ser Asp Glu Ser Phe Asn Pro Val Tyr Pro
1               5                   10                  15

Tyr Asp Thr Glu Ser Gly Pro Pro Ser Val Pro Phe Leu Thr Pro Pro
            20                  25                  30

Phe Val Ser Pro Asp Gly Phe Gln Glu Ser Pro Pro Gly Val Leu Ser
            35                  40                  45

Leu Asn Leu Ala Glu Pro Leu Val Thr Ser His Gly Met Leu Ala Leu
50                  55                  60

```
Lys Met Gly Ser Gly Leu Ser Leu Asp Asp Ala Gly Asn Leu Thr Ser
 65                  70                  75                  80

Gln Asp Ile Thr Thr Ala Ser Pro Pro Leu Lys Lys Thr Lys Thr Asn
                 85                  90                  95

Leu Ser Leu Glu Thr Ser Ser Pro Leu Thr Val Ser Thr Ser Gly Ala
                100                 105                 110

Leu Thr Val Ala Ala Ala Pro Leu Ala Val Ala Gly Thr Ser Leu
                115                 120                 125

Thr Met Gln Ser Glu Ala Pro Leu Thr Val Gln Asp Ala Lys Leu Thr
    130                 135                 140

Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Thr Leu Thr Val
                165                 170                 175

Ser Ala Thr Pro Pro Leu Ser Thr Ser Asn Gly Ser Leu Gly Ile Asp
                180                 185                 190

Met Gln Ala Pro Ile Tyr Thr Thr Asn Gly Lys Leu Gly Leu Asn Phe
    195                 200                 205

Gly Ala Pro Leu His Val Val Asp Ser Leu Asn Ala Leu Thr Val Val
210                 215                 220

Thr Gly Gln Gly Leu Thr Ile Asn Gly Thr Ala Leu Gln Thr Arg Val
225                 230                 235                 240

Ser Gly Ala Leu Asn Tyr Asp Thr Ser Gly Asn Leu Glu Leu Arg Ala
                245                 250                 255

Ala Gly Gly Met Arg Val Asp Ala Asn Gly Gln Leu Ile Leu Asp Val
                260                 265                 270

Ala Tyr Pro Phe Asp Ala Gln Asn Asn Leu Ser Leu Arg Leu Gly Gln
                275                 280                 285

Gly Pro Leu Phe Val Asn Ser Ala His Asn Leu Asp Val Asn Tyr Asn
                290                 295                 300

Arg Gly Leu Tyr Leu Phe Thr Ser Gly Asn Thr Lys Lys Leu Glu Val
305                 310                 315                 320

Asn Ile Lys Thr Ala Lys Gly Leu Ile Tyr Asp Asp Thr Ala Ile Ala
                325                 330                 335

Ile Asn Ala Gly Asp Gly Leu Gln Phe Asp Ser Gly Ser Asp Thr Asn
                340                 345                 350

Pro Leu Lys Thr Lys Leu Gly Leu Gly Leu Asp Tyr Asp Ser Ser Arg
                355                 360                 365

Ala Ile Ile Ala Lys Leu Gly Thr Gly Leu Ser Phe Asp Asn Thr Gly
                370                 375                 380

Ala Ile Thr Val Gly Asn Lys Asn Asp Asp Lys Leu Thr Leu Trp Thr
385                 390                 395                 400

Thr Pro Asp Pro Ser Pro Asn Cys Arg Ile Tyr Ser Glu Lys Asp Ala
                405                 410                 415

Lys Phe Thr Leu Val Leu Thr Lys Cys Gly Ser Gln Val Leu Ala Ser
                420                 425                 430

Val Ser Val Leu Ser Val Lys Gly Ser Leu Ala Pro Ile Ser Gly Thr
                435                 440                 445

Val Thr Ser Ala Gln Ile Val Leu Arg Phe Asp Glu Asn Gly Val Leu
                450                 455                 460

Leu Ser Asn Ser Ser Leu Asp Pro Gln Tyr Trp Asn Tyr Arg Lys Gly
465                 470                 475                 480

Asp Leu Thr Glu Gly Thr Ala Tyr Thr Asn Ala Val Gly Phe Met Pro
```

```
                  485                 490                 495
Asn Leu Thr Ala Tyr Pro Lys Thr Gln Ser Gln Thr Ala Lys Ser Asn
            500                 505                 510
Ile Val Ser Gln Val Tyr Leu Asn Gly Asp Lys Ser Lys Pro Met Thr
            515                 520                 525
Leu Thr Ile Thr Leu Asn Gly Thr Asn Glu Thr Gly Asp Ala Thr Val
            530                 535                 540
Ser Thr Tyr Ser Met Ser Phe Ser Trp Asn Trp Asn Gly Ser Asn Tyr
545                 550                 555                 560
Ile Asn Glu Thr Phe Gln Thr Asn Ser Phe Thr Phe Ser Tyr Ile Ala
            565                 570                 575
Gln Glu

<210> SEQ ID NO 34
<211> LENGTH: 578
<212> TYPE: PRT
<213> ORGANISM: Pan troglodytes

<400> SEQUENCE: 34

Met Lys Arg Thr Lys Thr Ser Asp Glu Ser Phe Asn Pro Val Tyr Pro
1               5                   10                  15
Tyr Asp Thr Glu Ser Gly Pro Pro Ser Val Pro Phe Leu Thr Pro Pro
            20                  25                  30
Phe Val Ser Pro Asp Gly Phe Gln Glu Ser Pro Pro Gly Val Leu Ser
        35                  40                  45
Leu Asn Leu Ala Glu Pro Leu Val Thr Ser His Gly Met Leu Ala Leu
    50                  55                  60
Lys Met Gly Ser Gly Leu Ser Leu Asp Asp Ala Gly Asn Leu Thr Ser
65                  70                  75                  80
Gln Asp Ile Thr Thr Ala Ser Pro Pro Leu Lys Lys Thr Lys Thr Asn
                85                  90                  95
Leu Ser Leu Glu Thr Ser Ser Pro Leu Thr Val Ser Thr Ser Gly Ala
            100                 105                 110
Leu Thr Val Ala Ala Ala Ala Pro Leu Ala Val Ala Gly Thr Ser Leu
        115                 120                 125
Thr Met Gln Ser Glu Ala Pro Leu Thr Val Gln Asp Ala Lys Leu Thr
    130                 135                 140
Leu Ala Thr Lys Gly Pro Leu Thr Val Ser Glu Gly Lys Leu Ala Leu
145                 150                 155                 160
Gln Thr Ser Ala Pro Leu Thr Ala Ala Asp Ser Ser Thr Leu Thr Val
                165                 170                 175
Ser Ala Thr Pro Pro Leu Ser Thr Ser Asn Gly Ser Leu Gly Ile Asp
            180                 185                 190
Met Gln Ala Pro Ile Tyr Thr Thr Asn Gly Lys Leu Gly Leu Asn Phe
        195                 200                 205
Gly Ala Pro Leu His Val Val Asp Ser Leu Asn Ala Leu Thr Val Val
    210                 215                 220
Thr Gly Gln Gly Leu Thr Ile Asn Gly Thr Ala Leu Gln Thr Arg Val
225                 230                 235                 240
Ser Gly Ala Leu Asn Tyr Asp Thr Ser Gly Asn Leu Glu Leu Arg Ala
                245                 250                 255
Ala Gly Gly Met Arg Val Asp Ala Asn Gly Gln Leu Ile Leu Asp Val
            260                 265                 270
Ala Tyr Pro Phe Asp Ala Gln Asn Asn Leu Ser Leu Arg Leu Gly Gln
```

```
                275                 280                 285
Gly Pro Leu Phe Val Asn Ser Ala His Asn Leu Asp Val Asn Tyr Asn
290                 295                 300

Arg Gly Leu Tyr Leu Phe Thr Ser Gly Asn Thr Lys Lys Leu Glu Val
305                 310                 315                 320

Asn Ile Lys Thr Ala Lys Gly Leu Ile Tyr Asp Asp Thr Ala Ile Ala
                325                 330                 335

Ile Asn Ala Gly Asp Gly Leu Gln Phe Asp Ser Gly Ser Asp Thr Asn
            340                 345                 350

Pro Leu Lys Thr Lys Leu Gly Leu Gly Leu Asp Tyr Asp Ser Ser Arg
        355                 360                 365

Ala Ile Ile Ala Lys Leu Gly Thr Gly Leu Ser Phe Asp Asn Thr Gly
    370                 375                 380

Ala Ile Thr Val Gly Asn Lys Asn Asp Asp Lys Leu Thr Leu Trp Thr
385                 390                 395                 400

Thr Pro Asp Pro Ser Pro Asn Cys Arg Ile Tyr Ser Glu Lys Asp Ala
                405                 410                 415

Lys Phe Thr Leu Val Leu Thr Lys Cys Gly Ser Gln Val Leu Ala Ser
            420                 425                 430

Val Ser Val Leu Ser Val Lys Gly Ser Leu Ala Pro Ile Ser Gly Thr
        435                 440                 445

Val Thr Ser Ala Gln Ile Val Leu Arg Phe Asp Glu Asn Gly Val Leu
    450                 455                 460

Leu Ser Asn Ser Ser Leu Asp Pro Gln Tyr Trp Asn Tyr Arg Lys Gly
465                 470                 475                 480

Asp Leu Thr Glu Gly Thr Ala Tyr Thr Asn Ala Val Gly Phe Met Pro
                485                 490                 495

Asn Leu Thr Ala Tyr Pro Lys Thr Gln Ser Gln Thr Ala Lys Ser Asn
            500                 505                 510

Ile Val Ser Gln Val Tyr Leu Asn Gly Asp Lys Ser Lys Pro Met Thr
        515                 520                 525

Leu Thr Ile Thr Leu Asn Gly Thr Asn Glu Thr Gly Asp Ala Thr Val
    530                 535                 540

Ser Thr Tyr Ser Met Ser Phe Ser Trp Asn Trp Asn Gly Ser Asn Tyr
545                 550                 555                 560

Ile Asn Glu Thr Phe Gln Thr Asn Ser Phe Thr Phe Ser Tyr Ile Ala
                565                 570                 575

Gln Glu

<210> SEQ ID NO 35
<211> LENGTH: 577
<212> TYPE: PRT
<213> ORGANISM: Pan paniscus

<400> SEQUENCE: 35

Met Lys Arg Ala Lys Thr Ser Asp Glu Thr Phe Asn Pro Val Tyr Pro
1               5                   10                  15

Tyr Asp Thr Glu Asn Gly Pro Pro Ser Val Pro Phe Leu Thr Pro Pro
            20                  25                  30

Phe Val Ser Pro Asp Gly Phe Gln Glu Ser Pro Pro Gly Val Leu Ser
        35                  40                  45

Leu Arg Leu Ser Glu Pro Leu Val Thr Ser His Gly Met Leu Ala Leu
    50                  55                  60

Lys Met Gly Asn Gly Leu Ser Leu Asp Asp Ala Gly Asn Leu Thr Ser
```

```
            65                   70                  75                  80
Gln Asp Val Thr Thr Val Thr Pro Pro Leu Lys Lys Thr Lys Thr Asn
                    85                  90                  95

Leu Ser Leu Gln Thr Ser Ala Pro Leu Thr Val Ser Ser Gly Ser Leu
                100                 105                 110

Thr Val Ala Ala Ala Pro Leu Ala Val Ala Gly Thr Ser Leu Thr
                115                 120                 125

Met Gln Ser Gln Ala Pro Leu Thr Val Gln Asp Ala Lys Leu Gly Leu
    130                 135                 140

Ala Thr Gln Gly Pro Leu Thr Val Ser Glu Gly Lys Leu Thr Leu Gln
145                 150                 155                 160

Thr Ser Ala Pro Leu Thr Ala Ala Asp Ser Ser Thr Leu Thr Val Ser
                165                 170                 175

Ala Thr Pro Pro Leu Ser Thr Ser Asn Gly Ser Leu Ser Ile Asp Met
                180                 185                 190

Gln Ala Pro Ile Tyr Thr Thr Asn Gly Lys Leu Ala Leu Asn Ile Gly
                195                 200                 205

Ala Pro Leu His Val Val Asp Thr Leu Asn Ala Leu Thr Val Val Thr
    210                 215                 220

Gly Gln Gly Leu Thr Ile Asn Gly Arg Ala Leu Gln Thr Arg Val Thr
225                 230                 235                 240

Gly Ala Leu Ser Tyr Asp Thr Glu Gly Asn Ile Gln Leu Gln Ala Gly
                245                 250                 255

Gly Gly Met Arg Ile Asp Asn Asn Gly Gln Leu Ile Leu Asn Val Ala
                260                 265                 270

Tyr Pro Phe Asp Ala Gln Asn Asn Leu Ser Leu Arg Leu Gly Gln Gly
                275                 280                 285

Pro Leu Ile Val Asn Ser Ala His Asn Leu Asp Leu Asn Leu Asn Arg
    290                 295                 300

Gly Leu Tyr Leu Phe Thr Ser Gly Asn Thr Lys Lys Leu Glu Val Asn
305                 310                 315                 320

Ile Lys Thr Ala Lys Gly Leu Phe Tyr Asp Gly Thr Ala Ile Ala Ile
                325                 330                 335

Asn Ala Gly Asp Gly Leu Gln Phe Gly Ser Gly Ser Asp Thr Asn Pro
                340                 345                 350

Leu Gln Thr Lys Leu Gly Leu Gly Leu Glu Tyr Asp Ser Asn Lys Ala
                355                 360                 365

Ile Ile Thr Lys Leu Gly Thr Gly Leu Ser Phe Asp Asn Thr Gly Ala
    370                 375                 380

Ile Thr Val Gly Asn Lys Asn Asp Asp Lys Leu Thr Leu Trp Thr Thr
385                 390                 395                 400

Pro Asp Pro Ser Pro Asn Cys Arg Ile Asn Ser Glu Lys Asp Ala Lys
                405                 410                 415

Leu Thr Leu Val Leu Thr Lys Cys Gly Ser Gln Val Leu Ala Ser Val
                420                 425                 430

Ser Val Leu Ser Val Lys Gly Ser Leu Ala Pro Ile Ser Gly Thr Val
                435                 440                 445

Thr Ser Ala Gln Ile Val Leu Arg Phe Asp Glu Asn Gly Val Leu Leu
    450                 455                 460

Ser Asn Ser Ser Leu Asp Pro Gln Tyr Trp Asn Tyr Arg Lys Gly Asp
465                 470                 475                 480

Ser Thr Glu Gly Thr Ala Tyr Thr Asn Ala Val Gly Phe Met Pro Asn
                485                 490                 495
```

```
Leu Thr Ala Tyr Pro Lys Thr Gln Ser Gln Thr Ala Lys Ser Asn Ile
                500                 505                 510

Val Ser Gln Val Tyr Leu Asn Gly Asp Lys Thr Lys Pro Met Thr Leu
            515                 520                 525

Thr Ile Thr Leu Asn Gly Thr Asn Glu Thr Gly Asp Ala Thr Val Ser
        530                 535                 540

Thr Tyr Ser Met Ser Phe Ser Trp Asn Trp Asn Gly Ser Asn Tyr Ile
545                 550                 555                 560

Asn Asp Thr Phe Gln Thr Asn Ser Phe Thr Phe Ser Tyr Ile Ala Gln
                565                 570                 575

Glu

<210> SEQ ID NO 36
<211> LENGTH: 577
<212> TYPE: PRT
<213> ORGANISM: Pan paniscus

<400> SEQUENCE: 36

Met Lys Arg Ala Lys Thr Ser Asp Glu Thr Phe Asn Pro Val Tyr Pro
1               5                   10                  15

Tyr Asp Thr Glu Asn Gly Pro Pro Ser Val Pro Phe Leu Thr Pro Pro
                20                  25                  30

Phe Val Ser Pro Asp Gly Phe Gln Glu Ser Pro Gly Val Leu Ser
            35                  40                  45

Leu Arg Leu Ser Glu Pro Leu Val Thr Ser His Gly Met Leu Ala Leu
        50                  55                  60

Lys Met Gly Asn Gly Leu Ser Leu Asp Asp Ala Gly Asn Leu Thr Ser
65                  70                  75                  80

Gln Asp Val Thr Thr Val Thr Pro Pro Leu Lys Lys Thr Lys Thr Asn
                85                  90                  95

Leu Ser Leu Gln Thr Ser Ala Pro Leu Thr Val Ser Ser Gly Ser Leu
            100                 105                 110

Thr Val Ala Ala Ala Ala Pro Leu Ala Val Ala Gly Thr Ser Leu Thr
        115                 120                 125

Met Gln Ser Gln Ala Pro Leu Thr Val Gln Asp Ala Lys Leu Gly Leu
130                 135                 140

Ala Thr Gln Gly Pro Leu Thr Val Ser Glu Gly Lys Leu Thr Leu Gln
145                 150                 155                 160

Thr Ser Ala Pro Leu Thr Ala Ala Asp Ser Ser Thr Leu Thr Val Ser
                165                 170                 175

Ala Thr Pro Pro Leu Ser Thr Ser Asn Gly Ser Leu Ser Ile Asp Met
            180                 185                 190

Gln Ala Pro Ile Tyr Thr Thr Asn Gly Lys Leu Ala Leu Asn Ile Gly
        195                 200                 205

Ala Pro Leu His Val Val Asp Thr Leu Asn Ala Leu Thr Val Val Thr
210                 215                 220

Gly Gln Gly Leu Thr Ile Asn Gly Arg Ala Leu Gln Thr Arg Val Thr
225                 230                 235                 240

Gly Ala Leu Ser Tyr Asp Thr Glu Gly Asn Ile Gln Leu Gln Ala Gly
                245                 250                 255

Gly Gly Met Arg Ile Asp Asn Asn Gly Gln Leu Ile Leu Asn Val Ala
            260                 265                 270

Tyr Pro Phe Asp Ala Gln Asn Asn Leu Ser Leu Arg Leu Gly Gln Gly
        275                 280                 285
```

Pro Leu Ile Val Asn Ser Ala His Asn Leu Asp Leu Asn Leu Asn Arg
    290                 295                 300

Gly Leu Tyr Leu Phe Thr Ser Gly Asn Thr Lys Leu Glu Val Asn
305                 310                 315                 320

Ile Lys Thr Ala Lys Gly Leu Phe Tyr Asp Gly Thr Ala Ile Ala Ile
                325                 330                 335

Asn Ala Gly Asp Gly Leu Gln Phe Gly Ser Gly Ser Asp Thr Asn Pro
            340                 345                 350

Leu Gln Thr Lys Leu Gly Leu Gly Leu Glu Tyr Asp Ser Asn Lys Ala
        355                 360                 365

Ile Ile Thr Lys Leu Gly Thr Gly Leu Ser Phe Asp Asn Thr Gly Ala
    370                 375                 380

Ile Thr Val Gly Asn Lys Asn Asp Asp Lys Leu Thr Leu Trp Thr Thr
385                 390                 395                 400

Pro Asp Pro Ser Pro Asn Cys Arg Ile Asn Ser Glu Lys Asp Ala Lys
                405                 410                 415

Leu Thr Leu Val Leu Thr Lys Cys Gly Ser Gln Val Leu Ala Ser Val
            420                 425                 430

Ser Val Leu Ser Val Lys Gly Ser Leu Ala Pro Ile Ser Gly Thr Val
        435                 440                 445

Thr Ser Ala Gln Ile Val Leu Arg Phe Asp Glu Asn Gly Val Leu Leu
    450                 455                 460

Ser Asn Ser Ser Leu Asp Pro Gln Tyr Trp Asn Tyr Arg Lys Gly Asp
465                 470                 475                 480

Ser Thr Glu Gly Thr Ala Tyr Thr Asn Ala Val Gly Phe Met Pro Asn
                485                 490                 495

Leu Thr Ala Tyr Pro Lys Thr Gln Ser Gln Thr Ala Lys Ser Asn Ile
            500                 505                 510

Val Ser Gln Val Tyr Leu Asn Gly Asp Lys Thr Lys Pro Met Thr Leu
        515                 520                 525

Thr Ile Thr Leu Asn Gly Thr Asn Glu Thr Gly Asp Ala Thr Val Ser
    530                 535                 540

Thr Tyr Ser Met Ser Phe Ser Trp Asn Trp Asn Gly Ser Asn Tyr Ile
545                 550                 555                 560

Asn Asp Thr Phe Gln Thr Asn Ser Phe Thr Phe Ser Tyr Ile Ala Gln
                565                 570                 575

Glu

<210> SEQ ID NO 37
<211> LENGTH: 845
<212> TYPE: DNA
<213> ORGANISM: Human cytomegalovirus

<400> SEQUENCE: 37
ccattgcata cgttgtatcc atatcataat atgtacattt atattggctc atgtccaaca      60
ttaccgccat gttgacattg attattgact agttattaat agtaatcaat tacgggtca     120 ttagttcata gcccatatat ggagttccgc gttacataac ttacggtaaa tggcccgcct    180
ggctgaccgc ccaacgaccc ccgcccattg acgtcaataa tgacgtatgt tcccatagta    240
acgccaatag ggactttcca ttgacgtcaa tgggtggagt atttacggta aactgcccac    300
ttggcagtac atcaagtgta tcatatgcca gtacgccccc ctattgacgt caatgacggt    360
aaatggcccg cctggcatta tgcccagtac atgaccttat gggactttcc tacttggcag    420

| | |
|---|---|
| tacatctacg tattagtcat cgctattacc atggtgatgc ggttttggca gtacatcaat | 480 |
| gggcgtggat agcggtttga ctcacgggga tttccaagtc tccacccat tgacgtcaat | 540 |
| gggagtttgt tttggcacca aaatcaacgg actttccaa aatgtcgtaa caactccgcc | 600 |
| ccattgacgc aaatgggcgg taggcgtgta cggtgggagg tctatataag cagagctctc | 660 |
| cctatcagtg atagagatct ccctatcagt gatagagatc gtcgacgagc tcgtttagtg | 720 |
| aaccgtcaga tcgcctggag acgccatcca cgctgttttg acctccatag aagacaccgg | 780 |
| gaccgatcca gcctccgcgg ccgggaacgg tgcattggaa cgcggattcc ccgtgccaag | 840 |
| agtga | 845 |

<210> SEQ ID NO 38
<211> LENGTH: 15422
<212> TYPE: DNA
<213> ORGANISM: Pan troglodytes

<400> SEQUENCE: 38

| | |
|---|---|
| tgcccgcttt ccagtcggga aacctgtcgt gccagctgca ttaatgaatc ggccaacgcg | 60 |
| cggggagagg cggtttgcgt attgggcgct agatctccca tcacatatac ctgccgttca | 120 |
| ctattattta gtgaaatgag atattatgat attttctgaa ttgtgattaa aaaggcaact | 180 |
| ttatgcccat gcaacagaaa ctataaaaaa tacagagaat gaaaagaaac agatagattt | 240 |
| tttagttctt taggcccgta gtctgcaaat ccttttatga ttttctatca aacaaaagag | 300 |
| gaaaatagac cagttgcaat ccaaacgaga gtctaataga atgaggtcga aaagtaaatc | 360 |
| gcgcgggttt gttactgata aagcaggcaa gacctaaaat gtgtaaaggg caaagtgtat | 420 |
| actttggcgt caccccttac atattttagg tcttttttta ttgtgcgtaa ctaacttgcc | 480 |
| atcttcaaac aggagggctg gaagaagcag accgctaaca cagtcacataa aaaggagac | 540 |
| atgaacgatg aacatcaaaa agtttgcaaa acaagcaaca gtattaacct ttactaccgc | 600 |
| actgctggca ggaggcgcaa ctcaagcgtt tgcgaaagaa acgaaccaaa agccatataa | 660 |
| ggaaacatac ggcatttccc atattacacg ccatgatatg ctgcaaatcc ctgaacagca | 720 |
| aaaaaatgaa aaatatcaag ttcctgaatt cgattcgtcc acaattaaaa atatctcttc | 780 |
| tgcaaaaggc ctggacgttt gggacagctg gccattacaa aacgctgacg gcactgtcgc | 840 |
| aaactatcac ggctaccaca tcgtctttgc attagccgga gatcctaaaa atgcggatga | 900 |
| cacatcgatt tacatgttct atcaaaaagt cggcgaaact tctattgaca gctggaaaaa | 960 |
| cgctggccgc gtctttaaag acagcgacaa attcgatgca aatgattcta tcctaaaaga | 1020 |
| ccaaacacaa gaatggtcag gttcagccac atttacatct gacggaaaaa tccgtttatt | 1080 |
| ctacactgat ttctccggta acattacgg caaacaaaca ctgacaactg cacaagttaa | 1140 |
| cgtatcagca tcagacagct ctttgaacat caacggtgta gaggattata atcaatctt | 1200 |
| tgacggtgac ggaaaaacgt atcaaaatgt acagcagttc atcgatgaag caactacag | 1260 |
| ctcaggcgac aaccatacgc tgagagatcc tcactacgta aagataaag ccacaaata | 1320 |
| cttagtattt gaagcaaaca ctggaactga agatggctac caaggcgaag atctttatt | 1380 |
| taacaaagca tactatggca aaagcacatc attcttccgt caagaaagtc aaaaacttct | 1440 |
| gcaaagcgat aaaaaacgca cggctgagtt agcaaacggc gctctcggta tgattgagct | 1500 |
| aaacgatgat tacacactga aaaagtgat gaaaccgctg attgcatcta acacagtaac | 1560 |
| agatgaaatt gaacgcgcga acgtctttaa aatgaacggc aaatggtacc tgttcactga | 1620 |
| ctcccgcgga tcaaaaatga cgattgacgg cattacgtct aacgatattt acatgcttgg | 1680 |

```
ttatgtttct aattctttaa ctggcccata caagccgctg aacaaaactg gccttgtgtt    1740
aaaaatggat cttgatccta acgatgtaac ctttacttac tcacacttcg ctgtacctca    1800
agcgaaagga aacaatgtcg tgattacaag ctatatgaca aacagaggat tctacgcaga    1860
caaacaatca acgtttgcgc caagcttcct gctgaacatc aaaggcaaga aaacatctgt    1920
tgtcaaagac agcatccttg aacaaggaca attaacagtt aacaataat agggataaca     1980 gggtaatgct agaagacccg agtcttacca gtaaaagaaa aaagatctct caacgcagca    2040
ccagcaccaa cacttcgcag tgtaaaaggc caagtgccga gagagtatat ataggaataa    2100
aaagtgacgt aaacgggcaa agtccaaaaa acgcccagaa aaaccgcacg cgaacctacg    2160
ccccgaaacg aaagccaaaa aacactagac actcccttcc ggcgtcaact tccgctttcc    2220
cacgctacgt cacttgcccc agtcaaacaa actacatatc ccgaacttcc aagtcgccac    2280
gcccaaaaca ccgcctacac ctccccgccc gccggcccgc cccaaaccc gcctcccgcc      2340 ccgcgccccg ccccgcgccg cccatctcat tatcatattg gcttcaatcc aaaataaggt    2400
atattattga tgatggttta acggatcct ctagagtcga cctgcaggca tgcaagcttg     2460
agtattctat agtgtcacct aaatagcttg gcgtaatcat ggtcatagct gtttcctgtg    2520
tgaaattgtt atccgctcac aattccacac aacatacgag ccggaagcat aaagtgtaaa    2580
gcctggggtg cctaatgagt gagctaactc acattaattg cgttgcgctc actgcccgct    2640
ttccagtcgg gaaacctgtc gtgccagctg cattaatgaa tcggccaacg cgaacccctt    2700
gcggccgccc gggccgtcga ccaattctca tgtttgacag cttatcatcg aatttctgcc    2760
attcatccgc ttattatcac ttattcaggc gtagcaacca ggcgtttaag ggcaccaata    2820
actgccttaa aaaaattacg ccccgccctg ccactcatcg cagtactgtt gtaattcatt    2880
aagcattctg ccgacatgga agccatcaca acggcatga tgaacctgaa tcgccagcgg     2940
catcagcacc ttgtcgcctt gcgtataata tttgcccatg gtgaaaacgg gggcgaagaa    3000
gttgtccata ttggccacgt ttaaatcaaa actggtgaaa ctcacccagg gattggctga    3060
gacgaaaaac atattctcaa taaacccttt agggaaatag gccaggtttt caccgtaaca    3120
cgccacatct gcgaatata tgtgtagaaa ctgccggaaa tcgtcgtggt attcactcca     3180
gagcgatgaa aacgtttcag tttgctcatg gaaaacggtg taacaagggt gaacactatc    3240
ccatatcacc agctcaccgt cttccattgc catacgaaat tccggatgag cattcatcag    3300
gcgggcaaga atgtgaataa aggccggata aaacttgtgc ttattttct ttacggtctt     3360 taaaaaggcc gtaatatcca gctgaacggt ctggttatag gtacattgag caactgactg    3420
aaatgcctca aaatgttctt tacgatgcca ttgggatata tcaacggtgg tatatccagt    3480
gatttttttc tccattttag cttccttagc tcctgaaaat ctcgataact caaaaaatac    3540
gcccggtagt gatcttattt cattatggtg aaagttggaa cctcttacgt gccgatcaac    3600
gtctcatttt cgccaaaagt tggcccaggg cttcccggta tcaacaggga caccaggatt    3660
tatttattct gcgaagtgat cttccgtcac aggtatttat tcgcgataag ctcatggagc    3720
ggcgtaaccg tcgcacagga aggacagaga aagcgcggat ctgggaagtg acggacagaa    3780
cggtcaggac ctggattggg gaggcggttg ccgccgctgc tgctgacggt gtgacgttct    3840
ctgttccggt cacaccacat acgttccgcc attcctatgc gatgcacatg ctgtatgccg    3900
gtataccgct gaaagttctg caaagccga tgggacataa gtccatcagt tcaacggaag     3960
tctacacgaa ggttttgcg ctggatgtgg ctgcccggca ccgggtgcag tttgcgatgc      4020
```

```
cggagtctga tgcggttgcg atgctgaaac aattatcctg agaataaatg ccttggcctt    4080
tatatggaaa tgtggaactg agtggatatg ctgtttttgt ctgttaaaca gagaagctgg    4140
ctgttatcca ctgagaagcg aacgaaacag tcgggaaaat ctcccattat cgtagagatc    4200
cgcattatta atctcaggag cctgtgtagc gtttatagga agtagtgttc tgtcatgatg    4260
cctgcaagcg gtaacgaaaa cgatttgaat atgccttcag gaacaataga aatcttcgtg    4320
cggtgttacg ttgaagtgga gcggattatg tcagcaatgg acagaacaac ctaatgaaca    4380
cagaaccatg atgtggtctg tccttttaca gccagtagtg ctcgccgcag tcgagcgaca    4440
gggcgaagcc ctcgagtgag cgaggaagca ccagggaaca gcacttatat attctgctta    4500
cacacgatgc ctgaaaaaac ttcccttggg gttatccact tatccacggg gatatttta    4560 taattatttt ttttatagtt tttagatctt ctttttttaga gcgccttgta ggcctttatc    4620
catgctggtt ctagagaagg tgttgtgaca aattgcccct tcagtgtgac aaatcaccct    4680
caaatgacag tcctgtctgt gacaaattgc ccttaaccct gtgacaaatt gccctcagaa    4740
gaagctgttt tttcacaaag ttatccctgc ttattgactc ttttttattt agtgtgacaa    4800
tctaaaaact tgtcacactt cacatggatc tgtcatggcg gaaacagcgg ttatcaatca    4860
caagaaacgt aaaaatagcc cgcgaatcgt ccagtcaaac gacctcactg aggcggcata    4920
tagtctctcc cgggatcaaa aacgtatgct gtatctgttc gttgaccaga tcagaaaatc    4980
tgatggcacc ctacaggaac atgacggtat ctgcgagatc catgttgcta aatatgctga    5040
aatattcgga ttgacctctg cggaagccag taaggatata cggcaggcat gaagagttt    5100 cgcggggaag gaagtggttt tttatcgccc tgaagaggat gccggcgatg aaaaaggcta    5160
tgaatctttt ccttggttta tcaaacgtgc gcacagtcca tccagagggc tttacagtgt    5220
acatatcaac ccatatctca ttcccttctt tatcgggtta cagaaccggt ttacgcagtt    5280
tcggcttagt gaaacaaaag aaatcaccaa tccgtatgcc atgcgtttat acgaatccct    5340
gtgtcagtat cgtaagccgg atggctcagg catcgtctct ctgaaaatcg actggatcat    5400
agagcgttac cagctgcctc aaagttacca gcgtatgcct gacttccgcc gccgcttcct    5460
gcaggtctgt gttaatgaga tcaacagcag aactccaatg cgcctctcat acattgagaa    5520
aaagaaaggc cgccagacga ctcatatcgt attttccttc cgcgatatca cttccatgac    5580
gacaggatag tctgagggtt atctgtcaca gatttgaggg tggttcgtca catttgttct    5640
gacctactga gggtaatttg tcacagtttt gctgtttcct tcagcctgca tggattttct    5700 catactttt gaactgtaat ttttaaggaa gccaaatttg agggcagttt gtcacagttg    5760
atttccttct ctttcccttc gtcatgtgac ctgatatcgg gggttagttc gtcatcattg    5820
atgagggttg attatcacag tttattactc tgaattggct atccgcgtgt gtacctctac    5880
ctggagtttt tcccacggtg gatatttctt cttgcgctga gcgtaagagc tatctgacag    5940
aacagttctt ctttgcttcc tcgccagttc gctcgctatg ctcggttaca cggctgcggc    6000
gagcgctagt gataataagt gactgaggta tgtgctcttc ttatctcctt ttgtagtgtt    6060
gctcttattt taaacaactt tgcggttttt tgatgacttt gcgattttgt tgttgctttg    6120
cagtaaattg caagatttaa taaaaaaacg caaagcaatg attaaaggat gttcagaatg    6180
aaactcatgg aaacacttaa ccagtgcata aacgctggtc atgaaatgac gaaggctatc    6240
gccattgcac agtttaatga tgacagcccg gaagcgagga aaataacccg gcgctggaga    6300
ataggtgaag cagcggattt agttgggggtt cttctcagg ctatcagaga tgccgagaaa    6360
gcagggcgac taccgcaccc ggatatggaa attcgaggac gggttgagca acgtgttggt    6420
```

```
tatacaattg aacaaattaa tcatatgcgt gatgtgtttg gtacgcgatt gcgacgtgct   6480
gaagacgtat ttccaccggt gatcggggtt gctgcccata aaggtggcgt ttacaaaacc   6540 tcagttttctg ttcatcttgc tcaggatctg gctctgaagg ggctacgtgt tttgctcgtg   6600
gaaggtaacg accccccaggg aacagcctca atgtatcacg gatgggtacc agatcttcat   6660
attcatgcag aagacactct cctgcctttc tatcttgggg aaaaggacga tgtcacttat   6720
gcaataaagc ccacttgctg gccggggctt gacattattc cttcctgtct ggctctgcac   6780
cgtattgaaa ctgagttaat gggcaaattt gatgaaggta aactgcccac cgatccacac   6840
ctgatgctcc gactggccat tgaaactgtt gctcatgact atgatgtcat agttattgac   6900
agcgcgccta acctgggtat cggcacgatt aatgtcgtat gtgctgctga tgtgctgatt   6960
gttcccacgc ctgctgagtt gtttgactac acctccgcac tgcagttttt cgatatgctt   7020
cgtgatctgc tcaagaacgt tgatcttaaa gggttcgagc ctgatgtacg tattttgctt   7080
accaaataca gcaatagtaa tggctctcag tccccgtgga tggaggagca aattcgggat   7140
gcctggggaa gcatggttct aaaaaatgtt gtacgtgaaa cggatgaagt tggtaaaggt   7200
cagatccgga tgagaactgt ttttgaacag gccattgatc aacgctcttc aactggtgcc   7260
tggagaaatg ctctttctat ttgggaacct gtctgcaatg aaattttcga tcgtctgatt   7320
aaaccacgct gggagattag ataatgaagc gtgcgcctgt tattccaaaa catacgctca   7380
atactcaacc ggttgaagat acttcgttat cgacaccagc tgccccgatg gtggattcgt   7440
taattgcgcg cgtaggagta atggctcgcg gtaatgccat tactttgcct gtatgtggtc   7500
gggatgtgaa gtttactctt gaagtgctcc ggggtgatag tgttgagaag acctctcggg   7560
tatggtcagg taatgaacgt gaccaggagc tgcttactga ggacgcactg gatgatctca   7620
tcccttcttt tctactgact ggtcaacaga caccggcgtt cggtcgaaga gtatctggtg   7680
tcatagaaat tgccgatggg agtcgccgtc gtaaagctgc tgcacttacc gaaagtgatt   7740
atcgtgttct ggttggcgag ctggatgatg agcagatggc tgcattatcc agattgggta   7800
acgattatcg cccaacaagt gcttatgaac gtggtcagcg ttatgcaagc cgattgcaga   7860
atgaatttgc tggaaatatt tctgcgctgg ctgatgcgga aaatatttca cgtaagatta   7920
ttacccgctg tatcaacacc gccaaattgc ctaaatcagt tgttgctctt ttttctcacc   7980
ccggtgaact atctgcccgg tcaggtgatg cacttcaaaa agcctttaca gataaagagg   8040
aattacttaa gcagcaggca tctaaccttc atgagcagaa aaaagctggg gtgatatttg   8100
aagctgaaga agttatcact cttttaactt ctgtgcttaa aacgtcatct gcatcaagaa   8160
ctagtttaag ctcacgacat cagtttgctc ctggagcgac agtattgtat aagggcgata   8220
aaatggtgct taacctggac aggtctcgtg ttccaactga gtgtatagag aaaattgagg   8280
ccattcttaa ggaacttgaa aagccagcac cctgatgcga ccacgtttta gtctacgttt   8340
atctgtcttt acttaatgtc cttttgttaca ggccagaaag cataactggc ctgaatattc   8400
tctctgggcc cactgttcca cttgtatcgt cggtctgata atcagactgg gaccacggtc   8460
ccactcgtat cgtcggtctg attattagtc tgggaccacg gtcccactcg tatcgtcggt   8520
ctgattatta gtctgggacc acggtcccac tcgtatcgtc ggtctgataa tcagactggg   8580
accacggtcc cactcgtatc gtcggtctga ttattagtct gggaccatgg tcccactcgt   8640
atcgtcggtc tgattattag tctgggacca cggtcccact cgtatcgtcg gtctgattat   8700
tagtctggaa ccacggtccc actcgtatcg tcggtctgat tattagtctg ggaccacggt   8760
```

```
cccactcgta tcgtcggtct gattattagt ctgggaccac gatcccactc gtgttgtcgg   8820
tctgattatc ggtctgggac cacggtccca cttgtattgt cgatcagact atcagcgtga   8880
gactacgatt ccatcaatgc ctgtcaaggg caagtattga catgtcgtcg taacctgtag   8940
aacggagtaa cctcggtgtg cggttgtatg cctgctgtgg attgctgctg tgtcctgctt   9000
atccacaaca ttttgcgcac ggttatgtgg acaaaatacc tggttaccca ggccgtgccg   9060
gcacgttaac cgggctgcat ccgatgcaag tgtgtcgctg tcgacgagct cgcgagctcg   9120
gacatgaggt tgccccgtat tcagtgtcgc tgatttgtat tgtctgaagt tgttttttacg  9180
ttaagttgat gcagatcaat taatacgata cctgcgtcat aattgattat ttgacgtggt   9240
ttgatggcct ccacgcacgt tgtgatatgt agatgataat cattatcact ttacgggtcc   9300
tttccggtga tccgacaggt tacggggcgg cgacctcgcg ggttttcgct atttatgaaa   9360
attttccggt ttaaggcgtt ccgttcttc ttcgtcataa cttaatgttt ttatttaaaa    9420
taccctctga aaagaaagga aacgacaggt gctgaaagcg agcttttttgg cctctgtcgt  9480
ttcctttctc tgttttttgtc cgtggaatga acaatggaag tccgagctca tcgctaataa  9540
cttcgtatag catacattat acgaagttat attcgatgcg ccgcaaggg gttcgcgtca    9600
gcgggtgttg gcgggtgtcg gggctggctt aactatgcgg catcagagca gattgtactg   9660
agagtgcacc atatgcggtg tgaaataccg cacagatgcg taaggagaaa ataccgcatc   9720
aggcgccatt cgccattcag gctgcgcaac tgttgggaag ggcgatcggt gcgggcctct   9780
tcgctattac gccagctggc gaaagggga tgtgctgcaa ggcgattaag ttgggtaacg    9840
ccagggtttt cccagtcacg acgttgtaaa acgacggcca gtgaattgta atacgactca   9900
ctatagggcg aattcgagct cggtacccgg ggatcctcgt ttaaaccatc atcaataata   9960
tacctttattt tggattgaag ccaatatgat aatgagatgg gcggcgcggg gcggggcgcg  10020
gggcgggagg cgggtttggg ggcgggccgg cgggcgggc ggtgtggcgg aagtggactt    10080
tgtaagtgtg gcgatgtga cttgctagtg ccggcgcgg taaaagtgac gttttccgtg     10140
cgcgacaacg cccccgggaa gtgacatttt tcccgcggtt tttaccggat gttgtagtga   10200
atttgggcgt aaccaagtaa gatttggcca ttttcgcggg aaaactgaaa cggggaagtg   10260
aaatctgatt aattttgcgt tagtcatacc gcgtaatatt tgtctagggc cgagggactt   10320
tggccgatta cgtggaggac tcgcccaggt gttttttgag gtgaatttcc gcgttccggg   10380
tcaaagtctg cgttttatta ttataggata tcccattgca tacgttgtat ccatatcata   10440
atatgtacat ttatattggc tcatgtccaa cattaccgcc atgttgacat tgattattga   10500
ctagttatta atagtaatca attacggggt cattagttca tagcccatat atggagttcc   10560
gcgttacata acttacggta aatggcccgc ctggctgacc gcccaacgac ccccgcccat   10620
tgacgtcaat aatgacgtat gttcccatag taacgccaat agggactttc cattgacgtc   10680
aatgggtgga gtatttacgg taaactgccc acttggcagt acatcaagtg tatcatatgc   10740
caagtacgcc ccctattgac gtcaatgacg gtaaatggcc cgcctggcat tatgcccagt   10800
acatgacctt atgggacttt cctacttggc agtacatcta cgtattagtc atcgctatta   10860
ccatggtgat gcggttttgg cagtacatca atgggcgtgg atagcggttt gactcacggg   10920
gatttccaag tctccacccc attgacgtca atgggagttt gttttggcac caaaatcaac   10980
gggactttcc aaaatgtcgt aacaactccg ccccattgac gcaaatgggc ggtaggcgtg   11040
tacggtggga ggtctatata agcagagctc tccctatcag tgatagagat ctccctatca   11100
gtgatagaga tcgtcgacga gctcgtttag tgaaccgtca gatcgcctgg agacgccatc   11160
```

```
cacgctgttt tgacctccat agaagacacc gggaccgatc cagcctccgc ggccgggaac   11220
ggtgcattgg aacgcggatt ccccgtgcca agagtgagat cttccgttta tctaggtacc   11280 gggcccccc tcgaggtcga cggtatcgat aagcttcacg ctgccgcaag cactcagggc   11340
gcaagggctg ctaaaggaag cggaacacgt agaaagccag tccgcagaaa cggtgctgac   11400
cccggatgaa tgtcagctac tgggctatct ggacaaggga aaacgcaagc gcaaagagaa   11460
agcaggtagc ttgcagtggg cttacatggc gatagctaga ctgggcggtt ttatggacag   11520
caagcgaacc ggaattgcca gctggggcgc cctctggtaa ggttgggaag ccctgcaaag   11580
taaactggat ggctttcttg ccgccaagga tctgatggcg caggggatca agatctaacc   11640
aggagctatt taatggcaac agttaaccag ctggtacgca aaccacgtgc tcgcaaagtt   11700
gcgaaaagca acgtgcctgc gctggaagca tgcccgcaaa acgtggcgt atgtactcgt   11760 gtatatacta ccactcctaa aaaaccgaac tccgcgctgc gtaaagtatg ccgtgttcgt   11820
ctgactaacg gtttcgaagt gacttcctac atcggtggtg aaggtcacaa cctgcaggag   11880
cactccgtga tcctgatccg tggcggtcgt gttaaagacc tcccgggtgt tcgttaccac   11940
accgtacgtg gtgcgcttga ctgctccggc gttaaagacc gtaagcaggc tcgttccaag   12000
tatggcgtga agcgtcctaa ggcttaatgg tagatctgat caagagacag gatgacggtc   12060
gtttcgcatg cttgaacaag atggattgca cgcaggttct ccggccgctt gggtggagag   12120
gctattcggc tatgactggg cacaacagac aatcggctgc tctgatgccg ccgtgttccg   12180
gctgtcagcg caggggcgcc cggttctttt tgtcaagacc gacctgtccg gtgccctgaa   12240
tgaactgcag gacgaggcag cgcggctatc gtggctggcc acgacgggcg ttccttgcgc   12300
agctgtgctc gacgttgtca ctgaagcggg aagggactgg ctgctattgg gcgaagtgcc   12360
ggggcaggat ctcctgtcat ctcaccttgc tcctgccgag aaagtatcca tcatggctga   12420
tgcaatgcgg cggctgcata cgcttgatcc ggctacctgc ccattcgacc accaagcgaa   12480
acatcgcatc gagcgagcac gtactcggat ggaagccggt cttgtcgatc aggatgatct   12540
ggacgaagag catcagggc tcgcgccagc cgaactgttc gccaggctca aggcgcgcat   12600
gcccgacggc gaggatctcg tcgtgaccca tggcgatgcc tgcttgccga atatcatggt   12660
ggaaaatggc cgcttttctg gattcatcga ctgtggccgg ctgggtgtgg cggaccgcta   12720
tcaggacata gcgttggcta cccgtgatat tgctgaagag cttggcggcg aatgggctga   12780
ccgcttcctc gtgctttacg gtatcgccgc tcccgattcg cagcgcatcg ccttctatcg   12840
ccttcttgac gagttcttct gagcgggact ctggggttcg aaatgaccga ccaagcgacg   12900
cccaacctgc catcacgaga tttcgattcc accgccgcct tctatgaaag gttgggcttc   12960
ggaatcgttt tccgggacgc cggctggatg atcctccagc gcggggatct catgctggag   13020
ttcttcgccc accccgggct cgatccctc gggggaatc agaattcagt cgacagcggc   13080
cgcgatctgt tgtgccttct agttgccagc catctgttgt ttgcccctcc ccgtgcctt   13140 ccttgaccct ggaaggtgcc actcccactg tcctttccta ataaaatgag gaaattgcat   13200
cgcattgtct gagtaggtgt cattctattc tggggggtgg ggtggggcag gacagcaagg   13260
gggaggattg ggaagacaat agcaggcatg ctggggatgc ggtgggctct atggccgatc   13320
agcgatcgct gaggtgggtg agtgggcgtg gcctggggtg gtcatgaaaa tatataagtt   13380
gggggtctta gggtctcttt atttgtgttg cagagaccgc cggagccatg agcgggagca   13440
gcagcagcag cagtagcagc agcgccttgg atggcagcat cgtgagccct tatttgacga   13500
```

| | |
|---|---|
| cgcggatgcc ccactgggcc ggggtgcgtc agaatgtgat gggctccagc atcgacggcc | 13560 |
| gacccgtcct gcccgcaaat tccgccacgc tgacctatgc gaccgtcgcg gggacgccgt | 13620 |
| tggacgccac cgccgccgcc gccgccaccg cagccgcctc ggccgtgcgc agcctggcca | 13680 |
| cggactttgc attcctggga ccactggcga caggggctac ttctcgggcc gctgctgccg | 13740 |
| ccgttcgcga tgacaagctg accgccctgc tggcgcagtt ggatgcgctt actcgggaac | 13800 |
| tgggtgacct ttctcagcag gtcatggccc tgcgccagca ggtctcctcc ctgcaagctg | 13860 |
| gcgggaatgc ttctcccaca aatgccgttt aagggcgcgc ctagggataa cagggtaata | 13920 |
| cccctatttg tttattttc taaatacatt caaatatgta tccgctcatg agacaataac | 13980 |
| cctgataaat gcttcaataa tattgaaaaa ggaagagtat gagtattcaa catttccgtg | 14040 |
| tcgcccttat tccctttttt gcggcatttt gccttcctgt ttttgctcac ccagaaacgc | 14100 |
| tggtgaaagt aaaagatgct gaagatcagt tgggtgcacg agtgggttac atcgaactgg | 14160 |
| atctcaacag cggtaagatc cttgagagtt ttcgccccga agaacgtttt ccaatgatga | 14220 |
| gcactttaa agttctgcta tgtggcgcgg tattatcccg tattgacgcc gggcaagagc | 14280 |
| aactcggtcg ccgcatacac tattctcaga atgacttggt tgagtactca ccagtcacag | 14340 |
| aaaagcatct tacggatggc atgacagtaa gagaattatg cagtgctgcc ataaccatga | 14400 |
| gtgataacac tgcggccaac ttacttctga caacgatcgg aggaccgaag gagctaaccg | 14460 |
| ctttttgca acaacatgggg gatcatgtaa ctcgccttga tcgttgggaa ccggagctga | 14520 |
| atgaagccat accaaacgac gagcgtgaca ccacgatgcc tgtagcaatg gcaacaacgt | 14580 |
| tgcgcaaact attaactggc gaactactta ctctagcttc ccggcaacaa ttaatagact | 14640 |
| ggatggaggc ggataaagtt gcaggaccac ttctgcgctc ggcccttccg gctggctggt | 14700 |
| ttattgctga taaatctgga gccggtgagc gtgggtctcg cggtatcatt gcagcactgg | 14760 |
| ggccagatgg taagccctcc cgtatcgtag ttatctacac gacggggagt caggcaacta | 14820 |
| tggatgaacg aaatagacag atcgctgaga taggtgcctc actgattaag cattggtaac | 14880 |
| tgtcagacca agtttactca tatatacttt agattgattt aaaatacgta tatgtatt | 14940 |
| agtcatcgct attaccatgg ttaatgcgcc gctacagggc gcgtccattc gccattcagg | 15000 |
| ctgcgcaact gttgggaagg gcgatcggtg cgggcctctt cgctattacg ccagctggcg | 15060 |
| aaagggggat gtgctgcaag gcgattaagt tgggtaacgc cagggttttc ccagtcacga | 15120 |
| cgttgtaaaa cgacggccag tgaattgtaa tacgactcac tatagggcga attgggccct | 15180 |
| ctagatgcat gctcgagcgg ccgccagtgt gatggatatc tgcagaattc cagcacactg | 15240 |
| gcggccgtta ctagtggatc cgagctcggt accaagcttg gcgtaatcat ggtcatagct | 15300 |
| gtttcctgtg tgaaattgtt atccgctcac aattccacac aacatacgag ccggaagcat | 15360 |
| aaagtgtaaa gcctggggtg cctaatgagt gagctaactc acattaattg cgttgcgctc | 15420 |
| ac | 15422 |

<210> SEQ ID NO 39
<211> LENGTH: 225
<212> TYPE: DNA
<213> ORGANISM: Bos taurus

<400> SEQUENCE: 39

| | |
|---|---|
| ctgtgccttc tagttgccag ccatctgttg tttgcccctc cccgtgcctt ccttgaccc | 60 |
| tggaaggtgc cactcccact gtcctttcct aataaaatga ggaaattgca tcgcattgtc | 120 |
| tgagtaggtg tcattctatt ctggggggtg ggtggggca ggacagcaag ggggaggatt | 180 | gggaagacaa tagcaggcat gctggggatg cggtgggctc tatgg        225

<210> SEQ ID NO 40
<211> LENGTH: 3983
<212> TYPE: DNA
<213> ORGANISM: Pan troglodytes

<400> SEQUENCE: 40

| | | | | | |
|---|---|---|---|---|---|
| catcatcaat | aatatacctt | attttggatt | gaagccaata | tgataatgag | atgggcggcg | 60 |
| cggggcgggg | cgcggggcgg | gaggcgggtt | tgggggcggg | ccggcgggcg | ggcggtgtg | 120 |
| gcggaagtgg | actttgtaag | tgtggcggat | gtgacttgct | agtgccgggc | gcggtaaaag | 180 |
| tgacgttttc | cgtgcgcgac | aacgcccccg | ggaagtgaca | ttttccgc | ggttttacc | 240 |
| ggatgttgta | gtgaatttgg | gcgtaaccaa | gtaagatttg | gccattttcg | cgggaaaact | 300 |
| gaaacgggga | agtgaaatct | gattaatttt | gcgttagtca | taccgcgtaa | tatttgtcta | 360 |
| gggccgaggg | actttggccg | attacgtgga | ggactcgccc | aggtgttttt | tgaggtgaat | 420 |
| ttccgcgttc | cgggtcaaag | tctccgtttt | attattatag | gatatcccat | tgcatacgtt | 480 |
| gtatccatat | cataatatgt | acaggcgcgc | caaagcatga | cactgatgtt | catttctgat | 540 |
| tcttatttta | ttattttcaa | acacaacaaa | atcattcaag | tcattcttcc | atcttagctt | 600 |
| aatagacaca | gtagcttaat | agacccagta | gtgcaaagcc | ccattctagc | ttataactag | 660 |
| tggagaagta | ctcgcctaca | tgggggtaga | gtcataatcg | tgcatcagga | tagggcggtg | 720 |
| gtgctgcagc | agcgcgcgaa | taaactgctg | ccgccgccgc | tccgtcctgc | aggaatacaa | 780 |
| catggcagtg | gtctcctcag | cgatgattcg | caccgcccgc | agcataaggc | gccttgtcct | 840 |
| ccgggcacag | cagcgcaccc | tgatctcact | taaatcagca | cagtaactgc | agcacagcac | 900 |
| cacaatattg | ttcaaaatcc | cacagtgcaa | ggcgctgtat | ccaaagctca | tggcggggac | 960 |
| cacagaaccc | acgtggccat | cataccacaa | gcgcaggtag | attaagtggc | gacccctcat | 1020 |
| aaacacgctg | gacataaaca | ttacctcttt | tggcatgttg | taattcacca | cctcccggta | 1080 |
| ccatataaac | ctctgattaa | acatggcgcc | atccaccacc | atcctaaacc | agctggccaa | 1140 |
| aacctgcccg | ccggctatac | actgcaggga | accgggactg | gaacaatgac | agtggagagc | 1200 |
| ccaggactcg | taaccatgga | tcatcatgct | cgtcatgata | tcaatgttgg | cacaacacag | 1260 |
| gcacacgtgc | atacacttcc | tcaggattac | aagctcctcc | cgcgttagaa | ccatatccca | 1320 |
| gggaacaacc | cattcctgaa | tcagcgtaaa | tcccacactg | cagggaagac | ctcgcacgta | 1380 |
| actcacgttg | tgcattgtca | aagtgttaca | ttcgggcagc | agcggatgat | cctccagtat | 1440 |
| ggtagcgcgg | gtttctgtct | caaaaggagg | tagacgatcc | ctactgtacg | gagtgcgccg | 1500 |
| agacaaccga | gatcgtgttg | gtcgtagtgt | catgccaaat | ggaacgccgg | acgtagtcat | 1560 |
| atttcctgaa | gtcttagatc | tctcaacgca | gcaccagcac | caacacttcg | cagtgtaaaa | 1620 |
| ggccaagtgc | cgagagagta | tatataggaa | taaaagtga | cgtaaacggg | caaagtccaa | 1680 |
| aaaacgccca | gaaaaccgc | acgcgaacct | acgccccgaa | acgaaagcca | aaaacacta | 1740 |
| gacactcect | tccggcgtca | acttccgctt | tcccacgcta | cgtcacttgc | cccagtcaaa | 1800 |
| caaactacat | atcccgaact | tccaagtcgc | cacgcccaaa | acaccgccta | cacctccccg | 1860 |
| cccgccggcc | cgcccccaaa | cccgcctccc | gcccgcgcc | ccgcccgcg | ccgcccatct | 1920 |
| cattatcata | ttggcttcaa | tccaaaataa | ggtatattat | tgatgatggt | ttaaacggat | 1980 |
| ccaattcttg | aagacgaaag | ggcctcgtga | tacgcctatt | tttataggtt | aatgtcatga | 2040 |

-continued

```
taataatggt tcttagacg tcaggtggca ctttcgggg aaatgtgcgc ggaacccta      2100 tttgtttatt tttctaaata cattcaaata tgtatccgct catgagacaa taaccctgat      2160
aaatgcttca ataatattga aaaggaaga gtatgagtat caacatttc cgtgtcgccc      2220 ttattccctt ttttgcggca ttttgccttc ctgttttgc tcacccagaa acgctggtga      2280
aagtaaaaga tgctgaagat cagttgggtg cacgagtggg ttacatcgaa ctggatctca      2340
acagcggtaa gatccttgag agtttcgcc ccgaagaacg ttttccaatg atgagcactt      2400
ttaaagttct gctatgtggc gcggtattat cccgtgttga cgccgggcaa gagcaactcg      2460
gtcgccgcat acactattct cagaatgact tggttgagta ctcaccagtc acagaaaagc      2520
atcttacgga tggcatgaca gtaagagaat tatgcagtgc tgccataacc atgagtgata      2580
acactgcggc caacttactt ctgacaacga tcggaggacc gaaggagcta accgcttttt      2640
tgcacaacat gggggatcat gtaactcgcc ttgatcgttg ggaaccggag ctgaatgaag      2700
ccataccaaa cgacgagcgt gacaccacga tgcctgtagc aatggcaaca acgttgcgca      2760
aactattaac tggcgaacta cttactctag cttcccggca acaattaata gactggatgg      2820
aggcggataa agttgcagga ccacttctgc gctcggccct tccggctggc tggtttattg      2880
ctgataaatc tggagccggt gagcgtgggt ctcgcggtat cattgcagca ctggggccag      2940
atggtaagcc ctcccgtatc gtagttatct acacgacggg gagtcaggca actatggatg      3000
aacgaaatag acagatcgct gagataggtg cctcactgat taagcattgg taactgtcag      3060
accaagttta ctcatatata ctttagattg atttaaaagg atctaggtga agatccttt      3120 tgataatctc atgaccaaaa tcccttaacg tgagttttcg ttccactgag cgtcagaccc      3180
cgtagaaaag atcaaaggat cttcttgaga tcctttttt ctgcgcgtaa tctgctgctt      3240
gcaaacaaaa aaaccaccgc taccagcggt ggtttgtttg ccggatcaag agctaccaac      3300
tctttttccg aaggtaactg gcttcagcag agcgcagata ccaaatactg tccttctagt      3360
gtagccgtag ttaggccacc acttcaagaa ctctgtagca ccgcctacat acctcgctct      3420
gctaatcctg ttaccagtgg ctgctgccag tggcgataag tcgtgtctta ccgggttgga      3480
ctcaagacga tagttaccgg ataaggcgca gcggtcgggc tgaacggggg gttcgtgcac      3540
acagcccagc ttggagcgaa cgacctacac cgaactgaga tacctacagc gtgagctatg      3600
agaaagcgcc acgcttcccg aagggagaaa ggcggacagg tatccggtaa gcggcagggt      3660
cggaacagga gagcgcacga gggagcttcc agggggaaac gcctggtatc tttatagtcc      3720
tgtcgggttt cgccacctct gacttgagcg tcgatttttg tgatgctcgt cagggggcg      3780 gagcctatgg aaaaacgcca gcaacgcggc cttttacgg ttcctggcct tttgctggcc      3840
ttgaagctgt ccctgatggt cgtcatctac ctgcctggac agcatggcct gcaacgcggg      3900
catcccgatg ccgccggaag cgagaagaat cataatgggg aaggccatcc agcctcgcgt      3960
cgcagatccg aattcgttta aac                                              3983
```

```
<210> SEQ ID NO 41
<211> LENGTH: 25
<212> TYPE: DNA
<213> ORGANISM: Human cytomegalovirus

<400> SEQUENCE: 41
acatcaatgg gcgtggatag cggtt                                             25

<210> SEQ ID NO 42
<211> LENGTH: 1187
```

<212> TYPE: DNA
<213> ORGANISM: Human cytomegalovirus

<400> SEQUENCE: 42

```
ccattgcata cgttgtatcc atatcataat atgtacattt atattggctc atgtccaaca      60
ttaccgccat gttgacattg attattgact agttattaat agtaatcaat tacggggtca     120
ttagttcata gcccatatat ggagttccgc gttacataac ttacggtaaa tggcccgcct     180
ggctgaccgc ccaacgaccc ccgcccattg acgtcaataa tgacgtatgt tcccatagta     240
acgccaatag ggactttcca ttgacgtcaa tgggtggagt atttacggta aactgcccac     300
ttggcagtac atcaagtgta tcatatgcca agtacgcccc ctattgacgt caatgacggt     360
aaatggcccg cctggcatta tgcccagtac atgaccttat gggactttcc tacttggcag     420
tacatctacg tattagtcat cgctattacc atggtgatgc ggttttggca gtacatcaat     480
gggcgtggat agcggtttga ctcacgggga tttccaagtc tccacccccat tgacgtcaat    540
gggagtttgt tttggcacca aaatcaacgg gactttccaa aatgtcgtaa caactccgcc     600
ccattgacgc aaatgggcgg taggcgtgta cggtgggagg tctatataag gcgaagcgct     660
ccctatcagt gatagagatc tccctatcag tgatagagat cgtcgacgag ctcgcggcgg     720
gcgggagtcg ctgcgcgctg ccttcgcccc gtgccccgct ccgccgccgc ctcgcgccgc     780
ccgcccggc tctgactgac cgcgttacta aaacaggtaa gtccgcctc cgcgccgggt       840
tttgcgcct cccgcgggcg ccccctcct cacggcgagc gctgccacgt cagacgaagg       900
gcgcagcgag cgtcctgatc cttccgcccg gacgctcagg acagcggccc gctgctcata    960
agactcggcc ttagaaccc agtatcagca gaaggacatt ttaggacggg acttgggtga    1020
ctctagggca ctggttttct ttccagagag cggaacaggc gaggaaaagt agtccttct     1080
cggcgattct gcggagggat ctccgtgggg cggtgaacgc cgatgatgcc tctactaacc    1140
atgttcatgt tttctttttt tttctacagg tcctgggtga cgaacag                  1187
```